United States Patent
Payne et al.

(10) Patent No.: US 9,296,996 B2
(45) Date of Patent: *Mar. 29, 2016

(54) GLUCOSYLTRANSFERASE ENZYMES FOR PRODUCTION OF GLUCAN POLYMERS

(71) Applicant: E I DU PONT DE NEMOURS AND COMPANY, Wilmington, DE (US)

(72) Inventors: Mark S Payne, Wilmington, DE (US); Yefim Brun, Wilmington, DE (US); Hongxian He, Wilmington, DE (US); Thomas Scholz, Bear, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/490,703

(22) Filed: Sep. 19, 2014

(65) Prior Publication Data

US 2015/0010954 A1    Jan. 8, 2015

Related U.S. Application Data

(62) Division of application No. 14/036,049, filed on Sep. 25, 2013, now Pat. No. 8,871,474.

(60) Provisional application No. 61/705,177, filed on Sep. 25, 2012, provisional application No. 61/705,178, filed on Sep. 25, 2012, provisional application No. 61/705,179, filed on Sep. 25, 2012, provisional application No. 61/705,180, filed on Sep. 25, 2012, provisional application No. 61/705,181, filed on Sep. 25, 2012.

(51) Int. Cl.
| | |
|---|---|
| *C12N 9/10* | (2006.01) |
| *C12P 19/18* | (2006.01) |
| *C08B 37/00* | (2006.01) |
| *C12P 19/04* | (2006.01) |

(52) U.S. Cl.
CPC .......... *C12N 9/1051* (2013.01); *C08B 37/0009* (2013.01); *C12N 9/1048* (2013.01); *C12P 19/04* (2013.01); *C12P 19/18* (2013.01); *C12Y 204/01005* (2013.01)

(58) Field of Classification Search
None
See application file for complete search history.

(56) References Cited

U.S. PATENT DOCUMENTS

| 5,952,205 A | 9/1999 | Catani et al. |
| 6,242,225 B1 | 6/2001 | Catani et al. |
| 6,660,502 B2 | 12/2003 | Catani et al. |
| 7,000,000 B1 | 2/2006 | O'Brien |
| 2013/0244287 A1 | 9/2013 | O'Brien et al. |
| 2013/0244288 A1 | 9/2013 | O'Brien et al. |

FOREIGN PATENT DOCUMENTS

WO  2013036918 A2  3/2013

OTHER PUBLICATIONS

Abo et al., Peptide Sequences for Sucrose Splitting and Glucan Binding Within *Streptococcus sobrinus* Glucosyltransferase (Water-Insoluble Glucan Synthetase), Journal of Bacteriology, vol. 173, No. 3 (1991), pp. 989-996.
Cantarel et al., The Carbohydrate-Active Enzymes Database (CAZY): An Expert Resource for Glycogenomics, Nucleic Acids Research, vol. 37 (2009), Database Issue pp. D233-D238.
Konishi et al., Structure and Enzymatic Properties of Genetically Truncated Forms of the Water-Insoluable Glucan-Synthesizing Glucosyltransferase From *Streptococcus sobrinus*, J. Biochem., vol. 126 (1999), pp. 287-295.
Leemhuis et al., Glucansucrases: Three-Dimensional Structures, Reactions, Mechanism, α-Glucan Analysis and Their Implications in Biotechnology and Food Applications, Journal of Biotechnology, vol. 163 (2013), pp. 250-272.
Monchois et al., Cloning and Sequencing of a Gene Coding for a Novel Dextransucrase From Leuconostoc Mesenteroids NRRL B-1299 Synthesizing Only α(1-6) and α(1-3) Linkages, Gene, Vol. 182 (1996), pp. 23-32.
Monchois et al., Isolation of an Active Catalytic Core of *Streptococcus downei* MFE28 GTF-I Glucosyltransferase, Journal of Bacteriology, vol. 181, No. 7(1A09). pp. 2290-2292.
Ogawa et al., Crystal Structure of (1->3)-α-D-Glucan, Fiber Differentiation Methods, vol. 47 (1980), pp. 353-362.
Simpson et al., Four Glucosyltransferases, GTFJ, GTFK, GTFL, and GTFM, From *Streptococcus salivarious* ATCC 25975, Microbiology, Vol. 141 (1995), pp. 1451-1460.
Yoshimi et al., Functional Analysis of the α-1,3-Glucan Synthase Genes AGSA and AGSB in Aspergillus Nidulans: AGSB Is the Major α-1,3-Glucan Sytnase in This Fungus, PLOS One, vol. 8, Issue 1 (2013), E54893, pp. 1-16.
Database Uniprot, Retrieved From EBI Accession No. Uniprot: Q0060, Database Accession No. Q00600 Sequence, Nov. 1, 1996 (XP002720581).
Giffard et al., Molecular Characterization of a Cluster of at Least Two Glucosyltransferase Genes in *Streptococcus salivarius* ATCC 25975, Journal of General Microbiology (1991), vol. 137, No. 11, pp. 2577-2593.
Kingston et al., Role of the C-Terminal YG Repeats of the Primer-Dependent Streptococcal Glucosyltransferase, GTFJ, in Binding to Dextran and Mutan, Microbiology (2002), vol. 148, No. Part 2, pp. 549-558.

*Primary Examiner* — Nashaat Nashed

(57) ABSTRACT

Reaction solutions are disclosed herein comprising water, sucrose and a glucosyltransferase enzyme that synthesizes poly alpha-1,3-glucan. The glucosyltransferase enzyme can synthesize insoluble glucan polymer having at least 50% alpha-1,3 glycosidic linkages and a number average degree of polymerization of at least 100. Further disclosed are methods of using such glucosyltransferase enzymes to produce insoluble poly alpha-1,3-glucan.

22 Claims, No Drawings

SEQUENCE LISTING

<160> NUMBER OF SEQ ID NOS: 64

<210> SEQ ID NO 1
<211> LENGTH: 4308
<212> TYPE: DNA
<213> ORGANISM: Streptococcus sobrinus

<400> SEQUENCE: 1

| | | | | | | |
|---|---|---|---|---|---|---|
| atggttgacg | gcaaatacta | ctattatgat | caggacggta | acgtaaagaa | gaatttcgcg | 60 |
| gtgagcgttg | gtgacaaaat | ctactacttc | gatgaaactg | gtgcatataa | ggataccagc | 120 |
| aaagtggacg | ccgacaagag | cagcagcgcg | gttagccaaa | acgcgaccat | ctttgcggcg | 180 |
| aataaccgtg | cgtacagcac | ctctgcaaag | aattttgaag | cggtggataa | ctacctgacc | 240 |
| gcagacagct | ggtatcgtcc | gaaatccatc | ctgaaggacg | gcaaaacctg | gaccgagagc | 300 |
| ggtaaggatg | atttccgtcc | actgctgatg | gcatggtggc | ctgacaccga | aactaagcgc | 360 |
| aactacgtga | actatatgaa | taaagtggtc | ggtattgaca | gacgtacac | tgcggaaacg | 420 |
| tcgcaagcgg | atttgaccgc | agcggcggag | ctggttcaag | cgcgtatcga | gcagaagatt | 480 |
| accagcgaaa | caacaccaa | atggctgcgc | gaagcaatct | ccgcgttcgt | taagacgcag | 540 |
| cctcagtgga | acggcgagtc | cgaaaagccg | tatgacgatc | acttgcagaa | cggtgcgctg | 600 |
| ctgtttgata | ccaaaccga | cctgacgcca | gacacccaaa | gcaattaccg | tttgctgaac | 660 |
| cgtaccccga | ccaatcagac | tggtagcctg | gatagccgtt | ttacgtataa | tccgaatgac | 720 |
| ccgttgggcg | gctacgattt | cttgctggcg | aacgacgttg | acaatagcaa | tccggtcgtc | 780 |
| caggctgaac | agttgaactg | gctgcattat | ctgctgaact | ttggctctat | ttacgctaac | 840 |
| gatgccgacg | ccaattttga | cagcattcgc | gttgatgccg | tcgataatgt | cgatgctgat | 900 |
| ctgctgcaaa | tcagcagcga | ttacctgaaa | gcagcgtatg | gcatcgacaa | gaataacaag | 960 |
| aatgcgaaca | accatgttag | catcgtcgaa | gcgtggagcg | acaatgatac | cccgtatttg | 1020 |
| cacgacgatg | gcgataatct | gatgaacatg | gacaacaaat | ttcgcctgtc | catgctgtgg | 1080 |
| agcctggcaa | agccgctgga | caaacgtagc | ggtttgaacc | cgctgattca | aatagcctg | 1140 |
| gtggaccgcg | aggtggacga | tcgtgaagtg | gaaaccgtgc | cgtcctacag | ctttgctcgt | 1200 |
| gcacatgata | gcgaggtgca | ggacatcatc | cgtgacatta | tcaaggctga | gattaaccca | 1260 |
| aatagctttg | gttatagctt | cactcaagaa | gagatcgagc | aagcctttaa | gatttacaac | 1320 |
| gaggatttga | agaaaacgga | caagaaatac | acccactaca | atgtgccgct | gagctacacc | 1380 |
| ctgctgctga | ccaacaaggg | cagcatcccg | cgtgtgtact | atggtgatat | gttcaccgat | 1440 |
| gatggccaat | acatggcaaa | caagaccgtc | aactacgacg | caatcgagag | cctgctgaaa | 1500 |
| gcccgtatga | aatatgtcag | cggtggccaa | gcaatgcaga | actatcaaat | tggtaatggc | 1560 |
| gagattttga | ccagcgtgcg | ctatggtaaa | ggtgccctga | gcagagcga | taagggtgac | 1620 |
| gcgacgacgc | gcactagcgg | tgttggcgtg | gttatgggta | atcagccgaa | cttctcctg | 1680 |
| gacggtaaag | ttgtggccct | gaatatgggt | gcggcccatg | cgaatcaaga | ataccgtgca | 1740 |
| ctgatggtca | gcactaaaga | cggtgtggca | acttacgcaa | ccgatgctga | cgcatccaaa | 1800 |
| gcgggcctgg | tcaagcgtac | cgacgagaac | ggctacctgt | acttcctgaa | tgatgatctg | 1860 |
| aagggcgtcg | cgaaccctca | ggtttccggc | ttcttgcaag | tgtgggttcc | agttggtgcc | 1920 |
| gccgatgacc | aggacattcg | cgtcgccgcc | agcgacacgg | cgagcacgga | tggtaaaagc | 1980 |
| ctgcatcaag | atgcggcgat | ggacagccgc | gtcatgtttg | agggtttcag | caattttcaa | 2040 |
| tccttcgcga | ccaaagaaga | agaatacacg | aatgttgtta | tcgcgaacaa | tgtcgataag | 2100 |

```
ttcgttagct ggggtatcac cgattttgaa atggctccgc agtatgttag cagcaccgac    2160
ggtcagttct tggacagcgt catccagaat ggctatgcgt ttactgatcg ctatgatctg    2220
ggtatgtcca aggcgaacaa gtatggcacg gcagaccaac tggttaaggc aatcaaagcc    2280
ctgcacgcta aggcctgaa  agttatggcg gactgggtcc cggatcaaat gtacacctttt   2340 ccaaaacagg aagttgtgac cgttacccgc accgacaaat tcggtaaacc gatcgccggc    2400
tctcaaatca atcacagctt gtatgtgacc gacaccaaat ccagcggcga cgactaccaa    2460
gcgaagtacg gcggtgcctt cctggatgaa ctgaaagaaa gtacccggaa ctgttcacg     2520 aaaaagcaaa ttagcacggg ccaagcgatt gatccgagcg tgaaaatcaa gcagtggagc    2580
gcaaaatact tcaatggttc gaatatcctg ggtcgcggtg cggactatgt gctgagcgac    2640
caggtcagca ataagtattt caacgtggcg agcgacacct tgttcctgcc gtccagcctg    2700
ctgggcaagg tcgtggagag cggcattcgt tacgacggca agggttacat ctacaacagc    2760
tccgcgaccg gcgatcaggt caaagcgtct tcattacgg  aagccggtaa cctgtattac    2820
ttcggcaaag acggttacat ggttactggt gcccagacga ttaatggcgc caactacttc    2880
ttcctggaaa acggtacggc actgcgtaat acgatttaca ccgatgctca aggtaatagc    2940
cactattacg cgaatgatgg caaacgctat gaaaatggct atcaacagtt cggtaacgat    3000
tggcgctact ttaaagatgg taacatggca gtcggcctga ccacggttga tgcaacgtg    3060 caatactttg acaaagacgg cgtccaggca aaggataaga ttatcgtcac ccgtgatggc    3120
aaggtccgtt acttcgatca gcacaacggt aacgcggcga ccaacacgtt cattgctgat    3180
aaaactggcc attggtatta cctgggtaaa gatggcgtcg cggtgactgg cgcccagacc    3240
gtcggcaaac aaaaactgta cttcgaggcc aacggtcaac aagttaaagg tgactttgtt    3300
acgtccgatg agggcaaact gtatttctat gacgttgatt ctggtgacat gtggacggac    3360
accttcatcg aggataaggc gggcaactgg ttctatttgg gcaaggatgg tgcggcagtt    3420
acgggtgccc aaacgattcg cggtcagaag ctgtacttca aggccaatgg tcaacaggtc    3480
aagggtgaca ttgttaaggg caccgacggt aaaatccgct actatgatgc aaaatccggt    3540
gaacaggtgt tcaacaaaac ggtgaaagct gcggatggca aaacgtatgt tatcggtaat    3600
gatggtgtcg cggtggaccc tagcgtggtt aaaggtcaaa cctttaagga cgcttcgggc    3660
gctctgcgtt tctacaactt gaagggtcaa ctggtcactg cagcggctg gtatgaaacc    3720 gcgaaccatg actgggttta cattcagtcc ggcaaggcac tgaccggcga acagaccatt    3780
aacggtcaac acctgtattt caagaagat  ggtcaccaag tcaagggtca gttggtcacg    3840
ggcaccgatg gtaaagtgcg ttactatgac gccaacagcg gtgaccaagc attcaacaag    3900
agcgtcactg tgaatggtaa aacctattac tttggcaacg atggtacggc gcagactgct    3960
ggcaacccga agggtcagac gttcaaggat ggctccgaca tccgttttta ctctatggaa    4020
ggccaactgg tgaccggctc gggttggtac gagaacgcgc aaggccagtg gctgtatgtg    4080
aaaaacggta aggtgctgac tggtctgcaa accgttggca gccagcgtgt ttacttcgac    4140
gagaatggta ttcaggccaa gggcaaagca gtgcgtacca gcgatggcaa aattcgttat    4200
ttcgacgaaa acagcggcag catgatcacg aatcaatgga agttcgtcta tggtcagtat    4260
tactactttg gtaacgacgg tgcacgtatt taccgtggtt ggaactaa                4308
```

<210> SEQ ID NO 2
<211> LENGTH: 1435
<212> TYPE: PRT

<213> ORGANISM: Streptococcus sobrinus

<400> SEQUENCE: 2

```
Met Val Asp Gly Lys Tyr Tyr Tyr Asp Gln Asp Gly Asn Val Lys
1               5                   10                  15

Lys Asn Phe Ala Val Ser Val Gly Asp Lys Ile Tyr Tyr Phe Asp Glu
            20                  25                  30

Thr Gly Ala Tyr Lys Asp Thr Ser Lys Val Asp Ala Asp Lys Ser Ser
                35                  40                  45

Ser Ala Val Ser Gln Asn Ala Thr Ile Phe Ala Ala Asn Asn Arg Ala
    50                  55                  60

Tyr Ser Thr Ser Ala Lys Asn Phe Glu Ala Val Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Gly Lys Asp Asp Phe Arg Pro Leu Leu Met Ala Trp
                100                 105                 110

Trp Pro Asp Thr Glu Thr Lys Arg Asn Tyr Val Asn Tyr Met Asn Lys
            115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Ser Glu Asn Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Leu Phe Asp Asn Gln Thr Asp Leu
            195                 200                 205

Thr Pro Asp Thr Gln Ser Asn Tyr Arg Leu Leu Asn Arg Thr Pro Thr
        210                 215                 220

Asn Gln Thr Gly Ser Leu Asp Ser Arg Phe Thr Tyr Asn Pro Asn Asp
225                 230                 235                 240

Pro Leu Gly Gly Tyr Asp Phe Leu Leu Ala Asn Asp Val Asp Asn Ser
                245                 250                 255

Asn Pro Val Val Gln Ala Glu Gln Leu Asn Trp Leu His Tyr Leu Leu
            260                 265                 270

Asn Phe Gly Ser Ile Tyr Ala Asn Asp Ala Asp Ala Asn Phe Asp Ser
            275                 280                 285

Ile Arg Val Asp Ala Val Asp Asn Val Asp Ala Asp Leu Leu Gln Ile
        290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
            340                 345                 350

Lys Phe Arg Leu Ser Met Leu Trp Ser Leu Ala Lys Pro Leu Asp Lys
            355                 360                 365

Arg Ser Gly Leu Asn Pro Leu Ile His Asn Ser Leu Val Asp Arg Glu
        370                 375                 380

Val Asp Asp Arg Glu Val Glu Thr Val Pro Ser Tyr Ser Phe Ala Arg
385                 390                 395                 400
```

```
Ala His Asp Ser Glu Val Gln Asp Ile Ile Arg Asp Ile Ile Lys Ala
            405                 410                 415

Glu Ile Asn Pro Asn Ser Phe Gly Tyr Ser Phe Thr Gln Glu Glu Ile
        420                 425                 430

Glu Gln Ala Phe Lys Ile Tyr Asn Glu Asp Leu Lys Lys Thr Asp Lys
        435                 440                 445

Lys Tyr Thr His Tyr Asn Val Pro Leu Ser Tyr Thr Leu Leu Leu Thr
    450                 455                 460

Asn Lys Gly Ser Ile Pro Arg Val Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ser Gly Gly Gln Ala Met
            500                 505                 510

Gln Asn Tyr Gln Ile Gly Asn Gly Glu Ile Leu Thr Ser Val Arg Tyr
        515                 520                 525

Gly Lys Gly Ala Leu Lys Gln Ser Asp Lys Gly Asp Ala Thr Thr Arg
    530                 535                 540

Thr Ser Gly Val Gly Val Met Gly Asn Gln Pro Asn Phe Ser Leu
545                 550                 555                 560

Asp Gly Lys Val Val Ala Leu Asn Met Gly Ala Ala His Ala Asn Gln
                565                 570                 575

Glu Tyr Arg Ala Leu Met Val Ser Thr Lys Asp Gly Val Ala Thr Tyr
            580                 585                 590

Ala Thr Asp Ala Asp Ala Ser Lys Ala Gly Leu Val Lys Arg Thr Asp
        595                 600                 605

Glu Asn Gly Tyr Leu Tyr Phe Leu Asn Asp Asp Leu Lys Gly Val Ala
    610                 615                 620

Asn Pro Gln Val Ser Gly Phe Leu Gln Val Trp Val Pro Val Gly Ala
625                 630                 635                 640

Ala Asp Asp Gln Asp Ile Arg Val Ala Ala Ser Asp Thr Ala Ser Thr
                645                 650                 655

Asp Gly Lys Ser Leu His Gln Asp Ala Ala Met Asp Ser Arg Val Met
            660                 665                 670

Phe Glu Gly Phe Ser Asn Phe Gln Ser Phe Ala Thr Lys Glu Glu Glu
        675                 680                 685

Tyr Thr Asn Val Val Ile Ala Asn Asn Val Asp Lys Phe Val Ser Trp
    690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Asp
            740                 745                 750

Gln Leu Val Lys Ala Ile Lys Ala Leu His Ala Lys Gly Leu Lys Val
        755                 760                 765

Met Ala Asp Trp Val Pro Asp Gln Met Tyr Thr Phe Pro Lys Gln Glu
    770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Thr Lys Ser Ser Gly
                805                 810                 815

Asp Asp Tyr Gln Ala Lys Tyr Gly Gly Ala Phe Leu Asp Glu Leu Lys
```

```
                   820                 825                 830
Glu Lys Tyr Pro Glu Leu Phe Thr Lys Lys Gln Ile Ser Thr Gly Gln
               835                 840                 845

Ala Ile Asp Pro Ser Val Lys Ile Lys Gln Trp Ser Ala Lys Tyr Phe
850                 855                 860

Asn Gly Ser Asn Ile Leu Gly Arg Gly Ala Asp Tyr Val Leu Ser Asp
865                 870                 875                 880

Gln Val Ser Asn Lys Tyr Phe Asn Val Ala Ser Asp Thr Leu Phe Leu
                885                 890                 895

Pro Ser Ser Leu Leu Gly Lys Val Val Glu Ser Gly Ile Arg Tyr Asp
                900                 905                 910

Gly Lys Gly Tyr Ile Tyr Asn Ser Ser Ala Thr Gly Asp Gln Val Lys
            915                 920                 925

Ala Ser Phe Ile Thr Glu Ala Gly Asn Leu Tyr Tyr Phe Gly Lys Asp
        930                 935                 940

Gly Tyr Met Val Thr Gly Ala Gln Thr Ile Asn Gly Ala Asn Tyr Phe
945                 950                 955                 960

Phe Leu Glu Asn Gly Thr Ala Leu Arg Asn Thr Ile Tyr Thr Asp Ala
                965                 970                 975

Gln Gly Asn Ser His Tyr Tyr Ala Asn Asp Gly Lys Arg Tyr Glu Asn
                980                 985                 990

Gly Tyr Gln Gln Phe Gly Asn Asp Trp Arg Tyr Phe Lys Asp Gly Asn
            995                 1000                1005

Met Ala Val Gly Leu Thr Thr Val Asp Gly Asn Val Gln Tyr Phe
    1010                1015                1020

Asp Lys Asp Gly Val Gln Ala Lys Asp Lys Ile Ile Val Thr Arg
    1025                1030                1035

Asp Gly Lys Val Arg Tyr Phe Asp Gln His Asn Gly Asn Ala Ala
    1040                1045                1050

Thr Asn Thr Phe Ile Ala Asp Lys Thr Gly His Trp Tyr Tyr Leu
    1055                1060                1065

Gly Lys Asp Gly Val Ala Val Thr Gly Ala Gln Thr Val Gly Lys
    1070                1075                1080

Gln Lys Leu Tyr Phe Glu Ala Asn Gly Gln Gln Val Lys Gly Asp
    1085                1090                1095

Phe Val Thr Ser Asp Glu Gly Lys Leu Tyr Phe Tyr Asp Val Asp
    1100                1105                1110

Ser Gly Asp Met Trp Thr Asp Thr Phe Ile Glu Asp Lys Ala Gly
    1115                1120                1125

Asn Trp Phe Tyr Leu Gly Lys Asp Gly Ala Ala Val Thr Gly Ala
    1130                1135                1140

Gln Thr Ile Arg Gly Gln Lys Leu Tyr Phe Lys Ala Asn Gly Gln
    1145                1150                1155

Gln Val Lys Gly Asp Ile Val Lys Gly Thr Asp Gly Lys Ile Arg
    1160                1165                1170

Tyr Tyr Asp Ala Lys Ser Gly Glu Gln Val Phe Asn Lys Thr Val
    1175                1180                1185

Lys Ala Ala Asp Gly Lys Thr Tyr Val Ile Gly Asn Asp Gly Val
    1190                1195                1200

Ala Val Asp Pro Ser Val Val Lys Gly Gln Thr Phe Lys Asp Ala
    1205                1210                1215

Ser Gly Ala Leu Arg Phe Tyr Asn Leu Lys Gly Gln Leu Val Thr
    1220                1225                1230
```

Gly Ser Gly Trp Tyr Glu Thr Ala Asn His Asp Trp Val Tyr Ile
    1235                1240                1245

Gln Ser Gly Lys Ala Leu Thr Gly Glu Gln Thr Ile Asn Gly Gln
    1250                1255                1260

His Leu Tyr Phe Lys Glu Asp Gly His Gln Val Lys Gly Gln Leu
    1265                1270                1275

Val Thr Gly Thr Asp Gly Lys Val Arg Tyr Tyr Asp Ala Asn Ser
    1280                1285                1290

Gly Asp Gln Ala Phe Asn Lys Ser Val Thr Val Asn Gly Lys Thr
    1295                1300                1305

Tyr Tyr Phe Gly Asn Asp Gly Thr Ala Gln Thr Ala Gly Asn Pro
    1310                1315                1320

Lys Gly Gln Thr Phe Lys Asp Gly Ser Asp Ile Arg Phe Tyr Ser
    1325                1330                1335

Met Glu Gly Gln Leu Val Thr Gly Ser Gly Trp Tyr Glu Asn Ala
    1340                1345                1350

Gln Gly Gln Trp Leu Tyr Val Lys Asn Gly Lys Val Leu Thr Gly
    1355                1360                1365

Leu Gln Thr Val Gly Ser Gln Arg Val Tyr Phe Asp Glu Asn Gly
    1370                1375                1380

Ile Gln Ala Lys Gly Lys Ala Val Arg Thr Ser Asp Gly Lys Ile
    1385                1390                1395

Arg Tyr Phe Asp Glu Asn Ser Gly Ser Met Ile Thr Asn Gln Trp
    1400                1405                1410

Lys Phe Val Tyr Gly Gln Tyr Tyr Tyr Phe Gly Asn Asp Gly Ala
    1415                1420                1425

Arg Ile Tyr Arg Gly Trp Asn
    1430                1435

<210> SEQ ID NO 3
<211> LENGTH: 4026
<212> TYPE: DNA
<213> ORGANISM: Streptococcus salivarius

<400> SEQUENCE: 3
atgatcgacg gcaaatacta ttatgttaat gaggacggta gccacaaaga aaactttgcg      60
attacggtta atggtcaact gctgtatttc ggtaaggacg gcgcactgac ctctagcagc     120
acttacagct ttaccccagg tacgacgaac atcgtggatg cttttctat caacaaccgc      180 gcgtatgact ccagcgaagc gtcctttgaa ctgattgatg ctacttgac tgccgactcc      240 tggtatcgtc cggcttccat catcaaggac ggtgtcacgt ggcaggccag caccgcagag     300
gactttcgcc cgctgctgat ggcgtggtgg ccaaacgtgg ataccaggt gaactatctg      360 aactacatgt ctaaagtgtt taacctggac gcaaagtata gcagcaccga taaacaagag     420
actctgaagg ttgcagctaa ggatattcag attaagatcg agcagaaaat tcaggcggag     480
aaaagcaccc aatggctgcg cgaaacgatc agcgcttttg tgaaaaccca accacagtgg     540
aacaaagaga ctgagaatta ctcgaaaggt ggtggtgagg atcatctgca aggcggtgca     600
ctgctgtacg tgaatgatag ccgtaccccg tgggcaaata gcgattatcg ccgcctgaac     660
cgcaccgcta ccaatcaaac gggtacgatt gacaagtcca ttctggacga gcagagcgac     720
ccaaatcaca tgggcggttt cgacttcctg ctggcgaatg atgttgacct gtccaacccg     780
gttgtgcagg cagagcagct gaaccagatt cactacttga tgaattgggg ctctatcgtg     840

-continued

```
atgggtgaca aagacgcaaa cttttgatggt atccgtgtcg atgcagttga caacgtcgat    900
gccgacatgc tgcaactgta taccaactac ttccgtgaat actacggtgt taacaaaagc    960
gaagcgaacg cactggcgca cattagcgtt ttggaagcgt ggagcttgaa tgataatcac   1020
tacaacgaca aaaccgatgg tgcagcattg gcgatggaga ataagcagcg tctggcgctg   1080
ctgtttagcc tggctaaacc gattaaagag cgcacccogg cagtgagccc gctgtataac   1140
aacaccttca atacgaccca acgcgatgag aaaaccgact ggatcaataa agacggttct   1200
aaggcctata acgaggatgg tactgtgaag cagagcacca ttggtaagta caatgaaaaa   1260
tatggtgatg catcgggcaa ttatgtgttc atccgtgccc atgataacaa tgtccaagac   1320
atcattgcgg agatcattaa gaaagaaatc aacccgaaaa gcgatggttt caccatcact   1380
gacgccgaaa tgaaacaagc gttcgagatt acaataagg acatgctgag cagcgacaag   1440
aagtacaccc tgaataacat cccggcagct tatgccgtga tgttgcagaa catggaaacg   1500
attacccgtg tctattatgg tgacctgtac accgacgacg ccactacat ggaaaccaag   1560 tccccgtatt acgacaccat cgttaacctg atgaaaagcc gtatcaagta cgtcagcggt   1620
ggccaggccc aacgtagcta ctggctgccg accgacggca agatggacaa tagcgacgtt   1680
gagctgtatc gcaccaacga agtgtatacc agcgtccgtt acggtaaaga cattatgacc   1740
gcgaacgata ccgagggtag caagtacagc cgcaccagcg gccaggtcac cctggttgca   1800
aacaacccga agctgaccct ggaccagagc gcgaagctga atgtggaaat gggtaagatt   1860
cacgcgaatc agaaataccg tgccctgatt gtgggcacgg ctgacggtat caagaatttc   1920
accagcgacg cagatgctat cgcggcaggc tacgtgaaag aaaccgactc caatggcgtt   1980 ctgactttg gcgctaatga catcaaaggt tatgaaacct tcgacatgtc cggctttgtt   2040
gctgtttggg tgccggtcgg cgcgagcgat gatcaggaca ttcgtgtcgc tcctagcact   2100
gaggccaaga agagggtga attgaccctg aaagcgaccg aagcatacga ttcccagctg   2160
atctatgaag gttttagcaa ttttcaaacc atcccggatg gtagcgaccc gagcgtgtac   2220
accaatcgca agatcgcaga gaacgtggac ctgttcaagt cctgggtgt tacctcgttt   2280 gaaatggcac cgcagttcgt ttccgcagat gatggcactt ttctggactc tgtgatccaa   2340
aacggctatg cgttttgccga tcgttacgat ttggcgatga gcaagaacaa caaatacggc   2400
agcaaagagg acttgcgtga cgcgctgaaa gccctgcata agcaggcat ccaggcgatt   2460 gcagactggg tcccggacca gatttatcag ttgccgggca agaagtggt cacggcgact   2520 cgcaccgacg gcgcaggccg taaaatcgcg gacgcgatca ttgatcatag cctgtacgtt   2580
gcgaacacta agagcagcgg caaagattac caggcgaagt acggtggtga gttcttggcg   2640
gagctgaagg ccaagtaccc ggagatgttc aaagtgaaca tgatttctac cggcaaaccg   2700
attgatgaca gcgtcaaact gaaacagtgg aaagcagaat actttaacgg caccaacgtc   2760
ttggagcgcg gtgtgggtta tgtcctgagc gatgaagcca cgggtaaata ctttaccgtc   2820
acgaaggatg gcaacttcat tccgttgcag ctgacgggta tgagaaagt cgtgaccggc   2880 tttagcaatg atggcaaagg tatcacctac ttcggtacga gcggcactca agcgaaatct   2940
gcgttcgtta cgttcaatgg taatacttac tattttgacg ctcgtggtca catggttacg   3000
aacggcgagt attcgccgaa cggtaaggat gtttaccgtt tcctgccgaa tggtattatg   3060
ctgtctaacg cttttttacgt tgatgcaaat ggtaacacgt acctgtacaa cagcaagggc   3120
caaatgtaca aggcggtta caccaaattt gacgttaccg aaacggacaa agatggtaag   3180
gaaagcaagg tggtgaagtt tcgttacttt acgaacgaag gtgtcatggc aaaaggcgtt   3240
```

-continued

```
accgtgattg acggcttcac gcaatacttt ggtgaagatg gtttccaagc gaaagacaag    3300
ctggtcacgt tcaagggcaa gacgtactac ttcgatgcac acaccggcaa tgcgatcaag    3360
gacacctggc gtaatatcaa tggcaagtgg tatcatttcg acgcgaacgg cgttgcagcg    3420
accggcgctc aggtcatcaa tggccaaaaa ctgtatttca acgaggacgg cagccaagtg    3480
aaaggcggtg ttgtcaaaaa cgcggacggt acgtattcta atacaaaga gggttctggt    3540 gaactggtta ccaacgagtt cttcacgacg gatggcaatg tttggtacta cgcaggcgcg    3600
aatggcaaga ccgttacggg tgcccaggtg attaacggcc aacacctgta cttcaatgcg    3660
gacggttcgc aagtgaaggg cggtgtggtc aagaacgcgg atggcaccta tagcaaatat    3720
gatgcgtcta ccggcgaacg cctgaccaat gagttttttca ccacgggtga taacaactgg    3780
tactacattg gcgcaaacgg caagagcgtg acgggcgagg tcaagatcgg tgacgatacc    3840
tatttctttg ccaaagatgg caagcaagtt aagggtcaaa ctgtcagcgc gggtaacggt    3900
cgtattagct actactatgg tgatagcggt aagcgtgcgg tgagcacttg gatcgaaatc    3960
caaccgggtg tttatgtcta cttcgacaag aacggcattg cctatccgcc tcgtgtgctg    4020
aattaa                                                                4026
```

<210> SEQ ID NO 4
<211> LENGTH: 1341
<212> TYPE: PRT
<213> ORGANISM: Streptococcus salivarius

<400> SEQUENCE: 4

```
Met Ile Asp Gly Lys Tyr Tyr Tyr Val Asn Glu Asp Gly Ser His Lys
 1               5                  10                  15

Glu Asn Phe Ala Ile Thr Val Asn Gly Gln Leu Leu Tyr Phe Gly Lys
            20                  25                  30

Asp Gly Ala Leu Thr Ser Ser Thr Tyr Ser Phe Thr Pro Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Ser Ser Thr Asp Lys Gln Glu Thr Leu Lys Val
    130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asp Tyr Arg Arg Leu Asn Arg Thr Ala Thr
    210                 215                 220
```

-continued

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
            245                 250                 255

Leu Ser Asn Pro Val Val Gln Ala Glu Gln Leu Asn Gln Ile His Tyr
        260                 265                 270

Leu Met Asn Trp Gly Ser Ile Val Met Gly Asp Lys Asp Ala Asn Phe
    275                 280                 285

Asp Gly Ile Arg Val Asp Ala Val Asp Asn Val Asp Ala Asp Met Leu
290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
        355                 360                 365

Lys Glu Arg Thr Pro Ala Val Ser Pro Leu Tyr Asn Asn Thr Phe Asn
    370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
        435                 440                 445

Glu Ile Asn Pro Lys Ser Asp Gly Phe Thr Ile Thr Asp Ala Glu Met
    450                 455                 460

Lys Gln Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr Tyr Asp Thr Ile Val
        515                 520                 525

Asn Leu Met Lys Ser Arg Ile Lys Tyr Val Ser Gly Gly Gln Ala Gln
    530                 535                 540

Arg Ser Tyr Trp Leu Pro Thr Asp Gly Lys Met Asp Asn Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asn Asp Thr Glu Gly Ser Lys Tyr Ser Arg Thr
            580                 585                 590

Ser Gly Gln Val Thr Leu Val Ala Asn Asn Pro Lys Leu Thr Leu Asp
        595                 600                 605

Gln Ser Ala Lys Leu Asn Val Glu Met Gly Lys Ile His Ala Asn Gln
    610                 615                 620

Lys Tyr Arg Ala Leu Ile Val Gly Thr Ala Asp Gly Ile Lys Asn Phe
625                 630                 635                 640

Thr Ser Asp Ala Asp Ala Ile Ala Ala Gly Tyr Val Lys Glu Thr Asp

-continued

```
              645                 650                 655
Ser Asn Gly Val Leu Thr Phe Gly Ala Asn Asp Ile Lys Gly Tyr Glu
              660                 665                 670

Thr Phe Asp Met Ser Gly Phe Val Ala Val Trp Val Pro Val Gly Ala
              675                 680                 685

Ser Asp Asp Gln Asp Ile Arg Val Ala Pro Ser Thr Glu Ala Lys Lys
690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                  725                 730                 735

Pro Ser Val Tyr Thr Asn Arg Lys Ile Ala Glu Asn Val Asp Leu Phe
              740                 745                 750

Lys Ser Trp Gly Val Thr Ser Phe Glu Met Ala Pro Gln Phe Val Ser
              755                 760                 765

Ala Asp Asp Gly Thr Phe Leu Asp Ser Val Ile Gln Asn Gly Tyr Ala
              770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                  805                 810                 815

Ile Gln Ala Ile Ala Asp Trp Val Pro Asp Gln Ile Tyr Gln Leu Pro
              820                 825                 830

Gly Lys Glu Val Val Thr Ala Thr Arg Thr Asp Gly Ala Gly Arg Lys
              835                 840                 845

Ile Ala Asp Ala Ile Ile Asp His Ser Leu Tyr Val Ala Asn Thr Lys
850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                  885                 890                 895

Thr Gly Lys Pro Ile Asp Asp Ser Val Lys Leu Lys Gln Trp Lys Ala
              900                 905                 910

Glu Tyr Phe Asn Gly Thr Asn Val Leu Glu Arg Gly Val Gly Tyr Val
              915                 920                 925

Leu Ser Asp Glu Ala Thr Gly Lys Tyr Phe Thr Val Thr Lys Asp Gly
930                 935                 940

Asn Phe Ile Pro Leu Gln Leu Thr Gly Asn Glu Lys Val Val Thr Gly
945                 950                 955                 960

Phe Ser Asn Asp Gly Lys Gly Ile Thr Tyr Phe Gly Thr Ser Gly Thr
                  965                 970                 975

Gln Ala Lys Ser Ala Phe Val Thr Phe Asn Gly Asn Thr Tyr Tyr Phe
              980                 985                 990

Asp Ala Arg Gly His Met Val Thr  Asn Gly Glu Tyr Ser Pro Asn Gly
              995                 1000                1005

Lys Asp  Val Tyr Arg Phe Leu  Pro Asn Gly Ile Met  Leu Ser Asn
    1010                 1015                1020

Ala Phe  Tyr Val Asp Ala Asn  Gly Asn Thr Tyr Leu  Tyr Asn Ser
    1025                 1030                1035

Lys Gly  Gln Met Tyr Lys Gly  Gly Tyr Thr Lys Phe  Asp Val Thr
    1040                 1045                1050

Glu Thr  Asp Lys Asp Gly Lys  Glu Ser Lys Val Val  Lys Phe Arg
    1055                 1060                1065
```

Tyr Phe Thr Asn Glu Gly Val Met Ala Lys Gly Val Thr Val Ile
1070              1075             1080

Asp Gly Phe Thr Gln Tyr Phe Gly Glu Asp Gly Phe Gln Ala Lys
1085              1090             1095

Asp Lys Leu Val Thr Phe Lys Gly Lys Thr Tyr Tyr Phe Asp Ala
1100              1105             1110

His Thr Gly Asn Ala Ile Lys Asp Thr Trp Arg Asn Ile Asn Gly
1115              1120             1125

Lys Trp Tyr His Phe Asp Ala Asn Gly Val Ala Ala Thr Gly Ala
1130              1135             1140

Gln Val Ile Asn Gly Gln Lys Leu Tyr Phe Asn Glu Asp Gly Ser
1145              1150             1155

Gln Val Lys Gly Gly Val Val Lys Asn Ala Asp Gly Thr Tyr Ser
1160              1165             1170

Lys Tyr Lys Glu Gly Ser Gly Glu Leu Val Thr Asn Glu Phe Phe
1175              1180             1185

Thr Thr Asp Gly Asn Val Trp Tyr Tyr Ala Gly Ala Asn Gly Lys
1190              1195             1200

Thr Val Thr Gly Ala Gln Val Ile Asn Gly Gln His Leu Tyr Phe
1205              1210             1215

Asn Ala Asp Gly Ser Gln Val Lys Gly Gly Val Val Lys Asn Ala
1220              1225             1230

Asp Gly Thr Tyr Ser Lys Tyr Asp Ala Ser Thr Gly Glu Arg Leu
1235              1240             1245

Thr Asn Glu Phe Phe Thr Thr Gly Asp Asn Asn Trp Tyr Tyr Ile
1250              1255             1260

Gly Ala Asn Gly Lys Ser Val Thr Gly Glu Val Lys Ile Gly Asp
1265              1270             1275

Asp Thr Tyr Phe Phe Ala Lys Asp Gly Lys Gln Val Lys Gly Gln
1280              1285             1290

Thr Val Ser Ala Gly Asn Gly Arg Ile Ser Tyr Tyr Tyr Gly Asp
1295              1300             1305

Ser Gly Lys Arg Ala Val Ser Thr Trp Ile Glu Ile Gln Pro Gly
1310              1315             1320

Val Tyr Val Tyr Phe Asp Lys Asn Gly Ile Ala Tyr Pro Pro Arg
1325              1330             1335

Val Leu Asn
1340

<210> SEQ ID NO 5
<211> LENGTH: 3744
<212> TYPE: DNA
<213> ORGANISM: Streptococcus salivarius

<400> SEQUENCE: 5
atgccaagcc acattaagac catcaacggc aaacaatact acgtggagga tgacggtacg      60
attcgcaaga attacgtcct ggagcgtatc ggtggcagcc aatactttaa tgcagaaacc     120
ggtgaactgt ctaatcagaa agagtatcgt ttcgacaaaa atggtggtac tggtagcagc     180
gcggacagca cgaacaccaa cgtgactgtg aacggtgaca aaaacgcatt ttacggtacc     240
acggacaaag acattgagct ggtcgacggc tatttcaccg cgaacacctg gtatcgcccg     300
aaagaaatcc tgaagacgg caagaatgg accgccagca cggagaacga taacgcccg      360 ctgctgaccg tctggtggcc tagcaaagca atccaggcgt cttatctgaa ctacatgaaa     420

```
gagcaaggcc tgggtaccaa ccaaacgtac acgagcttct ccagccaaac ccaaatggat    480
caagcagccc tggaagtgca aaagcgtatt gaagagcgca tcgcacgcga gggcaatacc    540
gactggctgc gcacgaccat caagaacttc gtgaaaaccc aaccgggttg aacagcacc     600 tctgaaaatc tggacaataa tgatcatctg caaggtggcg ccctgctgta caataacgac    660
tcccgcacga gccacgcgaa cagcgactat cgcctgctga atcgtacgcc gaccagccag    720
accggcaaac acaatccgaa ataccaccaaa gataccagca atggtggttt cgaatttctg    780
ctggcgaacg acatcgataa ctctaatccg gcggttcaag cagagcaact gaactggctg    840
cattacatta tgaacatcgg taccatcacg ggcggttctg aggatgaaaa cttcgacggc    900
gttcgtgttg acgctgtgga taatgtgaat gcggatctgc tgcaaatcgc gagcgactat    960
ttcaaagcaa aataccggtgc tgatcaaagc caagatcagg cgatcaaaca cttgagcatc   1020
ctggaagcgt ggtcccataa cgacgcctac tataacgaag ataccaaagg cgcgcagttg   1080
ccgatggatt atccgatgca cctggctctg gtctactcgc tgctgcgtcc gatcggcaat   1140
cgcagcggtg tggaaccgct gatttccaac agcctgaatg accgtagcga gtccggtaag   1200
aacagcaaac gtatggcgaa ctacgcgttc gtacgcgcgc atgatagcga ggtgcaatcg   1260
attattggcc agatcatcaa aaacgagatc aatccgcaaa gcaccggtaa tacgttcacc   1320
ctggatgaga tgaagaaagc gttgagatt tacaacaagg atatgcgtag cgcgaataag   1380
cagtatacgc agtacaacat cccgagcgcg tatgcgttga tgctgaccca aaggataccc   1440
gttccgcgtg tgtattacgg tgatatgtat acggacgacg gtcagtacat ggcgcaaaag   1500
agcccatact atgatgcgat cgaaacgctg ctgaaaggtc gcatccgcta tgccgcaggt   1560
ggtcaggaca tgaaggtcaa ctatattggt tacggtaaca ctaacggctg ggatgctgcg   1620
ggcgtgctga ccagcgtacg ttatggcacg ggcgcaaata gcgccagcga tacgggtacc   1680
gccgaaacgc gtaatcaagg tatggcagtg attgttagca accaaccggc gctgcgtctg   1740
actagcaatt tgaccattaa catgggtgcc gcacaccgta atcaggctta ccgtccgctg   1800
ctgctgacga ccaacgatgg cgtcgcgacc tatttgaacg atagcgatgc gaatggtatc   1860
gttaagtaca ccgacggtaa tggtaatctg accttctccg caaacgagat tcgtggcatc   1920
cgtaacccgc aagttgatgg ctatctggcc gtctgggttc cggtaggtgc gtcggagaat   1980
caggatgttc gtgtggcgcc gagcaaagag aagaacagct ccggtctggt ttacgagagc   2040
aatgctgccc tggatagcca agttatctac gaaggcttca gcaacttcca ggacttcgtt   2100
cagaatccga gccagtatac caacaaaaag attgcagaga atgcaaattt gttcaaatcc   2160
tggggtatta ccagctttga atttgcgccg cagtacgtga gctcggatga tggtagcttc   2220
ctggacagcg ttattcagaa cggttatgcg tttacggacc gctacgacat tggtatgagc   2280
aaagacaaca aatatggttc gctggcggat ttgaaggcag cactgaagag cttgcatgcc   2340
gttggtatta gcgcaatcgc ggattgggtt cctgatcaga tctacaatct gccaggcgac   2400
gaggtcgtca ccgcaacccg cgttaacaac tacggcgaaa ccaaagatgg tgcaatcatt   2460
gatcactctt tgtacgcggc caaaacccgt acttttggta acgactacca gggtaagtat   2520 ggtggtcgt tcctggacga gctgaaacgt ctgtatccgc agatctttga ccgcgttcag   2580
atttctaccg gtaagcgcat gaccacggac gagaagatca cccaatggtc tgcaaagtat   2640
atgaacggta cgaacatctt ggaccgtggc tctgaatacg ttttgaagaa tggtctgaat   2700
ggttactatg gcaccaatgg tggcaaagtt tcgctgccga agttgtgggg tagcaatcaa   2760
```

```
agcacgaatg cgacaatca aaacggcgac ggtagcggca agtttgaaaa gcgtctgttc    2820
agcgtgcgtt accgttataa caatggccag tacgcgaaaa atgcctttat caaagataac    2880
gacggcaatg tttactattt cgacaatagc ggtcgtatgg ctgtcggtga aaaacgatt     2940 gacggcaagc agtacttctt cctggctaat ggcgttcagc tgcgtgacgg ctaccgtcaa    3000
aatcgtcgcg gtcaggtgtt ttactacgac cagaatggtg tgctgaacgc aaacggtaaa    3060
caagacccga agcctgacaa caataacaat gcgagcggcc gtaatcaatt cgtccagatc    3120
ggtaacaacg tgtgggcgta ttatgatggc aatggtaaac gtgtcaccgg tcaccagaac    3180
atcaacggtc aggagttgtt tttcgataac aacggtgtcc aggttaaggg tcgtacggtg    3240
aatgagaacg gtgcaattcg ctactatgac gcgaatagcg gtgagatggc acgcaatcgt    3300
ttcgcggaga ttgaaccggg cgtctgggca tactttaaca atgacggcac cgcagtgaag    3360
ggttctcaga atatcaatgg tcaagacctg tacttcgacc agaacggtcg tcaggtcaag    3420
ggtgcgctgg ccaatgttga tgcaacctg cgctattacg acgttaacag cggtgagctg    3480
taccgtaatc gtttccacga aatcgacggc agctggtatt actttgatgg taacggtaat    3540
gcggtgaagg gtatggtcaa tatcaacggc caaaatctgt tgtttgacaa taacggcaaa    3600
cagattaagg gtcatctggt ccgcgtcaac ggcgtcgtgc gctattttga tccgaactct    3660
ggtgaaatgg cggttaatcg ttgggttgag gtgagcccag gttggtgggt ttactttgac    3720
ggtgaaggtc gtggtcagat ctaa                                          3744
```

<210> SEQ ID NO 6
<211> LENGTH: 1247
<212> TYPE: PRT
<213> ORGANISM: Streptococcus salivarius

<400> SEQUENCE: 6

```
Met Pro Ser His Ile Lys Thr Ile Asn Gly Lys Gln Tyr Tyr Val Glu
  1               5                  10                  15

Asp Asp Gly Thr Ile Arg Lys Asn Tyr Val Leu Glu Arg Ile Gly Gly
             20                  25                  30

Ser Gln Tyr Phe Asn Ala Glu Thr Gly Glu Leu Ser Asn Gln Lys Glu
         35                  40                  45

Tyr Arg Phe Asp Lys Asn Gly Thr Gly Ser Ser Ala Asp Ser Thr
     50                  55                  60

Asn Thr Asn Val Thr Val Asn Gly Asp Lys Asn Ala Phe Tyr Gly Thr
 65                  70                  75                  80

Thr Asp Lys Asp Ile Glu Leu Val Asp Gly Tyr Phe Thr Ala Asn Thr
                 85                  90                  95

Trp Tyr Arg Pro Lys Glu Ile Leu Lys Asp Gly Lys Glu Trp Thr Ala
            100                 105                 110

Ser Thr Glu Asn Asp Lys Arg Pro Leu Leu Thr Val Trp Trp Pro Ser
        115                 120                 125

Lys Ala Ile Gln Ala Ser Tyr Leu Asn Tyr Met Lys Glu Gln Gly Leu
    130                 135                 140

Gly Thr Asn Gln Thr Tyr Thr Ser Phe Ser Ser Gln Thr Gln Met Asp
145                 150                 155                 160

Gln Ala Ala Leu Glu Val Gln Lys Arg Ile Glu Arg Ile Ala Arg
                165                 170                 175

Glu Gly Asn Thr Asp Trp Leu Arg Thr Thr Ile Lys Asn Phe Val Lys
            180                 185                 190

Thr Gln Pro Gly Trp Asn Ser Thr Ser Glu Asn Leu Asp Asn Asn Asp
```

-continued

```
            195                 200                 205
His Leu Gln Gly Gly Ala Leu Leu Tyr Asn Asn Asp Ser Arg Thr Ser
210                 215                 220

His Ala Asn Ser Asp Tyr Arg Leu Leu Asn Arg Thr Pro Thr Ser Gln
225                 230                 235                 240

Thr Gly Lys His Asn Pro Lys Tyr Thr Lys Asp Thr Ser Asn Gly Gly
                245                 250                 255

Phe Glu Phe Leu Leu Ala Asn Asp Ile Asp Asn Ser Asn Pro Ala Val
                260                 265                 270

Gln Ala Glu Gln Leu Asn Trp Leu His Tyr Ile Met Asn Ile Gly Thr
                275                 280                 285

Ile Thr Gly Gly Ser Glu Asp Glu Asn Phe Asp Gly Val Arg Val Asp
290                 295                 300

Ala Val Asp Asn Val Asn Ala Asp Leu Leu Gln Ile Ala Ser Asp Tyr
305                 310                 315                 320

Phe Lys Ala Lys Tyr Gly Ala Asp Gln Ser Gln Asp Gln Ala Ile Lys
                325                 330                 335

His Leu Ser Ile Leu Glu Ala Trp Ser His Asn Asp Ala Tyr Tyr Asn
                340                 345                 350

Glu Asp Thr Lys Gly Ala Gln Leu Pro Met Asp Asp Pro Met His Leu
                355                 360                 365

Ala Leu Val Tyr Ser Leu Leu Arg Pro Ile Gly Asn Arg Ser Gly Val
370                 375                 380

Glu Pro Leu Ile Ser Asn Ser Leu Asn Asp Arg Ser Glu Ser Gly Lys
385                 390                 395                 400

Asn Ser Lys Arg Met Ala Asn Tyr Ala Phe Val Arg Ala His Asp Ser
                405                 410                 415

Glu Val Gln Ser Ile Ile Gly Gln Ile Lys Asn Glu Ile Asn Pro
                420                 425                 430

Gln Ser Thr Gly Asn Thr Phe Thr Leu Asp Glu Met Lys Lys Ala Phe
                435                 440                 445

Glu Ile Tyr Asn Lys Asp Met Arg Ser Ala Asn Lys Gln Tyr Thr Gln
                450                 455                 460

Tyr Asn Ile Pro Ser Ala Tyr Ala Leu Met Leu Thr His Lys Asp Thr
465                 470                 475                 480

Val Pro Arg Val Tyr Tyr Gly Asp Met Tyr Thr Asp Asp Gly Gln Tyr
                485                 490                 495

Met Ala Gln Lys Ser Pro Tyr Tyr Asp Ala Ile Glu Thr Leu Leu Lys
                500                 505                 510

Gly Arg Ile Arg Tyr Ala Ala Gly Gly Gln Asp Met Lys Val Asn Tyr
                515                 520                 525

Ile Gly Tyr Gly Asn Thr Asn Gly Trp Asp Ala Ala Gly Val Leu Thr
530                 535                 540

Ser Val Arg Tyr Gly Thr Gly Ala Asn Ser Ala Ser Asp Thr Gly Thr
545                 550                 555                 560

Ala Glu Thr Arg Asn Gln Gly Met Ala Val Ile Val Ser Asn Gln Pro
                565                 570                 575

Ala Leu Arg Leu Thr Ser Asn Leu Thr Ile Asn Met Gly Ala Ala His
                580                 585                 590

Arg Asn Gln Ala Tyr Arg Pro Leu Leu Leu Thr Thr Asn Asp Gly Val
                595                 600                 605

Ala Thr Tyr Leu Asn Asp Ser Asp Ala Asn Gly Ile Val Lys Tyr Thr
610                 615                 620
```

```
Asp Gly Asn Gly Asn Leu Thr Phe Ser Ala Asn Glu Ile Arg Gly Ile
625                 630                 635                 640

Arg Asn Pro Gln Val Asp Gly Tyr Leu Ala Val Trp Val Pro Val Gly
            645                 650                 655

Ala Ser Glu Asn Gln Asp Val Arg Val Ala Pro Ser Lys Glu Lys Asn
            660                 665                 670

Ser Ser Gly Leu Val Tyr Glu Ser Asn Ala Ala Leu Asp Ser Gln Val
            675                 680                 685

Ile Tyr Glu Gly Phe Ser Asn Phe Gln Asp Phe Val Gln Asn Pro Ser
            690                 695                 700

Gln Tyr Thr Asn Lys Lys Ile Ala Glu Asn Ala Asn Leu Phe Lys Ser
705                 710                 715                 720

Trp Gly Ile Thr Ser Phe Glu Phe Ala Pro Gln Tyr Val Ser Ser Asp
                725                 730                 735

Asp Gly Ser Phe Leu Asp Ser Val Ile Gln Asn Gly Tyr Ala Phe Thr
            740                 745                 750

Asp Arg Tyr Asp Ile Gly Met Ser Lys Asp Asn Lys Tyr Gly Ser Leu
            755                 760                 765

Ala Asp Leu Lys Ala Ala Leu Lys Ser Leu His Ala Val Gly Ile Ser
            770                 775                 780

Ala Ile Ala Asp Trp Val Pro Asp Gln Ile Tyr Asn Leu Pro Gly Asp
785                 790                 795                 800

Glu Val Val Thr Ala Thr Arg Val Asn Asn Tyr Gly Glu Thr Lys Asp
                805                 810                 815

Gly Ala Ile Ile Asp His Ser Leu Tyr Ala Ala Lys Thr Arg Thr Phe
            820                 825                 830

Gly Asn Asp Tyr Gln Gly Lys Tyr Gly Gly Ala Phe Leu Asp Glu Leu
            835                 840                 845

Lys Arg Leu Tyr Pro Gln Ile Phe Asp Arg Val Gln Ile Ser Thr Gly
850                 855                 860

Lys Arg Met Thr Thr Asp Glu Lys Ile Thr Gln Trp Ser Ala Lys Tyr
865                 870                 875                 880

Met Asn Gly Thr Asn Ile Leu Asp Arg Gly Ser Glu Tyr Val Leu Lys
                885                 890                 895

Asn Gly Leu Asn Gly Tyr Tyr Gly Thr Asn Gly Gly Lys Val Ser Leu
            900                 905                 910

Pro Lys Val Val Gly Ser Asn Gln Ser Thr Asn Gly Asp Asn Gln Asn
            915                 920                 925

Gly Asp Gly Ser Gly Lys Phe Glu Lys Arg Leu Phe Ser Val Arg Tyr
            930                 935                 940

Arg Tyr Asn Asn Gly Gln Tyr Ala Lys Asn Ala Phe Ile Lys Asp Asn
945                 950                 955                 960

Asp Gly Asn Val Tyr Tyr Phe Asp Asn Ser Gly Arg Met Ala Val Gly
            965                 970                 975

Glu Lys Thr Ile Asp Gly Lys Gln Tyr Phe Phe Leu Ala Asn Gly Val
            980                 985                 990

Gln Leu Arg Asp Gly Tyr Arg Gln Asn Arg Arg Gly Gln Val Phe Tyr
            995                 1000                1005

Tyr Asp Gln Asn Gly Val Leu Asn Ala Asn Gly Lys Gln Asp Pro
    1010                1015                1020

Lys Pro Asp Asn Asn Asn Asn Ala Ser Gly Arg Asn Gln Phe Val
    1025                1030                1035
```

| | | | | | | | | | |
|---|---|---|---|---|---|---|---|---|---|
|Gln|Ile|Gly|Asn|Asn|Val|Trp|Ala|Tyr|Tyr|Asp|Gly|Asn|Gly|Lys|
|1040| | | | |1045| | | | |1050|

Arg Val Thr Gly His Gln Asn Ile Asn Gly Gln Glu Leu Phe Phe
 1055                1060                1065

Asp Asn Asn Gly Val Gln Val Lys Gly Arg Thr Val Asn Glu Asn
 1070                1075                1080

Gly Ala Ile Arg Tyr Tyr Asp Ala Asn Ser Gly Glu Met Ala Arg
 1085                1090                1095

Asn Arg Phe Ala Glu Ile Glu Pro Gly Val Trp Ala Tyr Phe Asn
 1100                1105                1110

Asn Asp Gly Thr Ala Val Lys Gly Ser Gln Asn Ile Asn Gly Gln
 1115                1120                1125

Asp Leu Tyr Phe Asp Gln Asn Gly Arg Gln Val Lys Gly Ala Leu
 1130                1135                1140

Ala Asn Val Asp Gly Asn Leu Arg Tyr Tyr Asp Val Asn Ser Gly
 1145                1150                1155

Glu Leu Tyr Arg Asn Arg Phe His Glu Ile Asp Gly Ser Trp Tyr
 1160                1165                1170

Tyr Phe Asp Gly Asn Gly Asn Ala Val Lys Gly Met Val Asn Ile
 1175                1180                1185

Asn Gly Gln Asn Leu Leu Phe Asp Asn Asn Gly Lys Gln Ile Lys
 1190                1195                1200

Gly His Leu Val Arg Val Asn Gly Val Val Arg Tyr Phe Asp Pro
 1205                1210                1215

Asn Ser Gly Glu Met Ala Val Asn Arg Trp Val Glu Val Ser Pro
 1220                1225                1230

Gly Trp Trp Val Tyr Phe Asp Gly Glu Gly Arg Gly Gln Ile
 1235                1240                1245

<210> SEQ ID NO 7
<211> LENGTH: 4434
<212> TYPE: DNA
<213> ORGANISM: Streptococcus salivarius

<400> SEQUENCE: 7

```
atggacgaaa cgcaggataa gaccgtgacg cagagcaaca gcggcaccac cgcttccctg      60
gtcactagcc ctgaagccac gaaagaggcg gacaaacgca cgaacactaa agaggccgac     120
gttctgacgc ctgcaaaaga aacgaacgca gtcgagactg cgaccaccac taacacccag     180
gcgacggcgg aggccgccac gaccgcgacc accgcggacg tcgcggtggc tgcggtgccg     240
aacaaagaag cggtcgttac cacggatgct ccggcggtca cgaccgagaa agcggaagaa     300
cagccggcta ccgttaaagc agaagtcgtc aatacggaag tgaaagcgcc ggaagcggct     360
ctgaaagaca gcgaggttga ggcagcgctg agcctgaaga acatcaagaa cattgatggc     420
aagtattact atgttaatga ggatggcagc cacaaagaga atttcgctat taccgtgaat     480
ggccagctgc tgtactttgg taaagacggt gcgctgacgt cctctagcac gtattctttt     540
accccaggca ctaccaatat cgtggacggt tttagcatta caaccgcgc ttacgacagc     600
agcgaggcga gctttgagct gatcgacggt tacttgaccg cagacagctg gtatcgtccg     660
gctagcatca tcaaagatgg tgttacgtgg caagcgtcca ccgccgagga ttttcgtccg     720
ctgctgatgg catggtggcc gaatgtggat acgcaggtga actatttgaa ttacatgtcc     780
aaagtttca acctggacgc gaaatactct agcaccgaca acaggaaac cctgaaagtg     840
gcagcaaaag acattcaaat caagattgaa caaaagattc aagcggagaa gagcacgcag     900
```

```
tggctgcgtg aaactatcag cgcctttgtg aaaacccagc cgcagtggaa caaagaaacc    960
gagaattaca gcaagggtgg tggtgaggac cacctgcaag gtggcgcact gctgtatgtt   1020
aacgacagcc gtaccccttg ggcgaatagc gattaccgtc gtctgaatcg caccgcaacc   1080
aatcagacgg gcacgatcga taagtctatt ctggacgagc agtctgaccc aaaccacatg   1140
ggcggtttcg actttctgct ggcgaacgac gtcgacctga gcaatccggt cgtgcaggct   1200
gagcagctga atcaaatcca ctatctgatg aattggggtt ccattgtgat gggtgacaag   1260
gatgcgaact ttgacggcat tcgtgtcgat gcagttgaca acgtggacgc ggacatgttg   1320
caactgtata ccaattactt ccgtgagtac tacggtgtga acaagagcga agctaacgca   1380
ctggctcaca tcagcgttct ggaggcgtgg agcctgaatg ataatcatta caatgacaag   1440
accgatggtg cggcactggc aatggagaat aagcaacgtc tggcgctgtt gttttcgttg   1500
gcgaaaccga tcaaagagcg tacccccggca gtgagcccgc tgtataacaa caccttcaat   1560
accacccagc gtgatgaaaa gaccgattgg attaacaaag acggtagcaa ggcttacaac   1620
gaagatggca cggtcaaaca atcgaccatc ggtaagtaca cgagaaata cggtgacgca   1680
tccggtaact acgttttcat ccgtgcccac gataacaacg tccaggacat catcgccgag   1740
atcatcaaga aagagatcaa cccgaaaagc gacggcttca ccatcaccga cgccgaaatg   1800
aagcaagcct ttgaaatcta taacaaagat atgctgtcga cgacaaaaa gtataccctg   1860
aataacattc cggcagcgta tgccgtgatg ttgcagaata tggaaacgat acccgcgtc   1920
tattacggtg atctgtatac ggacgacggt cactacatgg aaaccaaatc tccgtattac   1980
gataccatcg tgaatttgat gaagagccgt atcaagtatg tttcgggtgg ccaggcgcaa   2040
cgtagctatt ggctgccgac cgacggtaag atggacaata gcgacgttga gctgtaccgc   2100
acgaatgagg tttacacgag cgtgcgctat ggtaaggata tcatgaccgc taatgatacc   2160
gaaggctcta gtattcccg caccagcggc caagtcacct tggtcgcgaa caatccgaag   2220
ctgaatctgg accaaagcgc caagttgaat gtggagatgg gcaaaatcca tgcgaatcag   2280
aagtatcgcg cactgattgt cggcactgcg gacggcatta gaactttac ttccgacgcg   2340
gacgccattg cagcgggtta tgtgaaagaa accgatagca acggcgtgct gaccttcggt   2400
gctaacgaca ttaagggcta cgaaacgttt gatatgagcg gtttcgtggc ggtgtgggtt   2460
ccggtgggtg catctgacaa tcaggacatt cgtgttgcgc cgagcaccga ggcaaagaaa   2520
gaaggtgagc tgaccttgaa ggcgacggaa gcgtatgata ccagctgat ttacgaaggc   2580
tttagcaatt ccagacgat cccagatggc agcgatccgt ccgtgtatac gaaccgcaag   2640
attgcggaga acgtggatct gttcaaaagc tggggtgtca ccagctttga gatggcaccg   2700
caatttgtct cggcggatga tggcaccttt ctggatagcg ttattcagaa tggctacgcc   2760
ttcgccgacc gttatgacct ggccatgtcc aagaacaaca gtatggtag caaagaggac   2820
ctgcgtgatg cactgaaagc actgcataag gcgggtattc aagctatcgc agactgggtt   2880
ccagaccaga tctaccagct gccgggcaaa gaagttgtca ccgccacccg tacggatggt   2940
gctggccgta agatcgcaga cgcgattatc gaccattctc tgtatgttgc aaacagcaaa   3000
agcagcggca agattatca gcaaagtac ggtggcgagt cctggccgga gctgaaagcc   3060
aaatacccgg aaatgttcaa agttaacatg attagcacgg taagccgat tgatgactcc   3120
gtgaaattga gcaatggaa agccgagtac ttcaatggca ccaacgtttt ggaacgtggt   3180
gtcggctatg ttctgagcga cgaggcgacc ggtaagtatt tcacggtgac caaagaaggc   3240
```

```
aatttcattc cgctgcaact gacgggtaaa gagaaagtta tcacgggttt ctccagcgat    3300
ggtaagggta tcacctattt cggtacgagc ggtacgcagg cgaagtctgc gtttgttacc    3360
ttcaatggta acacctacta tttcgacgcg cgtggccaca tggttaccaa tagcgaatac    3420
agcccgaatg caaggacgt ctaccgtttt ctgccgaacg gtatcatgct gagcaatgcg    3480
ttttacattg atgcgaacgg taatacctac ctgtacaact ctaagggtca aatgtacaaa    3540
ggcggttaca cgaaattcga tgtttctgaa acggataagg acggtaaaga gtccaaggtc    3600
gtcaagttcc gctactttac gaacgaaggc gtcatggcca agggtgttac cgtcattgat    3660
ggttttaccc aatacttcgg tgaggacggc tttcaagcga aggataagct ggtcaccttc    3720
aagggcaaga cgtattactt cgacgcacac actggtaatg gtatcaaaga tacctggcgc    3780
aatatcaatg gtaaatggta ctatttcgac gcgaatggcg ttgctgcgac cggtgcgcag    3840
gtgattaacg gccagaaact gtacttcaac gaggatggcc cccaagtcaa aggcggcgtg    3900
gttaagaacg cagacggcac ctatagcaaa tacaaagaag gttttggtga gctggttact    3960
aacgagtttt tcacgactga tggcaatgtt tggtactacg ccggtgcaaa tggtaaaacc    4020
gttaccggtg cacaagtgat caacggccaa catttgtact tcaatgcgga cggttcccag    4080
gtgaagggtg gcgttgtcaa gaacgcggat ggcacctaca gcagtacaa tgctagcact    4140 ggtgaacgtc tgacgaacga gttctttacg accggtgata acaattggta ttacattggc    4200
gcaaacggta gagcgtgac gggtgaggtc aagattggtg atgatactta ctttttcgcg    4260
aaggatggca acaagttaa aggtcaaacc gtcagcgccg gtaatggtcg cattagctac    4320
tactacggtg acagcggcaa gcgtgcggtt agcacctgga ttgagattca gccgggtgtt    4380
tatgtgtatt tcgacaaaaa cggtttggcg taccctccgc gtgttctgaa ttaa          4434
```

<210> SEQ ID NO 8
<211> LENGTH: 1477
<212> TYPE: PRT
<213> ORGANISM: Streptococcus salivarius

<400> SEQUENCE: 8

```
Met Asp Glu Thr Gln Asp Lys Thr Val Thr Gln Ser Asn Ser Gly Thr
1               5                   10                  15

Thr Ala Ser Leu Val Thr Ser Pro Glu Ala Thr Lys Glu Ala Asp Lys
            20                  25                  30

Arg Thr Asn Thr Lys Glu Ala Asp Val Leu Thr Pro Ala Lys Glu Thr
        35                  40                  45

Asn Ala Val Glu Thr Ala Thr Thr Thr Asn Thr Gln Ala Thr Ala Glu
    50                  55                  60

Ala Ala Thr Thr Ala Thr Thr Ala Asp Val Ala Val Ala Ala Val Pro
65                  70                  75                  80

Asn Lys Glu Ala Val Val Thr Thr Asp Ala Pro Ala Val Thr Thr Glu
                85                  90                  95

Lys Ala Glu Glu Gln Pro Ala Thr Val Lys Ala Glu Val Val Asn Thr
            100                 105                 110

Glu Val Lys Ala Pro Glu Ala Ala Leu Lys Asp Ser Glu Val Glu Ala
        115                 120                 125

Ala Leu Ser Leu Lys Asn Ile Lys Asn Ile Asp Gly Lys Tyr Tyr Tyr
    130                 135                 140

Val Asn Glu Asp Gly Ser His Lys Glu Asn Phe Ala Ile Thr Val Asn
145                 150                 155                 160

Gly Gln Leu Leu Tyr Phe Gly Lys Asp Gly Ala Leu Thr Ser Ser Ser
```

```
                    165                 170                 175
Thr Tyr Ser Phe Thr Pro Gly Thr Thr Asn Ile Val Asp Gly Phe Ser
                180                 185                 190

Ile Asn Asn Arg Ala Tyr Asp Ser Ser Glu Ala Ser Phe Glu Leu Ile
            195                 200                 205

Asp Gly Tyr Leu Thr Ala Asp Ser Trp Tyr Arg Pro Ala Ser Ile Ile
        210                 215                 220

Lys Asp Gly Val Thr Trp Gln Ala Ser Thr Ala Glu Asp Phe Arg Pro
225                 230                 235                 240

Leu Leu Met Ala Trp Pro Asn Val Asp Thr Gln Val Asn Tyr Leu
                245                 250                 255

Asn Tyr Met Ser Lys Val Phe Asn Leu Asp Ala Lys Tyr Ser Ser Thr
                260                 265                 270

Asp Lys Gln Glu Thr Leu Lys Val Ala Ala Lys Asp Ile Gln Ile Lys
            275                 280                 285

Ile Glu Gln Lys Ile Gln Ala Glu Lys Ser Thr Gln Trp Leu Arg Glu
        290                 295                 300

Thr Ile Ser Ala Phe Val Lys Thr Gln Pro Gln Trp Asn Lys Glu Thr
305                 310                 315                 320

Glu Asn Tyr Ser Lys Gly Gly Glu Asp His Leu Gln Gly Gly Ala
                325                 330                 335

Leu Leu Tyr Val Asn Asp Ser Arg Thr Pro Trp Ala Asn Ser Asp Tyr
                340                 345                 350

Arg Arg Leu Asn Arg Thr Ala Thr Asn Gln Thr Gly Thr Ile Asp Lys
            355                 360                 365

Ser Ile Leu Asp Glu Gln Ser Asp Pro Asn His Met Gly Gly Phe Asp
        370                 375                 380

Phe Leu Leu Ala Asn Asp Val Asp Leu Ser Asn Pro Val Val Gln Ala
385                 390                 395                 400

Glu Gln Leu Asn Gln Ile His Tyr Leu Met Asn Trp Gly Ser Ile Val
                405                 410                 415

Met Gly Asp Lys Asp Ala Asn Phe Asp Gly Ile Arg Val Asp Ala Val
                420                 425                 430

Asp Asn Val Asp Ala Asp Met Leu Gln Leu Tyr Thr Asn Tyr Phe Arg
            435                 440                 445

Glu Tyr Tyr Gly Val Asn Lys Ser Glu Ala Asn Ala Leu Ala His Ile
        450                 455                 460

Ser Val Leu Glu Ala Trp Ser Leu Asn Asp Asn His Tyr Asn Asp Lys
465                 470                 475                 480

Thr Asp Gly Ala Ala Leu Ala Met Glu Asn Lys Gln Arg Leu Ala Leu
                485                 490                 495

Leu Phe Ser Leu Ala Lys Pro Ile Lys Glu Arg Thr Pro Ala Val Ser
                500                 505                 510

Pro Leu Tyr Asn Asn Thr Phe Asn Thr Thr Gln Arg Asp Glu Lys Thr
            515                 520                 525

Asp Trp Ile Asn Lys Asp Gly Ser Lys Ala Tyr Asn Glu Asp Gly Thr
        530                 535                 540

Val Lys Gln Ser Thr Ile Gly Lys Tyr Asn Glu Lys Tyr Gly Asp Ala
545                 550                 555                 560

Ser Gly Asn Tyr Val Phe Ile Arg Ala His Asp Asn Asn Val Gln Asp
                565                 570                 575

Ile Ile Ala Glu Ile Ile Lys Lys Glu Ile Asn Pro Lys Ser Asp Gly
                580                 585                 590
```

```
Phe Thr Ile Thr Asp Ala Glu Met Lys Gln Ala Phe Glu Ile Tyr Asn
        595                 600                 605

Lys Asp Met Leu Ser Ser Asp Lys Lys Tyr Thr Leu Asn Asn Ile Pro
        610                 615                 620

Ala Ala Tyr Ala Val Met Leu Gln Asn Met Glu Thr Ile Thr Arg Val
625                 630                 635                 640

Tyr Tyr Gly Asp Leu Tyr Thr Asp Asp Gly His Tyr Met Glu Thr Lys
            645                 650                 655

Ser Pro Tyr Tyr Asp Thr Ile Val Asn Leu Met Lys Ser Arg Ile Lys
            660                 665                 670

Tyr Val Ser Gly Gly Gln Ala Gln Arg Ser Tyr Trp Leu Pro Thr Asp
        675                 680                 685

Gly Lys Met Asp Asn Ser Asp Val Glu Leu Tyr Arg Thr Asn Glu Val
        690                 695                 700

Tyr Thr Ser Val Arg Tyr Gly Lys Asp Ile Met Thr Ala Asn Asp Thr
705                 710                 715                 720

Glu Gly Ser Lys Tyr Ser Arg Thr Ser Gly Gln Val Thr Leu Val Ala
                725                 730                 735

Asn Asn Pro Lys Leu Asn Leu Asp Gln Ser Ala Lys Leu Asn Val Glu
            740                 745                 750

Met Gly Lys Ile His Ala Asn Gln Lys Tyr Arg Ala Leu Ile Val Gly
        755                 760                 765

Thr Ala Asp Gly Ile Lys Asn Phe Thr Ser Ala Asp Ala Ile Ala
        770                 775                 780

Ala Gly Tyr Val Lys Glu Thr Asp Ser Asn Gly Val Leu Thr Phe Gly
785                 790                 795                 800

Ala Asn Asp Ile Lys Gly Tyr Glu Thr Phe Asp Met Ser Gly Phe Val
            805                 810                 815

Ala Val Trp Val Pro Val Gly Ala Ser Asp Asn Gln Asp Ile Arg Val
            820                 825                 830

Ala Pro Ser Thr Glu Ala Lys Lys Glu Gly Glu Leu Thr Leu Lys Ala
        835                 840                 845

Thr Glu Ala Tyr Asp Ser Gln Leu Ile Tyr Glu Gly Phe Ser Asn Phe
        850                 855                 860

Gln Thr Ile Pro Asp Gly Ser Asp Pro Ser Val Tyr Thr Asn Arg Lys
865                 870                 875                 880

Ile Ala Glu Asn Val Asp Leu Phe Lys Ser Trp Gly Val Thr Ser Phe
                885                 890                 895

Glu Met Ala Pro Gln Phe Val Ser Ala Asp Asp Gly Thr Phe Leu Asp
            900                 905                 910

Ser Val Ile Gln Asn Gly Tyr Ala Phe Ala Asp Arg Tyr Asp Leu Ala
            915                 920                 925

Met Ser Lys Asn Asn Lys Tyr Gly Ser Lys Glu Asp Leu Arg Asp Ala
        930                 935                 940

Leu Lys Ala Leu His Lys Ala Gly Ile Gln Ala Ile Ala Asp Trp Val
945                 950                 955                 960

Pro Asp Gln Ile Tyr Gln Leu Pro Gly Lys Glu Val Val Thr Ala Thr
            965                 970                 975

Arg Thr Asp Gly Ala Gly Arg Lys Ile Ala Asp Ala Ile Ile Asp His
            980                 985                 990

Ser Leu Tyr Val Ala Asn Ser Lys  Ser Ser Gly Lys Asp  Tyr Gln Ala
        995                 1000                 1005
```

```
Lys Tyr Gly Gly Glu Phe Leu Ala Glu Leu Lys Ala Lys Tyr Pro
    1010                1015                1020

Glu Met Phe Lys Val Asn Met Ile Ser Thr Gly Lys Pro Ile Asp
    1025                1030                1035

Asp Ser Val Lys Leu Lys Gln Trp Lys Ala Glu Tyr Phe Asn Gly
    1040                1045                1050

Thr Asn Val Leu Glu Arg Gly Val Gly Tyr Val Leu Ser Asp Glu
    1055                1060                1065

Ala Thr Gly Lys Tyr Phe Thr Val Thr Lys Glu Gly Asn Phe Ile
    1070                1075                1080

Pro Leu Gln Leu Thr Gly Lys Glu Lys Val Ile Thr Gly Phe Ser
    1085                1090                1095

Ser Asp Gly Lys Gly Ile Thr Tyr Phe Gly Thr Ser Gly Thr Gln
    1100                1105                1110

Ala Lys Ser Ala Phe Val Thr Phe Asn Gly Asn Thr Tyr Tyr Phe
    1115                1120                1125

Asp Ala Arg Gly His Met Val Thr Asn Ser Glu Tyr Ser Pro Asn
    1130                1135                1140

Gly Lys Asp Val Tyr Arg Phe Leu Pro Asn Gly Ile Met Leu Ser
    1145                1150                1155

Asn Ala Phe Tyr Ile Asp Ala Asn Gly Asn Thr Tyr Leu Tyr Asn
    1160                1165                1170

Ser Lys Gly Gln Met Tyr Lys Gly Gly Tyr Thr Lys Phe Asp Val
    1175                1180                1185

Ser Glu Thr Asp Lys Asp Gly Lys Glu Ser Lys Val Val Lys Phe
    1190                1195                1200

Arg Tyr Phe Thr Asn Glu Gly Val Met Ala Lys Gly Val Thr Val
    1205                1210                1215

Ile Asp Gly Phe Thr Gln Tyr Phe Gly Glu Asp Gly Phe Gln Ala
    1220                1225                1230

Lys Asp Lys Leu Val Thr Phe Lys Gly Lys Thr Tyr Tyr Phe Asp
    1235                1240                1245

Ala His Thr Gly Asn Gly Ile Lys Asp Thr Trp Arg Asn Ile Asn
    1250                1255                1260

Gly Lys Trp Tyr Tyr Phe Asp Ala Asn Gly Val Ala Ala Thr Gly
    1265                1270                1275

Ala Gln Val Ile Asn Gly Gln Lys Leu Tyr Phe Asn Glu Asp Gly
    1280                1285                1290

Ser Gln Val Lys Gly Gly Val Val Lys Asn Ala Asp Gly Thr Tyr
    1295                1300                1305

Ser Lys Tyr Lys Glu Gly Phe Gly Glu Leu Val Thr Asn Glu Phe
    1310                1315                1320

Phe Thr Thr Asp Gly Asn Val Trp Tyr Tyr Ala Gly Ala Asn Gly
    1325                1330                1335

Lys Thr Val Thr Gly Ala Gln Val Ile Asn Gly Gln His Leu Tyr
    1340                1345                1350

Phe Asn Ala Asp Gly Ser Gln Val Lys Gly Gly Val Val Lys Asn
    1355                1360                1365

Ala Asp Gly Thr Tyr Ser Lys Tyr Asn Ala Ser Thr Gly Glu Arg
    1370                1375                1380

Leu Thr Asn Glu Phe Phe Thr Gly Asp Asn Asn Trp Tyr Tyr
    1385                1390                1395

Ile Gly Ala Asn Gly Lys Ser Val Thr Gly Glu Val Lys Ile Gly
```

-continued

```
Asp Asp Thr Tyr Phe Phe Ala Lys Asp Gly Lys Gln Val Lys Gly
    1415              1420                1425

Gln Thr Val Ser Ala Gly Asn Gly Arg Ile Ser Tyr Tyr Tyr Gly
    1430              1435                1440

Asp Ser Gly Lys Arg Ala Val Ser Thr Trp Ile Glu Ile Gln Pro
    1445              1450                1455

Gly Val Tyr Val Tyr Phe Asp Lys Asn Gly Leu Ala Tyr Pro Pro
    1460              1465                1470

Arg Val Leu Asn
    1475

<210> SEQ ID NO 9
<211> LENGTH: 4311
<212> TYPE: DNA
<213> ORGANISM: Streptococcus downei

<400> SEQUENCE: 9
```

```
atggttgacg gcaaatacta ctactacgat caggacggca acgtaaagaa aaacttcgcg      60
gttagcgtgg gcgagaaaat ctattacttt gacgaaactg cgcctacaa agacaccagc     120
aaagttgagg cggacaaaag cggcagcgac attagcaagg aagagactac cttcgcggca    180
aacaaccgcg cctacagcac cagcgcggag aattttgagg cgatcgacaa ttatctgacc    240
gcggactcct ggtatcgtcc taaatccatc ctgaaggatg caaaacgtg acggaaagc     300
agcaaagatg actttcgtcc gctgctgatg gcgtggtggc cggataccga acgaagcgc     360
aattacgtga actacatgaa caaagttgtt ggcatcgaca gacctatac cgcggaaacc    420
agccaggccg acttgaccgc tgcggcgaaa ctggtgcaag cacgcattga gcagaagatc    480
acgaccgaac agaacacgaa atggctgcgt gaggcaatct cggcatttgt aaaaacgcaa    540
ccgcagtgga acggtgaaag cgagaagccg tacgacgatc acctgcaaaa cggtgctctg    600
aaatttgata atcagagcga cctgaccccg gatacgcaaa gcaactaccg tctgttgaac    660
cgtaccccga ctaatcagac gggtagcctg acagccgct tcacttataa cgcgaacgac    720
cctttgggcg ttatgagct gctgctggca atgacgtcg ataacagcaa tccgatcgtg     780
caggcggagc agctgaactg gctgcattac ctgctgaatt ttggtacgat ctacgccaaa    840
gatgccgacg ctaacttcga tagcattcgt gtggacgcgg ttgataacgt cgatgcggat    900
ctgctgcaaa ttagcagcga ttacctgaaa gcagcctacg gcattgataa gaataacaaa    960
aacgcgaaca accacgtgag cattgtcgaa gcctggagcg ataatgatac cccgtacctg   1020
catgacgatg gtgacaacct gatgaatatg ataacaaat tcgcctgtc catgctgtgg     1080
tcgctggcca aaccgctgga caagcgtagc ggtctgaacc gctgattca taacagcttg   1140
gtggatcgtg aagttgatga ccgcgaggtt gaaacggttc gagctattc ttttgcacgt    1200
gcgcatgata gcgaggtcca ggacttgatc cgtgacatca tcaaggcaga gatcaatccg   1260
aacgcattcg gttatagctt tacccaagac gagattgacc aggccttta gatttacaat    1320
gaggatctga gaaaaacgga taagaaatac acccactata tgtgccgtt gagctacacc   1380
ctgctgctga cgaataaggg tagcatccca cgtgtctact atggtgatat gtttaccgac   1440
gatggtcagt atatggcgaa caaaccgtc aactatgacg ccattgaatc tctgctgaaa    1500
gcgcgtatga gtatgtcgc tggcggtcaa gcaatgcaga actaccaaat cggtaatggt   1560
gagatcctga ccagcgttcg ttatggtaag ggtgccctga acagagcga caaaggtgat    1620
```

```
gcgaccacgc gcaccagcgg tgtcggtgtc gttatgggca atcagccaaa ctttagcttg    1680
gacggcaaag tggtggctct gaacatgggc gcagctcatg cgaatcagga gtatcgtgcg    1740
ctgatggtta gcacgaaaga cggtgttgcc acgtatgcga ccgatgcaga tgcgagcaaa    1800
gccggtctgg tcaaacgtac cgacgaaaac ggctacctgt atttcctgaa tgacgacctg    1860
aagggtgtgg ccaatcctca ggtgagcggt ttcttgcagg tgtgggttcc ggtgggtgcc    1920
gcggatgatc aagatatccg tgttgcagct agcgataccg catccaccga tggcaagagc    1980
ctgcaccaag acgccgcgat ggatagccgt gttatgtttg aaggcttctc taactttcag    2040
tcctttgcca cgaaagaaga ggaatatacc aacgtcgtta tcgccaacaa tgtggataag    2100
ttcgttagct ggggtatcac ggatttcgag atggccccac aatatgtttc cagcaccgac    2160
ggtcaattcc tggactctgt cattcagaac ggttatgctt ttacggaccg ttatgacttg    2220
ggcatgtcta aggcaaacaa atacggcacg gccgatcaac tggttaaggc cattaaggcc    2280
ctgcacgcga agggcctgaa ggttatggca gattgggtgc cggatcagat gtataccttc    2340
ccgaaacagg aagtcgtgac cgttacccgt accgacaaat ttggcaaacc gatcgcaggt    2400
tcccaaatca atcatagcct gtatgttacc gataccaagt ccagcggcga tgactatcag    2460
gccaaatatg gtggtgcgtt tctggacgag ctgaaggaga aatatccgga gctgttcacg    2520
aagaaacaaa tcagcacggg tcaagctatt gacccgagcg tgaaaatcaa acagtggtct    2580
gctaagtatt tcaatggctc caacatcctg ggtcgcggtg cggactacgt actgtcggat    2640
caggcgagca acaaatacct gaacgtgtct gacgataaac tgttcctgcc gaaaaccttg    2700
ctgggccaag ttgtcgagag cggtatccgc tttgacggca ctggttatgt gtacaactct    2760
agcactacgg gtgaaaaagt taccgattcc ttcattacgg aggcaggtaa tctgtactac    2820
ttcggtcaag acggctatat ggtgaccggc gcacagaaca ttaagggcag caactattac    2880
ttcctggcca atggtgcggc cctgcgtaac accgtttaca ccgatgcgca aggtcagaat    2940
cactattacg gcaacgacgg caagcgttat gagaatggtt accaacagtt cggcaacgat    3000
tcttggcgtt acttcaaaaa tggcgtgatg gcgctgggtc tgactacggt ggatggtcac    3060
gtgcagtatt tcgataaaga tggtgtccag gccaaggata agatcattgt cacccgcgat    3120
ggcaaagtcc gctatttcga ccagcacaac ggtaatgcgg ttactaacac gttcgttgcg    3180
gacaagacgg gtcactggta ctatctgggc aaagacggcg tcgcggttac cggtgcgcag    3240
actgtgggta acagcatttt gtactttgaa gcgaacggtc aacaagtcaa gggtgacttc    3300
gtgacggcta agacggtaa actgtacttc tatgatgtgg acagcggcga catgtggacc    3360 aatacccttta tcgaggataa agcgggtaat tggttctacc tgggtaagga cggtgcggcc    3420
gtcaccggtg cacagacgat caaaggccag aaattgtatt tcaaagccaa cggtcagcaa    3480
gttaaaggtg acattgtcaa ggacgcggac ggtaagatcc gttattacga cgctcagacc    3540
ggtgaacagg tctttaacaa gtccgttagc gtcaacggta agacctacta tttcggtagc    3600
gacggcaccg cgcaaaccca ggcgaatccg aaaggccaaa cctttaagga tggtagcggc    3660
gttctgcgtt tctacaattt ggagggccag tatgtctcgg gcagcggctg gtacgaaacg    3720
gccgagcacg agtgggtata tgtgaaatcc ggtaaagttc tgaccggtgc ccagacgatt    3780
ggtaatcaac gtgtttactt caaggacaat ggtcaccagg tgaaaggcca gctggtcacg    3840
ggtaatgacg gtaaattgcg ttactacgac gcgaacagcg tgatcaagc attcaacaaa    3900 tccgtcacgg ttaacggtaa aacctactac tttggcagcg atggtacggc gcagacgcag    3960
gctaatccta agggtcagac cttcaaagat ggtagcggcg tgctgcgttt ttacaacttg    4020
```

-continued

```
gaaggccaat acgtgtctgg cagcggttgg tacaagaatg cgcagggcca gtggctgtac    4080
gtgaaagatg gcaaggtcct gaccggtctg caaacggtcg gcaatcagaa ggtctacttc    4140
gacaaaaatg gcatccaagc aaagggtaag gccgttcgca cgtccgatgg taaagtgcgc    4200
tactttgatg agaatagcgg tagcatgatt acgaaccaat ggaagttcgt ttacggtcaa    4260
tactattact tcggttctga cggcgcagcg gtttaccgtg gttggaacta a              4311
```

<210> SEQ ID NO 10
<211> LENGTH: 1436
<212> TYPE: PRT
<213> ORGANISM: Streptococcus downei

<400> SEQUENCE: 10

```
Met Val Asp Gly Lys Tyr Tyr Tyr Asp Gln Asp Gly Asn Val Lys
1               5                   10                  15

Lys Asn Phe Ala Val Ser Val Gly Glu Lys Ile Tyr Tyr Phe Asp Glu
                20                  25                  30

Thr Gly Ala Tyr Lys Asp Thr Ser Lys Val Glu Ala Asp Lys Ser Gly
            35                  40                  45

Ser Asp Ile Ser Lys Glu Glu Thr Thr Phe Ala Ala Asn Asn Arg Ala
        50                  55                  60

Tyr Ser Thr Ser Ala Glu Asn Phe Glu Ala Ile Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Ser Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Thr Glu Gln Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Gln Ser Asp Leu
        195                 200                 205

Thr Pro Asp Thr Gln Ser Asn Tyr Arg Leu Leu Asn Arg Thr Pro Thr
    210                 215                 220

Asn Gln Thr Gly Ser Leu Asp Ser Arg Phe Thr Tyr Asn Ala Asn Asp
225                 230                 235                 240

Pro Leu Gly Gly Tyr Glu Leu Leu Ala Asn Asp Val Asp Asn Ser
                245                 250                 255

Asn Pro Ile Val Gln Ala Glu Gln Leu Asn Trp Leu His Tyr Leu Leu
            260                 265                 270

Asn Phe Gly Thr Ile Tyr Ala Lys Asp Ala Asp Ala Asn Phe Asp Ser
        275                 280                 285

Ile Arg Val Asp Ala Val Asp Asn Val Asp Ala Asp Leu Leu Gln Ile
    290                 295                 300

Ser Ser Asp Tyr Leu Lys Ala Ala Tyr Gly Ile Asp Lys Asn Asn Lys
305                 310                 315                 320
```

-continued

Asn Ala Asn Asn His Val Ser Ile Val Glu Ala Trp Ser Asp Asn Asp
            325                 330                 335

Thr Pro Tyr Leu His Asp Asp Gly Asp Asn Leu Met Asn Met Asp Asn
            340                 345                 350

Lys Phe Arg Leu Ser Met Leu Trp Ser Leu Ala Lys Pro Leu Asp Lys
            355                 360                 365

Arg Ser Gly Leu Asn Pro Leu Ile His Asn Ser Leu Val Asp Arg Glu
            370                 375                 380

Val Asp Asp Arg Glu Val Glu Thr Val Pro Ser Tyr Ser Phe Ala Arg
385                 390                 395                 400

Ala His Asp Ser Glu Val Gln Asp Leu Ile Arg Asp Ile Ile Lys Ala
                405                 410                 415

Glu Ile Asn Pro Asn Ala Phe Gly Tyr Ser Phe Thr Gln Asp Glu Ile
                420                 425                 430

Asp Gln Ala Phe Lys Ile Tyr Asn Glu Asp Leu Lys Lys Thr Asp Lys
                435                 440                 445

Lys Tyr Thr His Tyr Asn Val Pro Leu Ser Tyr Thr Leu Leu Leu Thr
            450                 455                 460

Asn Lys Gly Ser Ile Pro Arg Val Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ala Gly Gly Gln Ala Met
            500                 505                 510

Gln Asn Tyr Gln Ile Gly Asn Gly Glu Ile Leu Thr Ser Val Arg Tyr
            515                 520                 525

Gly Lys Gly Ala Leu Lys Gln Ser Asp Lys Gly Asp Ala Thr Thr Arg
            530                 535                 540

Thr Ser Gly Val Gly Val Val Met Gly Asn Gln Pro Asn Phe Ser Leu
545                 550                 555                 560

Asp Gly Lys Val Val Ala Leu Asn Met Gly Ala Ala His Ala Asn Gln
                565                 570                 575

Glu Tyr Arg Ala Leu Met Val Ser Thr Lys Asp Gly Val Ala Thr Tyr
            580                 585                 590

Ala Thr Asp Ala Asp Ala Ser Lys Ala Gly Leu Val Lys Arg Thr Asp
            595                 600                 605

Glu Asn Gly Tyr Leu Tyr Phe Leu Asn Asp Asp Leu Lys Gly Val Ala
            610                 615                 620

Asn Pro Gln Val Ser Gly Phe Leu Gln Val Trp Val Pro Val Gly Ala
625                 630                 635                 640

Ala Asp Asp Gln Asp Ile Arg Val Ala Ala Ser Asp Thr Ala Ser Thr
                645                 650                 655

Asp Gly Lys Ser Leu His Gln Asp Ala Ala Met Asp Ser Arg Val Met
            660                 665                 670

Phe Glu Gly Phe Ser Asn Phe Gln Ser Phe Ala Thr Lys Glu Glu
            675                 680                 685

Tyr Thr Asn Val Val Ile Ala Asn Asn Val Asp Lys Phe Val Ser Trp
            690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Asp

-continued

```
                740                 745                 750
Gln Leu Val Lys Ala Ile Lys Ala Leu His Ala Lys Gly Leu Lys Val
                    755                 760                 765

Met Ala Asp Trp Val Pro Asp Gln Met Tyr Thr Phe Pro Lys Gln Glu
            770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Asp Thr Lys Ser Ser Gly
                    805                 810                 815

Asp Asp Tyr Gln Ala Lys Tyr Gly Gly Ala Phe Leu Asp Glu Leu Lys
                820                 825                 830

Glu Lys Tyr Pro Glu Leu Phe Thr Lys Lys Gln Ile Ser Thr Gly Gln
            835                 840                 845

Ala Ile Asp Pro Ser Val Lys Ile Lys Gln Trp Ser Ala Lys Tyr Phe
        850                 855                 860

Asn Gly Ser Asn Ile Leu Gly Arg Gly Ala Asp Tyr Val Leu Ser Asp
865                 870                 875                 880

Gln Ala Ser Asn Lys Tyr Leu Asn Val Ser Asp Lys Leu Phe Leu
                    885                 890                 895

Pro Lys Thr Leu Leu Gly Gln Val Val Glu Ser Gly Ile Arg Phe Asp
                900                 905                 910

Gly Thr Gly Tyr Val Tyr Asn Ser Ser Thr Thr Gly Glu Lys Val Thr
            915                 920                 925

Asp Ser Phe Ile Thr Glu Ala Gly Asn Leu Tyr Tyr Phe Gly Gln Asp
        930                 935                 940

Gly Tyr Met Val Thr Gly Ala Gln Asn Ile Lys Gly Ser Asn Tyr Tyr
945                 950                 955                 960

Phe Leu Ala Asn Gly Ala Ala Leu Arg Asn Thr Val Tyr Thr Asp Ala
                    965                 970                 975

Gln Gly Gln Asn His Tyr Tyr Gly Asn Asp Gly Lys Arg Tyr Glu Asn
                980                 985                 990

Gly Tyr Gln Gln Phe Gly Asn Asp Ser Trp Arg Tyr Phe Lys Asn Gly
            995                 1000                1005

Val Met Ala Leu Gly Leu Thr Thr Val Asp Gly His Val Gln Tyr
        1010                1015                1020

Phe Asp Lys Asp Gly Val Gln Ala Lys Asp Lys Ile Ile Val Thr
        1025                1030                1035

Arg Asp Gly Lys Val Arg Tyr Phe Asp Gln His Asn Gly Asn Ala
        1040                1045                1050

Val Thr Asn Thr Phe Val Ala Asp Lys Thr Gly His Trp Tyr Tyr
        1055                1060                1065

Leu Gly Lys Asp Gly Val Ala Val Thr Gly Ala Gln Thr Val Gly
        1070                1075                1080

Lys Gln His Leu Tyr Phe Glu Ala Asn Gly Gln Gln Val Lys Gly
        1085                1090                1095

Asp Phe Val Thr Ala Lys Asp Gly Lys Leu Tyr Phe Tyr Asp Val
        1100                1105                1110

Asp Ser Gly Asp Met Trp Thr Asn Thr Phe Ile Glu Asp Lys Ala
        1115                1120                1125

Gly Asn Trp Phe Tyr Leu Gly Lys Asp Gly Ala Ala Val Thr Gly
        1130                1135                1140

Ala Gln Thr Ile Lys Gly Gln Lys Leu Tyr Phe Lys Ala Asn Gly
        1145                1150                1155
```

```
Gln Gln Val Lys Gly Asp Ile Val Lys Asp Ala Asp Gly Lys Ile
    1160                1165                1170
Arg Tyr Tyr Asp Ala Gln Thr Gly Glu Gln Val Phe Asn Lys Ser
    1175                1180                1185
Val Ser Val Asn Gly Lys Thr Tyr Tyr Phe Gly Ser Asp Gly Thr
    1190                1195                1200
Ala Gln Thr Gln Ala Asn Pro Lys Gly Gln Thr Phe Lys Asp Gly
    1205                1210                1215
Ser Gly Val Leu Arg Phe Tyr Asn Leu Glu Gly Gln Tyr Val Ser
    1220                1225                1230
Gly Ser Gly Trp Tyr Glu Thr Ala Glu His Glu Trp Val Tyr Val
    1235                1240                1245
Lys Ser Gly Lys Val Leu Thr Gly Ala Gln Thr Ile Gly Asn Gln
    1250                1255                1260
Arg Val Tyr Phe Lys Asp Asn Gly His Gln Val Lys Gly Gln Leu
    1265                1270                1275
Val Thr Gly Asn Asp Gly Lys Leu Arg Tyr Tyr Asp Ala Asn Ser
    1280                1285                1290
Gly Asp Gln Ala Phe Asn Lys Ser Val Thr Val Asn Gly Lys Thr
    1295                1300                1305
Tyr Tyr Phe Gly Ser Asp Gly Thr Ala Gln Thr Gln Ala Asn Pro
    1310                1315                1320
Lys Gly Gln Thr Phe Lys Asp Gly Ser Gly Val Leu Arg Phe Tyr
    1325                1330                1335
Asn Leu Glu Gly Gln Tyr Val Ser Gly Ser Gly Trp Tyr Lys Asn
    1340                1345                1350
Ala Gln Gly Gln Trp Leu Tyr Val Lys Asp Gly Lys Val Leu Thr
    1355                1360                1365
Gly Leu Gln Thr Val Gly Asn Gln Lys Val Tyr Phe Asp Lys Asn
    1370                1375                1380
Gly Ile Gln Ala Lys Gly Lys Ala Val Arg Thr Ser Asp Gly Lys
    1385                1390                1395
Val Arg Tyr Phe Asp Glu Asn Ser Gly Ser Met Ile Thr Asn Gln
    1400                1405                1410
Trp Lys Phe Val Tyr Gly Gln Tyr Tyr Tyr Phe Gly Ser Asp Gly
    1415                1420                1425
Ala Ala Val Tyr Arg Gly Trp Asn
    1430                1435

<210> SEQ ID NO 11
<211> LENGTH: 3942
<212> TYPE: DNA
<213> ORGANISM: Streptococcus mutans

<400> SEQUENCE: 11
atgattgacg gcaaatacta ctactatgac aacaacggca agtacgcac caatttcacg      60 ttgatcgcgg acgtaaaat cctgcatttt gatgaaactg gcgcgtacac cgacactagc     120
attgataccg tgaacaagga tattgtcacg acgcgtagca acctgtataa gaaatacaat     180
caagtgtatg atcgcagcgc gcagagcttc gagcatgttg atcactacct gacggcggaa     240
tcttggtacc gtccgaaata cattctgaaa gatggcaaga cctggaccca gagcaccgag     300
aaggacttcc gtcctctgct gatgacctgg tggccgagcc aggaaacgca gcgccagtat     360
gtcaacttca tgaacgccca gttgggtatc aacaaaacgt acgacgacac cagcaatcag     420
```

```
ctgcaattga acatcgctgc tgcaacgatc aagcaaaga tcgaagccaa aatcacgacg    480
ctgaagaaca ccgattggct gcgtcaaacg atcagcgcgt tcgtcaaaac ccaaagcgct    540
tggaatagcg acagcgaaaa gccgtttgat gaccatctgc aaaacggtgc ggttctgtat    600
gataacgaag gtaaattgac gccgtatgcc aatagcaact atcgtattct gaaccgcacg    660
ccgaccaacc agaccggtaa gaaggacccg cgttataccg ccgacaacac gatcggcggc    720
tacgagtttc tgctggccaa cgacgtggat aatagcaacc cggtggttca ggccgagcag    780
ctgaactggc tgcacttcct gatgaacttt ggtaatatct acgcaaacga ccctgacgct    840
aacttcgact ccatccgcgt tgacgctgtc gataatgtgg acgccgatct gttacagatc    900
gcgggtgact atctgaaagc ggcaaagggc atccataaga atgacaaagc ggcgaacgac    960
cacctgtcca ttctggaagc gtggagcgac aatgacactc cgtatctgca tgatgatggc   1020
gacaacatga ttaacatgga taacaaactg cgcctgagcc tgctgttctc cctggcgaaa   1080
ccgctgaatc agcgtagcgg tatgaacccg ttgattacga acagcctggt caaccgtact   1140
gatgataatg ccgaaacggc ggcagtgcca agctactctt ttatccgtgc ccacgatagc   1200
gaggtccagg atttgattcg tgatatcatt aaggctgaga ttaacccgaa cgtcgtcggt   1260
tacagcttca cgatggaaga gattaagaag gcatttgaga tctacaataa ggacctgttg   1320
gccacggaga gaagtatac ccactataac accgcattga gctacgcgtt gctgctgacg    1380
aacaagagca gcgtgccgcg tgtctactat ggtgatatgt ttacggacga tggtcaatac   1440
atggcccaca agaccattaa ctacgaggca atcgaaaccc tgctgaaagc acgtatcaag   1500
tacgtgtccg gtggtcaggc tatgcgcaac cagcaagtgg gtaattcgga gatcatcacc   1560
agcgtgcgtt acggtaaagg tgcgctgaag gcgatggata cgggtgaccg cactacccgt   1620
acctctggtg tggcggtcat tgagggcaac aacccgagct tgcgcctgaa ggcttctgat   1680
cgtgtggttg tgaatatggg tgcggcccac aaaaatcaag cctatcgccc gctgctgttg   1740
acgaccgata acggcattaa ggcctatcac agcgaccaag aagcggcagg cctggtgcgt   1800
tacaccaacg accgtggcga actgatcttt accgcagccg acattaaggg ctacgcaaat   1860
ccgcaagtta gcggctacct gggcgtctgg gtccctgttg gcgcagcagc tgatcaggac   1920
gttcgtgttg cggcgagcac cgcgccaagc acggacggca agagcgttca ccagaacgcg   1980
gctctggaca gccgtgtgat gttcgagggt ttctcgaact tccaggcatt tgctaccaag   2040
aaagaagagt ataccaatgt ggtcatcgct aagaatgtgg ataagttcgc ggagtggggt   2100
gtcaccgatt tcgagatggc tccgcaatac gtttctagca ccgacggtag cttttttggat  2160 agcgtgattc aaaacggtta tgctttttacc gaccgttacg acctgggcat cagcaagccg   2220
aacaaatatg gcaccgcgga cgatctggtt aaagcgatta aggcattgca cagcaaaggc   2280
atcaaagtta tggcggattg ggttccggac cagatgtatg ccctgccgga aaagaggtt   2340 gtgacggcaa cccgtgttga caaatacggt acgccggtag ctggcagcca gatcaaaaac   2400
acgctgtacg tggtcgatgg taaatctagc ggtaaggacc agcaggcgaa gtacggtggt   2460
gccttcctgg aagagctgca agcgaagtat ccggaactgt tcgcgcgcaa acagattagc   2520
accggtgttc cgatggaccc gagcgtcaag attaagcaat ggagcgcaaa atacttcaac   2580
ggcacgaata tcctgggtcg tggtgctggt tacgtgctga agatcaggc aaccaacacc   2640 tactttaaca tcagcgacaa taagagatc aatttcctgc aaagacgtt gctgaaccag    2700 gattctcaag ttggctttag ctacgacggt aagggctatg tgtactacag cacctcgggc   2760
```

-continued

```
taccaggcta aaaacacgtt catcagcgag ggtgacaagt ggtattactt cgacaataac    2820
ggttatatgg ttaccggcgc acagagcatt aatggtgtga actattactt cctgccgaat    2880
ggtttacagc tgcgtgatgc gattctgaaa atgaggacg gtacgtacgc gtattatggc    2940
aatgatggtc gccgctacga gaatggctat tatcagttta tgagcggtgt ttggcgccat    3000
ttcaataatg gcgagatgtc cgttggtctg accgtcattg acggtcaagt tcaatacttt    3060
gacgagatgg gttaccaggc gaaaggcaaa ttcgttacca ccgcggatgg taagatccgt    3120
tacttcgata gcagagcgg caatatgtat cgtaatcgtt tcattgagaa cgaagagggc    3180
aaatggctgt acctgggtga ggacggcgcg gcagtcaccg tagccagac gatcaatggt    3240
cagcacctgt attttcgtgc taacggcgtt caggttaagg gtgagttcgt gaccgatcgt    3300
catggccgca tctcttatta cgacggcaac agcggtgatc agatccgcaa ccgtttcgtc    3360
cgcaatgcgc aaggccagtg gttttacttt gacaacaatg gctatgcagt aactggtgct    3420
cgtacgatca acggccagca cctgtatttc cgcgcgaacg gtgttcaggt aaaaggtgag    3480
tttgttacgg accgccacgg ccgcattagc tattatgatg gtaatagcgg tgaccaaatt    3540
cgcaatcgtt tcgtgcgtaa tgcacagggt cagtggttct acttcgacaa taatggttat    3600
gcagtcacgg gtgcacgtac cattaacggc caacacctgt actttcgcgc caatggtgtg    3660
caagtgaaag gcgaatttgt tactgatcgt tatggtcgta tcagctacta tgatggcaat    3720
tctggcgacc aaattcgcaa tcgctttgtt cgtaacgccc aaggtcaatg gttctatttc    3780
gacaacaacg ttacgcggt gaccggtgcc gcacgattaa atggtcaaca cttgtacttc    3840
cgtgccaaca gtgtccaggt gaagggtgaa tttgtgaccg accgctatgg tcgcatttct    3900
tactacgacg caaattccgg tgaacgcgtc cgtatcaatt aa                       3942
```

<210> SEQ ID NO 12
<211> LENGTH: 1313
<212> TYPE: PRT
<213> ORGANISM: Streptococcus mutans

<400> SEQUENCE: 12

```
Met Ile Asp Gly Lys Tyr Tyr Tyr Asp Asn Asn Gly Lys Val Arg
1               5                  10                  15

Thr Asn Phe Thr Leu Ile Ala Asp Gly Lys Ile Leu His Phe Asp Glu
            20                  25                  30

Thr Gly Ala Tyr Thr Asp Thr Ser Ile Asp Thr Val Asn Lys Asp Ile
        35                  40                  45

Val Thr Thr Arg Ser Asn Leu Tyr Lys Lys Tyr Asn Gln Val Tyr Asp
    50                  55                  60

Arg Ser Ala Gln Ser Phe Glu His Val Asp His Tyr Leu Thr Ala Glu
65                  70                  75                  80

Ser Trp Tyr Arg Pro Lys Tyr Ile Leu Lys Asp Gly Lys Thr Trp Thr
                85                  90                  95

Gln Ser Thr Glu Lys Asp Phe Arg Pro Leu Leu Met Thr Trp Trp Pro
            100                 105                 110

Ser Gln Glu Thr Gln Arg Gln Tyr Val Asn Phe Met Asn Ala Gln Leu
        115                 120                 125

Gly Ile Asn Lys Thr Tyr Asp Asp Thr Ser Asn Gln Leu Gln Leu Asn
    130                 135                 140

Ile Ala Ala Ala Thr Ile Gln Ala Lys Ile Glu Ala Lys Ile Thr Thr
145                 150                 155                 160

Leu Lys Asn Thr Asp Trp Leu Arg Gln Thr Ile Ser Ala Phe Val Lys
```

```
                165                 170                 175
Thr Gln Ser Ala Trp Asn Ser Asp Ser Glu Lys Pro Phe Asp Asp His
                180                 185                 190

Leu Gln Asn Gly Ala Val Leu Tyr Asp Asn Glu Gly Lys Leu Thr Pro
                195                 200                 205

Tyr Ala Asn Ser Asn Tyr Arg Ile Leu Asn Arg Thr Pro Thr Asn Gln
210                 215                 220

Thr Gly Lys Lys Asp Pro Arg Tyr Thr Ala Asp Asn Thr Ile Gly Gly
225                 230                 235                 240

Tyr Glu Phe Leu Leu Ala Asn Asp Val Asp Asn Ser Asn Pro Val Val
                245                 250                 255

Gln Ala Glu Gln Leu Asn Trp Leu His Phe Leu Met Asn Phe Gly Asn
                260                 265                 270

Ile Tyr Ala Asn Asp Pro Asp Ala Asn Phe Asp Ser Ile Arg Val Asp
                275                 280                 285

Ala Val Asp Asn Val Asp Ala Asp Leu Leu Gln Ile Ala Gly Asp Tyr
                290                 295                 300

Leu Lys Ala Ala Lys Gly Ile His Lys Asn Asp Lys Ala Ala Asn Asp
305                 310                 315                 320

His Leu Ser Ile Leu Glu Ala Trp Ser Asp Asn Asp Thr Pro Tyr Leu
                325                 330                 335

His Asp Asp Gly Asp Asn Met Ile Asn Met Asp Asn Lys Leu Arg Leu
                340                 345                 350

Ser Leu Leu Phe Ser Leu Ala Lys Pro Leu Asn Gln Arg Ser Gly Met
                355                 360                 365

Asn Pro Leu Ile Thr Asn Ser Leu Val Asn Arg Thr Asp Asp Asn Ala
370                 375                 380

Glu Thr Ala Ala Val Pro Ser Tyr Ser Phe Ile Arg Ala His Asp Ser
385                 390                 395                 400

Glu Val Gln Asp Leu Ile Arg Asp Ile Ile Lys Ala Glu Ile Asn Pro
                405                 410                 415

Asn Val Val Gly Tyr Ser Phe Thr Met Glu Glu Ile Lys Lys Ala Phe
                420                 425                 430

Glu Ile Tyr Asn Lys Asp Leu Leu Ala Thr Glu Lys Lys Tyr Thr His
                435                 440                 445

Tyr Asn Thr Ala Leu Ser Tyr Ala Leu Leu Thr Asn Lys Ser Ser
450                 455                 460

Val Pro Arg Val Tyr Tyr Gly Asp Met Phe Thr Asp Asp Gly Gln Tyr
465                 470                 475                 480

Met Ala His Lys Thr Ile Asn Tyr Glu Ala Ile Glu Thr Leu Leu Lys
                485                 490                 495

Ala Arg Ile Lys Tyr Val Ser Gly Gly Gln Ala Met Arg Asn Gln Gln
                500                 505                 510

Val Gly Asn Ser Glu Ile Ile Thr Ser Val Arg Tyr Gly Lys Gly Ala
                515                 520                 525

Leu Lys Ala Met Asp Thr Gly Asp Arg Thr Thr Arg Thr Ser Gly Val
                530                 535                 540

Ala Val Ile Glu Gly Asn Asn Pro Ser Leu Arg Leu Lys Ala Ser Asp
545                 550                 555                 560

Arg Val Val Val Asn Met Gly Ala Ala His Lys Asn Gln Ala Tyr Arg
                565                 570                 575

Pro Leu Leu Leu Thr Thr Asp Asn Gly Ile Lys Ala Tyr His Ser Asp
                580                 585                 590
```

-continued

```
Gln Glu Ala Ala Gly Leu Val Arg Tyr Thr Asn Asp Arg Gly Glu Leu
            595                 600                 605

Ile Phe Thr Ala Ala Asp Ile Lys Gly Tyr Ala Asn Pro Gln Val Ser
        610                 615                 620

Gly Tyr Leu Gly Val Trp Val Pro Val Gly Ala Ala Asp Gln Asp
625                 630                 635                 640

Val Arg Val Ala Ala Ser Thr Ala Pro Ser Thr Asp Gly Lys Ser Val
                645                 650                 655

His Gln Asn Ala Ala Leu Asp Ser Arg Val Met Phe Glu Gly Phe Ser
            660                 665                 670

Asn Phe Gln Ala Phe Ala Thr Lys Lys Glu Glu Tyr Thr Asn Val Val
        675                 680                 685

Ile Ala Lys Asn Val Asp Lys Phe Ala Glu Trp Gly Val Thr Asp Phe
    690                 695                 700

Glu Met Ala Pro Gln Tyr Val Ser Ser Thr Asp Gly Ser Phe Leu Asp
705                 710                 715                 720

Ser Val Ile Gln Asn Gly Tyr Ala Phe Thr Asp Arg Tyr Asp Leu Gly
                725                 730                 735

Ile Ser Lys Pro Asn Lys Tyr Gly Thr Ala Asp Leu Val Lys Ala
            740                 745                 750

Ile Lys Ala Leu His Ser Lys Gly Ile Lys Val Met Ala Asp Trp Val
        755                 760                 765

Pro Asp Gln Met Tyr Ala Leu Pro Glu Lys Glu Val Val Thr Ala Thr
    770                 775                 780

Arg Val Asp Lys Tyr Gly Thr Pro Val Ala Gly Ser Gln Ile Lys Asn
785                 790                 795                 800

Thr Leu Tyr Val Val Asp Gly Lys Ser Ser Gly Lys Asp Gln Gln Ala
                805                 810                 815

Lys Tyr Gly Gly Ala Phe Leu Glu Glu Leu Gln Ala Lys Tyr Pro Glu
            820                 825                 830

Leu Phe Ala Arg Lys Gln Ile Ser Thr Gly Val Pro Met Asp Pro Ser
        835                 840                 845

Val Lys Ile Lys Gln Trp Ser Ala Lys Tyr Phe Asn Gly Thr Asn Ile
    850                 855                 860

Leu Gly Arg Gly Ala Gly Tyr Val Leu Lys Asp Gln Ala Thr Asn Thr
865                 870                 875                 880

Tyr Phe Asn Ile Ser Asp Asn Lys Glu Ile Asn Phe Leu Pro Lys Thr
                885                 890                 895

Leu Leu Asn Gln Asp Ser Gln Val Gly Phe Ser Tyr Asp Gly Lys Gly
            900                 905                 910

Tyr Val Tyr Tyr Ser Thr Ser Gly Tyr Gln Ala Lys Asn Thr Phe Ile
        915                 920                 925

Ser Glu Gly Asp Lys Trp Tyr Tyr Phe Asp Asn Asn Gly Tyr Met Val
    930                 935                 940

Thr Gly Ala Gln Ser Ile Asn Gly Val Asn Tyr Tyr Phe Leu Pro Asn
945                 950                 955                 960

Gly Leu Gln Leu Arg Asp Ala Ile Leu Lys Asn Glu Asp Gly Thr Tyr
                965                 970                 975

Ala Tyr Tyr Gly Asn Asp Gly Arg Arg Tyr Glu Asn Gly Tyr Tyr Gln
            980                 985                 990

Phe Met Ser Gly Val Trp Arg His  Phe Asn Asn Gly Glu  Met Ser Val
        995                 1000                1005
```

| | | | | | | | | | | |
|---|---|---|---|---|---|---|---|---|---|---|
|Gly|Leu|Thr|Val|Ile|Asp|Gly|Gln|Val|Gln|Tyr|Phe|Asp|Glu|Met|
| |1010| | | |1015| | | |1020| |

Gly Tyr Gln Ala Lys Gly Lys Phe Val Thr Thr Ala Asp Gly Lys
    1025                      1030                      1035

Ile Arg Tyr Phe Asp Lys Gln Ser Gly Asn Met Tyr Arg Asn Arg
    1040                      1045                      1050

Phe Ile Glu Asn Glu Glu Gly Lys Trp Leu Tyr Leu Gly Glu Asp
    1055                      1060                      1065

Gly Ala Ala Val Thr Gly Ser Gln Thr Ile Asn Gly Gln His Leu
    1070                      1075                      1080

Tyr Phe Arg Ala Asn Gly Val Gln Val Lys Gly Glu Phe Val Thr
    1085                      1090                      1095

Asp Arg His Gly Arg Ile Ser Tyr Tyr Asp Gly Asn Ser Gly Asp
    1100                      1105                      1110

Gln Ile Arg Asn Arg Phe Val Arg Asn Ala Gln Gly Gln Trp Phe
    1115                      1120                      1125

Tyr Phe Asp Asn Asn Gly Tyr Ala Val Thr Gly Ala Arg Thr Ile
    1130                      1135                      1140

Asn Gly Gln His Leu Tyr Phe Arg Ala Asn Gly Val Gln Val Lys
    1145                      1150                      1155

Gly Glu Phe Val Thr Asp Arg His Gly Arg Ile Ser Tyr Tyr Asp
    1160                      1165                      1170

Gly Asn Ser Gly Asp Gln Ile Arg Asn Arg Phe Val Arg Asn Ala
    1175                      1180                      1185

Gln Gly Gln Trp Phe Tyr Phe Asp Asn Asn Gly Tyr Ala Val Thr
    1190                      1195                      1200

Gly Ala Arg Thr Ile Asn Gly Gln His Leu Tyr Phe Arg Ala Asn
    1205                      1210                      1215

Gly Val Gln Val Lys Gly Glu Phe Val Thr Asp Arg Tyr Gly Arg
    1220                      1225                      1230

Ile Ser Tyr Tyr Asp Gly Asn Ser Gly Asp Gln Ile Arg Asn Arg
    1235                      1240                      1245

Phe Val Arg Asn Ala Gln Gly Gln Trp Phe Tyr Phe Asp Asn Asn
    1250                      1255                      1260

Gly Tyr Ala Val Thr Gly Ala Arg Thr Ile Asn Gly Gln His Leu
    1265                      1270                      1275

Tyr Phe Arg Ala Asn Gly Val Gln Val Lys Gly Glu Phe Val Thr
    1280                      1285                      1290

Asp Arg Tyr Gly Arg Ile Ser Tyr Tyr Asp Ala Asn Ser Gly Glu
    1295                      1300                      1305

Arg Val Arg Ile Asn
    1310

<210> SEQ ID NO 13
<211> LENGTH: 3972
<212> TYPE: DNA
<213> ORGANISM: Streptococcus dentirousetti

<400> SEQUENCE: 13

```
atggttgacg gcaaatacta ctactacgat gcagacggca acgtaaagaa aaacttcgcg      60
gttagcgttg gcgatgccat tttctatttt gatgaaacgg gtgcctacaa agataccagc     120
aaagttgatg cggataagac cagctctagc gtcaatcaga ccacggaaac gttcgcagcg     180
aataaccgtg cgtatagcac cgcagccgag aactttgaag cgattgataa ctacctgact     240
```

| | |
|---|---|
| gcggatagct ggtatcgtcc gaagtctatc ttgaaagatg gtacgacgtg gaccgaaagc | 300 |
| accaaggatg attttcgccc gctgctgatg gcgtggtggc cggataccga aaccaaacgt | 360 |
| aactacgtga actatatgaa caaggtggtc ggtatcgaca aaacgtacac cgcggaaacg | 420 |
| tcccaagctg acctgacggc ggcagccgaa ctggtgcagg cgcgtatcga gcagaaaatc | 480 |
| actagcgaaa agaatacgaa gtggctgcgt gaggcgattt ccgcgttcgt taagactcaa | 540 |
| ccgcagtgga atggcgagag cgagaaacct tatgatgacc acctgcaaaa tggtgcgctg | 600 |
| aagttcgaca atgaaaccag cctgaccccg gatacgcaga gcggctatcg catcctgaac | 660 |
| cgtaccccga cgaatcaaac cggtagcctg acccgcgct tcacctttaa tcagaatgac | 720 |
| ccgctgggtg gttatgagta tttgctggct aatgatgtcg ataacagcaa cccggtcgtt | 780 |
| caggccgaga gcctgaactg gctgcattac ctgctgaatt ttggtagcat ttacgcgaat | 840 |
| gatccggagg ccaatttcga cagcatccgt gtggacgcgg tggacaatgt tgacgcagac | 900 |
| ctgctgcaaa ttagctcgga ttacctgaaa tcggcgtaca aaattgacaa gaacaacaaa | 960 |
| aatgcgaacg accacgttag catcgtcgag gcgtggagcg acaatgatac cccgtacctg | 1020 |
| aatgatgatg gcgacaatct gatgaacatg gataacaagt ttcgtctgag catgctgtgg | 1080 |
| agcctggcga agccaaccaa tgtccgtagc ggcttgaatc cgctgatcca caacagcgtg | 1140 |
| gttgaccgtg aggtggacga ccgtgaagtt gaggctaccc cgaattacag ctttgcacgc | 1200 |
| gcacacgaca gcgaagttca agatttgatt cgcgacatca tcaaagctga gatcaaccca | 1260 |
| aacagcttcg gttatagctt tacccaagag gaaatcgacc aggccttcaa gatctacaat | 1320 |
| gaggatttga agaaaaccaa taagaagtat acccactaca acgtcccgct gagctacacc | 1380 |
| ctgctgctga cgaacaaggg cagcattcca cgcatttact acggtgacat gtttacggat | 1440 |
| gacggtcagt atatggccaa caaaaccgtt aactatgacg ccattgagag cctgctgaaa | 1500 |
| gcacgtatga agtatgttag cggtggccaa gcgatgcaga attacaacat cggcaacggc | 1560 |
| gagattctga ccagcgtccg ttacggtaag ggtgccctga acagagcga caaaggcgat | 1620 |
| aagactactc gtaccagcgg tattggcgtt gtgatgggta accagagcaa tttcagcctg | 1680 |
| gagggcaagt tggtggccct gaatatgggt gcaacgcata ccaaacagaa gtatcgtgca | 1740 |
| ttgatggtgt ctacggaaac cggcgtggcg atttacaata gcgatgaaga agcagaggca | 1800 |
| gcaggcctga tcaaaacgac cgatgagaat ggttatttgt actttctgaa tgacgatctg | 1860 |
| aagggcgtgg ctaacccgca ggtcagcggc ttcctgcaag tgtgggttcc ggttggtgca | 1920 |
| ccggctgacc aggacattcg tgtggcggcg accgatgcgg cttctaccga cggtaagagc | 1980 |
| ctgcatcagg acgcagctct ggattctcgc gtcatgtttg aaggtttcag caacttccag | 2040 |
| agcttcgcaa ccaaggaaga ggaatacacc aacgttgtta ttgcaaagaa cgtggataag | 2100 |
| ttcgtgagct ggggtatcac cgacttcgag atggcaccgc agtacgttag ctctaccgat | 2160 |
| ggcaccttc tggatagcgt gattcaaaat ggctatgcct ttacggaccg ttacgacctg | 2220 |
| ggtatgagca aagcaaacaa gtatggtact gctgaccaac tggtggccgc gattaaagcg | 2280 |
| ctgcatgcga agggtctgcg tgtgatggcg gattgggtcc cagatcaaat gtacactttc | 2340 |
| cctaagaagg aagtggttac cgttacccgt acggacaaat ttggcaatcc agtggcaggc | 2400 |
| agccaaatca accacaccct tgtacgtcact gatactaagg gtagcggtga cgactaccag | 2460 |
| gcgaagtacg gtggcgcatt cctggatgaa ctgaaagaaa agtacccgga gctgtttacc | 2520 |
| aagaagcaaa tcagcaccgg tcaggcaatc gacccgagcg tgaaaatcaa gcagtggagc | 2580 |
| gcgaagtact tcaacggtag caatatcttg ggtcgcggtg cgaactacgt gctgtccgac | 2640 |

-continued

```
caggcgtcta acaagtactt taacgtggcc gaaggtaaag tctttctgcc agcggcgatg    2700
ctgggtaagg tcgtcgagag cggtatccgt ttcgacggta aaggttatat ctataacagc    2760
agcaccactg gcgaacaagt gaaggacagc ttcattaccg aagcgggtaa cttgtactat    2820
tttggcaaag atggttatat ggtcatgggt gcacagaata tccagggtgc taactactac    2880
ttcttggcga atggtgcggc cctgcgcaat agcatcctga cggatcagga tggcaaaagc    2940
cactattatg caaatgacgg caagcgttat gagaacggct actatcaatt cggtaacgac    3000
tcctggcgct attttgaaaa cggcgttatg ccgttggtt tgacgcgcgt tgcgggccac    3060
gaccaatact ttgataagga tggtatccaa gcgaagaata agatcattgt tacgcgtgac    3120
ggtaaggtcc gctacttcga cgaacacaac ggcaatgctg ccacgaatac gtttatcagc    3180
gatcaagccg ccattggta ctacctgggt aaagatggtg tcgccgtgac gggtgcgcag    3240
accgttggca agcaacacct gtacttcgag gctaacggcc aacaagtaaa aggcgatttt    3300
gttaccgcca aggacggtaa gttgtatttt ctggacggtg actctggcga catgtggacc    3360
gataccttcg tccaggataa ggctggtcat tggttctatc tgggcaaaga cggtgcggcg    3420
gtaaccggtg cccagaccgt ccgtggtcag aagctgtact tcaaagcgaa tggccagcag    3480
gttaagggtg acattgtgaa aggcgcggat ggtaaaatcc gttactatga tgcaaattcc    3540
ggtgaccagg tttacaatcg cacggtgaaa ggctccgacg gcaagaccta tatcattggt    3600
aatgacggcg tcgcaatcac gcaaaccatc gccaaaggcc agaccatcaa ggatggcagc    3660
gttctgcgct tctatagcat ggagggtcag ctggtgaccg gcagcggctg gtattccaac    3720
gcgaaaggtc aatggttgta tgtcaagaac ggtcaagtcc tgacgggttt gcagacggtg    3780
ggcagccagc gtgtgtactt tgacgcaaat ggtattcaag cgaaaggtaa agcagtgcgt    3840
acctccgatg gcaaactgcg ttacttcgat gcgaacagcg gcagcatgat caccaatcag    3900
tggaaagaag ttaatggtca gtactactat ttcgacaaca acggtgttgc gatctatcgc    3960
ggttggaact aa                                                         3972
```

<210> SEQ ID NO 14
<211> LENGTH: 1323
<212> TYPE: PRT
<213> ORGANISM: Streptococcus dentirousetti

<400> SEQUENCE: 14

```
Met Val Asp Gly Lys Tyr Tyr Tyr Asp Ala Asp Gly Asn Val Lys
1               5                  10                  15

Lys Asn Phe Ala Val Ser Val Gly Asp Ala Ile Phe Tyr Phe Asp Glu
                20                  25                  30

Thr Gly Ala Tyr Lys Asp Thr Ser Lys Val Asp Ala Asp Lys Thr Ser
            35                  40                  45

Ser Ser Val Asn Gln Thr Thr Glu Thr Phe Ala Ala Asn Asn Arg Ala
        50                  55                  60

Tyr Ser Thr Ala Ala Glu Asn Phe Glu Ala Ile Asp Asn Tyr Leu Thr
    65                  70                  75                  80

Ala Asp Ser Trp Tyr Arg Pro Lys Ser Ile Leu Lys Asp Gly Thr Thr
                85                  90                  95

Trp Thr Glu Ser Thr Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125
```

```
Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Ser Glu Lys Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Glu Thr Ser Leu
        195                 200                 205

Thr Pro Asp Thr Gln Ser Gly Tyr Arg Ile Leu Asn Arg Thr Pro Thr
    210                 215                 220

Asn Gln Thr Gly Ser Leu Asp Pro Arg Phe Thr Phe Asn Gln Asn Asp
225                 230                 235                 240

Pro Leu Gly Gly Tyr Glu Tyr Leu Leu Ala Asn Asp Val Asp Asn Ser
                245                 250                 255

Asn Pro Val Val Gln Ala Glu Ser Leu Asn Trp Leu His Tyr Leu Leu
            260                 265                 270

Asn Phe Gly Ser Ile Tyr Ala Asn Asp Pro Glu Ala Asn Phe Asp Ser
        275                 280                 285

Ile Arg Val Asp Ala Val Asp Asn Val Asp Ala Asp Leu Leu Gln Ile
    290                 295                 300

Ser Ser Asp Tyr Leu Lys Ser Ala Tyr Lys Ile Asp Lys Asn Asn Lys
305                 310                 315                 320

Asn Ala Asn Asp His Val Ser Ile Val Glu Ala Trp Ser Asp Asn Asp
                325                 330                 335

Thr Pro Tyr Leu Asn Asp Asp Gly Asp Asn Leu Met Asn Met Asp Asn
            340                 345                 350

Lys Phe Arg Leu Ser Met Leu Trp Ser Leu Ala Lys Pro Thr Asn Val
        355                 360                 365

Arg Ser Gly Leu Asn Pro Leu Ile His Asn Ser Val Val Asp Arg Glu
    370                 375                 380

Val Asp Asp Arg Glu Val Glu Ala Thr Pro Asn Tyr Ser Phe Ala Arg
385                 390                 395                 400

Ala His Asp Ser Glu Val Gln Asp Leu Ile Arg Asp Ile Ile Lys Ala
                405                 410                 415

Glu Ile Asn Pro Asn Ser Phe Gly Tyr Ser Phe Thr Gln Glu Glu Ile
            420                 425                 430

Asp Gln Ala Phe Lys Ile Tyr Asn Glu Asp Leu Lys Lys Thr Asn Lys
        435                 440                 445

Lys Tyr Thr His Tyr Asn Val Pro Leu Ser Tyr Thr Leu Leu Leu Thr
    450                 455                 460

Asn Lys Gly Ser Ile Pro Arg Ile Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ser Gly Gly Gln Ala Met
            500                 505                 510

Gln Asn Tyr Asn Ile Gly Asn Gly Glu Ile Leu Thr Ser Val Arg Tyr
        515                 520                 525

Gly Lys Gly Ala Leu Lys Gln Ser Asp Lys Gly Asp Lys Thr Thr Arg
    530                 535                 540

Thr Ser Gly Ile Gly Val Val Met Gly Asn Gln Ser Asn Phe Ser Leu
```

```
                    545                 550                 555                 560
            Glu Gly Lys Val Val Ala Leu Asn Met Gly Ala Thr His Thr Lys Gln
                            565                 570                 575

Lys Tyr Arg Ala Leu Met Val Ser Thr Glu Thr Gly Val Ala Ile Tyr
                            580                 585                 590

Asn Ser Asp Glu Glu Ala Glu Ala Gly Leu Ile Lys Thr Thr Asp
                        595                 600                 605

Glu Asn Gly Tyr Leu Tyr Phe Leu Asn Asp Asp Leu Lys Gly Val Ala
                            610                 615                 620

Asn Pro Gln Val Ser Gly Phe Leu Gln Val Trp Val Pro Val Gly Ala
            625                 630                 635                 640

Pro Ala Asp Gln Asp Ile Arg Val Ala Ala Thr Asp Ala Ala Ser Thr
                                645                 650                 655

Asp Gly Lys Ser Leu His Gln Asp Ala Ala Leu Asp Ser Arg Val Met
                            660                 665                 670

Phe Glu Gly Phe Ser Asn Phe Gln Ser Phe Ala Thr Lys Glu Glu Glu
                            675                 680                 685

Tyr Thr Asn Val Val Ile Ala Lys Asn Val Asp Lys Phe Val Ser Trp
                            690                 695                 700

Gly Ile Thr Asp Phe Glu Met Ala Pro Gln Tyr Val Ser Ser Thr Asp
            705                 710                 715                 720

Gly Thr Phe Leu Asp Ser Val Ile Gln Asn Gly Tyr Ala Phe Thr Asp
                                725                 730                 735

Arg Tyr Asp Leu Gly Met Ser Lys Ala Asn Lys Tyr Gly Thr Ala Asp
                            740                 745                 750

Gln Leu Val Ala Ala Ile Lys Ala Leu His Ala Lys Gly Leu Arg Val
                            755                 760                 765

Met Ala Asp Trp Val Pro Asp Gln Met Tyr Thr Phe Pro Lys Lys Glu
                            770                 775                 780

Val Val Thr Val Thr Arg Thr Asp Lys Phe Gly Asn Pro Val Ala Gly
            785                 790                 795                 800

Ser Gln Ile Asn His Thr Leu Tyr Val Thr Asp Thr Lys Gly Ser Gly
                                805                 810                 815

Asp Asp Tyr Gln Ala Lys Tyr Gly Gly Ala Phe Leu Asp Glu Leu Lys
                            820                 825                 830

Glu Lys Tyr Pro Glu Leu Phe Thr Lys Lys Gln Ile Ser Thr Gly Gln
                            835                 840                 845

Ala Ile Asp Pro Ser Val Lys Ile Lys Gln Trp Ser Ala Lys Tyr Phe
            850                 855                 860

Asn Gly Ser Asn Ile Leu Gly Arg Gly Ala Asn Tyr Val Leu Ser Asp
            865                 870                 875                 880

Gln Ala Ser Asn Lys Tyr Phe Asn Val Ala Glu Gly Lys Val Phe Leu
                            885                 890                 895

Pro Ala Ala Met Leu Gly Lys Val Val Glu Ser Gly Ile Arg Phe Asp
                            900                 905                 910

Gly Lys Gly Tyr Ile Tyr Asn Ser Ser Thr Thr Gly Glu Gln Val Lys
                            915                 920                 925

Asp Ser Phe Ile Thr Glu Ala Gly Asn Leu Tyr Phe Gly Lys Asp
                            930                 935                 940

Gly Tyr Met Val Met Gly Ala Gln Asn Ile Gln Gly Ala Asn Tyr Tyr
            945                 950                 955                 960

Phe Leu Ala Asn Gly Ala Ala Leu Arg Asn Ser Ile Leu Thr Asp Gln
                                965                 970                 975
```

Asp Gly Lys Ser His Tyr Tyr Ala Asn Asp Gly Lys Arg Tyr Glu Asn
        980                 985                 990

Gly Tyr Tyr Gln Phe Gly Asn Asp Ser Trp Arg Tyr Phe Glu Asn Gly
    995                 1000                1005

Val Met Ala Val Gly Leu Thr Arg Val Ala Gly His Asp Gln Tyr
    1010                1015                1020

Phe Asp Lys Asp Gly Ile Gln Ala Lys Asn Lys Ile Ile Val Thr
    1025                1030                1035

Arg Asp Gly Lys Val Arg Tyr Phe Asp Glu His Asn Gly Asn Ala
    1040                1045                1050

Ala Thr Asn Thr Phe Ile Ser Asp Gln Ala Gly His Trp Tyr Tyr
    1055                1060                1065

Leu Gly Lys Asp Gly Val Ala Val Thr Gly Ala Gln Thr Val Gly
    1070                1075                1080

Lys Gln His Leu Tyr Phe Glu Ala Asn Gly Gln Gln Val Lys Gly
    1085                1090                1095

Asp Phe Val Thr Ala Lys Asp Gly Lys Leu Tyr Phe Leu Asp Gly
    1100                1105                1110

Asp Ser Gly Asp Met Trp Thr Asp Thr Phe Val Gln Asp Lys Ala
    1115                1120                1125

Gly His Trp Phe Tyr Leu Gly Lys Asp Gly Ala Ala Val Thr Gly
    1130                1135                1140

Ala Gln Thr Val Arg Gly Gln Lys Leu Tyr Phe Lys Ala Asn Gly
    1145                1150                1155

Gln Gln Val Lys Gly Asp Ile Val Lys Gly Ala Asp Gly Lys Ile
    1160                1165                1170

Arg Tyr Tyr Asp Ala Asn Ser Gly Asp Gln Val Tyr Asn Arg Thr
    1175                1180                1185

Val Lys Gly Ser Asp Gly Lys Thr Tyr Ile Ile Gly Asn Asp Gly
    1190                1195                1200

Val Ala Ile Thr Gln Thr Ile Ala Lys Gly Gln Thr Ile Lys Asp
    1205                1210                1215

Gly Ser Val Leu Arg Phe Tyr Ser Met Glu Gly Gln Leu Val Thr
    1220                1225                1230

Gly Ser Gly Trp Tyr Ser Asn Ala Lys Gly Gln Trp Leu Tyr Val
    1235                1240                1245

Lys Asn Gly Gln Val Leu Thr Gly Leu Gln Thr Val Gly Ser Gln
    1250                1255                1260

Arg Val Tyr Phe Asp Ala Asn Gly Ile Gln Ala Lys Gly Lys Ala
    1265                1270                1275

Val Arg Thr Ser Asp Gly Lys Leu Arg Tyr Phe Asp Ala Asn Ser
    1280                1285                1290

Gly Ser Met Ile Thr Asn Gln Trp Lys Glu Val Asn Gly Gln Tyr
    1295                1300                1305

Tyr Tyr Phe Asp Asn Asn Gly Val Ala Ile Tyr Arg Gly Trp Asn
    1310                1315                1320

<210> SEQ ID NO 15
<211> LENGTH: 4047
<212> TYPE: DNA
<213> ORGANISM: Streptococcus oralis

<400> SEQUENCE: 15
atgatcgacg gcaaaaacta ctacgtacag gatgatggca cggtaaagaa gaatttcgcg    60

```
gtagaactga atggtcgtat cctgtatttt gatgcagaaa ccggcgctct ggttgatagc      120
aacgagtatc agttccaaca gggtacgagc agcctgaaca atgaattttc tcagaagaac      180
gcattctatg gtacgaccga taaggatatt gagactgtgg atggctacct gaccgcagat      240
agctggtatc gcccgaaatt catcctgaag gatggcaaga cgtggaccgc gagcacggaa      300
acggatctgc gtccgctgtt gatggcatgg tggccggaca agcgtaccca aatcaactat      360
ctgaactaca tgaaccagca gggtctgggt gcgggtgcgt ttgagaacaa agtggagcag      420
gccctgctga cgggtgcaag ccaacaggta aacgcaaga tcgaagagaa gattggtaaa       480
gagggtgata ccaagtggct gcgcaccctg atgggtgcgt cgtgaaaaac gcaaccaaac      540
tggaatatca aaccgagtc tgaaacgacc ggcacgaaaa aggaccatct gcaaggcggt       600
gcactgctgt atacgaacaa cgagaaatcc ccgcacgcgg acagcaaatt tcgtctgctg      660
aatcgtaccc cgaccagcca aaccggcacg ccgaagtatt tcatcgacaa gtctaacggt      720
ggctacgaat ttctgctggc gaacgatttt gacaatagca atcctgcggt acaagctgag      780
cagctgaatt ggctgcacta catgatgaac tttggcagca ttgttgcgaa tgatccgacc      840
gcgaatttcg acggcgttcg tgtggatgct gttgataacg tcaatgcgga cttgttgcaa      900
attgcaagcg attactttaa gagccgttac aaagtcggtg agagcgaaga agaagcgatc      960
aagcacctgt ccatcctgga agcatggagc gataacgacc cggactacaa caaagatacc     1020
aagggtgcac agttggcgat tgataacaaa ctgcgcctga gcctgctgta ctctttcatg     1080
cgtaatctga gcatccgtag cggtgttgaa ccgacgatta ccaatagcct gaatgaccgt     1140
tccagcgaaa agaagaacgg cgagcgtatg gcaaattaca tcttcgtgcg tgcccacgat     1200
agcgaggtcc aaacggtgat cgccgacatc attcgcgaaa acatcaatcc gaacaccgac     1260
ggcctgacgt ttacgatgga cgagctgaag caggcattca agatttacaa cgaggacatg     1320
cgcaaggcgg acaaaaagta tacccagttt aacattccta ccgcacacgc gctgatgctg     1380
tctaataagg attctattac ccgcgtgtac tatggtgatc tgtatactga cgatggtcag     1440
tacatggaga agaaaagccc gtatcacgat gcgattgacg ctctgctgcg tgcacgtatt     1500
aaatacgtcg cgggtggcca ggatatgaaa gtgacctata tgggcgtgcc gcgtgaagcg     1560
gataagtgga gctataacgg cattctgacc agcgtgcgct atggcacggg cgctaacgaa     1620
gccacggatg agggcactgc ggaaacgcgc acgcaaggta tggcagtgat tgcgagcaat     1680
aatccaaatc tgaaactgaa tgaatgggac aagttgcaag tcaacatggg tgcggcgcat     1740
aagaatcaat attaccgtcc ggttctgctg accactaagg acggtatcag ccgttatctg     1800
accgatgaag aagtgcctca gagcctgtgg aaaagacgg acgcaaacgg tattctgacc     1860
ttcgacatga atgatattgc tggctacagc aacgtgcaag ttagcggtta cctggccgtc     1920
tgggtcccgg tcggtgcgaa ggcggatcaa gatgcgcgca cgaccgcatc caagaagaaa     1980
aatgcgtcgg gtcaggtgta cgaaagcagc gcggctctgg atagccagct gatttacgaa     2040
ggtttcagca actttcaaga ctttgccact cgcgatgatc agtacacgaa caaggtcatt     2100
gcgaaaaacg tgaatctgtt caagaatgg ggtgtgacca gcttcgagct gccgccgcag      2160
tacgtgagca gccaagatgg caccttcctg gacagcatta tccaaaacgg ctatgcattt     2220
gaagaccgtt acgatatggc gatgagcaag aataacaagt atggtagcct gaaagacctg     2280
ttgaacgcgc tgcgcgcact gcacagcgtc aacattcaag caatcgccga ttgggtgccg     2340
gaccaaattt acaacttgcc gggcaaagag gtggtgaccg caactcgtgt caacaactac     2400
```

```
ggcacctacc gtgagggtgc tgaaatcaaa gaaaagctgt atgtcgccaa tagcaagacc      2460
aacgaaaccg atttccaagg taaatacggt ggtgcgttcc tggatgagct gaaggcgaag      2520
tacccggaga ttttcgagcg tgtccaaatc agcaacggcc aaaagatgac taccgatgaa      2580
aagatcacca atggagcgc gaaatacttt aatggcacca atattctggg tcgtggcgcg       2640
tactatgtcc tgaaagattg ggccagcaat gattacctga cgaaccgtaa cggcgagatt      2700
gttttgccga agcaactggt taacaagaat agctataccg ctttgtcag cgacgcgaac       2760 ggcacgaagt tctattctac ctctggctac caggcgaaga acagcttcat tcaagacgaa      2820
aacggtaatt ggtattactt tgacaaacgt ggttatctgg ttacgggcgc acacgagatt      2880
gatggcaagc atgtctactt cctgaaaaac ggtatccaac tgcgtgacag catccgtgag      2940
gatgagaacg gtaatcaata ctattacgac cagaccggcg cacaagtgct gaaccgttac      3000
tacacgacgg acggtcagaa ttggcgctat ttcgatgcga aaggtgttat ggcacgcggc      3060
ctggtaaaga ttggtgacgg ccaacagttt ttcgatgaaa acggttacca ggtcaagggc      3120
aagattgtta gcgcaaaaga cggcaagctg cgctactttg ataaagactc tggcaatgct      3180
gtcattaatc gtttcgcgca gggtgacaat ccgagcgact ggtactattt cggtgtggaa      3240
tttgctaaac tgacgggttt gcaaaagatc ggccagcaga cgctgtattt tgaccaagac      3300
ggtaagcaag tcaaaggtaa gatcgtaact ctgtcggaca aaagcattcg ttacttcgat      3360
gccaacagcg gtgaaatggc ggttggcaag ttcgcggaag gtgcaaagaa tgagtggtat      3420
tatttcgata aaaccggcaa agcggttact ggtttgcaga aaattggtaa gcagaccctg      3480
tactttgacc aggacggtaa acaggttaaa ggcaaggttg tcacgctggc tgataaaagc      3540
atccgctact cgacgcagac tccggcgag atggcggtcg gtaagtttgc agagggtgcg      3600
aagaacgagt ggtactattt tgatcagact ggcaaggccg tgactggttt gcaaaagatt      3660
gacaagcaaa ccttgtactt cgaccaggac ggtaaacaag tcaagggtaa gattgtgacg      3720
ttgagcgaca agtcgatccg ttactttgat gctaatagcg gtgagatggc tactaacaaa      3780
ttcgtcgagg gctcgcagaa tgaatggtac tacttcgatc aagcgggtaa ggctgttacg      3840
ggcttgcaac aggtcggtca gcaaactctg tacttcaccc aggatggtaa gcaagtgaag      3900
ggtaaggtcg tggacgtgaa cggtgtttct cgttatttcg acgcaaactc cggtgacatg      3960
gctcgttcta aatggattca actgaagat ggcagctgga tgtatttcga ccgtgacggt       4020
cgtggccaga ttttggccg taactaa                                           4047
```

<210> SEQ ID NO 16
<211> LENGTH: 1348
<212> TYPE: PRT
<213> ORGANISM: Streptococcus oralis

<400> SEQUENCE: 16

```
Met Ile Asp Gly Lys Asn Tyr Tyr Val Gln Asp Asp Gly Thr Val Lys
1               5                   10                  15

Lys Asn Phe Ala Val Glu Leu Asn Gly Arg Ile Leu Tyr Phe Asp Ala
            20                  25                  30

Glu Thr Gly Ala Leu Val Asp Ser Asn Glu Tyr Gln Phe Gln Gln Gly
        35                  40                  45

Thr Ser Ser Leu Asn Asn Glu Phe Ser Gln Lys Asn Ala Phe Tyr Gly
    50                  55                  60

Thr Thr Asp Lys Asp Ile Glu Thr Val Asp Gly Tyr Leu Thr Ala Asp
65                  70                  75                  80
```

```
Ser Trp Tyr Arg Pro Lys Phe Ile Leu Lys Asp Gly Lys Thr Trp Thr
                 85                  90                  95

Ala Ser Thr Glu Thr Asp Leu Arg Pro Leu Leu Met Ala Trp Trp Pro
            100                 105                 110

Asp Lys Arg Thr Gln Ile Asn Tyr Leu Asn Tyr Met Asn Gln Gln Gly
            115                 120                 125

Leu Gly Ala Gly Ala Phe Glu Asn Lys Val Glu Gln Ala Leu Leu Thr
            130                 135                 140

Gly Ala Ser Gln Gln Val Gln Arg Lys Ile Glu Lys Ile Gly Lys
145                 150                 155                 160

Glu Gly Asp Thr Lys Trp Leu Arg Thr Leu Met Gly Ala Phe Val Lys
                165                 170                 175

Thr Gln Pro Asn Trp Asn Ile Lys Thr Glu Ser Glu Thr Thr Gly Thr
            180                 185                 190

Lys Lys Asp His Leu Gln Gly Gly Ala Leu Leu Tyr Thr Asn Asn Glu
            195                 200                 205

Lys Ser Pro His Ala Asp Ser Lys Phe Arg Leu Leu Asn Arg Thr Pro
    210                 215                 220

Thr Ser Gln Thr Gly Thr Pro Lys Tyr Phe Ile Asp Lys Ser Asn Gly
225                 230                 235                 240

Gly Tyr Glu Phe Leu Leu Ala Asn Asp Phe Asp Asn Ser Asn Pro Ala
                245                 250                 255

Val Gln Ala Glu Gln Leu Asn Trp Leu His Tyr Met Met Asn Phe Gly
            260                 265                 270

Ser Ile Val Ala Asn Asp Pro Thr Ala Asn Phe Asp Gly Val Arg Val
            275                 280                 285

Asp Ala Val Asp Asn Val Asn Ala Asp Leu Leu Gln Ile Ala Ser Asp
    290                 295                 300

Tyr Phe Lys Ser Arg Tyr Lys Val Gly Glu Ser Glu Glu Ala Ile
305                 310                 315                 320

Lys His Leu Ser Ile Leu Glu Ala Trp Ser Asn Asp Pro Asp Tyr
                325                 330                 335

Asn Lys Asp Thr Lys Gly Ala Gln Leu Ala Ile Asp Asn Lys Leu Arg
            340                 345                 350

Leu Ser Leu Leu Tyr Ser Phe Met Arg Asn Leu Ser Ile Arg Ser Gly
            355                 360                 365

Val Glu Pro Thr Ile Thr Asn Ser Leu Asn Asp Arg Ser Ser Glu Lys
            370                 375                 380

Lys Asn Gly Glu Arg Met Ala Asn Tyr Ile Phe Val Arg Ala His Asp
385                 390                 395                 400

Ser Glu Val Gln Thr Val Ile Ala Asp Ile Ile Arg Glu Asn Ile Asn
                405                 410                 415

Pro Asn Thr Asp Gly Leu Thr Phe Thr Met Asp Glu Leu Lys Gln Ala
            420                 425                 430

Phe Lys Ile Tyr Asn Glu Asp Met Arg Lys Ala Asp Lys Lys Tyr Thr
            435                 440                 445

Gln Phe Asn Ile Pro Thr Ala His Ala Leu Met Leu Ser Asn Lys Asp
    450                 455                 460

Ser Ile Thr Arg Val Tyr Tyr Gly Asp Leu Tyr Thr Asp Asp Gly Gln
465                 470                 475                 480

Tyr Met Glu Lys Lys Ser Pro Tyr His Asp Ala Ile Asp Ala Leu Leu
                485                 490                 495

Arg Ala Arg Ile Lys Tyr Val Ala Gly Gly Gln Asp Met Lys Val Thr
```

-continued

```
                500             505             510
Tyr Met Gly Val Pro Arg Glu Ala Asp Lys Trp Ser Tyr Asn Gly Ile
            515                 520                 525
Leu Thr Ser Val Arg Tyr Gly Thr Gly Ala Asn Glu Ala Thr Asp Glu
            530                 535                 540
Gly Thr Ala Glu Thr Arg Thr Gln Gly Met Ala Val Ile Ala Ser Asn
545                 550                 555                 560
Asn Pro Asn Leu Lys Leu Asn Glu Trp Asp Lys Leu Gln Val Asn Met
            565                 570                 575
Gly Ala Ala His Lys Asn Gln Tyr Tyr Arg Pro Val Leu Leu Thr Thr
            580                 585                 590
Lys Asp Gly Ile Ser Arg Tyr Leu Thr Asp Glu Val Pro Gln Ser
            595                 600                 605
Leu Trp Lys Lys Thr Asp Ala Asn Gly Ile Leu Thr Phe Asp Met Asn
            610                 615                 620
Asp Ile Ala Gly Tyr Ser Asn Val Gln Val Ser Gly Tyr Leu Ala Val
625                 630                 635                 640
Trp Val Pro Val Gly Ala Lys Ala Asp Gln Asp Ala Arg Thr Thr Ala
            645                 650                 655
Ser Lys Lys Lys Asn Ala Ser Gly Gln Val Tyr Glu Ser Ser Ala Ala
            660                 665                 670
Leu Asp Ser Gln Leu Ile Tyr Glu Gly Phe Ser Asn Phe Gln Asp Phe
            675                 680                 685
Ala Thr Arg Asp Asp Gln Tyr Thr Asn Lys Val Ile Ala Lys Asn Val
            690                 695                 700
Asn Leu Phe Lys Glu Trp Gly Val Thr Ser Phe Glu Leu Pro Pro Gln
705                 710                 715                 720
Tyr Val Ser Ser Gln Asp Gly Thr Phe Leu Asp Ser Ile Ile Gln Asn
            725                 730                 735
Gly Tyr Ala Phe Glu Asp Arg Tyr Asp Met Ala Met Ser Lys Asn Asn
            740                 745                 750
Lys Tyr Gly Ser Leu Lys Asp Leu Leu Asn Ala Leu Arg Ala Leu His
            755                 760                 765
Ser Val Asn Ile Gln Ala Ile Ala Asp Trp Val Pro Asp Gln Ile Tyr
770                 775                 780
Asn Leu Pro Gly Lys Glu Val Thr Ala Thr Arg Val Asn Asn Tyr
785                 790                 795                 800
Gly Thr Tyr Arg Glu Gly Ala Glu Ile Lys Glu Lys Leu Tyr Val Ala
            805                 810                 815
Asn Ser Lys Thr Asn Glu Thr Asp Phe Gln Gly Lys Tyr Gly Gly Ala
            820                 825                 830
Phe Leu Asp Glu Leu Lys Ala Lys Tyr Pro Glu Ile Phe Glu Arg Val
            835                 840                 845
Gln Ile Ser Asn Gly Gln Lys Met Thr Thr Asp Glu Lys Ile Thr Lys
            850                 855                 860
Trp Ser Ala Lys Tyr Phe Asn Gly Thr Asn Ile Leu Gly Arg Gly Ala
865                 870                 875                 880
Tyr Tyr Val Leu Lys Asp Trp Ala Ser Asn Asp Tyr Leu Thr Asn Arg
            885                 890                 895
Asn Gly Glu Ile Val Leu Pro Lys Gln Leu Val Asn Lys Asn Ser Tyr
            900                 905                 910
Thr Gly Phe Val Ser Asp Ala Asn Gly Thr Lys Phe Tyr Ser Thr Ser
            915                 920                 925
```

```
Gly Tyr Gln Ala Lys Asn Ser Phe Ile Gln Asp Glu Asn Gly Asn Trp
        930                 935                 940

Tyr Tyr Phe Asp Lys Arg Gly Tyr Leu Val Thr Gly Ala His Glu Ile
945                 950                 955                 960

Asp Gly Lys His Val Tyr Phe Leu Lys Asn Gly Ile Gln Leu Arg Asp
            965                 970                 975

Ser Ile Arg Glu Asp Glu Asn Gly Asn Gln Tyr Tyr Tyr Asp Gln Thr
            980                 985                 990

Gly Ala Gln Val Leu Asn Arg Tyr Tyr Thr Thr Asp Gly Gln Asn Trp
        995                 1000                1005

Arg Tyr Phe Asp Ala Lys Gly Val Met Ala Arg Gly Leu Val Lys
    1010                1015                1020

Ile Gly Asp Gly Gln Gln Phe Phe Asp Glu Asn Gly Tyr Gln Val
    1025                1030                1035

Lys Gly Lys Ile Val Ser Ala Lys Asp Gly Lys Leu Arg Tyr Phe
    1040                1045                1050

Asp Lys Asp Ser Gly Asn Ala Val Ile Asn Arg Phe Ala Gln Gly
    1055                1060                1065

Asp Asn Pro Ser Asp Trp Tyr Tyr Phe Gly Val Glu Phe Ala Lys
    1070                1075                1080

Leu Thr Gly Leu Gln Lys Ile Gly Gln Gln Thr Leu Tyr Phe Asp
    1085                1090                1095

Gln Asp Gly Lys Gln Val Lys Gly Lys Ile Val Thr Leu Ser Asp
    1100                1105                1110

Lys Ser Ile Arg Tyr Phe Asp Ala Asn Ser Gly Glu Met Ala Val
    1115                1120                1125

Gly Lys Phe Ala Glu Gly Ala Lys Asn Glu Trp Tyr Tyr Phe Asp
    1130                1135                1140

Lys Thr Gly Lys Ala Val Thr Gly Leu Gln Lys Ile Gly Lys Gln
    1145                1150                1155

Thr Leu Tyr Phe Asp Gln Asp Gly Lys Gln Val Lys Gly Lys Val
    1160                1165                1170

Val Thr Leu Ala Asp Lys Ser Ile Arg Tyr Phe Asp Ala Asp Ser
    1175                1180                1185

Gly Glu Met Ala Val Gly Lys Phe Ala Glu Gly Ala Lys Asn Glu
    1190                1195                1200

Trp Tyr Tyr Phe Asp Gln Thr Gly Lys Ala Val Thr Gly Leu Gln
    1205                1210                1215

Lys Ile Asp Lys Gln Thr Leu Tyr Phe Asp Gln Asp Gly Lys Gln
    1220                1225                1230

Val Lys Gly Lys Ile Val Thr Leu Ser Asp Lys Ser Ile Arg Tyr
    1235                1240                1245

Phe Asp Ala Asn Ser Gly Glu Met Ala Thr Asn Lys Phe Val Glu
    1250                1255                1260

Gly Ser Gln Asn Glu Trp Tyr Tyr Phe Asp Gln Ala Gly Lys Ala
    1265                1270                1275

Val Thr Gly Leu Gln Gln Val Gly Gln Gln Thr Leu Tyr Phe Thr
    1280                1285                1290

Gln Asp Gly Lys Gln Val Lys Gly Lys Val Val Asp Val Asn Gly
    1295                1300                1305

Val Ser Arg Tyr Phe Asp Ala Asn Ser Gly Asp Met Ala Arg Ser
    1310                1315                1320
```

Lys Trp Ile Gln Leu Glu Asp Gly Ser Trp Met Tyr Phe Asp Arg
1325                1330                    1335

Asp Gly Arg Gly Gln Asn Phe Gly Arg Asn
    1340            1345

<210> SEQ ID NO 17
<211> LENGTH: 4047
<212> TYPE: DNA
<213> ORGANISM: Streptococcus sanguinis

<400> SEQUENCE: 17

| | | | | | |
|---|---|---|---|---|---|
| atgattgatg | gtaaaaagta | ttacgtacag | gacgacggca | cggttaagaa | gaatttcgcg | 60 |
| gttgagctga | atggcaagat | cctgtacttc | gatgcagaga | ctggtgcgtt | gattgacagc | 120 |
| gcggagtatc | aattccaaca | aggcaccagc | agcctgaata | tgagttcac | tcaaaagaac | 180 |
| gcctttacg | gtacgaccga | taaggatgtg | gaaaccattg | atggttactt | gaccgccgat | 240 |
| tcctggtatc | gtccgaagtt | cattctgaaa | gatggcaaaa | cctggacggc | gagcacggaa | 300 |
| attgacttgc | gtccgttgtt | gatggcgtgg | tggccggaca | aacagaccca | ggttagctac | 360 |
| ctgaattaca | tgaaccagca | aggcttgggt | gcaggcgcct | tcgaaaacaa | agtagagcag | 420 |
| gcaattctga | ccggtgcgtc | ccaacaggta | caacgtaaaa | tcgaagaacg | catcggtaaa | 480 |
| gagggtgata | ccaagtggct | gcgtaccctg | atgggtgcat | tgtaaagac | ccagccgaac | 540 |
| tggaacatta | gaccgagtc | cgaaaccact | ggcacgaata | agatcatct | gcaaggtggc | 600 |
| gcactgctgt | atagcaattc | gacaagacg | agccatgcca | actctaagta | ccgtatcctg | 660 |
| aaccgcaccc | cgaccaacca | aacgggcacg | ccgaaatact | ttattgacaa | gagcaatggt | 720 |
| ggttatgaat | tctgctggc | gaatgacttt | gacaatagca | atccggcagt | gcaagcggaa | 780 |
| cagctgaact | ggttgcactt | tatgatgaat | tttggctcca | tcgttgcaaa | tgatccgacg | 840 |
| gccaacttcg | acggcgtccg | cgttgacgct | gtggataacg | tgaatgcgga | tctgttgcaa | 900 |
| attgcgagcg | actatttcaa | gagccgctat | aaagtcggcg | aaagcgaaga | gaggccatt | 960 |
| aagcacctgt | ccatcctgga | agcgtggagc | gacaacgacc | cggactacaa | caaggatact | 1020 |
| aaaggtgccc | aactgccgat | cgacaacaaa | ctgcgtctga | gcctgctgta | ctccttcatg | 1080 |
| cgtaagctga | gcatccgtag | cggcgtcgag | ccgaccatca | ccaactctct | gaatgatcgc | 1140 |
| agcacgagga | agaagaatgg | tgagcgtatg | gcaaactata | tcttcgttcg | tgcacatgat | 1200 |
| agcgaggtgc | aaacggtcat | cgccgacatt | atccgtgaga | catcaatcc | gaataccgac | 1260 |
| ggcctgacgt | tcacgatgga | tgaactgaag | caggccttta | aaatttacaa | tgaggatatg | 1320 |
| cgtaaagccg | acaaaaagta | cacgcagttc | aatatcccga | ccgcgcacgc | gctgatgctg | 1380 |
| agcaacaaag | attctatcac | ccgcgtttac | tacggtgacc | tgtatacgga | tgacggtcag | 1440 |
| tatatggaaa | agaaaagccc | gtatcacgac | gccattgacg | ctctgctgcg | tgcgcgtatc | 1500 |
| aaatatgttg | cggtggtca | ggacatgaag | gtgacctata | tgggcgtgcc | gcgtgaggca | 1560 |
| gataaatgga | gctataacgg | catcctgacc | agcgttcgtt | atggtacggg | tgccaacgag | 1620 |
| gcaaccgacg | agggtacggc | agaaacccgt | acccagggca | tggccgtcat | tgccagcaac | 1680 |
| aatccgaacc | tgaaactgaa | cgagtgggac | aagttgcagg | tcaacatggg | tgcagctcac | 1740 |
| aaaaaccaat | actatcgtcc | ggtgctgctg | accaccaagg | acggcatctc | gcgctacctg | 1800 |
| accgacgaag | aagtcccgca | gagcctgtgg | aaaaagaccg | atgcgaacgg | catcttgacg | 1860 |
| tttgacatga | atgatattgc | gggttacagc | aacgtccaag | tgagcggtta | tctgccgtc | 1920 |
| tgggttcctg | tgggtgcgaa | ggcggaccag | gacgctcgtg | ttacggcatc | taagaagaaa | 1980 |

```
aatgcctctg gccaagttta cgaaagcagc gcagccctgg actcccagct gatctatgag    2040
ggcttcagca attttcagga ctttgccacc cgtgacgacc agtacactaa caaggttatc    2100
gcgaaaaacg tcaatctgtt taaagagtgg ggcgtcacca gcttcgaatt gccgccacag    2160
tatgtgagca gccaagacgg tacgttcctg gatagcatca tccagaatgg ttatgcattc    2220
gaagatcgct atgatatggc gatgagcaaa acaataagt acggtagctt gaacgacctg    2280
ttgaacgcct gcgtgcact gcatagcgtg aatatccaag cgattgcgga ttgggtgccg    2340
gaccagattt acaatctgcc gggtaaagaa gttgtcactg caacccgtgt taacaattat    2400
ggcacgtatc gtgagggtag cgagattaaa gagaacctgt acgttgctaa caccaaaacc    2460
aatggtacgg actaccaagg taagtatggt ggtgcgttct tggacgagct gaaagccaaa    2520
taccctgaga tttttgagcg cgtccaaatc agcaacggcc agaagatgac caccgacgag    2580
aagattacga atggtccgc caaacacttt aacggcacga acattctggg tcgtggtgcg    2640
tattatgtgc tgaaagactg ggcgagcaac gagtacctga ataacaaaaa tggcgagatg    2700
gttctgccga agcagctggt taataaaaat gcatataccg gcttcgtcag cgacgcgagc    2760
ggcaccaaat actattctac cagcggctat caggctcgta atagctttat tcaagatgaa    2820
aatggtaatt ggtactactt caataaccgt ggttattgg tgacgggtgc acaggaaatc    2880
gacggtaagc aactgtattt cctgaaaaac ggcattcagc tgcgtgattc tctgcgtgag    2940
gacgaaaacg gcaaccagta ttactatgat aagacgggtg cgcaagttct gaatcgttat    3000
tacactacgg acggccaaaa ttggcgctac ttcgacgtta aaggcgtcat ggcccgtggt    3060
ctggtcacga tgggtggtaa ccaacaattc tttgaccaaa acggttacca ggttaaaggc    3120
aaaattgcgc gtgcaaaaga cggtaaactg cgttacttcg ataaagacag cggtaatgcg    3180
gcagctaacc gtttcgccca aggcgataac cctagcgact ggtactattt cggtgcagat    3240
ggtgttgcgg ttacgggcct gcaaaaggtt ggtcagcaaa ctctgtactt tgatcaggac    3300
ggcaagcagg tgaaaggtaa agttgttacc ttggcggaca aaagcattcg ttatttcgat    3360
gcaaacagcg gcgagatggc ggtgaacaag tttgtggaag gtgctaagaa cgtgtggtac    3420
tacttcgatc aagcaggcaa agcggtgacc ggcctgcaaa ccatcaataa acaagtgctg    3480
tatttcgacc aggatggtaa acaagtcaaa ggtaaggtgg tcacgctggc tgataagtct    3540
atccgctact tcgacgcgaa cagcggtgag atggcagtgg gcaaattcgc cgaaggcgca    3600
aagaatgagt ggtattactt tgaccaggcg ggcaaggctg ttaccggtct gcaaaagatc    3660
ggccaacaga cgctgtattt cgaccagaac ggtaaacagg ttaagggtaa agtggtcacc    3720
ctggcggata agagcatccg ctatttcgac gctaactctg gcgaaatggc aagcaataag    3780
ttcgttgagg gtgccaaaaa tgaatggtac tatttcgatc aggctggcaa ggcagtgacg    3840
ggtctgcaac aaattggcca gcagaccctg tattttgacc agaatggcaa acaggtgaag    3900
ggtaagattg tgtatgttaa tggtgcgaat cgctactttg atgccaatag cggtgaaatg    3960
gcgcgtaaca agtggattca gctggaagat ggcagctgga tgtattttga ccgcaatggt    4020
cgtggtcgtc gtttcggttg gaactaa                                       4047
```

<210> SEQ ID NO 18
<211> LENGTH: 1348
<212> TYPE: PRT
<213> ORGANISM: Streptococcus sanguinis

<400> SEQUENCE: 18

-continued

```
Met Ile Asp Gly Lys Lys Tyr Tyr Val Gln Asp Asp Gly Thr Val Lys
1               5                   10                  15

Lys Asn Phe Ala Val Glu Leu Asn Gly Lys Ile Leu Tyr Phe Asp Ala
            20                  25                  30

Glu Thr Gly Ala Leu Ile Asp Ser Ala Glu Tyr Gln Phe Gln Gln Gly
        35                  40                  45

Thr Ser Ser Leu Asn Asn Glu Phe Thr Gln Lys Asn Ala Phe Tyr Gly
    50                  55                  60

Thr Thr Asp Lys Asp Val Glu Thr Ile Asp Gly Tyr Leu Thr Ala Asp
65                  70                  75                  80

Ser Trp Tyr Arg Pro Lys Phe Ile Leu Lys Asp Gly Lys Thr Trp Thr
                85                  90                  95

Ala Ser Thr Glu Ile Asp Leu Arg Pro Leu Leu Met Ala Trp Trp Pro
            100                 105                 110

Asp Lys Gln Thr Gln Val Ser Tyr Leu Asn Tyr Met Asn Gln Gln Gly
            115                 120                 125

Leu Gly Ala Gly Ala Phe Glu Asn Lys Val Glu Gln Ala Ile Leu Thr
130                 135                 140

Gly Ala Ser Gln Gln Val Gln Arg Lys Ile Glu Glu Arg Ile Gly Lys
145                 150                 155                 160

Glu Gly Asp Thr Lys Trp Leu Arg Thr Leu Met Gly Ala Phe Val Lys
                165                 170                 175

Thr Gln Pro Asn Trp Asn Ile Lys Thr Glu Ser Glu Thr Thr Gly Thr
            180                 185                 190

Asn Lys Asp His Leu Gln Gly Gly Ala Leu Leu Tyr Ser Asn Ser Asp
            195                 200                 205

Lys Thr Ser His Ala Asn Ser Lys Tyr Arg Ile Leu Asn Arg Thr Pro
210                 215                 220

Thr Asn Gln Thr Gly Thr Pro Lys Tyr Phe Ile Asp Lys Ser Asn Gly
225                 230                 235                 240

Gly Tyr Glu Phe Leu Leu Ala Asn Asp Phe Asn Ser Asn Pro Ala
                245                 250                 255

Val Gln Ala Glu Gln Leu Asn Trp Leu His Phe Met Met Asn Phe Gly
            260                 265                 270

Ser Ile Val Ala Asn Asp Pro Thr Ala Asn Phe Asp Gly Val Arg Val
            275                 280                 285

Asp Ala Val Asp Asn Val Asn Ala Asp Leu Leu Gln Ile Ala Ser Asp
            290                 295                 300

Tyr Phe Lys Ser Arg Tyr Lys Val Gly Glu Ser Glu Glu Ala Ile
305                 310                 315                 320

Lys His Leu Ser Ile Leu Glu Ala Trp Ser Asp Asn Asp Pro Asp Tyr
                325                 330                 335

Asn Lys Asp Thr Lys Gly Ala Gln Leu Pro Ile Asp Asn Lys Leu Arg
            340                 345                 350

Leu Ser Leu Leu Tyr Ser Phe Met Arg Lys Leu Ser Ile Arg Ser Gly
            355                 360                 365

Val Glu Pro Thr Ile Thr Asn Ser Leu Asn Asp Arg Ser Thr Glu Lys
370                 375                 380

Lys Asn Gly Glu Arg Met Ala Asn Tyr Ile Phe Val Arg Ala His Asp
385                 390                 395                 400

Ser Glu Val Gln Thr Val Ile Ala Asp Ile Ile Arg Glu Asn Ile Asn
                405                 410                 415

Pro Asn Thr Asp Gly Leu Thr Phe Thr Met Asp Glu Leu Lys Gln Ala
```

```
                420             425             430
    Phe Lys Ile Tyr Asn Glu Asp Met Arg Lys Asp Lys Lys Tyr Thr
                435             440             445
    Gln Phe Asn Ile Pro Thr Ala His Ala Leu Met Leu Ser Asn Lys Asp
        450             455             460
    Ser Ile Thr Arg Val Tyr Tyr Gly Asp Leu Tyr Thr Asp Asp Gly Gln
    465             470             475             480
    Tyr Met Glu Lys Lys Ser Pro Tyr His Asp Ala Ile Asp Ala Leu Leu
                485             490             495
    Arg Ala Arg Ile Lys Tyr Val Ala Gly Gly Gln Asp Met Lys Val Thr
                500             505             510
    Tyr Met Gly Val Pro Arg Glu Ala Asp Lys Trp Ser Tyr Asn Gly Ile
                515             520             525
    Leu Thr Ser Val Arg Tyr Gly Thr Gly Ala Asn Glu Ala Thr Asp Glu
                530             535             540
    Gly Thr Ala Glu Thr Arg Thr Gln Gly Met Ala Val Ile Ala Ser Asn
    545             550             555             560
    Asn Pro Asn Leu Lys Leu Asn Glu Trp Asp Lys Leu Gln Val Asn Met
                565             570             575
    Gly Ala Ala His Lys Asn Gln Tyr Tyr Arg Pro Val Leu Leu Thr Thr
                580             585             590
    Lys Asp Gly Ile Ser Arg Tyr Leu Thr Asp Glu Glu Val Pro Gln Ser
                595             600             605
    Leu Trp Lys Lys Thr Asp Ala Asn Gly Ile Leu Thr Phe Asp Met Asn
                610             615             620
    Asp Ile Ala Gly Tyr Ser Asn Val Gln Val Ser Gly Tyr Leu Ala Val
    625             630             635             640
    Trp Val Pro Val Gly Ala Lys Ala Asp Gln Asp Ala Arg Val Thr Ala
                645             650             655
    Ser Lys Lys Lys Asn Ala Ser Gly Gln Val Tyr Glu Ser Ser Ala Ala
                660             665             670
    Leu Asp Ser Gln Leu Ile Tyr Glu Gly Phe Ser Asn Phe Gln Asp Phe
                675             680             685
    Ala Thr Arg Asp Asp Gln Tyr Thr Asn Lys Val Ile Ala Lys Asn Val
                690             695             700
    Asn Leu Phe Lys Glu Trp Gly Val Thr Ser Phe Glu Leu Pro Pro Gln
    705             710             715             720
    Tyr Val Ser Ser Gln Asp Gly Thr Phe Leu Asp Ser Ile Ile Gln Asn
                725             730             735
    Gly Tyr Ala Phe Glu Asp Arg Tyr Asp Met Ala Met Ser Lys Asn Asn
                740             745             750
    Lys Tyr Gly Ser Leu Asn Asp Leu Leu Asn Ala Leu Arg Ala Leu His
                755             760             765
    Ser Val Asn Ile Gln Ala Ile Ala Asp Trp Val Pro Asp Gln Ile Tyr
                770             775             780
    Asn Leu Pro Gly Lys Glu Val Val Thr Ala Thr Arg Val Asn Asn Tyr
    785             790             795             800
    Gly Thr Tyr Arg Glu Gly Ser Glu Ile Lys Glu Asn Leu Tyr Val Ala
                805             810             815
    Asn Thr Lys Thr Asn Gly Thr Asp Tyr Gln Gly Lys Tyr Gly Gly Ala
                820             825             830
    Phe Leu Asp Glu Leu Lys Ala Lys Tyr Pro Glu Ile Phe Glu Arg Val
                835             840             845
```

```
Gln Ile Ser Asn Gly Gln Lys Met Thr Thr Asp Glu Lys Ile Thr Lys
            850                 855                 860
Trp Ser Ala Lys His Phe Asn Gly Thr Asn Ile Leu Gly Arg Gly Ala
865                 870                 875                 880
Tyr Tyr Val Leu Lys Asp Trp Ala Ser Asn Glu Tyr Leu Asn Asn Lys
                885                 890                 895
Asn Gly Glu Met Val Leu Pro Lys Gln Leu Val Asn Lys Asn Ala Tyr
            900                 905                 910
Thr Gly Phe Val Ser Asp Ala Ser Gly Thr Lys Tyr Tyr Ser Thr Ser
            915                 920                 925
Gly Tyr Gln Ala Arg Asn Ser Phe Ile Gln Asp Glu Asn Gly Asn Trp
            930                 935                 940
Tyr Tyr Phe Asn Asn Arg Gly Tyr Leu Val Thr Gly Ala Gln Glu Ile
945                 950                 955                 960
Asp Gly Lys Gln Leu Tyr Phe Leu Lys Asn Gly Ile Gln Leu Arg Asp
                965                 970                 975
Ser Leu Arg Glu Asp Glu Asn Gly Asn Gln Tyr Tyr Asp Lys Thr
            980                 985                 990
Gly Ala Gln Val Leu Asn Arg Tyr Tyr Thr Thr Asp Gly Gln Asn Trp
            995                 1000                1005
Arg Tyr Phe Asp Val Lys Gly Val Met Ala Arg Gly Leu Val Thr
    1010                1015                1020
Met Gly Gly Asn Gln Gln Phe Phe Asp Gln Asn Gly Tyr Gln Val
    1025                1030                1035
Lys Gly Lys Ile Ala Arg Ala Lys Asp Gly Lys Leu Arg Tyr Phe
    1040                1045                1050
Asp Lys Asp Ser Gly Asn Ala Ala Ala Asn Arg Phe Ala Gln Gly
    1055                1060                1065
Asp Asn Pro Ser Asp Trp Tyr Tyr Phe Gly Ala Asp Gly Val Ala
    1070                1075                1080
Val Thr Gly Leu Gln Lys Val Gly Gln Gln Thr Leu Tyr Phe Asp
    1085                1090                1095
Gln Asp Gly Lys Gln Val Lys Gly Lys Val Val Thr Leu Ala Asp
    1100                1105                1110
Lys Ser Ile Arg Tyr Phe Asp Ala Asn Ser Gly Glu Met Ala Val
    1115                1120                1125
Asn Lys Phe Val Glu Gly Ala Lys Asn Val Trp Tyr Tyr Phe Asp
    1130                1135                1140
Gln Ala Gly Lys Ala Val Thr Gly Leu Gln Thr Ile Asn Lys Gln
    1145                1150                1155
Val Leu Tyr Phe Asp Gln Gly Lys Gln Val Lys Gly Lys Val
    1160                1165                1170
Val Thr Leu Ala Asp Lys Ser Ile Arg Tyr Phe Asp Ala Asn Ser
    1175                1180                1185
Gly Glu Met Ala Val Gly Lys Phe Ala Glu Gly Ala Lys Asn Glu
    1190                1195                1200
Trp Tyr Tyr Phe Asp Gln Ala Gly Lys Ala Val Thr Gly Leu Gln
    1205                1210                1215
Lys Ile Gly Gln Gln Thr Leu Tyr Phe Asp Gln Asn Gly Lys Gln
    1220                1225                1230
Val Lys Gly Lys Val Val Thr Leu Ala Asp Lys Ser Ile Arg Tyr
    1235                1240                1245
```

```
Phe Asp Ala Asn Ser Gly Glu Met Ala Ser Asn Lys Phe Val Glu
    1250            1255            1260

Gly Ala Lys Asn Glu Trp Tyr Tyr Phe Asp Gln Ala Gly Lys Ala
1265            1270            1275

Val Thr Gly Leu Gln Gln Ile Gly Gln Gln Thr Leu Tyr Phe Asp
    1280            1285            1290

Gln Asn Gly Lys Gln Val Lys Gly Lys Ile Val Tyr Val Asn Gly
1295            1300            1305

Ala Asn Arg Tyr Phe Asp Ala Asn Ser Gly Glu Met Ala Arg Asn
    1310            1315            1320

Lys Trp Ile Gln Leu Glu Asp Gly Ser Trp Met Tyr Phe Asp Arg
1325            1330            1335

Asn Gly Arg Gly Arg Arg Phe Gly Trp Asn
    1340            1345

<210> SEQ ID NO 19
<211> LENGTH: 4023
<212> TYPE: DNA
<213> ORGANISM: Unknown
<220> FEATURE:
<223> OTHER INFORMATION: unknown Streptococcus species

<400> SEQUENCE: 19
atgatcgacg gcaaatacta ctacgtaaac gaggacggca gccacaaaga gaatttcgcg      60
atcacggtta atggtcaact gctgtatttt ggtaaggatg gcgcgctgac cagcagcagc     120
acgtacagct tcacccaagg cactaccaat attgtggacg gttttagcat taacaaccgt     180
gcgtatgact ccagcgaggc ctctttcgag ctgattgacg gttatctgac tgcggactct     240
tggtaccgtc cggcgagcat tatcaaagac ggtgtgacgt ggcaagcatc caccgccgag     300
gacttccgcc cgttgctgat ggcgtggtgg ccgaacgttg atactcaggt gaactacctg     360
aactacatgt ccaaagtctt taatctggat gctaaataca gctcgactga taaacaggaa     420
accctgaagg tggcggcgaa agatatccag atcaaaattg aacaaaagat tcaggcggaa     480
aagtccacgc aatggctgcg tgaaacgatc agcgcctttg taaaaaccca gccgcaatgg     540
aacaaagaga ctgagaacta cagcaagggc ggtggtgagg accatctgca aggtggtgcc     600
ctgctgtatg ttaatgactc tcgtaccccg tgggcgaaca gcaactatcg tttgctgaac     660
cgcacggcga ccaaccagac cggtacgatc gacaagagca tcctggacga gcagagcgat     720
ccgaatcaca tgggtggttt tgatttcttg ctggctaatg acgttgactt gagcaatccg     780
gtcgtccagg cggaacaact gaatcagatc cactacctga tgaattgggg ttctattgtc     840
atgggtgata agacgcgaa ttttgacggt attcgtgtag acgcggtgga taatgttgat     900
gcggacatgc tgcaattgta caccaactat ttccgcgaat actatggtgt caacaaaagc     960
gaggcaaacg cgctggcgca cattagcgtc ctggaagcct ggagcctgaa tgacaaccat    1020
tacaatgata agactgatgt tgcggcgctg gcaatggaga ataagcagcg cttggcactg    1080
ttgtttagcc tggcgaaacc gattaaagaa cgcacgcctg ccgtgtctcc gctgtacaac    1140
aatacgttta acaccactca gcgtgatgaa aagacggact ggatcaataa agatggttcg    1200
aaagcctaca tgaggatgg cactgtcaag aaaagcacca tcggcaagta acgagaag     1260
tatggtgatg ctagcggcaa ctacgttttc atccgcgctc acgacaataa cgtgcaagac    1320
atcatcgcgg agatcattaa gaaagagatt aacgagaaat ctgacggttt taccattacg    1380
gattcggaga tgaagcgtgc atttgagatc tataacaaag acatgctgtc taatgacaaa    1440
```

```
aagtacacgc tgaataacat cccggcggcg tacgcggtta tgctgcaaaa catggaaacg    1500
attacccgcg tgtattacgg cgatctgtac acggacgacg gtaattacat ggaagcgaaa    1560
agcccgtact acgatacgat tgttaacttg atgaagtctc gcatcaaata cgtgagcggt    1620
ggccaggcgc agcgcagcta ctggctgccg accgatggta agatggataa gtcggatgtt    1680
gagctgtacc gtacgaacga agtgtacacg agcgtccgtt acggcaaaga cattatgacc    1740
gccgatgaca cgcaaggtag caaatacagc cgtaccagcg gtcaggtgac cctggtcgtc    1800
aacaacccaa aactgacctt ggaccaaagc gcaaagctga acgtggttat gggcaagatt    1860
catgctaatc agaagtaccg cgcactgatt gtcggtaccc cgaacggtat taagaatttc    1920
accagcgacg cagaggctat tgccgcaggc tatgtcaaag aaaccgatgg caatggcgtg    1980
ctgaccttcg gtgcaaacga catcaagggt tatgaaactt cgatatgag cggcttcgtc    2040 gctgtttggg ttccggtcgg tgcgagcgac gaccaagata ttcgtgtggc ggcgtctacg    2100
gcagcaaaga aagagggtga gctgacgctg aaagcgaccg aagcctatga ctcccaactg    2160
atctatgaag gctttagcaa tttccagacc atcccagatg gcagcgatcc ttctgtttat    2220
accaatcgta agatcgcgga aaatgttgat tgttcaaga gctggggtgt cacgagcttc    2280
gaaatggctc cgcagttcgt ttctgcggac gatggcacgt ttctggacag cgtcattcaa    2340
aacggctatg cgttcgcaga ccgttatgat ctggccatga gcaaaaacaa taagtacggt    2400
agcaaagaag atctgcgtaa cgcgctgaag gcactgcaca aagcaggcat tcaggcgatt    2460
gcagattggg tgccagacca aatctaccag ctgcctggca agaagttgt tactgccacc    2520 cgcacggacg gtgctggtcg caaaatcagc gatgcaatca tcgatcattc cctgtacgtt    2580
gcgaactcca agagctccgg taaggactac caagcgaagt acggtggcga gttcttggcg    2640
gaactgaagg cgaaataccc ggaaatgttc aaagtgaaca tgattagcac cggcaaaccg    2700
attgatgata gcgtgaaact gaagcagtgg aaagcagaat acttcaacgg caccaatgtg    2760
ctggatcgcg tgtcggtta tgttctgagc gatgaggcaa ccggtaagta tttcaccgtt    2820
accaaagagg gtaactttat cccgttgcag ctgaagggta caagaaggt gattaccggc    2880 ttttccagcg acggtaaggg cattacctat ttcggtacta gcggtaacca agctaaatcc    2940
gcgttcgtca cttttaacgg taacacgtac tacttcgacg cacgtggcca catggttacc    3000
aacggtgagt actcgccgaa tggtaaagat gtgtatcgtt ttctgccgaa cggcattatg    3060
ctgagcaacg cgttctatgt tgacggcaat ggcaacacct acctgtacaa ctccaaaggc    3120
caaatgtata aggtggcta tagcaaattt gacgtcacgg aaacgaagga cggtaaagag    3180
agcaaagttg tcaagttccg ctactttacg aacgagggcg tgatggcgaa aggtgtcacg    3240
gttgtggatg gcttcactca gtactttaac gaggatggca ttcaaagcaa agacgagctg    3300
gtcacttaca atggcaagac ctattacttc gaagcacaca cgggcaatgc cattaagaat    3360
acgtggcgta atatcaaggg caaatggtac cattttgatg ctaacggtgt cgcggctact    3420
ggcgcacagg ttatcaacgg tcagcacctg tacttcaatg aagatggctc tcaagtaaaa    3480
ggtagcatcg tcaaaaacgc tgatggtacg ttcagcaagt acaaggacag ctctggcgat    3540
ctggtggtga acgagttttt cacgacgggt gataacgtct ggtactatgc tggtgccaat    3600
ggcaaaacgg ttactggtgc acaggtgatt aatggccagc acttgttctt caaagaggat    3660
ggcagccagg tcaagggcga ctttgtgaag aatagcgacg gcacctactc caagtatgac    3720
gctgcgagcg gcgaacgtct gaccaacgag ttcttcacta cgggcgacaa tcattggtac    3780
tatattggcg ccaacggtaa gaccgttacc ggtgaagtta agattggtga cgacacgtat    3840
```

-continued

```
ttcttcgcaa aagacggtaa gcaactgaaa ggtcaaatcg ttaccacccg tagcggtcgt    3900
atcagctact actttggtga tagcggtaag aaggctatta gcacgtgggt ggagatccag    3960
ccgggtgtgt ttgttttctt cgacaaaaac ggcctggctt acccaccgga gaatatgaac    4020
tga                                                                  4023
```

<210> SEQ ID NO 20
<211> LENGTH: 1340
<212> TYPE: PRT
<213> ORGANISM: Unknown
<220> FEATURE:
<223> OTHER INFORMATION: unknown Streptococcus species

<400> SEQUENCE: 20

```
Met Ile Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr Tyr Ser Phe Thr Gln Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Ser Ser Thr Asp Lys Gln Glu Thr Leu Lys Val
    130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asn Tyr Arg Leu Leu Asn Arg Thr Ala Thr
    210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
    290                 295                 300

Gln Leu Tyr Thr Asn Tyr Phe Arg Glu Tyr Tyr Gly Val Asn Lys Ser
305                 310                 315                 320
```

```
Glu Ala Asn Ala Leu Ala His Ile Ser Val Leu Glu Ala Trp Ser Leu
            325                 330                 335

Asn Asp Asn His Tyr Asn Asp Lys Thr Asp Val Ala Ala Leu Ala Met
        340                 345                 350

Glu Asn Lys Gln Arg Leu Ala Leu Leu Phe Ser Leu Ala Lys Pro Ile
            355                 360                 365

Lys Glu Arg Thr Pro Ala Val Ser Pro Leu Tyr Asn Asn Thr Phe Asn
    370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Lys Ser Thr Ile Gly Lys
            405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
        435                 440                 445

Glu Ile Asn Glu Lys Ser Asp Gly Phe Thr Ile Thr Asp Ser Glu Met
    450                 455                 460

Lys Arg Ala Phe Glu Ile Tyr Asn Lys Asp Met Leu Ser Asn Asp Lys
465                 470                 475                 480

Lys Tyr Thr Leu Asn Asn Ile Pro Ala Ala Tyr Ala Val Met Leu Gln
            485                 490                 495

Asn Met Glu Thr Ile Thr Arg Val Tyr Tyr Gly Asp Leu Tyr Thr Asp
            500                 505                 510

Asp Gly Asn Tyr Met Glu Ala Lys Ser Pro Tyr Tyr Asp Thr Ile Val
        515                 520                 525

Asn Leu Met Lys Ser Arg Ile Lys Tyr Val Ser Gly Gly Gln Ala Gln
    530                 535                 540

Arg Ser Tyr Trp Leu Pro Thr Asp Gly Lys Met Asp Lys Ser Asp Val
545                 550                 555                 560

Glu Leu Tyr Arg Thr Asn Glu Val Tyr Thr Ser Val Arg Tyr Gly Lys
            565                 570                 575

Asp Ile Met Thr Ala Asp Asp Thr Gln Gly Ser Lys Tyr Ser Arg Thr
            580                 585                 590

Ser Gly Gln Val Thr Leu Val Val Asn Asn Pro Lys Leu Thr Leu Asp
        595                 600                 605

Gln Ser Ala Lys Leu Asn Val Val Met Gly Lys Ile His Ala Asn Gln
    610                 615                 620

Lys Tyr Arg Ala Leu Ile Val Gly Thr Pro Asn Gly Ile Lys Asn Phe
625                 630                 635                 640

Thr Ser Asp Ala Glu Ala Ile Ala Ala Gly Tyr Val Lys Glu Thr Asp
            645                 650                 655

Gly Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Ala Ser Thr Ala Ala Lys Lys
    690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
            725                 730                 735

Pro Ser Val Tyr Thr Asn Arg Lys Ile Ala Glu Asn Val Asp Leu Phe
```

```
                    740                 745                 750
Lys Ser Trp Gly Val Thr Ser Phe Glu Met Ala Pro Gln Phe Val Ser
            755                 760                 765

Ala Asp Asp Gly Thr Phe Leu Asp Ser Val Ile Gln Asn Gly Tyr Ala
        770                 775                 780

Phe Ala Asp Arg Tyr Asp Leu Ala Met Ser Lys Asn Asn Lys Tyr Gly
785                 790                 795                 800

Ser Lys Glu Asp Leu Arg Asn Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ser Asp Ala Ile Ile Asp His Ser Leu Tyr Val Ala Asn Ser Lys
        850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
            900                 905                 910

Glu Tyr Phe Asn Gly Thr Asn Val Leu Asp Arg Gly Val Gly Tyr Val
        915                 920                 925

Leu Ser Asp Glu Ala Thr Gly Lys Tyr Phe Thr Val Thr Lys Glu Gly
        930                 935                 940

Asn Phe Ile Pro Leu Gln Leu Lys Gly Asn Lys Lys Val Ile Thr Gly
945                 950                 955                 960

Phe Ser Ser Asp Gly Lys Gly Ile Thr Tyr Phe Gly Thr Ser Gly Asn
                965                 970                 975

Gln Ala Lys Ser Ala Phe Val Thr Phe Asn Gly Asn Thr Tyr Tyr Phe
            980                 985                 990

Asp Ala Arg Gly His Met Val Thr Asn Gly Glu Tyr Ser Pro Asn Gly
        995                 1000                1005

Lys Asp Val Tyr Arg Phe Leu Pro Asn Gly Ile Met Leu Ser Asn
    1010                1015                1020

Ala Phe Tyr Val Asp Gly Asn Gly Asn Thr Tyr Leu Tyr Asn Ser
    1025                1030                1035

Lys Gly Gln Met Tyr Lys Gly Gly Tyr Ser Lys Phe Asp Val Thr
    1040                1045                1050

Glu Thr Lys Asp Gly Lys Glu Ser Lys Val Val Lys Phe Arg Tyr
    1055                1060                1065

Phe Thr Asn Glu Gly Val Met Ala Lys Gly Val Thr Val Val Asp
    1070                1075                1080

Gly Phe Thr Gln Tyr Phe Asn Glu Asp Gly Ile Gln Ser Lys Asp
    1085                1090                1095

Glu Leu Val Thr Tyr Asn Gly Lys Thr Tyr Tyr Phe Glu Ala His
    1100                1105                1110

Thr Gly Asn Ala Ile Lys Asn Thr Trp Arg Asn Ile Lys Gly Lys
    1115                1120                1125

Trp Tyr His Phe Asp Ala Asn Gly Val Ala Ala Thr Gly Ala Gln
    1130                1135                1140

Val Ile Asn Gly Gln His Leu Tyr Phe Asn Glu Asp Gly Ser Gln
    1145                1150                1155
```

-continued

```
Val Lys Gly Ser Ile Val Lys Asn Ala Asp Gly Thr Phe Ser Lys
    1160            1165                1170

Tyr Lys Asp Ser Ser Gly Asp Leu Val Val Asn Glu Phe Phe Thr
    1175            1180                1185

Thr Gly Asp Asn Val Trp Tyr Ala Gly Ala Asn Gly Lys Thr
    1190            1195                1200

Val Thr Gly Ala Gln Val Ile Asn Gly Gln His Leu Phe Phe Lys
    1205            1210                1215

Glu Asp Gly Ser Gln Val Lys Gly Asp Phe Val Lys Asn Ser Asp
    1220            1225                1230

Gly Thr Tyr Ser Lys Tyr Asp Ala Ala Ser Gly Glu Arg Leu Thr
    1235            1240                1245

Asn Glu Phe Phe Thr Thr Gly Asp Asn His Trp Tyr Tyr Ile Gly
    1250            1255                1260

Ala Asn Gly Lys Thr Val Thr Gly Glu Val Lys Ile Gly Asp Asp
    1265            1270                1275

Thr Tyr Phe Phe Ala Lys Asp Gly Lys Gln Leu Lys Gly Gln Ile
    1280            1285                1290

Val Thr Thr Arg Ser Gly Arg Ile Ser Tyr Tyr Phe Gly Asp Ser
    1295            1300                1305

Gly Lys Lys Ala Ile Ser Thr Trp Val Glu Ile Gln Pro Gly Val
    1310            1315                1320

Phe Val Phe Phe Asp Lys Asn Gly Leu Ala Tyr Pro Pro Glu Asn
    1325            1330                1335

Met Asn
    1340

<210> SEQ ID NO 21
<211> LENGTH: 4479
<212> TYPE: DNA
<213> ORGANISM: Leuconostoc mesenteroides

<400> SEQUENCE: 21
atgaccccat ccgtattagg tgattcttcc gtcccagatg tatcggctaa caatgtgcaa      60
tccgcgagcg ataatacgac ggacacccag caaaatacca ccatcaccga ggaaaatgat     120
aaggtccaga gcgctgcgac caacgataac gtgaccacgg cagcgtccga cacgacgcag     180
agcgccgata caacgttac cgagaaacaa tctgatgatc acgcgctgga taatgaaaag     240
gttgacaata agcaggacga ggtcgcccag accaacgtga ctagcaaaaa cgaggagagc     300
gcggtggcct ctaccgacac cgatccggca gagactacca cggacgaaac gcaacaggtt     360
agcggcaagt atgtggaaaa ggatggttct tggtattact actttgacga cggtaagaac     420
gcgaagggtc tgagcacgat tgacaacaat atccaatact tgatgaaag cggtaagcag     480 gtcaaaggtc agtatgtgac gattgataac cagacctatt actttgataa agatagcgt     540 gatgaactga ccggcctgca atctattgac ggtaacattg ttgccttcaa tgacgagggc     600
cagcagatct ttaatcaata ctaccagagc gagaacggta cgacctacta ttttgatgat     660
aagggccacg ctgccaccgg tattaagaat attgagggca agaactacta ttttgacaat     720
ctgggtcaac tgaaaaaggg cttctccggc gtgatcgacg gtcagattat gacgtttgac     780
caggaaactg gtcaagaggt ttccaatacc acgtccgaga tcaaagaggg cctgacgact     840
cagaacactg attactctga acataatgcg gcgcacggta ccgacgccga agattttgag     900
aacatcgatg gctatctgac cgccagctcc tggtaccgtc cgacggacat tctgcgcaat     960
```

```
ggcactgact gggaaccgag caccgacacg gactttcgtc caatcttgag cgtttggtgg    1020
ccggataaga atacgcaggt caactatctg aactacatgg cggacctggg cttcattagc    1080
aacgcagaca gcttcgaaac gggtgactct cagagcctgc tgaacgaggc gtccaattac    1140
gtccagaaaa gcatcgagat gaaaatctcc gcgcaacaga gcaccgagtg gctgaaagac    1200
gccatggccg cgtttattgt tacgcagccg caatggaatg aaacttccga agatatgagc    1260
aacgaccact tgcaaaacgg tgcgctgacc tacgttaaca gcccgctgac cccggacgca    1320
aacagcaact ttcgcctgct gaatcgtacc cctaccaacc agaccggcga acaggcgtac    1380
aacctggata attctaaagg tggctttgag ctgctgctgg caaatgatgt ggataacagc    1440
aacccggtgg ttcaagcgga acaactgaat tggctgtact acctgatgaa tttcggtacg    1500
attaccgcca atgacgcgga tgccaacttt gacggcattc gcgtcgatgc agtggataac    1560
gtggatgctg atctgttgca gattgcggca gactacttta aactggccta cggtgtggac    1620
cagaatgata gcaccgcaaa ccaacacctg tctatcctgg aagattggag ccacaacgac    1680
ccgctgtatg tcacggatca aggcagcgac cagctgacta tggacgacta cgtgcatacg    1740
caattgattt ggagcctgac caaaagcagc gatatccgtg gtaccatgca acgttttgtg    1800
gattactata tggtggaccg ttccaatgac tccacggaga atgaagcgat cccgaattac    1860
agctttgtcc gcgcacacga tagcgaagtt caaaccgtta tcgcgcaaat cgtgagcgat    1920
ctgtatccag atgttgagaa tagcctggct ccgaccaccg agcagctggc agcagcattc    1980
aaggtgtata atgaagatga gaaattggcc gacaaaaagt atacccaata caacatggcg    2040
agcgcctatg cgatgctgct gaccaataaa gacacggtgc gcgtgtcta ctatggcgac     2100 ctgtataccg atgacggtca atacatggca acgaagagcc cgtattacga cgcgattaac    2160
accctgctga agctcgtgt tcaatatgtc gcgggtggcc aaagcatgag cgtggatagc     2220
aacgatgtgc tgaccagcgt tcgctatggc aaagacgcga tgacggcgag cgacacgggc    2280
accagcgaga ctcgtaccga gggcgtcggt gtcattgtgt ccaacaatgc ggagctgcaa    2340
ctggaagatg gtcatacggt taccctgcac atgggtgccg cgcacaaaaa tcaggcatac    2400
cgtgcgttgt tgtccaccac ggccgacggt ctggcgtatt atgatacgga cgagaatgcc    2460
ccggtggcat atacgatgc gaacggtgac ttgattttca ccaatgagtc catctacggc     2520
gttcagaatc cgcaagtcag cggttacctg gcggtgtggg tcccggttgg tgcacaacag    2580
gaccaggacg cgcgcacggc aagcgatacc accactaaca ccagcgataa agttttccac    2640
agcaacgcgg ctctggacag ccaagtgatc tacgagggct tcagcaactt ccaagcgttt    2700
gcgactgatt ccagcgaata caccaatgtt gttattgctc agaacgctga tcaattcaaa    2760
caatggggcg tgacctcgtt tcagctggct ccgcagtacc gcagcagcac ggacacttcc    2820
ttcctggata gcatcatcca aaatggttac gcgtttacgg accgctatga tctgggttat    2880
ggcacgccga cgaagtacgg taccgcggac caactgcgtg atgcaatcaa agcactgcat    2940
gcgagcggca tccaagcgat tgcagattgg gttccggacc agatttacaa tctgccggag    3000
caagaactgg cgactgtcac gcgcacgaat agcttcggtg atgatgatac tgacagcgac    3060
attgataatg ctctgtatgt ggttcaaagc cgcggtggtg gtcagtacca agagatgtat    3120
ggcggtgcgt ttctggagga gttgcaagcg ctgtacccta gcctgtttaa ggtgaaccag    3180
atttctactg gtgtcccgat cgatggtagc gtgaagatta ccgagtgggc tgcgaaatac    3240
ttcaacggca gcaatatcca gggtaagggt gcgggttacg tgttgaaaga catgggtagc    3300
```

-continued

```
aataagtact tcaaggtcgt gagcaatacc gaggacggcg actatctgcc gaaacagctg    3360
accaacgacc tgagcgaaac cggtttcacc cacgacgaca agggtatcat ctactacacc    3420
ctgagcggct atcgtgcaca gaacgccttc attcaagacg atgataacaa ttactattac    3480
tttgacaaga ccggtcacct ggtcacgggt ttgcagaaaa tcaacaacca tacgtacttc    3540
ttcctgccga atggcattga gctggtgaaa tccttcttgc agaacgagga tggcacgatc    3600
gtttacttcg ataagaaagg tcatcaagtc tttgatcaat acattacgga tcaaaatggc    3660
aacgcgtact atttcgacga tgccggtgtt atgctgaagt ctggtctggc aacgattgat    3720
ggtcatcagc agtacttcga tcagaatggc gttcaagtta aggacaagtt cgttatcggt    3780
acggatggct acaagtacta cttcgagccg ggttgcggca atttggcaat tttgcgttac    3840
gtgcaaaata gcaagaacca atggttctat ttcgatggca atggccacgc agtcacgggt    3900
ttccaaacca tcaacggcaa gaagcagtat ttctacaacg atggtcacca agcaagggc    3960 gaatttatca atgcggacgg tgacaccttc tacaccagcg ccaccgacgg tcgtttggtg    4020
acgggtgttc agaagatcaa cggtatcacc tacgcgtttg acaataccgg caacctgatc    4080
acgaaccagt attatcagct ggcggacggt aagtacatgc tgctggacga ctctggtcgc    4140
gcaaaaacgg gctttgtcct gcaagacggt gtcctgcgtt atttcgacca gaacggtgaa    4200
caagtgaagg acgccattat cgtcgacccg gacaccaacc tgtcttatta ctttaacgcg    4260
acccagggtg tcgcggtgaa aaacgattac ttcgagtacc aaggcaactg gtacctgacc    4320
gatgcaaact accagctgat taaaggcttc aaagcagttg acgactcgct gcaacacttc    4380
gacgaagtta cgggtgtgca gaccaaggaa agcgctctga ttagcgcaca gggcaaagtt    4440
taccagttcg acaacaatgg taacgcggtg agcgcataa                          4479
```

<210> SEQ ID NO 22
<211> LENGTH: 1492
<212> TYPE: PRT
<213> ORGANISM: Leuconostoc mesenteroides

<400> SEQUENCE: 22

```
Met Thr Pro Ser Val Leu Gly Asp Ser Ser Val Pro Asp Val Ser Ala
1               5                   10                  15

Asn Asn Val Gln Ser Ala Ser Asp Asn Thr Thr Asp Thr Gln Gln Asn
            20                  25                  30

Thr Thr Ile Thr Glu Glu Asn Asp Lys Val Gln Ser Ala Ala Thr Asn
        35                  40                  45

Asp Asn Val Thr Thr Ala Ala Ser Asp Thr Thr Gln Ser Ala Asp Asn
    50                  55                  60

Asn Val Thr Glu Lys Gln Ser Asp Asp His Ala Leu Asp Asn Glu Lys
65                  70                  75                  80

Val Asp Asn Lys Gln Asp Glu Val Ala Gln Thr Asn Val Thr Ser Lys
                85                  90                  95

Asn Glu Glu Ser Ala Val Ala Ser Thr Asp Thr Asp Pro Ala Glu Thr
            100                 105                 110

Thr Thr Asp Glu Thr Gln Gln Val Ser Gly Lys Tyr Val Glu Lys Asp
        115                 120                 125

Gly Ser Trp Tyr Tyr Phe Asp Asp Gly Lys Asn Ala Lys Gly Leu
    130                 135                 140

Ser Thr Ile Asp Asn Asn Ile Gln Tyr Phe Asp Glu Ser Gly Lys Gln
145                 150                 155                 160

Val Lys Gly Gln Tyr Val Thr Ile Asp Asn Gln Thr Tyr Tyr Phe Asp
```

-continued

```
                165                 170                 175
Lys Asp Ser Gly Asp Glu Leu Thr Gly Leu Gln Ser Ile Asp Gly Asn
            180                 185                 190
Ile Val Ala Phe Asn Asp Glu Gly Gln Gln Ile Phe Asn Gln Tyr Tyr
            195                 200                 205
Gln Ser Glu Asn Gly Thr Thr Tyr Tyr Phe Asp Lys Gly His Ala
        210                 215                 220
Ala Thr Gly Ile Lys Asn Ile Glu Gly Lys Asn Tyr Tyr Phe Asp Asn
225                 230                 235                 240
Leu Gly Gln Leu Lys Lys Gly Phe Ser Gly Val Ile Asp Gly Gln Ile
                245                 250                 255
Met Thr Phe Asp Gln Glu Thr Gly Gln Glu Val Ser Asn Thr Thr Ser
            260                 265                 270
Glu Ile Lys Glu Gly Leu Thr Thr Gln Asn Thr Asp Tyr Ser Glu His
        275                 280                 285
Asn Ala Ala His Gly Thr Asp Ala Glu Asp Phe Glu Asn Ile Asp Gly
        290                 295                 300
Tyr Leu Thr Ala Ser Ser Trp Tyr Arg Pro Thr Asp Ile Leu Arg Asn
305                 310                 315                 320
Gly Thr Asp Trp Glu Pro Ser Thr Asp Thr Asp Phe Arg Pro Ile Leu
                325                 330                 335
Ser Val Trp Trp Pro Asp Lys Asn Thr Gln Val Asn Tyr Leu Asn Tyr
                340                 345                 350
Met Ala Asp Leu Gly Phe Ile Ser Asn Ala Asp Ser Phe Glu Thr Gly
            355                 360                 365
Asp Ser Gln Ser Leu Leu Asn Glu Ala Ser Asn Tyr Val Gln Lys Ser
        370                 375                 380
Ile Glu Met Lys Ile Ser Ala Gln Gln Ser Thr Glu Trp Leu Lys Asp
385                 390                 395                 400
Ala Met Ala Ala Phe Ile Val Thr Gln Pro Gln Trp Asn Glu Thr Ser
                405                 410                 415
Glu Asp Met Ser Asn Asp His Leu Gln Asn Gly Ala Leu Thr Tyr Val
            420                 425                 430
Asn Ser Pro Leu Thr Pro Asp Ala Asn Ser Asn Phe Arg Leu Leu Asn
        435                 440                 445
Arg Thr Pro Thr Asn Gln Thr Gly Glu Gln Ala Tyr Asn Leu Asp Asn
        450                 455                 460
Ser Lys Gly Gly Phe Glu Leu Leu Leu Ala Asn Asp Val Asp Asn Ser
465                 470                 475                 480
Asn Pro Val Val Gln Ala Glu Gln Leu Asn Trp Leu Tyr Tyr Leu Met
                485                 490                 495
Asn Phe Gly Thr Ile Thr Ala Asn Asp Ala Asp Ala Asn Phe Asp Gly
            500                 505                 510
Ile Arg Val Asp Ala Val Asp Asn Val Asp Ala Asp Leu Leu Gln Ile
            515                 520                 525
Ala Ala Asp Tyr Phe Lys Leu Ala Tyr Gly Val Asp Gln Asn Asp Ser
        530                 535                 540
Thr Ala Asn Gln His Leu Ser Ile Leu Glu Asp Trp Ser His Asn Asp
545                 550                 555                 560
Pro Leu Tyr Val Thr Asp Gln Gly Ser Asp Gln Leu Thr Met Asp Asp
                565                 570                 575
Tyr Val His Thr Gln Leu Ile Trp Ser Leu Thr Lys Ser Ser Asp Ile
            580                 585                 590
```

```
Arg Gly Thr Met Gln Arg Phe Val Asp Tyr Tyr Met Val Asp Arg Ser
        595                 600                 605

Asn Asp Ser Thr Glu Asn Glu Ala Ile Pro Asn Tyr Ser Phe Val Arg
610                 615                 620

Ala His Asp Ser Glu Val Gln Thr Val Ile Ala Gln Ile Val Ser Asp
625                 630                 635                 640

Leu Tyr Pro Asp Val Glu Asn Ser Leu Ala Pro Thr Thr Glu Gln Leu
                645                 650                 655

Ala Ala Ala Phe Lys Val Tyr Asn Glu Asp Glu Lys Leu Ala Asp Lys
                660                 665                 670

Lys Tyr Thr Gln Tyr Asn Met Ala Ser Ala Tyr Ala Met Leu Leu Thr
        675                 680                 685

Asn Lys Asp Thr Val Pro Arg Val Tyr Tyr Gly Asp Leu Tyr Thr Asp
        690                 695                 700

Asp Gly Gln Tyr Met Ala Thr Lys Ser Pro Tyr Tyr Asp Ala Ile Asn
705                 710                 715                 720

Thr Leu Leu Lys Ala Arg Val Gln Tyr Val Ala Gly Gln Ser Met
                725                 730                 735

Ser Val Asp Ser Asn Asp Val Leu Thr Ser Val Arg Tyr Gly Lys Asp
        740                 745                 750

Ala Met Thr Ala Ser Asp Thr Gly Thr Ser Glu Thr Arg Thr Glu Gly
        755                 760                 765

Val Gly Val Ile Val Ser Asn Asn Ala Glu Leu Gln Leu Glu Asp Gly
        770                 775                 780

His Thr Val Thr Leu His Met Gly Ala Ala His Lys Asn Gln Ala Tyr
785                 790                 795                 800

Arg Ala Leu Leu Ser Thr Thr Ala Asp Gly Leu Ala Tyr Tyr Asp Thr
                805                 810                 815

Asp Glu Asn Ala Pro Val Ala Tyr Thr Asp Ala Asn Gly Asp Leu Ile
                820                 825                 830

Phe Thr Asn Glu Ser Ile Tyr Gly Val Gln Asn Pro Gln Val Ser Gly
        835                 840                 845

Tyr Leu Ala Val Trp Val Pro Val Gly Ala Gln Asp Gln Asp Ala
        850                 855                 860

Arg Thr Ala Ser Asp Thr Thr Asn Thr Ser Asp Lys Val Phe His
865                 870                 875                 880

Ser Asn Ala Ala Leu Asp Ser Gln Val Ile Tyr Glu Gly Phe Ser Asn
                885                 890                 895

Phe Gln Ala Phe Ala Thr Asp Ser Ser Glu Tyr Thr Asn Val Val Ile
                900                 905                 910

Ala Gln Asn Ala Asp Gln Phe Lys Gln Trp Gly Val Thr Ser Phe Gln
                915                 920                 925

Leu Ala Pro Gln Tyr Arg Ser Ser Thr Asp Thr Ser Phe Leu Asp Ser
        930                 935                 940

Ile Ile Gln Asn Gly Tyr Ala Phe Thr Asp Arg Tyr Asp Leu Gly Tyr
945                 950                 955                 960

Gly Thr Pro Thr Lys Tyr Gly Thr Ala Asp Gln Leu Arg Asp Ala Ile
                965                 970                 975

Lys Ala Leu His Ala Ser Gly Ile Gln Ala Ile Ala Asp Trp Val Pro
                980                 985                 990

Asp Gln Ile Tyr Asn Leu Pro Glu Gln Glu Leu Ala Thr Val Thr Arg
        995                 1000                1005
```

-continued

```
Thr Asn Ser Phe Gly Asp Asp Thr Asp Ser Asp Ile Asp Asn
1010                1015                1020

Ala Leu Tyr Val Val Gln Ser Arg Gly Gly Gln Tyr Gln Glu
1025                1030                1035

Met Tyr Gly Gly Ala Phe Leu Glu Glu Leu Gln Ala Leu Tyr Pro
1040                1045                1050

Ser Leu Phe Lys Val Asn Gln Ile Ser Thr Gly Val Pro Ile Asp
1055                1060                1065

Gly Ser Val Lys Ile Thr Glu Trp Ala Ala Lys Tyr Phe Asn Gly
1070                1075                1080

Ser Asn Ile Gln Gly Lys Gly Ala Gly Tyr Val Leu Lys Asp Met
1085                1090                1095

Gly Ser Asn Lys Tyr Phe Lys Val Val Ser Asn Thr Glu Asp Gly
1100                1105                1110

Asp Tyr Leu Pro Lys Gln Leu Thr Asn Asp Leu Ser Glu Thr Gly
1115                1120                1125

Phe Thr His Asp Asp Lys Gly Ile Ile Tyr Tyr Thr Leu Ser Gly
1130                1135                1140

Tyr Arg Ala Gln Asn Ala Phe Ile Gln Asp Asp Asn Asn Tyr
1145                1150                1155

Tyr Tyr Phe Asp Lys Thr Gly His Leu Val Thr Gly Leu Gln Lys
1160                1165                1170

Ile Asn Asn His Thr Tyr Phe Phe Leu Pro Asn Gly Ile Glu Leu
1175                1180                1185

Val Lys Ser Phe Leu Gln Asn Glu Asp Gly Thr Ile Val Tyr Phe
1190                1195                1200

Asp Lys Lys Gly His Gln Val Phe Asp Gln Tyr Ile Thr Asp Gln
1205                1210                1215

Asn Gly Asn Ala Tyr Tyr Phe Asp Asp Ala Gly Val Met Leu Lys
1220                1225                1230

Ser Gly Leu Ala Thr Ile Asp Gly His Gln Gln Tyr Phe Asp Gln
1235                1240                1245

Asn Gly Val Gln Val Lys Asp Lys Phe Val Ile Gly Thr Asp Gly
1250                1255                1260

Tyr Lys Tyr Tyr Phe Glu Pro Gly Cys Gly Asn Leu Ala Ile Leu
1265                1270                1275

Arg Tyr Val Gln Asn Ser Lys Asn Gln Trp Phe Tyr Phe Asp Gly
1280                1285                1290

Asn Gly His Ala Val Thr Gly Phe Gln Thr Ile Asn Gly Lys Lys
1295                1300                1305

Gln Tyr Phe Tyr Asn Asp Gly His Gln Ser Lys Gly Glu Phe Ile
1310                1315                1320

Asn Ala Asp Gly Asp Thr Phe Tyr Thr Ser Ala Thr Asp Gly Arg
1325                1330                1335

Leu Val Thr Gly Val Gln Lys Ile Asn Gly Ile Thr Tyr Ala Phe
1340                1345                1350

Asp Asn Thr Gly Asn Leu Ile Thr Asn Gln Tyr Tyr Gln Leu Ala
1355                1360                1365

Asp Gly Lys Tyr Met Leu Leu Asp Asp Ser Gly Arg Ala Lys Thr
1370                1375                1380

Gly Phe Val Leu Gln Asp Gly Val Leu Arg Tyr Phe Asp Gln Asn
1385                1390                1395

Gly Glu Gln Val Lys Asp Ala Ile Ile Val Asp Pro Asp Thr Asn
```

Leu Ser Tyr Tyr Phe Asn Ala Thr Gln Gly Val Ala Val Lys Asn
    1415            1420                1425

Asp Tyr Phe Glu Tyr Gln Gly Asn Trp Tyr Leu Thr Asp Ala Asn
        1430            1435                1440

Tyr Gln Leu Ile Lys Gly Phe Lys Ala Val Asp Asp Ser Leu Gln
    1445            1450                1455

His Phe Asp Glu Val Thr Gly Val Gln Thr Lys Glu Ser Ala Leu
    1460            1465                1470

Ile Ser Ala Gln Gly Lys Val Tyr Gln Phe Asp Asn Asn Gly Asn
    1475            1480                1485

Ala Val Ser Ala
    1490

<210> SEQ ID NO 23
<211> LENGTH: 3972
<212> TYPE: DNA
<213> ORGANISM: Streptococcus criceti

<400> SEQUENCE: 23

| | | | | | |
|---|---|---|---|---|---|
| atggttgatg | caaatacta | ctactacgac | gcagatggca | acgttaagaa | gaatttcgcg | 60 |
| attagcgtcg | gtgacgcaat | cttctacttt | gacgaaaccg | gtgcttacaa | ggacaccagc | 120 |
| aaagttggtg | cggataaaac | cagcagcagc | gcgaatcaaa | ccacggccac | cttcgcggca | 180 |
| aacaaccgtg | cctatagcac | tgcggcggag | aactttgagg | caattgacaa | ctatttgacc | 240 |
| gcagacagct | ggtatcgtcc | gaagagcatt | ctgaaagatg | gtaagacgtg | gaccgaatcc | 300 |
| accaaagacg | acttccgtcc | gctgctgatg | gcttggtggc | cggataccga | aactaaacgc | 360 |
| aactatgtca | actatatgaa | taaggtcgtc | ggcattgata | aaacctatac | cgcggagact | 420 |
| agccaagccg | acctgacggc | agctgcggag | ctggttcaag | cgcgcattga | gcaacgcatc | 480 |
| acgtctgaga | agaacacgaa | atggctgcgc | gaggctatta | gcgcgtttgt | caagacccag | 540 |
| ccgcaatgga | atggcgagtc | cgaaaagccg | tatgatgatc | atttgcagaa | cggtgcactg | 600 |
| aagttcgaca | cgaaaccctc | tctgaccccg | gacacccagt | ctggttatcg | tatcttgaat | 660 |
| cgcacgccga | ccaatcaaac | gggcagcctg | gacccgcgtt | tcacctttaa | tcaaaatgat | 720 |
| ccgctgggtg | gctatgaata | tctgctggca | aacgacgtgg | ataatagcaa | cccggtggtg | 780 |
| caagcggaga | gcttgaattg | gctgcactac | ctgctgaact | tcggcagcat | ctacgcgaat | 840 |
| gatccggaag | cgaatttcga | ttccattcgt | gtagacgccg | tggataacgt | ggatgcggat | 900 |
| ctgttgcaga | ttagcagcga | ctacctgaaa | tctgcgtaca | aaatcgataa | gaacaacaaa | 960 |
| aatgcgaatg | accacgtgag | catcgttgag | gcgtggagcg | ataacgacac | cccgtacctg | 1020 |
| cacgatgaag | gcgataactt | gatgaatatg | gacaataagt | ttcgcctgag | catgttgcgc | 1080 |
| tccctggcga | agcctctgga | caaacgtagc | ggcctgaacc | ctctgatcca | taatagcgtc | 1140 |
| gttgatcgcg | aggtggatga | ccgtgaggtt | gagaaaattc | cgagctactc | ttttgcacgc | 1200 |
| gctcacgaca | gcgaggttca | ggatctgatt | cgtgacatca | ttaaggcaga | aatcaatccg | 1260 |
| aacagcttcg | gctacagctt | tacccaagaa | gaaatcgatc | aagcgttcaa | gatctacaac | 1320 |
| gaggacctga | agaaaaccaa | caagaagtac | acccattaca | atgtcccgct | gtcttacacc | 1380 |
| ttgctgctga | cgaataaggg | tagcattccg | cgtatttact | acggcgacat | gtttaccgac | 1440 |
| gatggccagt | atatggcgaa | caaaacggtg | aattacaatg | ctattgagag | cctgctgaag | 1500 |
| gctcgtatga | agtatgtgag | cggtggtcag | gcgatgcaaa | actatcaaat | tggtaatggt | 1560 |

```
gaaattctga cgtcggtgcg ctacggtaaa ggtgcgctga agcaatcgga caagggcgac    1620
gcaacgacgc gtacctctgg tattggtatt gtcatgggca accagccgaa tttctcgctg    1680
gaaggtaaag tcgttgccct gaacatgggt gcagcgcatg ccaatcagga gtatcgtgcc    1740
ctgatggtga gcactaaaga cggcgtggcg acctatgcga cggatgcaga cgcgagcaaa    1800
gcgggtatga cgaaacgtac cgacgagaac ggctacttgt atttcctgaa tgacgacttg    1860
aagggtgttg caaatccaca gatctccggt tttctgcaag tatgggtgcc ggtcggtgct    1920
cctgccgacc aggatattcg cgttgccgcg acgaacgctg caagcacgga tggtaagtcc    1980
ctgcaccaag atgcgcgat ggatagccgt gttatgttcg agggttttc caactttcag     2040 gcgttcgcaa cgaaagaaga tgagtatgct aatgttgtta ttgcgaaaaa tgtggataag    2100
tttgttagct ggggcatcac tgactttgag atggcaccgc agtatacctc tagcgatgac    2160
ggtcagttcc tggatagcgt tattcagaat ggttatgcat tcacggaccg ttatgatctg    2220
ggtatgagca aggcaaacaa atatggtacg gcggaacacc tggtcaaagc tatcaaagcg    2280
ttgcacaaag caggtctgaa agttatggcg gattgggtcc cggaccagat gtatacccttt    2340 ccgaagaaag aggttgtcac cgttacgcgt acggacaagt tcggtaaacc ggttgcgggc    2400
agccaaatca atcatacccct gtatgtgact gacaccaaag gtagcggtga tgactatcag    2460
gccaaatacg gtggtgcgtt tctggacgag ctgaaagaga atacccggga attgtttacg    2520
aaaaagcaga tttctacggg ccaagcaatc gacccaagcg tcaagattaa gcagtggagc    2580
gcgaaatact ttaacggcag caatatcttg ggtcgtggtg caaattacgt cctgagcgac    2640
caggccagca acaagtattt caatgtggcg gaaggtaagg tttttctgcc aggcgccatg    2700
ctgggcaagg tggtggaaag cggcatccgt tttgacggca agggctacat ctataacagc    2760
tcgaccaccg gcgaacaagt caaagatagc ttcatcacgg aagcaggtaa tttgtattac    2820
ttcggtaaag acggttacat ggtcatgggt gcgcagaaca ttcaaggcgc caattactac    2880
ttcctggcca acggtgcggc actgcgtaat agcatcctga ccgatcaaga cggcaagtcc    2940
cactactacg cgaacgacgg caaacgttat gaaaacggct attatcagtt tggtaacgat    3000
tcctggcgct acttcgagaa tggtgtaatg gccgtcggcg tgacccgtgt ggctggccat    3060
gaccagtact cgataagga tggtattcaa gcgaagaaca agatcatcgt tacccgcgat    3120
ggtaaggttc gttacttcga tgagcacaat ggcaatgcag tcaccaacac gttcattagc    3180
gatcaggcag gtcactggta ctatctgggt aaggacggtg tggcggtgac gggtgcccaa    3240
acggtgggca aacagcacct gtatttcgag gccaacggcc agcaggtcaa aggcgatttt    3300
gtgaccgcga agacggtaa actgtatttc ttcgatggcg atagcggtga catgtggacc    3360
gacacgttcg tccaagacaa aactggccat tggttttacc tgggtaaaga tggtgcggcg    3420
gtcaccggtg cacagaccgt gcgcggtcag aaattgtact ttaaagccaa cggtcagcaa    3480
gttaagggcg acattgtcaa aggtgctgat ggtaaaatcc gttactatga tgcaaattcg    3540
ggcgatcagg tctacaaccg tactgtgaag ggttccgacg gtaaaaccta catcatcggc    3600
aaagacggtg ttgccattac gcagaccatc gcgaagggtc aaaccattaa ggacggcagc    3660
gttctgcgtt tctacagcat ggaaggccag ctggttaccg gtagcggctg gtattctaac    3720
gcgaaaggtc agtggctgta cgtgaagaat ggtcaggttc tgaccggtct gcaaaccgtt    3780
ggttcccaac gtgtgtactt cgacgctaac ggtatccaag cgaagggcaa ggccgtgcgc    3840
accagcgacg gtaagctgcg ttactttgat gcgaacagcg gtagcatgat cactaaccag    3900
```

```
tggaaagagg tgaacggtca atactattac tttgacaaca atggcgtcgc catctaccgc      3960
ggctggaact aa                                                          3972
```

<210> SEQ ID NO 24
<211> LENGTH: 1323
<212> TYPE: PRT
<213> ORGANISM: Streptococcus criceti

<400> SEQUENCE: 24

```
Met Val Asp Gly Lys Tyr Tyr Tyr Asp Ala Asp Gly Asn Val Lys
1               5                   10                  15

Lys Asn Phe Ala Ile Ser Val Gly Asp Ala Ile Phe Tyr Phe Asp Glu
            20                  25                  30

Thr Gly Ala Tyr Lys Asp Thr Ser Lys Val Gly Ala Asp Lys Thr Ser
        35                  40                  45

Ser Ser Ala Asn Gln Thr Thr Ala Thr Phe Ala Ala Asn Asn Arg Ala
    50                  55                  60

Tyr Ser Thr Ala Ala Glu Asn Phe Glu Ala Ile Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Thr Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Arg Ile
145                 150                 155                 160

Thr Ser Glu Lys Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Glu Thr Ser Leu
        195                 200                 205

Thr Pro Asp Thr Gln Ser Gly Tyr Arg Ile Leu Asn Arg Thr Pro Thr
    210                 215                 220

Asn Gln Thr Gly Ser Leu Asp Pro Arg Phe Thr Phe Asn Gln Asn Asp
225                 230                 235                 240

Pro Leu Gly Gly Tyr Glu Tyr Leu Leu Ala Asn Asp Val Asp Asn Ser
                245                 250                 255

Asn Pro Val Val Gln Ala Glu Ser Leu Asn Trp Leu His Tyr Leu Leu
            260                 265                 270

Asn Phe Gly Ser Ile Tyr Ala Asn Asp Pro Glu Ala Asn Phe Asp Ser
        275                 280                 285

Ile Arg Val Asp Ala Val Asp Asn Val Asp Ala Asp Leu Leu Gln Ile
    290                 295                 300

Ser Ser Asp Tyr Leu Lys Ser Ala Tyr Lys Ile Asp Lys Asn Lys
305                 310                 315                 320

Asn Ala Asn Asp His Val Ser Ile Val Glu Ala Trp Ser Asp Asn Asp
                325                 330                 335

Thr Pro Tyr Leu His Asp Glu Gly Asp Asn Leu Met Asn Met Asp Asn
            340                 345                 350

Lys Phe Arg Leu Ser Met Leu Arg Ser Leu Ala Lys Pro Leu Asp Lys
```

```
                355                 360                 365
Arg Ser Gly Leu Asn Pro Leu Ile His Asn Ser Val Val Asp Arg Glu
    370                 375                 380

Val Asp Asp Arg Glu Val Glu Lys Ile Pro Ser Tyr Ser Phe Ala Arg
385                 390                 395                 400

Ala His Asp Ser Glu Val Gln Asp Leu Ile Arg Asp Ile Ile Lys Ala
                405                 410                 415

Glu Ile Asn Pro Asn Ser Phe Gly Tyr Ser Phe Thr Gln Glu Glu Ile
                420                 425                 430

Asp Gln Ala Phe Lys Ile Tyr Asn Glu Asp Leu Lys Lys Thr Asn Lys
            435                 440                 445

Lys Tyr Thr His Tyr Asn Val Pro Leu Ser Tyr Thr Leu Leu Leu Thr
            450                 455                 460

Asn Lys Gly Ser Ile Pro Arg Ile Tyr Tyr Gly Asp Met Phe Thr Asp
465                 470                 475                 480

Asp Gly Gln Tyr Met Ala Asn Lys Thr Val Asn Tyr Asn Ala Ile Glu
                485                 490                 495

Ser Leu Leu Lys Ala Arg Met Lys Tyr Val Ser Gly Gly Gln Ala Met
            500                 505                 510

Gln Asn Tyr Gln Ile Gly Asn Gly Glu Ile Leu Thr Ser Val Arg Tyr
            515                 520                 525

Gly Lys Gly Ala Leu Lys Gln Ser Asp Lys Gly Asp Ala Thr Thr Arg
        530                 535                 540

Thr Ser Gly Ile Gly Ile Val Met Gly Asn Gln Pro Asn Phe Ser Leu
545                 550                 555                 560

Glu Gly Lys Val Val Ala Leu Asn Met Gly Ala Ala His Ala Asn Gln
                565                 570                 575

Glu Tyr Arg Ala Leu Met Val Ser Thr Lys Asp Gly Val Ala Thr Tyr
            580                 585                 590

Ala Thr Asp Ala Asp Ala Ser Lys Ala Gly Met Thr Lys Arg Thr Asp
        595                 600                 605

Glu Asn Gly Tyr Leu Tyr Phe Leu Asn Asp Asp Leu Lys Gly Val Ala
    610                 615                 620

Asn Pro Gln Ile Ser Gly Phe Leu Gln Val Trp Val Pro Val Gly Ala
625                 630                 635                 640

Pro Ala Asp Gln Asp Ile Arg Val Ala Ala Thr Asn Ala Ala Ser Thr
                645                 650                 655

Asp Gly Lys Ser Leu His Gln Asp Ala Ala Met Asp Ser Arg Val Met
            660                 665                 670

Phe Glu Gly Phe Ser Asn Phe Gln Ala Phe Ala Thr Lys Glu Asp Glu
        675                 680                 685

Tyr Ala Asn Val Val Ile Ala Lys Asn Val Asp Lys Phe Val Ser Trp
    690                 695                 700

Gly Ile Thr Asp Phe Glu Met Ala Pro Gln Tyr Thr Ser Ser Asp Asp
705                 710                 715                 720

Gly Gln Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Glu
            740                 745                 750

His Leu Val Lys Ala Ile Lys Ala Leu His Lys Ala Gly Leu Lys Val
        755                 760                 765

Met Ala Asp Trp Val Pro Asp Gln Met Tyr Thr Phe Pro Lys Lys Glu
    770                 775                 780
```

```
Val Val Thr Val Thr Arg Thr Asp Lys Phe Gly Lys Pro Val Ala Gly
785                 790                 795                 800

Ser Gln Ile Asn His Thr Leu Tyr Val Thr Asp Thr Lys Gly Ser Gly
            805                 810                 815

Asp Asp Tyr Gln Ala Lys Tyr Gly Gly Ala Phe Leu Asp Glu Leu Lys
            820                 825                 830

Glu Lys Tyr Pro Glu Leu Phe Thr Lys Gln Ile Ser Thr Gly Gln
            835                 840                 845

Ala Ile Asp Pro Ser Val Lys Ile Lys Gln Trp Ser Ala Lys Tyr Phe
850                 855                 860

Asn Gly Ser Asn Ile Leu Gly Arg Gly Ala Asn Tyr Val Leu Ser Asp
865                 870                 875                 880

Gln Ala Ser Asn Lys Tyr Phe Asn Val Ala Glu Gly Lys Val Phe Leu
            885                 890                 895

Pro Gly Ala Met Leu Gly Lys Val Val Glu Ser Gly Ile Arg Phe Asp
            900                 905                 910

Gly Lys Gly Tyr Ile Tyr Asn Ser Ser Thr Thr Gly Glu Gln Val Lys
            915                 920                 925

Asp Ser Phe Ile Thr Glu Ala Gly Asn Leu Tyr Tyr Phe Gly Lys Asp
            930                 935                 940

Gly Tyr Met Val Met Gly Ala Gln Asn Ile Gln Gly Ala Asn Tyr Tyr
945                 950                 955                 960

Phe Leu Ala Asn Gly Ala Ala Leu Arg Asn Ser Ile Leu Thr Asp Gln
                965                 970                 975

Asp Gly Lys Ser His Tyr Tyr Ala Asn Asp Gly Lys Arg Tyr Glu Asn
            980                 985                 990

Gly Tyr Tyr Gln Phe Gly Asn Asp Ser Trp Arg Tyr Phe Glu Asn Gly
            995                 1000                1005

Val Met Ala Val Gly Val Thr Arg Val Ala Gly His Asp Gln Tyr
    1010                1015                1020

Phe Asp Lys Asp Gly Ile Gln Ala Lys Asn Lys Ile Ile Val Thr
    1025                1030                1035

Arg Asp Gly Lys Val Arg Tyr Phe Asp Glu His Asn Gly Asn Ala
    1040                1045                1050

Val Thr Asn Thr Phe Ile Ser Asp Gln Ala Gly His Trp Tyr Tyr
    1055                1060                1065

Leu Gly Lys Asp Gly Val Ala Val Thr Gly Ala Gln Thr Val Gly
    1070                1075                1080

Lys Gln His Leu Tyr Phe Glu Ala Asn Gly Gln Gln Val Lys Gly
    1085                1090                1095

Asp Phe Val Thr Ala Lys Asp Gly Lys Leu Tyr Phe Phe Asp Gly
    1100                1105                1110

Asp Ser Gly Asp Met Trp Thr Asp Thr Phe Val Gln Asp Lys Thr
    1115                1120                1125

Gly His Trp Phe Tyr Leu Gly Lys Asp Gly Ala Ala Val Thr Gly
    1130                1135                1140

Ala Gln Thr Val Arg Gly Gln Lys Leu Tyr Phe Lys Ala Asn Gly
    1145                1150                1155

Gln Gln Val Lys Gly Asp Ile Val Lys Gly Ala Asp Gly Lys Ile
    1160                1165                1170

Arg Tyr Tyr Asp Ala Asn Ser Gly Asp Gln Val Tyr Asn Arg Thr
    1175                1180                1185
```

| Val | Lys | Gly | Ser | Asp | Gly | Lys | Thr | Tyr | Ile | Ile | Gly | Lys | Asp | Gly |
|---|---|---|---|---|---|---|---|---|---|---|---|---|---|---|
| | 1190 | | | | | 1195 | | | | | 1200 | | | |

| Val | Ala | Ile | Thr | Gln | Thr | Ile | Ala | Lys | Gly | Gln | Thr | Ile | Lys | Asp |
|---|---|---|---|---|---|---|---|---|---|---|---|---|---|---|
| | 1205 | | | | | 1210 | | | | | 1215 | | | |

| Gly | Ser | Val | Leu | Arg | Phe | Tyr | Ser | Met | Glu | Gly | Gln | Leu | Val | Thr |
|---|---|---|---|---|---|---|---|---|---|---|---|---|---|---|
| | 1220 | | | | | 1225 | | | | | 1230 | | | |

| Gly | Ser | Gly | Trp | Tyr | Ser | Asn | Ala | Lys | Gly | Gln | Trp | Leu | Tyr | Val |
|---|---|---|---|---|---|---|---|---|---|---|---|---|---|---|
| | 1235 | | | | | 1240 | | | | | 1245 | | | |

| Lys | Asn | Gly | Gln | Val | Leu | Thr | Gly | Leu | Gln | Thr | Val | Gly | Ser | Gln |
|---|---|---|---|---|---|---|---|---|---|---|---|---|---|---|
| | 1250 | | | | | 1255 | | | | | 1260 | | | |

| Arg | Val | Tyr | Phe | Asp | Ala | Asn | Gly | Ile | Gln | Ala | Lys | Gly | Lys | Ala |
|---|---|---|---|---|---|---|---|---|---|---|---|---|---|---|
| | 1265 | | | | | 1270 | | | | | 1275 | | | |

| Val | Arg | Thr | Ser | Asp | Gly | Lys | Leu | Arg | Tyr | Phe | Asp | Ala | Asn | Ser |
|---|---|---|---|---|---|---|---|---|---|---|---|---|---|---|
| | 1280 | | | | | 1285 | | | | | 1290 | | | |

| Gly | Ser | Met | Ile | Thr | Asn | Gln | Trp | Lys | Glu | Val | Asn | Gly | Gln | Tyr |
|---|---|---|---|---|---|---|---|---|---|---|---|---|---|---|
| | 1295 | | | | | 1300 | | | | | 1305 | | | |

| Tyr | Tyr | Phe | Asp | Asn | Asn | Gly | Val | Ala | Ile | Tyr | Arg | Gly | Trp | Asn |
|---|---|---|---|---|---|---|---|---|---|---|---|---|---|---|
| | 1310 | | | | | 1315 | | | | | 1320 | | | |

<210> SEQ ID NO 25
<211> LENGTH: 4308
<212> TYPE: DNA
<213> ORGANISM: Streptococcus sobrinus

<400> SEQUENCE: 25

```
atggttgacg gcaaatacta ctattatgat caggatggca acgttaagaa gaatttcgcg      60
gttagcgttg gtgacaagat ctactacttt gacgagactg gtgcctacaa agacacctct     120
aaagtggacg cggacaagtc tagcagcgcc gttagccaaa atgcgacgat ctttgcggct     180
aacaatcgtg cgtatagcac ctctgctgag aactttgagg ccgttgataa ctatctgacg     240
gcagatagct ggtatcgtcc taaatctatt ctgaaagatg caagacgtga gaccgagtcg     300
ggtaaggacg acttccgtcc gctgctgatg gcgtggtggc cggacacgga gactaaacgc     360
aattacgtga attacatgaa cctggttgtc ggcatcgaca agacgtacac cgcggaaacc     420
tctcaagcag atttgaccgc agcggcggag ctggtccagg cgcgtattga acagaaaatc     480
accacggaac agaatacgaa atggctgcgc gaggcgatct ctgctttcgt caagacccag     540
ccgcagtgga atggtgaaag cgagaagccg tatgacgacc acctgcaaaa cggtgctctg     600
aaattcgata tcagagcga cctgaccccg gacacccaga gcaactatcg cctgctgaat     660
cgcacccccga ctaaccagac tggcagcctg acagccgtt tcacctataa tgcgaacgat     720
ccgttgggtg gctacgaatt tctgctggct aacgacgtgg ataatagcaa ccctgtggtg     780
caggcagaac aactgaactg gttgcattac ctgttgaatt tggtagcat ttacgcgaaa     840
gatgcggatg caaacttcga ttccatccgt gtggacgccg tggacaacgt cgatgcagat     900
ctgttgcaga ttagcagcga ttacctgaag gcagcctatg gcattgacaa gaacaataag     960
aacgcgaaca accatgttag cattgttgag gcttggagcg ataacgatac gccgtacctg    1020
cacgatgacg tgataaacct gatgaacatg gacaataagt ccgcttgag catgctgtgg    1080
agcctggcca agccgctgga caagcgcagc ggtctgaatc ctctgattca taacagcctg    1140
gtggaccgtg aggttgatga ccgtgaagtg gaaacggttc cgagctactc ttttgcgcgt    1200
gcgcatgatt ccgaggtcca agacattatc cgcgacatta tcaaggccga aatcaacccg    1260
aatagctttg gttatagctt cacccaagaa gagattgacc aggcgtttaa gatctataat    1320
```

```
gaagatctga agaaaaccga caagaaatac acccactata atgtcccgtt gagctatact    1380
ttgctgctga cgaataaagg ttcgattccg cgtgtgtatt acggtgatat gttcaccgat    1440
gatggtcaat acatggcgaa caaaacggtt aactatgatg ccattgagtc gctgctgaaa    1500
gcgcgcatga agtacgttag cggcggtcaa gcgatgcaaa actatcaaat cggcaatggt    1560
gagattctga ccagcgttcg ttatggtaag ggtgcattga agcaatccga caagggtgac    1620
gcgaccacgc gtacgtccgg tgtgggcgtc gtgatgggca accagccgaa ctttagcctg    1680
gacggcaagg tggtggcatt gaacatgggt gccgctcatg caaatcagga gtatcgtgcg    1740
ctgatggtga gcaccaagga tggcgttgcc acgtatgcca ccgacgcgga cgcaagcaag    1800
gcaggtctgg tcaaacgcac cgatgaaaat ggttatttgt actttctgaa cgacgatctg    1860
aagggtgtgg caaacccaca agtcagcggt tccttgcagg tgtgggtccc agtgggtgcg    1920
gctgacgatc aggacattcg tgttgcagcg agcgacacgg ctagcacgga cggtaagtcc    1980
ctgcatcaag atgcggcaat ggatagccgt gttatgtttg agggttttag caacttccag    2040
agctttgcaa ccaaagaaga agagtacacc aacgtagtta ttgcgaacaa cgtggacaaa    2100
ttcgttagct ggggtattac cgactttgag atggcaccgc aatatgtcag ctccaccgat    2160
ggccagtttc tggatagcgt tatccagaat ggttacgcgt tcaccgaccg ttatgatctg    2220
ggtatgagca agccaacaa atacggtacc gcggatcagc tggttaaagc aatcaaagcg    2280
ttgcacgcga agggtctgaa ggtgatggcg gactgggttc cagaccagat gtacacgttt    2340
ccgaagcagg aagttgtcac tgtcacgcgc accgacaaat ttggtaagcc gattgcgggc    2400
agccaaatca atcacagcct gtacgtgacg gacaccaaat ccagcggtga tgattaccag    2460
gccaaatatg gtggtgcgtt cctggatgag ctgaaagaga atacccgga gctgttcacc    2520 aaaaagcaga tctcgaccgg tcaggcgatc gacccgagcg tgaagattaa gcagtggagc    2580
gcgaaatact ttaatggtag caacattctg ggtcgtggtg ccgactacgt cctgtccgat    2640
caagttagca caagtatt caatgtggcc agcgacacg tgtttctgcc gtctagcctg    2700
ttgggtaagg ttgtcgaaag cggtattcgt tacgatggca aaggttatat ctataacagc    2760
agcgcgactg gcgaccaagt caaggcgtct tttatcacgg aagcaggcaa tctgtactac    2820
ttcggcaaag acggttacat ggttactggt gcgcagacca ttaacggtgc gaattacttc    2880
ttcttggaaa atggtacggc cctgcgtaat accatctaca ccgatgcaca gggcaactcc    2940
cactattatg ctaatgatgg caagcgttac gagaacggtt accagcagtt cggcaacgat    3000
tggcgttact tcaaagatgg taacatggcc gtcggtctga ccacggtgga tggtaacgtt    3060
cagtatttcg acaaggacgg tgtccaagct aaagacaaga ttattgtgac ccgcgatggt    3120
aaggtgcgct actttgatca acacaatggc aacgcggtca cgaataccct tatcgccgac    3180
aagaccggtc actggtacta cctgggcaaa gatggcgtcg cggtcaccgg cgctcaaacc    3240
gtcggtaagc aaaaactgta ttttgaggcg aacggtgagc aggtgaaagg cgactttgtg    3300
actagccatg aaggcaaact gtactttat gatgttgaca cgcgcgacat gtggaccgat    3360
accttcatcg aggataaggc cggcaactgg ttctacctgg gtaaagacgg cgcagcagtt    3420
agcggtgcac agaccattcg cggtcaaaag ctgtacttca aggcgtacgg tcaacaggtc    3480
aaaggtgaca tcgttaaagg caccgacggc aagatccgtt actacgatgc gaaatccggc    3540
gagcaggttt tcaataagac ggtcaaagcc gctgatggca aaacctatgt gatcggcaac    3600
aatggtgtgg cggtcgatcc gagcgttgtt aagggtcaga cgttcaaaga cgccagcggc    3660
gcactgcgtt tttacaatct gaaaggtcaa ctggttacgg gctccggttg gtatgaaacg    3720
```

-continued

```
gccaatcacg attgggtgta tattcagagc ggtaaagcac tgaccggtga gcaaaccatc   3780
aatggtcagc acctgtactt taaagaagat ggccaccaag ttaaaggtca gctggtcacc   3840
cgtacggacg gcaaagtgcg ttactatgac gcaaattctg gcgatcaagc gttcaacaag   3900
tccgtgacgg ttaacggcaa aacgtattac ttcggtaatg atggtaccgc gcaaaccgcg   3960
ggtaacccga aaggccaaat cttcaaggac ggcagcgttc tgcgtttcta tagcatggaa   4020
ggccagctgg taattggcag cggctggtat tccaacgcgc aaggccaatg gctgtatgtg   4080
aagaatggta aagtgttgac cggttttgcag accgtcggtt cccagcgcgt gtactttgat   4140
gagaatggca ttcaagcaaa aggcaaagcg gttcgcacga gcgacggcaa aattcgctac   4200
ttcgacgaga acagcggtag catgatcacc aatcaatgga agtttgttta cggtcaatac   4260
tattactttg gtaatgacgg tgcggcaatc taccgtggtt ggaattaa                4308
```

<210> SEQ ID NO 26
<211> LENGTH: 1435
<212> TYPE: PRT
<213> ORGANISM: Streptococcus sobrinus

<400> SEQUENCE: 26

```
Met Val Asp Gly Lys Tyr Tyr Tyr Asp Gln Asp Gly Asn Val Lys
1               5                   10                  15

Lys Asn Phe Ala Val Ser Val Gly Asp Lys Ile Tyr Tyr Phe Asp Glu
                20                  25                  30

Thr Gly Ala Tyr Lys Asp Thr Ser Lys Val Asp Ala Asp Lys Ser Ser
            35                  40                  45

Ser Ala Val Ser Gln Asn Ala Thr Ile Phe Ala Ala Asn Asn Arg Ala
        50                  55                  60

Tyr Ser Thr Ser Ala Glu Asn Phe Glu Ala Val Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Gly Lys Asp Asp Phe Arg Pro Leu Leu Met Ala Trp
            100                 105                 110

Trp Pro Asp Thr Glu Thr Lys Arg Asn Tyr Val Asn Tyr Met Asn Leu
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Thr Glu Gln Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Gln Ser Asp Leu
        195                 200                 205

Thr Pro Asp Thr Gln Ser Asn Tyr Arg Leu Leu Asn Arg Thr Pro Thr
    210                 215                 220

Asn Gln Thr Gly Ser Leu Asp Ser Arg Phe Thr Tyr Asn Ala Asn Asp
225                 230                 235                 240

Pro Leu Gly Gly Tyr Glu Phe Leu Leu Ala Asn Asp Val Asp Asn Ser
                245                 250                 255

Asn Pro Val Val Gln Ala Glu Gln Leu Asn Trp Leu His Tyr Leu Leu
            260                 265                 270
```

```
Asn Phe Gly Ser Ile Tyr Ala Lys Asp Ala Asp Ala Asn Phe Asp Ser
            275                 280                 285

Ile Arg Val Asp Ala Val Asp Asn Val Asp Ala Asp Leu Leu Gln Ile
290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
            340                 345                 350

Lys Phe Arg Leu Ser Met Leu Trp Ser Leu Ala Lys Pro Leu Asp Lys
            355                 360                 365

Arg Ser Gly Leu Asn Pro Leu Ile His Asn Ser Leu Val Asp Arg Glu
370                 375                 380

Val Asp Asp Arg Glu Val Glu Thr Val Pro Ser Tyr Ser Phe Ala Arg
385                 390                 395                 400

Ala His Asp Ser Glu Val Gln Asp Ile Ile Arg Asp Ile Ile Lys Ala
                405                 410                 415

Glu Ile Asn Pro Asn Ser Phe Gly Tyr Ser Phe Thr Gln Glu Glu Ile
            420                 425                 430

Asp Gln Ala Phe Lys Ile Tyr Asn Glu Asp Leu Lys Lys Thr Asp Lys
            435                 440                 445

Lys Tyr Thr His Tyr Asn Val Pro Leu Ser Tyr Thr Leu Leu Leu Thr
450                 455                 460

Asn Lys Gly Ser Ile Pro Arg Val Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ser Gly Gly Gln Ala Met
            500                 505                 510

Gln Asn Tyr Gln Ile Gly Asn Gly Glu Ile Leu Thr Ser Val Arg Tyr
            515                 520                 525

Gly Lys Gly Ala Leu Lys Gln Ser Asp Lys Gly Asp Ala Thr Thr Arg
530                 535                 540

Thr Ser Gly Val Gly Val Met Gly Asn Gln Pro Asn Phe Ser Leu
545                 550                 555                 560

Asp Gly Lys Val Val Ala Leu Asn Met Gly Ala Ala His Ala Asn Gln
                565                 570                 575

Glu Tyr Arg Ala Leu Met Val Ser Thr Lys Asp Gly Val Ala Thr Tyr
            580                 585                 590

Ala Thr Asp Ala Asp Ala Ser Lys Ala Gly Leu Val Lys Arg Thr Asp
            595                 600                 605

Glu Asn Gly Tyr Leu Tyr Phe Leu Asn Asp Asp Leu Lys Gly Val Ala
610                 615                 620

Asn Pro Gln Val Ser Gly Phe Leu Gln Val Trp Val Pro Val Gly Ala
625                 630                 635                 640

Ala Asp Asp Gln Asp Ile Arg Val Ala Ala Ser Asp Thr Ala Ser Thr
                645                 650                 655

Asp Gly Lys Ser Leu His Gln Asp Ala Ala Met Asp Ser Arg Val Met
            660                 665                 670

Phe Glu Gly Phe Ser Asn Phe Gln Ser Phe Ala Thr Lys Glu Glu
            675                 680                 685
```

-continued

```
Tyr Thr Asn Val Val Ile Ala Asn Asn Val Asp Lys Phe Val Ser Trp
    690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
            725                 730                 735

Arg Tyr Asp Leu Gly Met Ser Lys Ala Asn Lys Tyr Gly Thr Ala Asp
            740                 745                 750

Gln Leu Val Lys Ala Ile Lys Ala Leu His Ala Lys Gly Leu Lys Val
            755                 760                 765

Met Ala Asp Trp Val Pro Asp Gln Met Tyr Thr Phe Pro Lys Gln Glu
    770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Asp Thr Lys Ser Ser Gly
            805                 810                 815

Asp Asp Tyr Gln Ala Lys Tyr Gly Gly Ala Phe Leu Asp Glu Leu Lys
            820                 825                 830

Glu Lys Tyr Pro Glu Leu Phe Thr Lys Lys Gln Ile Ser Thr Gly Gln
            835                 840                 845

Ala Ile Asp Pro Ser Val Lys Ile Lys Gln Trp Ser Ala Lys Tyr Phe
    850                 855                 860

Asn Gly Ser Asn Ile Leu Gly Arg Gly Ala Asp Tyr Val Leu Ser Asp
865                 870                 875                 880

Gln Val Ser Asn Lys Tyr Phe Asn Val Ala Ser Asp Thr Leu Phe Leu
            885                 890                 895

Pro Ser Ser Leu Leu Gly Lys Val Val Glu Ser Gly Ile Arg Tyr Asp
            900                 905                 910

Gly Lys Gly Tyr Ile Tyr Asn Ser Ser Ala Thr Gly Asp Gln Val Lys
            915                 920                 925

Ala Ser Phe Ile Thr Glu Ala Gly Asn Leu Tyr Tyr Phe Gly Lys Asp
    930                 935                 940

Gly Tyr Met Val Thr Gly Ala Gln Thr Ile Asn Gly Ala Asn Tyr Phe
945                 950                 955                 960

Phe Leu Glu Asn Gly Thr Ala Leu Arg Asn Thr Ile Tyr Thr Asp Ala
            965                 970                 975

Gln Gly Asn Ser His Tyr Tyr Ala Asn Asp Gly Lys Arg Tyr Glu Asn
            980                 985                 990

Gly Tyr Gln Gln Phe Gly Asn Asp Trp Arg Tyr Phe Lys Asp Gly Asn
            995                 1000                1005

Met Ala Val Gly Leu Thr Thr Val Asp Gly Asn Val Gln Tyr Phe
    1010                1015                1020

Asp Lys Asp Gly Val Gln Ala Lys Asp Lys Ile Ile Val Thr Arg
    1025                1030                1035

Asp Gly Lys Val Arg Tyr Phe Asp Gln His Asn Gly Asn Ala Val
    1040                1045                1050

Thr Asn Thr Phe Ile Ala Asp Lys Thr Gly His Trp Tyr Tyr Leu
    1055                1060                1065

Gly Lys Asp Gly Val Ala Val Thr Gly Ala Gln Thr Val Gly Lys
    1070                1075                1080

Gln Lys Leu Tyr Phe Glu Ala Asn Gly Glu Gln Val Lys Gly Asp
    1085                1090                1095

Phe Val Thr Ser His Glu Gly Lys Leu Tyr Phe Tyr Asp Val Asp
```

|  | 1100 |  |  | 1105 |  |  | 1110 |  |  |
| --- | --- | --- | --- | --- | --- | --- | --- | --- | --- |

Ser Gly Asp Met Trp Thr Asp Thr Phe Ile Glu Asp Lys Ala Gly
     1115                1120                1125

Asn Trp Phe Tyr Leu Gly Lys Asp Gly Ala Ala Val Ser Gly Ala
     1130                1135                1140

Gln Thr Ile Arg Gly Gln Lys Leu Tyr Phe Lys Ala Tyr Gly Gln
     1145                1150                1155

Gln Val Lys Gly Asp Ile Val Lys Gly Thr Asp Gly Lys Ile Arg
     1160                1165                1170

Tyr Tyr Asp Ala Lys Ser Gly Glu Gln Val Phe Asn Lys Thr Val
     1175                1180                1185

Lys Ala Ala Asp Gly Lys Thr Tyr Val Ile Gly Asn Asn Gly Val
     1190                1195                1200

Ala Val Asp Pro Ser Val Val Lys Gly Gln Thr Phe Lys Asp Ala
     1205                1210                1215

Ser Gly Ala Leu Arg Phe Tyr Asn Leu Lys Gly Gln Leu Val Thr
     1220                1225                1230

Gly Ser Gly Trp Tyr Glu Thr Ala Asn His Asp Trp Val Tyr Ile
     1235                1240                1245

Gln Ser Gly Lys Ala Leu Thr Gly Glu Gln Thr Ile Asn Gly Gln
     1250                1255                1260

His Leu Tyr Phe Lys Glu Asp Gly His Gln Val Lys Gly Gln Leu
     1265                1270                1275

Val Thr Arg Thr Asp Gly Lys Val Arg Tyr Tyr Asp Ala Asn Ser
     1280                1285                1290

Gly Asp Gln Ala Phe Asn Lys Ser Val Thr Val Asn Gly Lys Thr
     1295                1300                1305

Tyr Tyr Phe Gly Asn Asp Gly Thr Ala Gly Thr Ala Gly Asn Pro
     1310                1315                1320

Lys Gly Gln Ile Phe Lys Asp Gly Ser Val Leu Arg Phe Tyr Ser
     1325                1330                1335

Met Glu Gly Gln Leu Val Ile Gly Ser Gly Trp Tyr Ser Asn Ala
     1340                1345                1350

Gln Gly Gln Trp Leu Tyr Val Lys Asn Gly Lys Val Leu Thr Gly
     1355                1360                1365

Leu Gln Thr Val Gly Ser Gln Arg Val Tyr Phe Asp Glu Asn Gly
     1370                1375                1380

Ile Gln Ala Lys Gly Lys Ala Val Arg Thr Ser Asp Gly Lys Ile
     1385                1390                1395

Arg Tyr Phe Asp Glu Asn Ser Gly Ser Met Ile Thr Asn Gln Trp
     1400                1405                1410

Lys Phe Val Tyr Gly Gln Tyr Tyr Tyr Phe Gly Asn Asp Gly Ala
     1415                1420                1425

Ala Ile Tyr Arg Gly Trp Asn
     1430                1435

<210> SEQ ID NO 27
<211> LENGTH: 4023
<212> TYPE: DNA
<213> ORGANISM: Streptococcus salivarius

<400> SEQUENCE: 27
atgattgacg gcaaatacta ctacgtaaac aaagatggct cgcacaaaga gaatttcgca      60
attaccgtga atggtcagtt gttgtatttc ggtaaggacg gtgcattgac gtctagcagc     120

```
acctacagct ttacgcaggg caccaccaac atcgttgatg ctttagcaa aaacaaccgt      180 gcgtacgatt ccagcgaggc gagctttgaa ctgatcgacg ttatctgac cgcggactcc      240 tggtatcgtc cggtgagcat tatcaaggac ggcgttacgt ggcaagccag caccaaagag      300
gactttcgcc cgctgctgat ggcctggtgg ccgaatgttg cacccaggt caactacctg       360 aattacatgt cgaaggtgtt taacctggac gcgaagtata cgagcaccga caaacaggtt      420
gacctgaatc gcgcagccaa ggacattcag gttaagattg agcaaaagat tcaggccgag      480
aagagcactc aatggctgcg tgaagcgatt tcggccttcg tcaaaaccca gccgcagtgg      540
aataaagaaa cggagaactt ctccaagggt ggtggtgagg atcatctgca aggtggtgca      600
ctgctgtacg ttaacgaccc gcgtaccccg tgggctaact ccaactaccg cctgctgaat      660
cgtactgcga ccaaccagac cggcacgatc gacaagagcg ttctggacga acagagcgat      720
cctaaccaca tgggcggctt cgattttctg ctggcgaatg acgtcgatac cagcaatccg      780
gtggtgcagg cggaacaact gaatcagatc cactacctga tgaattgggg ttccattgtt      840
atgggcgaca aagatgcaaa cttcgatggt atccgcgtgg acgcggtcga taacgttgac      900
gcagatatgc tgcaactgta caccaactac tttcgtgagt attatggcgt gaacaaaagc      960
gaggcaaacg ctttggcgca catctcggtg ctggaagcgt ggagcttgaa tgataatcac     1020
tataatgaca agactgacgg tgcggccctg gcgatggaga caaacagcg tttggccctg     1080 ctgtttagct tggcgaaacc gatcaaagaa cgtacccctg cggtgagccc gctgtacaac     1140
aacactttca acacgacgca gcgtgacgaa aagaccgatt ggattaacaa agacggtagc     1200
aaagcctata atgaggacgg caccgtcaag cagtccacca tcggcaagta caacgagaaa     1260
tacggcgacg cgtccggcaa ttatgtgttc attcgcgccc acgataacaa cgtccaagac     1320
attattgcag agatcattaa gaaagaaatc aatccgaaaa gcgacggttt caccattacc     1380
gacgccgaaa tgaaaaaggc attcgaaatc tacaacaaag atatgctgtc ctctgataag     1440
aaatacaccc tgaacaacat cccagcggcc tacgcggtga tgctgcaaaa catggaaacc     1500
attactcgtg tgtattacgg cgatctgtat accgacgatg ccattacat ggaaaccaag     1560 agcccgtact acgacaccat tgtgaacctg atgaagaacc gtatcaaata cgtgtccggt     1620
ggtcaagcgc aacgttccta ttggctgccg accgacggta agatggataa aagcgatgtc     1680
gaactgtatc gcaccaacga ggtgtacacc agcgtccgtt acggtaagga catcatgact     1740
gccgatgaca cccaaggtag caagtacagc cgtaccagcg gtcaggtgac cctggtggtg     1800
aacaacccga agctgtcttt ggataagagc gcgaagctgg acgtcgaaat gggcaagatc     1860
catgcaaacc agaaataccg tgctctgatc gtgggtacgc cgaacggcat caaaaacttc     1920
acgagcgacg ccgaggcaat cgcggctggc tacgtgaaag aaaccgacgg caatggtgtg     1980
ctgaccttcg gtgcaaatga catcaaaggt tacgaaacgt tgacatgag cggtttcgtt     2040 gcagtttggg ttccggtagg tgcaagcgat gatcaagaca tccgtgtcgc cgcaagcacc     2100
gcggcaaaga aagaaggtga gctgactttg aaggcaactg aggcgtatga ctctcagctg     2160
atttacgaag gttttcgaa ttttcagacc attccggatg gtagcgatcc gagcgtttac     2220
accaatcgta agatcgcgga aaatgttgat ttgttcaaga gctggggtgt gacctctttc     2280
gaaatggcgc cacagtttgt gagcgcagac gacggtacgt ttctggacag cgttatccag     2340
aacggctatg cgtttgcgga ccgttatgat ctggcgatgt ccaaaaacaa taagtacggt     2400
tcgaaagaag atctgcgtaa cgcgttgaag gctttgcaca aggccggcat ccaagccatt     2460
```

-continued

```
gcggactggg ttccggatca gatctaccaa ctgccgggca agaagtagt gaccgccact    2520
cgtaccgatg gtgccggtcg taagattagc gatgcaatta tcgatcacag cctgtacgtc    2580
gcaaacagca agtcgtctgg caaagactat caagctaaat acggtggtga gttcctggcc    2640
gagctgaaag caaagtaccc ggaaatgttt aaagtcaaca tgattagcac gggtaaaccg    2700
atcgacgact ctgtcaaact gaagcaatgg aaggcggagt actttaacgg tacgaatgtt    2760
ctggaccgtg tgttggtta cgtcctgagc gatgaggcga cgggcaagta ctttaccgtt    2820
acgaaagagg gtaactttat cccactgcaa ttgaaaggta cgagaaagt tatcacgggc    2880
ttcagctctg acggcaaggg cattacctat ttcggcacct cggtaatca agcgaaaagc    2940
gcttttgtca cgttcaatgg taatacctac tattttgacg cgcgtggcca catggttacc    3000
aacggcgaat atagccctaa tggtaaggat gtgtatcgtt tcctgccgaa tggtattatg    3060
ttgagcaatg cattctacgt tgacggtaac ggcaatacct acctgtacaa ctccaagggc    3120
caaatgtaca aggtggtta tagcaaattc gacgttacgg aaaccaaaga tggtaaagag    3180
agcaaagtgg tgaaatttcg ctactttacc aatgaaggtg tgatggcaaa aggtgttacc    3240
gtggtggacg gcttcactca atacttcaac gaagatggca ttcagagcaa ggacgaactg    3300
gtgacctaca atggtaaaac ctattacttc gaagcgcata ccggtaatgc gatcaaaaac    3360
acgtggcgca atatcaaggg taagtggtat cactttgatg cgaatggcgt ggcggcaacg    3420
ggtgcacagg ttatcaatgg tcagcacctg tactttaatg aggatggttc ccaggtgaag    3480
ggtggcgtcg tgaagaatgc ggatggtacc ttcagcaagt ataaagatgg ttccggtgac    3540
ctggtggtca atgagttctt cactactggt gataacgtgt ggtactacgc tggtgccaac    3600
ggcaaaactg tgacgggtgc ccaggtcatc aatggccaac acctgttttt caaagaggac    3660
ggtagccagg ttaagggtga tttcgttaag aacagcgacg gcacctactc taagtatgat    3720
gcggccagcg gcgaacgcct gacgaatgag tttttcacga ccggtgacaa ccactggtac    3780
tatattggtg ccaatggcaa aaccgttacc ggcgaagtca gatcggtga tgatacgtac    3840
ttcttcgcaa agatggcaa gcagctgaag ggccagatcg tgacgacccg cagcggtcgt    3900
atcagctact acttcggcga ctctggtaag aaggcgatta gcacctgggt ggagattcag    3960
ccgggtgttt tcgtgttttt cgacaaaaat ggcctggcat atccgccgga aaacatgaat    4020
taa                                                                   4023
```

<210> SEQ ID NO 28
<211> LENGTH: 1340
<212> TYPE: PRT
<213> ORGANISM: Streptococcus salivarius

<400> SEQUENCE: 28

```
Met Ile Asp Gly Lys Tyr Tyr Val Asn Lys Asp Gly Ser His Lys
1               5                   10                  15

Glu Asn Phe Ala Ile Thr Val Asn Gly Gln Leu Leu Tyr Phe Gly Lys
                20                  25                  30

Asp Gly Ala Leu Thr Ser Ser Thr Tyr Ser Phe Thr Gln Gly Thr
            35                  40                  45

Thr Asn Ile Val Asp Gly Phe Ser Lys Asn Asn Arg Ala Tyr Asp Ser
        50                  55                  60

Ser Glu Ala Ser Phe Glu Leu Ile Asp Gly Tyr Leu Thr Ala Asp Ser
65                  70                  75                  80

Trp Tyr Arg Pro Val Ser Ile Ile Lys Asp Gly Val Thr Trp Gln Ala
                85                  90                  95
```

```
Ser Thr Lys Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Thr Ser Thr Asp Lys Gln Val Asp Leu Asn Arg
    130                 135                 140

Ala Ala Lys Asp Ile Gln Val Lys Ile Glu Gln Lys Ile Gln Ala Glu
145                 150                 155                 160

Lys Ser Thr Gln Trp Leu Arg Glu Ala Ile Ser Ala Phe Val Lys Thr
                165                 170                 175

Gln Pro Gln Trp Asn Lys Glu Thr Glu Asn Phe Ser Lys Gly Gly Gly
            180                 185                 190

Glu Asp His Leu Gln Gly Gly Ala Leu Leu Tyr Val Asn Asp Pro Arg
        195                 200                 205

Thr Pro Trp Ala Asn Ser Asn Tyr Arg Leu Leu Asn Arg Thr Ala Thr
    210                 215                 220

Asn Gln Thr Gly Thr Ile Asp Lys Ser Val Leu Asp Glu Gln Ser Asp
225                 230                 235                 240

Pro Asn His Met Gly Gly Phe Asp Phe Leu Leu Ala Asn Asp Val Asp
                245                 250                 255

Thr Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
        355                 360                 365

Lys Glu Arg Thr Pro Ala Val Ser Pro Leu Tyr Asn Asn Thr Phe Asn
    370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
        435                 440                 445

Glu Ile Asn Pro Lys Ser Asp Gly Phe Thr Ile Thr Asp Ala Glu Met
    450                 455                 460

Lys Lys Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510
```

```
Asp Gly His Tyr Met Glu Thr Lys Ser Pro Tyr Tyr Asp Thr Ile Val
            515                 520                 525

Asn Leu Met Lys Asn Arg Ile Lys Tyr Val Ser Gly Gly Gln Ala Gln
        530                 535                 540

Arg Ser Tyr Trp Leu Pro Thr Asp Gly Lys Met Asp Lys Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asp Asp Thr Gln Gly Ser Lys Tyr Ser Arg Thr
            580                 585                 590

Ser Gly Gln Val Thr Leu Val Val Asn Asn Pro Lys Leu Ser Leu Asp
        595                 600                 605

Lys Ser Ala Lys Leu Asp Val Glu Met Gly Lys Ile His Ala Asn Gln
610                 615                 620

Lys Tyr Arg Ala Leu Ile Val Gly Thr Pro Asn Gly Ile Lys Asn Phe
625                 630                 635                 640

Thr Ser Asp Ala Glu Ala Ile Ala Ala Gly Tyr Val Lys Glu Thr Asp
                645                 650                 655

Gly Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Ala Ser Thr Ala Ala Lys Lys
690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
770                 775                 780

Phe Ala Asp Arg Tyr Asp Leu Ala Met Ser Lys Asn Asn Lys Tyr Gly
785                 790                 795                 800

Ser Lys Glu Asp Leu Arg Asn Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ser Asp Ala Ile Ile Asp His Ser Leu Tyr Val Ala Asn Ser Lys
850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
            900                 905                 910

Glu Tyr Phe Asn Gly Thr Asn Val Leu Asp Arg Gly Val Gly Tyr Val
        915                 920                 925

Leu Ser Asp Glu Ala Thr Gly Lys Tyr Phe Thr Val Thr Lys Glu Gly
```

-continued

```
              930                 935                 940
Asn Phe Ile Pro Leu Gln Leu Lys Gly Asn Glu Lys Val Ile Thr Gly
945                 950                 955                 960

Phe Ser Ser Asp Gly Lys Gly Ile Thr Tyr Phe Gly Thr Ser Gly Asn
                965                 970                 975

Gln Ala Lys Ser Ala Phe Val Thr Phe Asn Gly Asn Thr Tyr Tyr Phe
            980                 985                 990

Asp Ala Arg Gly His Met Val Thr Asn Gly Glu Tyr Ser Pro Asn Gly
        995                 1000                1005

Lys Asp Val Tyr Arg Phe Leu Pro Asn Gly Ile Met Leu Ser Asn
    1010                1015                1020

Ala Phe Tyr Val Asp Gly Asn Gly Asn Thr Tyr Leu Tyr Asn Ser
    1025                1030                1035

Lys Gly Gln Met Tyr Lys Gly Gly Tyr Ser Lys Phe Asp Val Thr
    1040                1045                1050

Glu Thr Lys Asp Gly Lys Glu Ser Lys Val Val Lys Phe Arg Tyr
    1055                1060                1065

Phe Thr Asn Glu Gly Val Met Ala Lys Gly Val Thr Val Val Asp
    1070                1075                1080

Gly Phe Thr Gln Tyr Phe Asn Glu Asp Gly Ile Gln Ser Lys Asp
    1085                1090                1095

Glu Leu Val Thr Tyr Asn Gly Lys Thr Tyr Tyr Phe Glu Ala His
    1100                1105                1110

Thr Gly Asn Ala Ile Lys Asn Thr Trp Arg Asn Ile Lys Gly Lys
    1115                1120                1125

Trp Tyr His Phe Asp Ala Asn Gly Val Ala Ala Thr Gly Ala Gln
    1130                1135                1140

Val Ile Asn Gly Gln His Leu Tyr Phe Asn Glu Asp Gly Ser Gln
    1145                1150                1155

Val Lys Gly Gly Val Val Lys Asn Ala Asp Gly Thr Phe Ser Lys
    1160                1165                1170

Tyr Lys Asp Gly Ser Gly Asp Leu Val Val Asn Glu Phe Phe Thr
    1175                1180                1185

Thr Gly Asp Asn Val Trp Tyr Tyr Ala Gly Ala Asn Gly Lys Thr
    1190                1195                1200

Val Thr Gly Ala Gln Val Ile Asn Gly Gln His Leu Phe Phe Lys
    1205                1210                1215

Glu Asp Gly Ser Gln Val Lys Gly Asp Phe Val Lys Asn Ser Asp
    1220                1225                1230

Gly Thr Tyr Ser Lys Tyr Asp Ala Ala Ser Gly Glu Arg Leu Thr
    1235                1240                1245

Asn Glu Phe Phe Thr Thr Gly Asp Asn His Trp Tyr Tyr Ile Gly
    1250                1255                1260

Ala Asn Gly Lys Thr Val Thr Gly Glu Val Lys Ile Gly Asp Asp
    1265                1270                1275

Thr Tyr Phe Phe Ala Lys Asp Gly Lys Gln Leu Lys Gly Gln Ile
    1280                1285                1290

Val Thr Thr Arg Ser Gly Arg Ile Ser Tyr Tyr Phe Gly Asp Ser
    1295                1300                1305

Gly Lys Lys Ala Ile Ser Thr Trp Val Glu Ile Gln Pro Gly Val
    1310                1315                1320

Phe Val Phe Phe Asp Lys Asn Gly Leu Ala Tyr Pro Pro Glu Asn
    1325                1330                1335
```

Met Asn
        1340

<210> SEQ ID NO 29
<211> LENGTH: 4026
<212> TYPE: DNA
<213> ORGANISM: Streptococcus salivarius

<400> SEQUENCE: 29

| | | | | | | |
|---|---|---|---|---|---|---|
| atgacggacg | gtaaatacta | ttatgtaaat | gaggacggca | gccacaaaga | gaatttcgca | 60 |
| attacggtaa | acggtcaact | gttgtacttt | ggcaaggacg | gcgctctgac | gagcagcagc | 120 |
| acgcacagct | tcacgccggg | tactacgaat | attgtggacg | gtttctcgat | caacaaccgt | 180 |
| gcgtacgata | gcagcgaagc | gagctttgag | ctgatcaacg | gttacctgac | ggcggattcc | 240 |
| tggtatcgcc | cggtttctat | catcaaggat | ggcgtcacgt | ggcaggcaag | cactgccgag | 300 |
| gattttcgtc | cgctgttgat | ggcctggtgg | ccgaacgttg | atacccaggt | gaactatctg | 360 |
| aactatatgt | ccaaggtctt | taacctggaa | gccagtaca | ccagcaccga | taaacaggct | 420 |
| gatctgaacc | gtgctgcaaa | ggatatccag | gtcaagatcg | aacagaagat | ccaggcggaa | 480 |
| aagagcacgc | agtggctgcg | tgagactatc | tccgcgtttg | ttaaaaccca | gccgcaatgg | 540 |
| aacaaagaga | ctgagaatta | ctccaagggt | ggtggcgaag | atcatctgca | aggcggtgcg | 600 |
| ctgttgtacg | tgaacgacag | ccgtaccccg | tgggcgaata | gcaattaccg | cctgctgaat | 660 |
| cgcacggcaa | cgaaccagac | cggtaccatt | aacaagtcgg | tgttggacga | gcaatccgat | 720 |
| ccaaatcaca | tgggtggctt | cgacttcctg | ctggcaaacg | atgtggatct | gagcaatcct | 780 |
| gttgtgcagg | ccgagcagct | gaatcaaatc | cattatctga | tgaactgggg | cagcattgtt | 840 |
| atgggtgaca | agacgcgaa | ttttgatggt | atccgtgtgg | acgccgttga | caacgtgaac | 900 |
| gctgacatgt | tgcagctgta | cacgaactac | tttcgtgagt | attacggcgt | caacaaaagc | 960 |
| gaagcgcaag | cgctggcgca | cattagcgtt | ctggaagcgt | ggagcttgaa | cgataaccac | 1020 |
| tataacgaca | aaaccgatgg | tgcggcactg | gcgatggaga | taagcaacg | tctggccttg | 1080 |
| ctgttctctc | tggccaagcc | gatcaaagat | cgtactccgg | cagtgagccc | actgtataac | 1140 |
| aatactttca | ataccaccca | acgtgacttc | aagacggatt | ggattaacaa | ggacggtagc | 1200 |
| accgcctaca | atgaggatgg | caccgcgaaa | caatctacca | tcggtaagta | caatgagaaa | 1260 |
| tatggtgatg | caagcggtaa | ctatgtgttt | attcgtgccc | atgacaataa | cgtccaagac | 1320 |
| attattgcgg | agatcattaa | gaaagaaatc | aataagaaga | gcgatggttt | taccatcagc | 1380 |
| gatagcgaaa | tgaaacaggc | gttcgaaatc | tacaacaaag | atatgctgag | cagcaataag | 1440 |
| aaatacactc | tgaataacat | tccggcagcg | tacgccgtga | tgctgcaaaa | catggagact | 1500 |
| atcacccgtg | tgtattatgg | tgacctgtac | accgacgacg | gtcactatat | ggaaaccaag | 1560 |
| agcccgtatc | atgacaccat | tgtgaacctg | atgaaaaacc | gtatcaagta | cgtttctggt | 1620 |
| ggccaggccc | aacgctccta | ttggctgccg | accgacggta | aaatggacaa | tagcgatgtc | 1680 |
| gaactgtacc | gtactagcga | ggtctatacc | agcgttcgct | acggtaagga | cattatgacg | 1740 |
| gcggatgaca | ccgagggtag | caagtactcc | cgcacgagcg | gtcaggttac | cctggttgtt | 1800 |
| aacaacccga | agctgactct | gcatgaaagc | gccaaactga | acgtcgagat | gggtaagatc | 1860 |
| cacgcaaacc | agaaataccg | tgcgctgatt | gtgggtaccg | ccgatggcat | caaaaacttt | 1920 |
| acgtctgatg | ccgaagcgat | cgcggcaggc | tacgtaaaag | aaacggacag | caatggtgtt | 1980 |
| ctgaccttcg | gcgcaaatga | tatcaaaggt | tacgagactt | tcgatatgag | cggtttcgtc | 2040 |

```
gcagtttggg tgccggtggg tgcgagcgat gatcaggaca tccgcgtggc gccgtcgacg    2100
gaagcgaaga aagaaggtga actgacgctg aaagccacgg aagcgtatga tagccagttg    2160
atttatgaag gcttctccaa tttccagacc attccggatg gcagcgaccc gagcgtttat    2220
accaaccgca aaattgctga gaatgttgat ctgtttaagt cctggggtgt cactagcttc    2280
gaaatggctc cgcagtttgt ttcggcggac gacggcacct tcctggatag cgttatccag    2340
aacggttacg cctttgcgga ccgttatgat ttggccatga gcaagaacaa caagtacggt    2400
tctaaagagg atctgcgcga cgcactgaaa gcgctgcaca agctggcat tcaggcaatc    2460 gcggactggg tcccagacca aatctaccaa ctgccaggca agaagtggt tacggcgacg    2520 cgcacggacg gtgcgggtcg caagatcgcg gacgccatca ttgatcatag cctgtatgtt    2580
gctaactcca gagctccgg tcgcgattac caagcgcagt atggtggcga gtttctggca    2640
gagctgaaag cgaagtaccc gaaaatgttc acggaaaaca tgattagcac gggtaagccg    2700
atcgatgaca gcgtcaaact gaagcaatgg aaagccaagt atttcaatgg tacgaatgtg    2760
ctggaccgtg gtgtcggtta cgtcctgtcc gacgaggcga ccggcaaata cttcaccgtt    2820
accaaagagg gtaacttcat tccgctgcaa ctgaccggca tgaaaaagc ggtgaccggt    2880 ttcagcaacg acggcaaggg tatcacctac tttggtacga gcggtaatca ggccaagagc    2940
gcgttcgtca cctttaacgg caatacgtac tatttcgacg cgcgtggcca catggtcacg    3000
aacggcgagt atagcccgaa cggcaaagat gtctaccgtt ttctgccaaa tggtattatg    3060
ttgtcgaacg cgttttatgt cgacgcaaac ggtaatacgt acttgtacaa ctacaagggc    3120
cagatgtaca aggtggtta tacgaaattt gatgtcaccg aaactgataa agatggtaat    3180
gagagcaagg tggtcaagtt tcgttatttc accaatgagg gcgtcatggc taagggtctg    3240
accgtcattg acggtagcac ccagtacttt ggtgaggatg gttttcaaac gaaggacaag    3300
ctggcgacct ataaaggtaa gacttattac ttcgaggcac acacgggcaa tgcgatcaaa    3360
aacacctggc gtaacatcga cggtaagtgg tatcacttcg atgagaatgg cgttgccgcg    3420
accggtgcac aagtgattaa cggtcaaaaa ctgtatttca cgaggatgg ctcgcaagtg    3480 aagggcggtg ttgttaagaa cgccgacggt acctacagca aatacaaaga gggcagcggt    3540
gagctggtta ccaacgagtt tttcacgacc gacggtaatg tgtggtacta tgctggtgcg    3600
gatggcaaga ctgtgaccgg tgctcaggtc attaatggtc agcacctgta ctttaaagaa    3660
gatggcagcc aggtgaaagg tggtgtggtg aaaaacgcgg acggtacgta cagcaagtat    3720
gacgccgcca ccggtgaacg cttgaccaat gagttcttta ccacgggcga taacaattgg    3780
tactatattg gttctaatgg taagaccgta accggtgaag tcaaaatcgg tgcggacacc    3840
tattactttg ccaaagatgg caaacaggtc aagggccaaa ccgtcaccgc aggcaatggc    3900
cgcatctcct attactacgg cgattctggt aagaaagcaa tcagcacgtg gatcgaaatt    3960
caaccgggta tctatgtcta ttttgataag acgggcatcg cgtacccacc gcgtgtgctg    4020
aattaa                                                                4026
```

<210> SEQ ID NO 30
<211> LENGTH: 1341
<212> TYPE: PRT
<213> ORGANISM: Streptococcus salivarius

<400> SEQUENCE: 30

Met Thr Asp Gly Lys Tyr Tyr Tyr Val Asn Glu Asp Gly Ser His Lys
1               5                   10                  15

```
Glu Asn Phe Ala Ile Thr Val Asn Gly Gln Leu Leu Tyr Phe Gly Lys
             20                  25                  30

Asp Gly Ala Leu Thr Ser Ser Thr His Ser Phe Thr Pro Gly Thr
         35                  40                  45

Thr Asn Ile Val Asp Gly Phe Ser Ile Asn Asn Arg Ala Tyr Asp Ser
     50                  55                  60

Ser Glu Ala Ser Phe Glu Leu Ile Asn Gly Tyr Leu Thr Ala Asp Ser
 65                  70                  75                  80

Trp Tyr Arg Pro Val Ser Ile Ile Lys Asp Gly Val Thr Trp Gln Ala
             85                  90                  95

Ser Thr Ala Glu Asp Phe Arg Pro Leu Leu Met Ala Trp Trp Pro Asn
             100                 105                 110

Val Asp Thr Gln Val Asn Tyr Leu Asn Tyr Met Ser Lys Val Phe Asn
             115                 120                 125

Leu Glu Ala Lys Tyr Thr Ser Thr Asp Lys Gln Ala Asp Leu Asn Arg
 130                 135                 140

Ala Ala Lys Asp Ile Gln Val Lys Ile Glu Gln Lys Ile Gln Ala Glu
 145                 150                 155                 160

Lys Ser Thr Gln Trp Leu Arg Glu Thr Ile Ser Ala Phe Val Lys Thr
             165                 170                 175

Gln Pro Gln Trp Asn Lys Glu Thr Glu Asn Tyr Ser Lys Gly Gly Gly
             180                 185                 190

Glu Asp His Leu Gln Gly Gly Ala Leu Leu Tyr Val Asn Asp Ser Arg
             195                 200                 205

Thr Pro Trp Ala Asn Ser Asn Tyr Arg Leu Leu Asn Arg Thr Ala Thr
             210                 215                 220

Asn Gln Thr Gly Thr Ile Asn Lys Ser Val Leu Asp Glu Gln Ser Asp
 225                 230                 235                 240

Pro Asn His Met Gly Gly Phe Asp Phe Leu Leu Ala Asn Asp Val Asp
             245                 250                 255

Leu Ser Asn Pro Val Val Gln Ala Glu Gln Leu Asn Gln Ile His Tyr
             260                 265                 270

Leu Met Asn Trp Gly Ser Ile Val Met Gly Asp Lys Asp Ala Asn Phe
             275                 280                 285

Asp Gly Ile Arg Val Asp Ala Val Asp Asn Val Asn Ala Asp Met Leu
             290                 295                 300

Gln Leu Tyr Thr Asn Tyr Phe Arg Glu Tyr Tyr Gly Val Asn Lys Ser
 305                 310                 315                 320

Glu Ala Gln Ala Leu Ala His Ile Ser Val Leu Glu Ala Trp Ser Leu
             325                 330                 335

Asn Asp Asn His Tyr Asn Asp Lys Thr Asp Gly Ala Ala Leu Ala Met
             340                 345                 350

Glu Asn Lys Gln Arg Leu Ala Leu Leu Phe Ser Leu Ala Lys Pro Ile
             355                 360                 365

Lys Asp Arg Thr Pro Ala Val Ser Pro Leu Tyr Asn Asn Thr Phe Asn
             370                 375                 380

Thr Thr Gln Arg Asp Phe Lys Thr Asp Trp Ile Asn Lys Asp Gly Ser
 385                 390                 395                 400

Thr Ala Tyr Asn Glu Asp Gly Thr Ala Lys Gln Ser Thr Ile Gly Lys
             405                 410                 415

Tyr Asn Glu Lys Tyr Gly Asp Ala Ser Gly Asn Tyr Val Phe Ile Arg
             420                 425                 430
```

```
Ala His Asp Asn Asn Val Gln Asp Ile Ile Ala Glu Ile Lys Lys
            435                 440                 445

Glu Ile Asn Lys Lys Ser Asp Gly Phe Thr Ile Ser Asp Ser Glu Met
450                 455                 460

Lys Gln Ala Phe Glu Ile Tyr Asn Lys Asp Met Leu Ser Ser Asn Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr His Asp Thr Ile Val
        515                 520                 525

Asn Leu Met Lys Asn Arg Ile Lys Tyr Val Ser Gly Gly Gln Ala Gln
    530                 535                 540

Arg Ser Tyr Trp Leu Pro Thr Asp Gly Lys Met Asp Asn Ser Asp Val
545                 550                 555                 560

Glu Leu Tyr Arg Thr Ser Glu Val Tyr Thr Ser Val Arg Tyr Gly Lys
                565                 570                 575

Asp Ile Met Thr Ala Asp Asp Thr Glu Gly Ser Lys Tyr Ser Arg Thr
            580                 585                 590

Ser Gly Gln Val Thr Leu Val Val Asn Asn Pro Lys Leu Thr Leu His
        595                 600                 605

Glu Ser Ala Lys Leu Asn Val Glu Met Gly Lys Ile His Ala Asn Gln
    610                 615                 620

Lys Tyr Arg Ala Leu Ile Val Gly Thr Ala Asp Gly Ile Lys Asn Phe
625                 630                 635                 640

Thr Ser Asp Ala Glu Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Pro Ser Thr Glu Ala Lys Lys
    690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
    770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ala Asp Ala Ile Ile Asp His Ser Leu Tyr Val Ala Asn Ser Lys
```

-continued

```
            850                 855                 860
Ser Ser Gly Arg Asp Tyr Gln Ala Gln Tyr Gly Gly Glu Phe Leu Ala
865                 870                 875                 880
Glu Leu Lys Ala Lys Tyr Pro Lys Met Phe Thr Glu Asn Met Ile Ser
                    885                 890                 895
Thr Gly Lys Pro Ile Asp Asp Ser Val Lys Leu Lys Gln Trp Lys Ala
                900                 905                 910
Lys Tyr Phe Asn Gly Thr Asn Val Leu Asp Arg Gly Val Gly Tyr Val
            915                 920                 925
Leu Ser Asp Glu Ala Thr Gly Lys Tyr Phe Thr Val Thr Lys Glu Gly
930                 935                 940
Asn Phe Ile Pro Leu Gln Leu Thr Gly Asn Glu Lys Ala Val Thr Gly
945                 950                 955                 960
Phe Ser Asn Asp Gly Lys Gly Ile Thr Tyr Phe Gly Ser Gly Asn
                965                 970                 975
Gln Ala Lys Ser Ala Phe Val Thr Phe Asn Gly Asn Thr Tyr Tyr Phe
                980                 985                 990
Asp Ala Arg Gly His Met Val Thr Asn Gly Glu Tyr Ser Pro Asn Gly
            995                 1000                1005
Lys Asp Val Tyr Arg Phe Leu Pro Asn Gly Ile Met Leu Ser Asn
            1010                1015                1020
Ala Phe Tyr Val Asp Ala Asn Gly Asn Thr Tyr Leu Tyr Asn Tyr
            1025                1030                1035
Lys Gly Gln Met Tyr Lys Gly Tyr Thr Lys Phe Asp Val Thr
            1040                1045                1050
Glu Thr Asp Lys Asp Gly Asn Glu Ser Lys Val Val Lys Phe Arg
            1055                1060                1065
Tyr Phe Thr Asn Glu Gly Val Met Ala Lys Gly Leu Thr Val Ile
            1070                1075                1080
Asp Gly Ser Thr Gln Tyr Phe Gly Glu Asp Gly Phe Gln Thr Lys
            1085                1090                1095
Asp Lys Leu Ala Thr Tyr Lys Gly Lys Thr Tyr Tyr Phe Glu Ala
            1100                1105                1110
His Thr Gly Asn Ala Ile Lys Asn Thr Trp Arg Asn Ile Asp Gly
            1115                1120                1125
Lys Trp Tyr His Phe Asp Glu Asn Gly Val Ala Ala Thr Gly Ala
            1130                1135                1140
Gln Val Ile Asn Gly Gln Lys Leu Tyr Phe Asn Glu Asp Gly Ser
            1145                1150                1155
Gln Val Lys Gly Gly Val Val Lys Asn Ala Asp Gly Thr Tyr Ser
            1160                1165                1170
Lys Tyr Lys Glu Gly Ser Gly Glu Leu Val Thr Asn Glu Phe Phe
            1175                1180                1185
Thr Thr Asp Gly Asn Val Trp Tyr Tyr Ala Gly Ala Asp Gly Lys
            1190                1195                1200
Thr Val Thr Gly Ala Gln Val Ile Asn Gly Gln His Leu Tyr Phe
            1205                1210                1215
Lys Glu Asp Gly Ser Gln Val Lys Gly Gly Val Val Lys Asn Ala
            1220                1225                1230
Asp Gly Thr Tyr Ser Lys Tyr Asp Ala Ala Thr Gly Glu Arg Leu
            1235                1240                1245
Thr Asn Glu Phe Phe Thr Thr Gly Asp Asn Asn Trp Tyr Tyr Ile
            1250                1255                1260
```

| Gly | Ser | Asn | Gly | Lys | Thr | Val | Thr | Gly | Glu | Val | Lys | Ile | Gly | Ala |
| | 1265 | | | | 1270 | | | | 1275 | | | | | |

| Asp | Thr | Tyr | Tyr | Phe | Ala | Lys | Asp | Gly | Lys | Gln | Val | Lys | Gly | Gln |
| | 1280 | | | | | 1285 | | | | 1290 | | | | |

| Thr | Val | Thr | Ala | Gly | Asn | Gly | Arg | Ile | Ser | Tyr | Tyr | Tyr | Gly | Asp |
| | 1295 | | | | | 1300 | | | | | 1305 | | | |

| Ser | Gly | Lys | Lys | Ala | Ile | Ser | Thr | Trp | Ile | Glu | Ile | Gln | Pro | Gly |
| | 1310 | | | | | 1315 | | | | 1320 | | | | |

| Ile | Tyr | Val | Tyr | Phe | Asp | Lys | Thr | Gly | Ile | Ala | Tyr | Pro | Pro | Arg |
| | 1325 | | | | | 1330 | | | | 1335 | | | | |

| Val | Leu | Asn |
| | 1340 | |

<210> SEQ ID NO 31
<211> LENGTH: 3918
<212> TYPE: DNA
<213> ORGANISM: Streptococcus salivarius

<400> SEQUENCE: 31

```
atgatcgacg gcaaacagta ttatgtagag aacggtgtgg ttaagaaaaa tgcggcaatt      60
gaactggatg gccgcctgta ctactttgat gagactggcg caatggtcga tcagagcaaa     120
ccgttgtatc gtgcggacgc gattccgaac aactctatct acgccgtgta caaccaagcg     180
tatgatacca gcagcaaatc cttcgagcat ttggataact tcctgaccgc ggatagctgg     240
tatcgcccga acagattcgt gaaggacggt aaaaactgga ccgcaagcac tgagaaagac     300
tatcgtcctc tgctgatgac ctggtggccg gacaaggtga cccaggtgaa ttacctgaac     360
tatatgtctc aacagggttt tggtaacaaa acgtacacca cggatatgat gagctacgac     420
ctggcggctg cggcagaaac ggtgcagcgt ggcatcgaag agcgtatcgg tcgcgagggt     480
aacaccacgt ggctgcgcca gctgatgagc gatttcatca aaacccagcc gggttggaat     540
agcgagagcg aggacaatct gctggttggt aaggaccatc tgcaaggtgg tgcgctgacc     600
tttctgaaca atagcgcaac gagccacgcg aatagcgact tcgtctgat gaaccgtacc     660
ccgaccaatc agaccggtac ccgtaaatac cacatcgatc gtagcaatgg cggctatgag     720
ctgctgctgg ctaacgacat tgataatagc aatccggcag ttcaagcaga gcaactgaat     780
tggctgcact acattatgaa tattggcagc atcttgggta tgacccgag cgcgaatttt     840
gacggtgttc gtatcgatgc ggtggataat gtggacgcgg atttgctgca aatcgcgtct     900
gattacttca agagaagta ccgtgtcgcg gacaacgagg caaacgcgat tgcccacctg     960
agcattctgg aagcgtggag ctataatgat catcagtaca caaggacac gaagggcgca    1020
cagctgtcca tcgataaccc gctgcgcgaa accctgctga ctaccttcct gcgtaaaagc    1080
aattatcgtg gtagcttgga gcgcgttatt accaactccc tgaataaccg ctctagcgag    1140
caaaagcaca ctccgcgcga cgcgaactac atctttgtac gtgcgcatga cagcgaagtt    1200
caagacgtgc tggcgaatat cattagcaaa cagatcaacc caaagacgga tggcttcacg    1260
ttcaccatgg atgaactgaa gcaggcgttc gagatctaca atgcggatat tgcgaaggcg    1320
gacaagaagt ataccaata caacattccg gcagcttacg caaccatgct gacgaacaag    1380
gatagcatta cccgcgttta ctacggcgac ctgtttacgg atgacggtca gtatatggcc    1440
gagaaatccc cgtactataa cgcaattgac gctctgctgc gtgcgcgcat taagtacgtc    1500
gcgggtggtc aggacatgaa ggtgactaaa ctgaatggtt atgagattat gagcagcgtg    1560
```

```
cgttatggta aaggtgcaga agaggctaac cagctgggta cggcagaaac ccgcaatcaa    1620
ggtatgctgg ttctgacggc taaccgtccg acatgaaac tgggtgcaaa cgatcgcctg     1680
gtcgtgaata tgggcgctgc ccacaaaaac caggcctacc gcccgttgct gttgtccaaa    1740
tctactggcc tggcgacgta tctgaaagat agcgacgttc cggcaggcct ggtgcgttat    1800
accgataacc agggtaatct gacctttacg gcggacgata ttgcaggcca tagcacggtt    1860
gaagtgagcg gttacttggc ggtctgggtt ccggtcggcg cgagcgagaa ccaggacgcg    1920
cgcacgaagg ccagctctac caagaagggc gagcaagttt tcgaatctag cgccgctctg    1980
gacagccagg ttatctacga aggtttctcc aatttccaag attttgtcaa gacccccgagc   2040 cagtacacca accgcgtgat cgcgcaaaat gcgaagctgt ttaaagaatg gggcatcact    2100
agctttgagt tcgcgcctca gtatgttttct agccaagacg gcaccttttt ggatagcatc    2160
attgaaaacg gctacgcgtt cgaggatcgt tacgatatcg caatgagcaa gaacaataag    2220
tatggcagcc tgaaagattt gatggacgca ctgcgtgcgt tgcatgcgga aggcatcagc    2280
gcaatcgccg attgggtccc ggaccaaatc tataatctgc cgggtaaaga agttgtcacg    2340
gcgagccgta ccaacagcta tggtaccccg cgtccgaatg cggaaatcta caatagcctg    2400
tacgctgcta aaacgcgcac gttcggtaat gacttccagg gtaagtatgg tggcgcattt    2460
ctggacgaac tgaaagcaaa gtacccggcc atctttgagc gtgttcaaat cagcaacggt    2520
cgtaaattga ccacgaatga aagattacc cagtggagcg ccaaatactt taatggtagc     2580
aatattcagg gcacgggtgc gcgttacgtt ttgcaggaca cgctaccaa tcagtacttt     2640 agcgttaagg cgggtcagac tttcctgccg aagcagatga ccgaaattac cggcagcggt    2700
ttccgtcgtg tcggtgacga tgtccaatat ctgagcattg gtggttatct ggcgaagaat    2760
acctttatcc aggtcggtgc gaatcagtgg tattattttg acaaaaacgg caatatggtt    2820
acgggtgaac aggtgatcga tggtaaaaag tacttcttct tggataacgg tctgcaactg    2880
cgtcatgttc tgcgccaggg ctccgatggt cacgtctatt actatgaccc taaaggtgtg    2940
caagcgttca atggtttcta cgactttgca ggccctcgcc aagacgttcg ttacttcgat    3000
ggcaatggtc agatgtatcg cggcctgcac gatatgtacg gtacgacctt ttacttcgac    3060
gagaaaaccg gcatccaagc aaaagacaag ttcattcgct tcgcagacgg tcgtacccgt    3120
tacttcattc cggacaccgg taatctggca gtgaatcgtt tcgcccaaaa cccggagaac    3180
aaagcctggt attacctgga tagcaacggt tacgctgtca ccggcttgca gacgattaat    3240
ggcaagcagt attactttga caacgaaggc cgtcaggtta aaggccactt tgtgaccatt    3300
aacaaccagc gttactttct ggatggtgac tcgggcgaga tcgcgccatc gcgtttcgtt    3360
accgagaaca caagtggta ctacgtcgac ggtaatggta agctggtcaa gggtgcacag    3420
gtgattaacg gtaaccacta ctacttcaat aacgactata gccaggtgaa gggtgcatgg    3480
gcgaacggtc gttactacga tggcgacagc ggtcaagcgg tcagcaacca gtttattcaa    3540
attgcggcga accaatgggc atatctgaat caagatggcc acaaggtcac gggtctgcaa    3600
aacatcaaca ataaagtgta ctattttggc tctaatggcg cgcaagttaa gggtaaactg    3660
ctgaccgtgc aaggcaagaa atgctacttt gacgcccaca ccggtgagca agtcgttaat    3720
cgcttcgtgg aagctgcccg tggttgctgg tactatttca attccgctgg ccaggccgtt    3780 accggccaaac aagtcatcaa cggtaagcag ttgtattttg atggttctgg tcgtcaagtc    3840
aaaggccgtt atgtgtacgt gggtggtaaa cgtttgttct gtgatgcgaa aacgggcgag    3900
ctgcgtcaac gccgttaa                                                  3918
```

<210> SEQ ID NO 32
<211> LENGTH: 1305
<212> TYPE: PRT
<213> ORGANISM: Streptococcus salivarius

<400> SEQUENCE: 32

```
Met Ile Asp Gly Lys Gln Tyr Tyr Val Glu Asn Gly Val Val Lys Lys
1               5                   10                  15

Asn Ala Ala Ile Glu Leu Asp Gly Arg Leu Tyr Tyr Phe Asp Glu Thr
            20                  25                  30

Gly Ala Met Val Asp Gln Ser Lys Pro Leu Tyr Arg Ala Asp Ala Ile
        35                  40                  45

Pro Asn Asn Ser Ile Tyr Ala Val Tyr Asn Gln Ala Tyr Asp Thr Ser
    50                  55                  60

Ser Lys Ser Phe Glu His Leu Asp Asn Phe Leu Thr Ala Asp Ser Trp
65                  70                  75                  80

Tyr Arg Pro Lys Gln Ile Leu Lys Asp Gly Lys Asn Trp Thr Ala Ser
                85                  90                  95

Thr Glu Lys Asp Tyr Arg Pro Leu Leu Met Thr Trp Trp Pro Asp Lys
            100                 105                 110

Val Thr Gln Val Asn Tyr Leu Asn Tyr Met Ser Gln Gln Gly Phe Gly
        115                 120                 125

Asn Lys Thr Tyr Thr Thr Asp Met Met Ser Tyr Asp Leu Ala Ala Ala
    130                 135                 140

Ala Glu Thr Val Gln Arg Gly Ile Glu Glu Arg Ile Gly Arg Glu Gly
145                 150                 155                 160

Asn Thr Thr Trp Leu Arg Gln Leu Met Ser Asp Phe Ile Lys Thr Gln
                165                 170                 175

Pro Gly Trp Asn Ser Glu Ser Glu Asp Asn Leu Leu Val Gly Lys Asp
            180                 185                 190

His Leu Gln Gly Gly Ala Leu Thr Phe Leu Asn Asn Ser Ala Thr Ser
        195                 200                 205

His Ala Asn Ser Asp Phe Arg Leu Met Asn Arg Thr Pro Thr Asn Gln
    210                 215                 220

Thr Gly Thr Arg Lys Tyr His Ile Asp Arg Ser Asn Gly Gly Tyr Glu
225                 230                 235                 240

Leu Leu Leu Ala Asn Asp Ile Asp Asn Ser Asn Pro Ala Val Gln Ala
                245                 250                 255

Glu Gln Leu Asn Trp Leu His Tyr Ile Met Asn Ile Gly Ser Ile Leu
            260                 265                 270

Gly Asn Asp Pro Ser Ala Asn Phe Asp Gly Val Arg Ile Asp Ala Val
        275                 280                 285

Asp Asn Val Asp Ala Asp Leu Leu Gln Ile Ala Ser Asp Tyr Phe Lys
    290                 295                 300

Glu Lys Tyr Arg Val Ala Asp Asn Glu Asn Ala Ile Ala His Leu
305                 310                 315                 320

Ser Ile Leu Glu Ala Trp Ser Tyr Asn Asp His Gln Tyr Asn Lys Asp
                325                 330                 335

Thr Lys Gly Ala Gln Leu Ser Ile Asp Asn Pro Leu Arg Glu Thr Leu
            340                 345                 350

Leu Thr Thr Phe Leu Arg Lys Ser Asn Tyr Arg Gly Ser Leu Glu Arg
        355                 360                 365

Val Ile Thr Asn Ser Leu Asn Asn Arg Ser Ser Glu Gln Lys His Thr
```

```
              370                 375                 380
Pro Arg Asp Ala Asn Tyr Ile Phe Val Arg Ala His Asp Ser Glu Val
385                 390                 395                 400

Gln Asp Val Leu Ala Asn Ile Ile Ser Lys Gln Ile Asn Pro Lys Thr
                405                 410                 415

Asp Gly Phe Thr Phe Thr Met Asp Glu Leu Lys Gln Ala Phe Glu Ile
                420                 425                 430

Tyr Asn Ala Asp Ile Ala Lys Ala Asp Lys Lys Tyr Thr Gln Tyr Asn
                435                 440                 445

Ile Pro Ala Ala Tyr Ala Thr Met Leu Thr Asn Lys Asp Ser Ile Thr
450                 455                 460

Arg Val Tyr Tyr Gly Asp Leu Phe Thr Asp Asp Gly Gln Tyr Met Ala
465                 470                 475                 480

Glu Lys Ser Pro Tyr Tyr Asn Ala Ile Asp Ala Leu Leu Arg Ala Arg
                485                 490                 495

Ile Lys Tyr Val Ala Gly Gly Gln Asp Met Lys Val Thr Lys Leu Asn
                500                 505                 510

Gly Tyr Glu Ile Met Ser Ser Val Arg Tyr Gly Lys Gly Ala Glu Glu
                515                 520                 525

Ala Asn Gln Leu Gly Thr Ala Glu Thr Arg Asn Gln Gly Met Leu Val
530                 535                 540

Leu Thr Ala Asn Arg Pro Asp Met Lys Leu Gly Ala Asn Asp Arg Leu
545                 550                 555                 560

Val Val Asn Met Gly Ala Ala His Lys Asn Gln Ala Tyr Arg Pro Leu
                565                 570                 575

Leu Leu Ser Lys Ser Thr Gly Leu Ala Thr Tyr Leu Lys Asp Ser Asp
                580                 585                 590

Val Pro Ala Gly Leu Val Arg Tyr Thr Asp Asn Gln Gly Asn Leu Thr
                595                 600                 605

Phe Thr Ala Asp Asp Ile Ala Gly His Ser Thr Val Glu Val Ser Gly
                610                 615                 620

Tyr Leu Ala Val Trp Val Pro Val Gly Ala Ser Glu Asn Gln Asp Ala
625                 630                 635                 640

Arg Thr Lys Ala Ser Ser Thr Lys Lys Gly Glu Gln Val Phe Glu Ser
                645                 650                 655

Ser Ala Ala Leu Asp Ser Gln Val Ile Tyr Glu Gly Phe Ser Asn Phe
                660                 665                 670

Gln Asp Phe Val Lys Thr Pro Ser Gln Tyr Thr Asn Arg Val Ile Ala
                675                 680                 685

Gln Asn Ala Lys Leu Phe Lys Glu Trp Gly Ile Thr Ser Phe Glu Phe
                690                 695                 700

Ala Pro Gln Tyr Val Ser Ser Gln Asp Gly Thr Phe Leu Asp Ser Ile
705                 710                 715                 720

Ile Glu Asn Gly Tyr Ala Phe Glu Asp Arg Tyr Asp Ile Ala Met Ser
                725                 730                 735

Lys Asn Asn Lys Tyr Gly Ser Leu Lys Asp Leu Met Asp Ala Leu Arg
                740                 745                 750

Ala Leu His Ala Glu Gly Ile Ser Ala Ile Ala Asp Trp Val Pro Asp
                755                 760                 765

Gln Ile Tyr Asn Leu Pro Gly Lys Glu Val Val Thr Ala Ser Arg Thr
                770                 775                 780

Asn Ser Tyr Gly Thr Pro Arg Pro Asn Ala Glu Ile Tyr Asn Ser Leu
785                 790                 795                 800
```

```
Tyr Ala Ala Lys Thr Arg Thr Phe Gly Asn Asp Phe Gln Gly Lys Tyr
                805                 810                 815

Gly Gly Ala Phe Leu Asp Glu Leu Lys Ala Lys Tyr Pro Ala Ile Phe
            820                 825                 830

Glu Arg Val Gln Ile Ser Asn Gly Arg Lys Leu Thr Thr Asn Glu Lys
        835                 840                 845

Ile Thr Gln Trp Ser Ala Lys Tyr Phe Asn Gly Ser Asn Ile Gln Gly
    850                 855                 860

Thr Gly Ala Arg Tyr Val Leu Gln Asp Asn Ala Thr Asn Gln Tyr Phe
865                 870                 875                 880

Ser Val Lys Ala Gly Gln Thr Phe Leu Pro Lys Gln Met Thr Glu Ile
                885                 890                 895

Thr Gly Ser Gly Phe Arg Arg Val Gly Asp Asp Val Gln Tyr Leu Ser
            900                 905                 910

Ile Gly Gly Tyr Leu Ala Lys Asn Thr Phe Ile Gln Val Gly Ala Asn
        915                 920                 925

Gln Trp Tyr Tyr Phe Asp Lys Asn Gly Asn Met Val Thr Gly Glu Gln
    930                 935                 940

Val Ile Asp Gly Lys Lys Tyr Phe Phe Leu Asp Asn Gly Leu Gln Leu
945                 950                 955                 960

Arg His Val Leu Arg Gln Gly Ser Asp Gly His Val Tyr Tyr Tyr Asp
                965                 970                 975

Pro Lys Gly Val Gln Ala Phe Asn Gly Phe Tyr Asp Phe Ala Gly Pro
            980                 985                 990

Arg Gln Asp Val Arg Tyr Phe Asp  Gly Asn Gly Gln Met  Tyr Arg Gly
        995                 1000                1005

Leu His Asp Met Tyr Gly Thr  Thr Phe Tyr Phe Asp  Glu Lys Thr
    1010                1015                1020

Gly Ile Gln Ala Lys Asp Lys  Phe Ile Arg Phe Ala  Asp Gly Arg
    1025                1030                1035

Thr Arg Tyr Phe Ile Pro Asp  Thr Gly Asn Leu Ala  Val Asn Arg
    1040                1045                1050

Phe Ala Gln Asn Pro Glu Asn  Lys Ala Trp Tyr Tyr  Leu Asp Ser
    1055                1060                1065

Asn Gly Tyr Ala Val Thr Gly  Leu Gln Thr Ile Asn  Gly Lys Gln
    1070                1075                1080

Tyr Tyr Phe Asp Asn Glu Gly  Arg Gln Val Lys Gly  His Phe Val
    1085                1090                1095

Thr Ile Asn Asn Gln Arg Tyr  Phe Leu Asp Gly Asp  Ser Gly Glu
    1100                1105                1110

Ile Ala Pro Ser Arg Phe Val  Thr Glu Asn Asn Lys  Trp Tyr Tyr
    1115                1120                1125

Val Asp Gly Asn Gly Lys Leu  Val Lys Gly Ala Gln  Val Ile Asn
    1130                1135                1140

Gly Asn His Tyr Tyr Phe Asn  Asn Asp Tyr Ser Gln  Val Lys Gly
    1145                1150                1155

Ala Trp Ala Asn Gly Arg Tyr  Tyr Asp Gly Asp Ser  Gly Gln Ala
    1160                1165                1170

Val Ser Asn Gln Phe Ile Gln  Ile Ala Ala Asn Gln  Trp Ala Tyr
    1175                1180                1185

Leu Asn Gln Asp Gly His Lys  Val Thr Gly Leu Gln  Asn Ile Asn
    1190                1195                1200
```

| | | | | | | | | | | |
|---|---|---|---|---|---|---|---|---|---|---|
| Asn | Lys | Val | Tyr | Tyr | Phe | Gly | Ser | Asn | Gly | Ala | Gln | Val | Lys | Gly |
| | 1205 | | | | 1210 | | | | 1215 | |

Lys Leu Leu Thr Val Gln Gly Lys Lys Cys Tyr Phe Asp Ala His
    1220                1225                1230

Thr Gly Glu Gln Val Val Asn Arg Phe Val Glu Ala Ala Arg Gly
    1235                1240                1245

Cys Trp Tyr Tyr Phe Asn Ser Ala Gly Gln Ala Val Thr Gly Gln
    1250                1255                1260

Gln Val Ile Asn Gly Lys Gln Leu Tyr Phe Asp Gly Ser Gly Arg
    1265                1270                1275

Gln Val Lys Gly Arg Tyr Val Tyr Val Gly Gly Lys Arg Leu Phe
    1280                1285                1290

Cys Asp Ala Lys Thr Gly Glu Leu Arg Gln Arg Arg
    1295                1300                1305

<210> SEQ ID NO 33
<211> LENGTH: 4026
<212> TYPE: DNA
<213> ORGANISM: Streptococcus salivarius

<400> SEQUENCE: 33

```
atgatcgacg gcaaatacta ctatgtaaac gaggacggca gccacaaaga gaatttcgcg      60
attacggtaa acggtcagct gctgtacttt ggtaaggacg gtgctctgac gagcagctcc     120
acgtacagct ttaccccggg tacgaccaat attgtcgatg gcttcagcat taacaaccgt     180
gcgtatgaca gcagcgaggc atcctttgag ctgatcgatg ttatttgac cgcggatagc     240
tggtatcgtc cggcgagcat cattaaggac ggcgttacgt ggcaggcctc gaccgcagaa     300
gattttcgtc cgctgctgat ggcttggtgg ccgaatgttg acacccaggt gaattatctg     360
aattacatgt ccaaggtttt caacctggat gcaaagtaca ccagcaccga caagcaggaa     420
accctgaacg tggctgcgaa agatatccaa gtcaagattg agcaaaagat tcaggcagag     480
aaatctaccc agtggctgcg tgaaacgatt agcgcgtttg ttaaaactca gccgcaatgg     540
aataaagaaa cggaaaacta ttccaagggt ggtggcgagg accatctgca aggcggtgcc     600
ctgttgtacg ttaacgattc gcgcacccg tgggcgaact cgaactatcg cttgctgaac     660
cataccgcta ccaatcaaaa aggcactatt gacaaatctg tcctggacga gcagagcgac     720
ccgaaccaca tgggcggttt cgatttctg ctggcgaacg acgtcgacct gagcaacccg     780
gtggtgcagg ccgaacaact gaaccagatt cactacctga tgaattgggg tagcatcgtg     840
atgggtgata agatgcgaa cttgacggc attcgtgtcg atgcggtcga taacgtggac     900
gccgacatgt tgcagctgta cacgaactac tttcgtgagt actacggcgt taacaagagc     960
gaagcaaatg ccctggcgca tcagcgtt ctggaagcgt ggagcctgaa tgacaatcac    1020
tataacgata agacggacgg tgcggccctg gcaatggaga taaacaacg tctggcgctg    1080
ctgttcagcc tggcgaaacc gatcaaagag cgtacgccgg ctgtgagccc actgtataac    1140
aacaccttca atactacgca gcgtgacgag aaaacggact ggattaacaa agacggtagc    1200
aaagcgtata acgaggatgg taccgtcaag caatcgacca ttggtaagta caatgagaag    1260
tatgcgacg caagcggtaa ttacgtgttc attcgtgccc acgacaacaa tgttcaagac    1320
atcatcgccg aaatcatcaa gaaagagatc aaccctaaga gcgacggttt caccatcacc    1380
gacgcagaga tgaagaaggc ctttgaaatc tacaacaagg acatgttgag cagcgataag    1440
aagtatactc tgaacaacat tccggctgcg tacgcggtga tgttgcagaa tatggaaacc    1500
```

-continued

```
atcacgcgtg tttactatgg tgatctgtat accgataatg gcaactacat ggaaacgaaa    1560
agcccgtact atgacaccat tgttaatctg atgaagaatc gcatcaagta tgtgtctggc    1620
ggtcaagcgc agcgttctta ctggctgccg accgatggta agatggacaa tagcgatgtg    1680
gaactgtacc gcaccaacga ggtatacgct tctgtgcgct atggtaaaga cattatgacc    1740
gccgatgata ccgagggttc caagtactcc cgtacgagcg gccaagttac cttggtggca    1800
aacaacccga aattgaccct ggaccaaagc gcgaaactga agtggagat gggtaagatc     1860 cacgcaaatc aaaagtaccg tgcactgatt gtcggtaccg ccgacggtat caagaatttc    1920
accagcgatg cggatgcgat tgcagcaggc tatgttaaag agactgatag caatggtgtg    1980
ctgacgtttg gtgcgaacga cattaaaggc tatgaaacgt tgacatgag cggtttcgtt     2040 gcggtgtggg tgcctgtggg tgctagcgat gatcaggata tccgtgtcgc gccgagcacc    2100
gaggcaaaga aagaaggtga gctgacgttg aaagcgaccg aggcctatga cagccagttg    2160
atttacgaag gtttcagcaa tttccaaacc attccagacg gttccgatcc gagcgtctac    2220
accaatcgca aaatcgcgga aaacgttgat ctgttcaaaa gctggggtgt gaccagcttc    2280
gaaatggcac cgcaattcgt tagcgcggac gatggtacgt tcttggacag cgttatccaa    2340
aatggctatg cgttcgccga tcgttatgac ttggcgatga gcaaaaacaa caaatacggc    2400
agcaaagagg atctgcgcga cgccctgaaa gcgctgcata agcgggtat tcaagccatc     2460 gctgactggg ttccggacca gatctaccag ctgccgggta agaagtcgt taccgcgacc     2520 cgcaccgatg gcgctggccg taagatcgcg gatgcaatta tcgatcatag cttgtatgtg    2580
gccaatacta aaagctccgg taaggattac caggcgaaat atggtggtga atttctggct    2640
gagctgaagg ccaaataccc ggagatgttc aaggtcaaca tgattagcac cggcaaacct    2700
attgatgact ctgtcaaatt gaaacaatgg aaggcagagt atttcaatgg cactaacgtc    2760
ctggaacgtg gtgttggtta cgtgctgagc gacgaggcga ccggtaaata cttcaccgtt    2820
acgaaggacg gcaatttcat cccgctgcaa ctgaccggta tgagaaggt tgtgacgggt     2880 ttttctaatg acggtaaggg cattacctac ttcggtacct cgggtaccca ggcaaagagc    2940
gcattcgtga cgtttaacgg taacacctac tactttgatg cacgcggcca catggtgacg    3000
aacggcgagt acagcccgaa cggcaaggat gtttatcgct tcctgccgaa tggcatcatg    3060
ctgtccaatg cgttttacgt cgatgcaaat ggtaatactt acctgtacaa cagcaagggt    3120
cagatgtata agggcggtta taccaagttc gacgttactg aaacggacaa ggacggtaaa    3180
gagagcaaag tagtgaagtt tcgttatttc acgaacgaag cgtcatggc gaaaggtgtc     3240 accgttattg atggctttac ccagtatttc ggtgaagatg gctttcaagc gaaggacaag    3300
ctggtgacct taagggcaa aacctactat tttgacgcgc acacgggcaa cgccatcaag    3360
aacacctggc gtaatatcga cggtaagtgg tatcattttg atgcgaacgg tgtggcggcg    3420
accggcgcac aggtcattaa tggtcaaaaa ctgtacttta tgaggacgg tagccaagtc    3480 aaaggtggcg tcgtcaagaa tgcagatggc acctatagca aatacaaaga gggctccggt    3540
gagctggtta ccaacgagtt ctttaccacg gatggtaacg tctggtacta tgctggtgcg    3600
aatggcaaga ccgttaccgg tgcacaggtt atcaacggcc agcacctgta cttcaatgcg    3660
gatggctctc aagtgaaggg cggtgtcgtc aaaaacgcgg acggtacgta ctccaaatac    3720
gatgccgcga ccggtgaacg tctgaccaat gagttttca cgactggtga caacaattgg    3780
tactacatcg gcgccaacgg taagacggtt acggcgaag tgaaaattgg cgacgatacg    3840
tactacttcg caaaagatgg taaacaggtg aaaggtcaga cggtttccgc tggtaatggc    3900
```

```
cgcatcagct actattacgg tgactctggt aaacgtgcgg ttagcacgtg ggttgaaatt    3960
caaccgggcg tgtatgtcta tttttgataag aatggcctgg catatccacc gcgcgttttg    4020
aattaa                                                                 4026
```

<210> SEQ ID NO 34
<211> LENGTH: 1341
<212> TYPE: PRT
<213> ORGANISM: Streptococcus salivarius

<400> SEQUENCE: 34

```
Met Ile Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
                20                  25                  30

Asp Gly Ala Leu Thr Ser Ser Thr Tyr Ser Phe Thr Pro Gly Thr
            35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Thr Ser Thr Asp Lys Gln Glu Thr Leu Asn Val
    130                 135                 140

Ala Ala Lys Asp Ile Gln Val Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asn Tyr Arg Leu Leu Asn His Thr Ala Thr
    210                 215                 220

Asn Gln Lys Gly Thr Ile Asp Lys Ser Val Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
```

```
                340                 345                 350
Glu Asn Lys Gln Arg Leu Ala Leu Leu Phe Ser Leu Ala Lys Pro Ile
            355                 360                 365
Lys Glu Arg Thr Pro Ala Val Ser Pro Leu Tyr Asn Asn Thr Phe Asn
        370                 375                 380
Thr Thr Gln Arg Asp Glu Lys Thr Asp Trp Ile Asn Lys Asp Gly Ser
385                 390                 395                 400
Lys Ala Tyr Asn Glu Asp Gly Thr Val Lys Gln Ser Thr Ile Gly Lys
                405                 410                 415
Tyr Asn Glu Lys Tyr Gly Asp Ala Ser Gly Asn Tyr Val Phe Ile Arg
            420                 425                 430
Ala His Asp Asn Asn Val Gln Asp Ile Ile Ala Glu Ile Ile Lys Lys
        435                 440                 445
Glu Ile Asn Pro Lys Ser Asp Gly Phe Thr Ile Thr Asp Ala Glu Met
    450                 455                 460
Lys Lys Ala Phe Glu Ile Tyr Asn Lys Asp Met Leu Ser Ser Asp Lys
465                 470                 475                 480
Lys Tyr Thr Leu Asn Asn Ile Pro Ala Ala Tyr Ala Val Met Leu Gln
                485                 490                 495
Asn Met Glu Thr Ile Thr Arg Val Tyr Tyr Gly Asp Leu Tyr Thr Asp
            500                 505                 510
Asn Gly Asn Tyr Met Glu Thr Lys Ser Pro Tyr Asp Thr Ile Val
        515                 520                 525
Asn Leu Met Lys Asn Arg Ile Lys Tyr Val Ser Gly Gly Gln Ala Gln
    530                 535                 540
Arg Ser Tyr Trp Leu Pro Thr Asp Gly Lys Met Asp Asn Ser Asp Val
545                 550                 555                 560
Glu Leu Tyr Arg Thr Asn Glu Val Tyr Ala Ser Val Arg Tyr Gly Lys
                565                 570                 575
Asp Ile Met Thr Ala Asp Asp Thr Glu Gly Ser Lys Tyr Ser Arg Thr
            580                 585                 590
Ser Gly Gln Val Thr Leu Val Ala Asn Asn Pro Lys Leu Thr Leu Asp
        595                 600                 605
Gln Ser Ala Lys Leu Lys Val Glu Met Gly Lys Ile His Ala Asn Gln
    610                 615                 620
Lys Tyr Arg Ala Leu Ile Val Gly Thr Ala Asp Gly Ile Lys Asn Phe
625                 630                 635                 640
Thr Ser Asp Ala Asp Ala Ile Ala Ala Gly Tyr Val Lys Glu Thr Asp
                645                 650                 655
Ser Asn Gly Val Leu Thr Phe Gly Ala Asn Asp Ile Lys Gly Tyr Glu
            660                 665                 670
Thr Phe Asp Met Ser Gly Phe Ala Val Trp Val Pro Val Gly Ala
        675                 680                 685
Ser Asp Asp Gln Asp Ile Arg Val Ala Pro Ser Thr Glu Ala Lys Lys
    690                 695                 700
Glu Gly Glu Leu Thr Leu Lys Ala Thr Glu Ala Tyr Asp Ser Gln Leu
705                 710                 715                 720
Ile Tyr Glu Gly Phe Ser Asn Phe Gln Thr Ile Pro Asp Gly Ser Asp
                725                 730                 735
Pro Ser Val Tyr Thr Asn Arg Lys Ile Ala Glu Asn Val Asp Leu Phe
            740                 745                 750
Lys Ser Trp Gly Val Thr Ser Phe Glu Met Ala Pro Gln Phe Val Ser
        755                 760                 765
```

```
Ala Asp Asp Gly Thr Phe Leu Asp Ser Val Ile Gln Asn Gly Tyr Ala
        770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ala Asp Ala Ile Ile Asp His Ser Leu Tyr Val Ala Asn Thr Lys
        850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
                900                 905                 910

Glu Tyr Phe Asn Gly Thr Asn Val Leu Glu Arg Gly Val Gly Tyr Val
            915                 920                 925

Leu Ser Asp Glu Ala Thr Gly Lys Tyr Phe Thr Val Thr Lys Asp Gly
        930                 935                 940

Asn Phe Ile Pro Leu Gln Leu Thr Gly Asn Glu Lys Val Val Thr Gly
945                 950                 955                 960

Phe Ser Asn Asp Gly Lys Gly Ile Thr Tyr Phe Gly Thr Ser Gly Thr
                965                 970                 975

Gln Ala Lys Ser Ala Phe Val Thr Phe Asn Gly Asn Thr Tyr Tyr Phe
                980                 985                 990

Asp Ala Arg Gly His Met Val Thr Asn Gly Glu Tyr Ser Pro Asn Gly
            995                 1000                1005

Lys Asp Val Tyr Arg Phe Leu Pro Asn Gly Ile Met Leu Ser Asn
        1010                1015                1020

Ala Phe Tyr Val Asp Ala Asn Gly Asn Thr Tyr Leu Tyr Asn Ser
        1025                1030                1035

Lys Gly Gln Met Tyr Lys Gly Gly Tyr Thr Lys Phe Asp Val Thr
        1040                1045                1050

Glu Thr Asp Lys Asp Gly Lys Glu Ser Lys Val Val Lys Phe Arg
        1055                1060                1065

Tyr Phe Thr Asn Glu Gly Val Met Ala Lys Gly Val Thr Val Ile
        1070                1075                1080

Asp Gly Phe Thr Gln Tyr Phe Gly Glu Asp Gly Phe Gln Ala Lys
        1085                1090                1095

Asp Lys Leu Val Thr Phe Lys Gly Lys Thr Tyr Tyr Phe Asp Ala
        1100                1105                1110

His Thr Gly Asn Ala Ile Lys Asn Thr Trp Arg Asn Ile Asp Gly
        1115                1120                1125

Lys Trp Tyr His Phe Asp Ala Asn Gly Val Ala Ala Thr Gly Ala
        1130                1135                1140

Gln Val Ile Asn Gly Gln Lys Leu Tyr Phe Asn Glu Asp Gly Ser
        1145                1150                1155

Gln Val Lys Gly Gly Val Val Lys Asn Ala Asp Gly Thr Tyr Ser
        1160                1165                1170
```

| | | | | | | | | | | |
|---|---|---|---|---|---|---|---|---|---|---|
| Lys | Tyr | Lys | Glu | Gly | Ser | Gly | Glu | Leu | Val | Thr | Asn | Glu | Phe | Phe |
| | 1175 | | | | 1180 | | | | 1185 | |

Thr Thr Asp Gly Asn Val Trp Tyr Tyr Ala Gly Ala Asn Gly Lys
    1190                1195                1200

Thr Val Thr Gly Ala Gln Val Ile Asn Gly Gln His Leu Tyr Phe
    1205                1210                1215

Asn Ala Asp Gly Ser Gln Val Lys Gly Gly Val Val Lys Asn Ala
    1220                1225                1230

Asp Gly Thr Tyr Ser Lys Tyr Asp Ala Ala Thr Gly Glu Arg Leu
    1235                1240                1245

Thr Asn Glu Phe Phe Thr Thr Gly Asp Asn Asn Trp Tyr Tyr Ile
    1250                1255                1260

Gly Ala Asn Gly Lys Thr Val Thr Gly Glu Val Lys Ile Gly Asp
    1265                1270                1275

Asp Thr Tyr Tyr Phe Ala Lys Asp Gly Lys Gln Val Lys Gly Gln
    1280                1285                1290

Thr Val Ser Ala Gly Asn Gly Arg Ile Ser Tyr Tyr Tyr Gly Asp
    1295                1300                1305

Ser Gly Lys Arg Ala Val Ser Thr Trp Val Glu Ile Gln Pro Gly
    1310                1315                1320

Val Tyr Val Tyr Phe Asp Lys Asn Gly Leu Ala Tyr Pro Pro Arg
    1325                1330                1335

Val Leu Asn
    1340

```
<210> SEQ ID NO 35
<211> LENGTH: 3996
<212> TYPE: DNA
<213> ORGANISM: Streptococcus salivarius

<400> SEQUENCE: 35
atggtcgacg gcaaatacta ctacgtgaaa gaggatggca gctacaaaac gaacttcgca      60
gtttccgtca acggccaact gctgtatttc ggcaaggatg gcgcgctgac gtccaccagc     120
acccatagct ttacgccagg cactaccaat ctggttgatg cgttcagctc ccataaccgc     180
gcctacgact ccaaaaagga gagcttcgaa ctggtggatg gttatctgac gccgaactct     240
tggtatcgtc cggtcactat cctggaaaat ggtgaaaaat ggcgtgttag caccgagaag     300
gactttcgcc cgttgttgat ggcctggtgg ccggatgtcg acacgcaagt tgcctatctg     360
aacacctttt ctaaacactt caacctgaac gcgacgtact ctacttctca gagccaaagc     420
gagctgaatg cggcagctaa aaccatccaa atcaaaatcg aacaggagat tagcgcgaaa     480
aagagcacgg agtggctgcg ccaggcaatt gagtcctttg tcaaggagca ggatcagtgg     540
aacaccacga ccgagaacta caccctggcg gatcatttgc agggcggtgc gctgctgtat     600
gtgaacaatg acaagacgcc gtgggcgaac agcgactatc gtctgctgaa ccgtactccg     660
agcaaccagg acggcagcct gaacggtact ggccgttatc tgggtggtta cgagtttctg     720
ctggcgaatg acgtggacaa tagcaatccg gtggtccagg ctgagcagct gaatcaaatt     780
cactatctgg tcaactgggg cagcattgtc atgggtgaca aggacgcgaa tttcgacggc     840
attcgtgttg acgccgttga caatgtggac gccgatctgt tgcaggttta cacgaactac     900
ttccgtgcgg cgtttggtgt ggataaaagc gaagcgaacg cactggccca catcagcatt     960
ctggaggcgt gggatctgaa cgacaatgcg tacaaccaga acatgacgg tgcggccttg    1020
gcaatggata caacctgcg ttacgcgatc atgggtgcac tgtatggtag cggtagctcg    1080
```

```
ctgaaagatc tgattaccag cagcctgacc gaccgtacga ataactccaa atatggtgat    1140
acccaagcaa actacatctt cgcccgtgct catgataatc tggtccagga cattattcgt    1200
gacatcgtgc agaaagagat caatccgaag agcgacggct acacgatgac cgatgcggag    1260
ctgaagcgtg cgtttgaaat ctacaacgag gatatgaaaa aggccgaaaa acgctacact    1320
atcaacaaca tcccggcagc gtatgcactg attttgcaga acatggaaca ggttactcgt    1380
gtgtactacg gtgatctgta taccgacaat ggtcagtaca tggcgaccaa aagcccgtac    1440
tacgacgcga ttacgaccct gctgaaaaat cgtatgaagt atgtgagcgg cggtcagagc    1500
atgaaagttg acactttcaa cggtaaagaa attctgtcgt ctgttcgtta cggtaaggac    1560
atcatgaccg cggaccaaac gaccggtgtc gcagaaacca gcaagcacag cggcatgctg    1620
accctgatcg ccaataacca ggattttttct ctgggcgatg gcaccttgaa agtgaacatg    1680
ggcaagctgc acgcgaacca ggcgtatcgc ccgctgctgc tgggcacgga taagggcatc    1740
gttacctatg aaaatgacgc ggctgcggca ggcaaaatca agtacacgga cgcagagggt    1800
aatctgacct tcagcggtga cgagatcaag ggctatcgca ccgtggacat gcgcggctac    1860
ctgggtgtgt gggtcccggt cggcgcaccg gacaatcaag acattcgcgt taagggtagc    1920
gataagaaac tggacaagac tttcagcgca accgaagctc tggatagcca ggtgatttac    1980
gaaggtttta gcaactttca ggacttcgtg gaaaaagaca gccagtacac caacaagctg    2040
attgcggaaa acgcggaact gtttaagagc tggggtatta ctagctttga aatggcccct    2100
cagtttgtca gcgcagacga tcgtaccttc ctggatagcg ttatccaaaa cggttatgcg    2160
tttaccgatc gttacgatct ggccatgtct aagaataaca agtatggcag caaagaagat    2220
ctgcgtgatg cgctgaaggc gctgcacaag cagggcattc aagcaattgc cgactgggtt    2280
ccggatcaac tgtaccaact gccgggtcaa gaggttgtca ccgctacccg tgcaaatagc    2340
tacggcaccc cgaaggccaa tgcctacatt aacaatacgc tgtatgttgc caatagcaag    2400
agcagcggta aagacttcca ggctcaatac ggtggcgagt cctggatgaa attgcagaag    2460
aagtacccgc agttgttcga ggatgtgatg atcagcacgg gtaaaaagat tgacccgagc    2520
gtgaaaatca gcagtggag cgccaaatac atgaatggca ccaacattct gggtcgtggc    2580
aaccgttacg ttctgtcgaa tgacgccacc ggtcgctatt atcaagtgac cgacaacggc    2640
attttcttgc cgaagccgct gacggatcag ggtggtaaga ccggcttcta ttacgatggt    2700
aagggcatgg cctatttcga caattccggc tttcaagcga aaaatgcgtt catcaagtac    2760
gcgggtaact actactactt cgataaagag ggctatatgc tgacgggccg tcaagatatt    2820
gacagcaaga cgtatttctt tctgccgaat ggtatccaac tgcgtgatag catttaccaa    2880
caagatggca agtactacta ttttggtagc ttcggcgaac aatacaaaga cggttatttc    2940
gtctttgacg tgccaaaaga gggcaccagc gaaaccgagg ctaagttccg ctactttctt    3000
ccgacgggtg agatggcagt gggtttgacc tatgcgggtg tggtctgca atactttgat    3060 gagaacggtt ccaggcgaa gggtacgaag tatgttacgc cggatggtaa gttgtatttc    3120
ttcgacaaga atagcggcaa cgcgtacacc aatcgttggg cggagatcga tggtatttgg    3180
tacgagttta atgaccaagg ttacgcgcag gcgaagaaag gtgagtttta caccacggat    3240
ggtagcacgt ggttttaccg cgacgcagca ggtaaaaacg ttaccggtgc cctgaccctg    3300
gacggtcacg agtattactt tcgtgcgaac ggtgcgcagg tgaaggcga gttcgtcacc    3360 gaaaacggta agattagcta ttacaccgtt gataacggtt acaaggtaaa agacaagttc    3420
```

-continued

```
ttcgaagtca atggtaagtg gtatcacgct gataaggacg gtaatttggc gacgggtcgt      3480
cagaccatcg accatctgaa ttactacttc aacgccgacg gctcccaggt taagtccgat      3540
ttcttcactc tggatggtgg taaaacctgg tattatgcca agacaacgg tgagattgtg       3600 accggtgcgt actcggtgcg tggcaagaac tattacttca agaggacgg tagccaagtt       3660 aagggcgatt tcgtcaaaaa tgcggacggt tccctgagct attatgacaa ggatagcggc      3720
gaacgtctga caaccgtttc cttgaccacg ggtaacaatg tctggtatta ctttaaggat      3780
ggtaaagcgg tcacgggtcg ccagaacatc gacggtaagg agtactactt tgatcacctg      3840
ggtcgtcaag tcaaaggctc cccgattagc actccgaagg gcgttgagta ttatgagtct      3900
gtgctgggtg agcgtgtcac caacacctgg atcaccttcc aagacggcaa aaccgtgttc      3960
tttgatgaaa atggctacgc ggactttgat aagtaa                                3996
```

```
<210> SEQ ID NO 36
<211> LENGTH: 1331
<212> TYPE: PRT
<213> ORGANISM: Streptococcus salivarius

<400> SEQUENCE: 36
```

Met Val Asp Gly Lys Tyr Tyr Tyr Val Lys Glu Asp Gly Ser Tyr Lys
1               5                   10                  15

Thr Asn Phe Ala Val Ser Val Asn Gly Gln Leu Leu Tyr Phe Gly Lys
            20                  25                  30

Asp Gly Ala Leu Thr Ser Thr Ser His Ser Phe Thr Pro Gly Thr
        35                  40                  45

Thr Asn Leu Val Asp Ala Phe Ser Ser His Asn Arg Ala Tyr Asp Ser
    50                  55                  60

Lys Lys Glu Ser Phe Glu Leu Val Asp Gly Tyr Leu Thr Pro Asn Ser
65                  70                  75                  80

Trp Tyr Arg Pro Val Thr Ile Leu Glu Asn Gly Glu Lys Trp Arg Val
                85                  90                  95

Ser Thr Glu Lys Asp Phe Arg Pro Leu Leu Met Ala Trp Trp Pro Asp
            100                 105                 110

Val Asp Thr Gln Val Ala Tyr Leu Asn Thr Phe Ser Lys His Phe Asn
        115                 120                 125

Leu Asn Ala Thr Tyr Ser Thr Ser Gln Ser Gln Ser Glu Leu Asn Ala
    130                 135                 140

Ala Ala Lys Thr Ile Gln Ile Lys Ile Glu Gln Glu Ile Ser Ala Lys
145                 150                 155                 160

Lys Ser Thr Glu Trp Leu Arg Gln Ala Ile Glu Ser Phe Val Lys Glu
                165                 170                 175

Gln Asp Gln Trp Asn Thr Thr Glu Asn Tyr Thr Leu Ala Asp His
            180                 185                 190

Leu Gln Gly Gly Ala Leu Leu Tyr Val Asn Asn Asp Lys Thr Pro Trp
        195                 200                 205

Ala Asn Ser Asp Tyr Arg Leu Leu Asn Arg Thr Pro Ser Asn Gln Asp
    210                 215                 220

Gly Ser Leu Asn Gly Thr Gly Arg Tyr Leu Gly Gly Tyr Glu Phe Leu
225                 230                 235                 240

Leu Ala Asn Asp Val Asp Asn Ser Asn Pro Val Val Gln Ala Glu Gln
                245                 250                 255

Leu Asn Gln Ile His Tyr Leu Val Asn Trp Gly Ser Ile Val Met Gly
            260                 265                 270

-continued

```
Asp Lys Asp Ala Asn Phe Asp Gly Ile Arg Val Asp Val Asp Asn
            275                 280                 285

Val Asp Ala Asp Leu Leu Gln Val Tyr Thr Asn Tyr Phe Arg Ala Ala
    290                 295                 300

Phe Gly Val Asp Lys Ser Glu Ala Asn Ala Leu Ala His Ile Ser Ile
305                 310                 315                 320

Leu Glu Ala Trp Asp Leu Asn Asp Asn Ala Tyr Asn Gln Lys His Asp
                325                 330                 335

Gly Ala Ala Leu Ala Met Asp Asn Leu Arg Tyr Ala Ile Met Gly
            340                 345                 350

Ala Leu Tyr Gly Ser Gly Ser Ser Leu Lys Asp Leu Ile Thr Ser Ser
            355                 360                 365

Leu Thr Asp Arg Thr Asn Asn Ser Lys Tyr Gly Asp Thr Gln Ala Asn
370                 375                 380

Tyr Ile Phe Ala Arg Ala His Asp Asn Leu Val Gln Asp Ile Ile Arg
385                 390                 395                 400

Asp Ile Val Gln Lys Glu Ile Asn Pro Lys Ser Asp Gly Tyr Thr Met
                405                 410                 415

Thr Asp Ala Glu Leu Lys Arg Ala Phe Glu Ile Tyr Asn Glu Asp Met
            420                 425                 430

Lys Lys Ala Glu Lys Arg Tyr Thr Ile Asn Asn Ile Pro Ala Ala Tyr
            435                 440                 445

Ala Leu Ile Leu Gln Asn Met Glu Gln Val Thr Arg Val Tyr Tyr Gly
    450                 455                 460

Asp Leu Tyr Thr Asp Asn Gly Gln Tyr Met Ala Thr Lys Ser Pro Tyr
465                 470                 475                 480

Tyr Asp Ala Ile Thr Thr Leu Leu Lys Asn Arg Met Lys Tyr Val Ser
                485                 490                 495

Gly Gly Gln Ser Met Lys Val Asp Thr Phe Asn Gly Lys Glu Ile Leu
            500                 505                 510

Ser Ser Val Arg Tyr Gly Lys Asp Ile Met Thr Ala Asp Gln Thr Thr
            515                 520                 525

Gly Val Ala Glu Thr Ser Lys His Ser Gly Met Leu Thr Leu Ile Ala
530                 535                 540

Asn Asn Gln Asp Phe Ser Leu Gly Asp Gly Thr Leu Lys Val Asn Met
545                 550                 555                 560

Gly Lys Leu His Ala Asn Gln Ala Tyr Arg Pro Leu Leu Leu Gly Thr
                565                 570                 575

Asp Lys Gly Ile Val Thr Tyr Glu Asn Asp Ala Ala Ala Gly Lys
            580                 585                 590

Ile Lys Tyr Thr Asp Ala Glu Gly Asn Leu Thr Phe Ser Gly Asp Glu
            595                 600                 605

Ile Lys Gly Tyr Arg Thr Val Asp Met Arg Gly Tyr Leu Gly Val Trp
    610                 615                 620

Val Pro Val Gly Ala Pro Asp Asn Gln Asp Ile Arg Val Lys Gly Ser
625                 630                 635                 640

Asp Lys Lys Leu Asp Lys Thr Phe Ser Ala Thr Glu Ala Leu Asp Ser
                645                 650                 655

Gln Val Ile Tyr Glu Gly Phe Ser Asn Phe Gln Asp Phe Val Glu Lys
            660                 665                 670

Asp Ser Gln Tyr Thr Asn Lys Leu Ile Ala Glu Asn Ala Glu Leu Phe
            675                 680                 685

Lys Ser Trp Gly Ile Thr Ser Phe Glu Met Ala Pro Gln Phe Val Ser
```

-continued

```
            690             695             700
Ala Asp Asp Arg Thr Phe Leu Asp Ser Val Ile Gln Asn Gly Tyr Ala
705             710             715             720
Phe Thr Asp Arg Tyr Asp Leu Ala Met Ser Lys Asn Lys Tyr Gly
            725             730             735
Ser Lys Glu Asp Leu Arg Asp Ala Leu Lys Ala Leu His Lys Gln Gly
                740             745             750
Ile Gln Ala Ile Ala Asp Trp Val Pro Asp Gln Leu Tyr Gln Leu Pro
            755             760             765
Gly Gln Glu Val Val Thr Ala Thr Arg Ala Asn Ser Tyr Gly Thr Pro
            770             775             780
Lys Ala Asn Ala Tyr Ile Asn Asn Thr Leu Tyr Val Ala Asn Ser Lys
785             790             795             800
Ser Ser Gly Lys Asp Phe Gln Ala Gln Tyr Gly Gly Glu Phe Leu Asp
                805             810             815
Glu Leu Gln Lys Lys Tyr Pro Gln Leu Phe Glu Asp Val Met Ile Ser
                820             825             830
Thr Gly Lys Lys Ile Asp Pro Ser Val Lys Ile Lys Gln Trp Ser Ala
                835             840             845
Lys Tyr Met Asn Gly Thr Asn Ile Leu Gly Arg Gly Asn Arg Tyr Val
                850             855             860
Leu Ser Asn Asp Ala Thr Gly Arg Tyr Tyr Gln Val Thr Asp Asn Gly
865             870             875             880
Ile Phe Leu Pro Lys Pro Leu Thr Asp Gln Gly Gly Lys Thr Gly Phe
                885             890             895
Tyr Tyr Asp Gly Lys Gly Met Ala Tyr Phe Asp Asn Ser Gly Phe Gln
                900             905             910
Ala Lys Asn Ala Phe Ile Lys Tyr Ala Gly Asn Tyr Tyr Phe Asp
                915             920             925
Lys Glu Gly Tyr Met Leu Thr Gly Arg Gln Asp Ile Asp Ser Lys Thr
                930             935             940
Tyr Phe Phe Leu Pro Asn Gly Ile Gln Leu Arg Asp Ser Ile Tyr Gln
945             950             955             960
Gln Asp Gly Lys Tyr Tyr Phe Gly Ser Phe Gly Glu Gln Tyr Lys
                965             970             975
Asp Gly Tyr Phe Val Phe Asp Val Pro Lys Glu Gly Thr Ser Glu Thr
                980             985             990
Glu Ala Lys Phe Arg Tyr Phe Ser Pro Thr Gly Glu Met Ala Val Gly
                995             1000            1005
Leu Thr Tyr Ala Gly Gly Gly Leu Gln Tyr Phe Asp Glu Asn Gly
    1010            1015            1020
Phe Gln Ala Lys Gly Thr Lys Tyr Val Thr Pro Asp Gly Lys Leu
    1025            1030            1035
Tyr Phe Phe Asp Lys Asn Ser Gly Asn Ala Tyr Thr Asn Arg Trp
    1040            1045            1050
Ala Glu Ile Asp Gly Ile Trp Tyr Glu Phe Asn Asp Gln Gly Tyr
    1055            1060            1065
Ala Gln Ala Lys Lys Gly Glu Phe Tyr Thr Thr Asp Gly Ser Thr
    1070            1075            1080
Trp Phe Tyr Arg Asp Ala Ala Gly Lys Asn Val Thr Gly Ala Leu
    1085            1090            1095
Thr Leu Asp Gly His Glu Tyr Tyr Phe Arg Ala Asn Gly Ala Gln
    1100            1105            1110
```

| | | | | | | | | | | |
|---|---|---|---|---|---|---|---|---|---|---|
| Val | Lys | Gly | Glu | Phe | Val | Thr | Glu | Asn | Gly | Lys | Ile | Ser | Tyr | Tyr |
| | 1115 | | | | 1120 | | | | 1125 | |

Thr Val Asp Asn Gly Tyr Lys Val Lys Asp Lys Phe Phe Glu Val
    1130                1135                1140

Asn Gly Lys Trp Tyr His Ala Asp Lys Asp Gly Asn Leu Ala Thr
    1145                1150                1155

Gly Arg Gln Thr Ile Asp His Leu Asn Tyr Tyr Phe Asn Ala Asp
    1160                1165                1170

Gly Ser Gln Val Lys Ser Asp Phe Phe Thr Leu Asp Gly Gly Lys
    1175                1180                1185

Thr Trp Tyr Tyr Ala Lys Asp Asn Gly Glu Ile Val Thr Gly Ala
    1190                1195                1200

Tyr Ser Val Arg Gly Lys Asn Tyr Tyr Phe Lys Glu Asp Gly Ser
    1205                1210                1215

Gln Val Lys Gly Asp Phe Val Lys Asn Ala Asp Gly Ser Leu Ser
    1220                1225                1230

Tyr Tyr Asp Lys Asp Ser Gly Glu Arg Leu Asn Asn Arg Phe Leu
    1235                1240                1245

Thr Thr Gly Asn Asn Val Trp Tyr Tyr Phe Lys Asp Gly Lys Ala
    1250                1255                1260

Val Thr Gly Arg Gln Asn Ile Asp Gly Lys Glu Tyr Tyr Phe Asp
    1265                1270                1275

His Leu Gly Arg Gln Val Lys Gly Ser Pro Ile Ser Thr Pro Lys
    1280                1285                1290

Gly Val Glu Tyr Tyr Glu Ser Val Leu Gly Glu Arg Val Thr Asn
    1295                1300                1305

Thr Trp Ile Thr Phe Gln Asp Gly Lys Thr Val Phe Phe Asp Glu
    1310                1315                1320

Asn Gly Tyr Ala Asp Phe Asp Lys
    1325                1330

<210> SEQ ID NO 37
<211> LENGTH: 3918
<212> TYPE: DNA
<213> ORGANISM: Streptococcus salivarius

<400> SEQUENCE: 37

| | |
|---|---|
| atgattgacg gcaaacagta ttatgtagag aacggtgtgg ttaagaagaa tacggcgatt | 60 |
| gaactggatg gccgtctgta ttactttgac gaaaccggtg caatggttga tcaatctaag | 120 |
| ccgctgtatc gcgcggatgc aatcccgaac aactctatct acgcagtttta caaccaggct | 180 |
| tacgacacca gcagcaagag ctttgaacac ctggacaact ttctgacggc cgatagctgg | 240 |
| taccgtccga agcagatttt gaaagacggc aagaattgga ccgcctcgac ggagaaggac | 300 |
| tatcgtcctt tgctgatgac gtggtggccg gataaagtca cgcaagtcaa ctacctgaac | 360 |
| tatatgtccc aacagggctt tggtaacaag acctacacca cggatatgat gagctacgac | 420 |
| ctggcggcag cggcggaaac ggttcagcgt ggcatcgaag agcgtattgg tcgtgagggt | 480 |
| aatacgacgt ggctgcgtca gttgatgagc gacttcatca aaacccagcc gggctggaat | 540 |
| agcgagagcg aagataatct gctggtcggt aaggatcatc tgcaaggtgg tgcactgacg | 600 |
| tttctgaaca atagcaccac gagccatgcg aacagcgatt ccgcctgat gaatcgtacc | 660 |
| ccgacgaacc agaccggcac ccgcaaatac cacatcgatc gtagcaatgg tggctacgaa | 720 |
| ctgctgctgg cgaacgacat cgacaatagc aatccggccg tccaagcgga acagctgaac | 780 |

-continued

```
tggctgcatt acatcatgaa catcggctct atcctgggca atgacccaag cgcgaatttt    840
gatggcgtcc gtatcgatgc agttgacaat gtggatgcgg acttgttgca aattgcgtct    900
gactacttta aggaaaagta ccgtgttgcc gataacgagg caaacgctat tgcgcacctg    960
tcgattctgg aggcatggtc ctacaatgat catcaataca acaaagacac gaagggcgct    1020
caactgagca ttgataatcc gctgcgtgag actttgctga cgaccttcct gcgcaagtct    1080
aactaccgtg gttccctgga gcgtgtgatc accaactcgt tgaacaaccg tagcagcgaa    1140
cagaagcaca cgccgcgtga cgccaactac attttgtgc gtgctcacga cagcgaagtt    1200
caagcggtgc tggcaaacat catctctaaa cagatcaacc cgaaaaccga cggttttacc    1260
tttacgatgg atgagctgaa gcaggcgttt gagatttaca acgcagacat gcgtaaggcg    1320
gataagaagt acacgcagta caacattccg gcagcttacg ccaccatgct gaccaataag    1380
gatagcatca cccgtgtgta ctatggtgat tgtttaccg acgacggtca atacatggcg    1440
gagaaaagcc cgtactataa cgcaattgac gccctgctgc gtgctcgcat caaatacgtc    1500
gcgggtggtc aggacatgaa ggtgaccaaa ttgaacggct atgagatcat gtcctccgtt    1560
cgctacggta aggcgcaga ggaagctaat cagctgggca ccgcagaaac ccgcaatcaa    1620
ggcatgctgg tcctgaccgc gaatcgccca gacatgaagc tgggtacgaa tgatcgcctg    1680
gtcgtcaata tgggtgcagc ccacaagaat caggcgtatc gtccgctgct gctgtccaag    1740
tccaccggct tggcaaccta cctgaaagac agcgacgtcc ctgcgggcct ggtgcgttac    1800
acggacaatc aagtaatct gaccttcacg gcggacgaca tcaccggcca tagcaccgta    1860
gaggtgagcg gttacctggc ggtttgggtg ccggtgggtg cgagcgagaa ccaagatgcg    1920
cgcacgaaag cgagcacgac gaaaaagggc gaacaagttt ttgaaagctc cgcagcgctg    1980
gatagccagg tcatctatga gggtttctcc aacttccagg attttgttaa gacccccttcc    2040
cagtacacga tcgcgttat cgcacagaac gcgaagcgct ttaaggagtg gggtatcacc    2100
agctttgagt tcgcgcctca atatgttagc agccaagacg gtacctttct ggatagcatt    2160
attgagaacg gctacgcgtt cgaggaccgt tacgatatcg cgatgagcaa aaacaacaag    2220
tacggcagcc tgaaggatct gatggacgcg ctgcgtgcac tgcacgcgga gggtatcagc    2280
gccattgctg actgggttcc ggaccaaatc tataacctgc cgggtaagga agttgtaacc    2340
gcaagccgca cgaatagcta cggtacgccg cgtccgaacg cggaaatcta taacagcctg    2400
tatgcggcga aaacgcgtac gtttggcaat gattttcagg gtaaatacgg tggcgcgttt    2460
ctggatgaac tgaaagcaaa gtacccggcg atcttcgagc gtgtgcaaat ttcgaatggt    2520
cgtaagctga ctaccaatga gaaaatcacg caatggagcg cgaagtactt taatggcagc    2580
aacattcaag gtaccggtgc gcgttacgtt ctgcaagata tgccacgaa ccagtatttc    2640
aacctgaagg ccggtcaaac ctttctgcca aagcagatga ccgagattac cgcaacgggc    2700
ttccgtcgtg tcggtgacaa agtgcaatac ctgtccacgt ccggctacct ggcgaagaat    2760
acctttatcc agattggtgc gaaccagtgg tattacttcg acaagaatgg caacatggtg    2820
accggtgagc aagtgattga tgtaaaaaag tatttcttcc tggataacgg tctgcaactg    2880
cgtcatgtct tgcgtcaagg ttctgacggt cacgtgtatt actacgatcc gaaaggcgtc    2940
caggcgttta atggtttcta tgactttgcg ggtccgcgcc aagatgtccg ttatttcgac    3000
ggtaatggtc agatgtaccg tggtctgcat gatatgtatg gtaccacgtt ctactttgat    3060
gaaaagacgg gtatccaggc taaggataag tttatccgtt tcgccgacgg ccgtacccgt    3120
```

-continued

```
tactttattc cggacaccgg caatttggct gtgaatcgct tcgctcagaa tccggaaaac    3180
aaggcgtggt actacctgga cagcaacggt tatgcagtga cgggtttgca gaccattaat    3240
ggcaaacaat actatttcga caacgagggc cgtcaggtca agggccactt cgttactatc    3300
aacaatcagc gctacttctt ggacggtgac tcgggtgaga tcgcacgtag ccgcttcgtg    3360
acggagaaca caaatggta ctatgtggat ggtaacggta aattggtcaa gggtgcacaa    3420
gtcatcaacg gtaaccacta ttacttcaat aatgattatt ctcaggtgaa aggtgcttgg    3480
gccaatggcc gctactacga cggcgatagc ggccaggcgg tcacgaatcg tttcgtgcag    3540
gtcggtgcaa accagtgggc ctatctgaat cagaacggtc agaaggttgt gggcttgcaa    3600
cacatcaatg gcaagctgta ctactttgaa ggcaacggtg tccaagcaaa aggcaagctg    3660
ctgacctata agggtaagaa atactacttc gatgctaaca gcggtgaggc agtcaccaac    3720
cgctttattc aaatctctcg cggtgtttgg tactatttca atgcgagcgg tcaagcagtg    3780
accggcgagc aagttatcaa tggtcaacac ctgtacttcg acgcaagcgg tcgccaggtt    3840
aaaggccgct atgtctggat taaaggccag cgccgttatt acgacgcgaa cactggtgcc    3900
tgggtacgta atcgttaa                                                  3918
```

<210> SEQ ID NO 38
<211> LENGTH: 1305
<212> TYPE: PRT
<213> ORGANISM: Streptococcus salivarius

<400> SEQUENCE: 38

```
Met Ile Asp Gly Lys Gln Tyr Tyr Val Glu Asn Gly Val Val Lys Lys
1               5                   10                  15

Asn Thr Ala Ile Glu Leu Asp Gly Arg Leu Tyr Tyr Phe Asp Glu Thr
            20                  25                  30

Gly Ala Met Val Asp Gln Ser Lys Pro Leu Tyr Arg Ala Asp Ala Ile
        35                  40                  45

Pro Asn Asn Ser Ile Tyr Ala Val Tyr Asn Gln Ala Tyr Asp Thr Ser
    50                  55                  60

Ser Lys Ser Phe Glu His Leu Asp Asn Phe Leu Thr Ala Asp Ser Trp
65                  70                  75                  80

Tyr Arg Pro Lys Gln Ile Leu Lys Asp Gly Lys Asn Trp Thr Ala Ser
                85                  90                  95

Thr Glu Lys Asp Tyr Arg Pro Leu Leu Met Thr Trp Trp Pro Asp Lys
            100                 105                 110

Val Thr Gln Val Asn Tyr Leu Asn Tyr Met Ser Gln Gln Gly Phe Gly
        115                 120                 125

Asn Lys Thr Tyr Thr Thr Asp Met Met Ser Tyr Asp Leu Ala Ala Ala
    130                 135                 140

Ala Glu Thr Val Gln Arg Gly Ile Glu Glu Arg Ile Gly Arg Glu Gly
145                 150                 155                 160

Asn Thr Thr Trp Leu Arg Gln Leu Met Ser Asp Phe Ile Lys Thr Gln
                165                 170                 175

Pro Gly Trp Asn Ser Glu Ser Glu Asp Asn Leu Leu Val Gly Lys Asp
            180                 185                 190

His Leu Gln Gly Gly Ala Leu Thr Phe Leu Asn Asn Ser Thr Thr Ser
        195                 200                 205

His Ala Asn Ser Asp Phe Arg Leu Met Asn Arg Thr Pro Thr Asn Gln
    210                 215                 220

Thr Gly Thr Arg Lys Tyr His Ile Asp Arg Ser Asn Gly Gly Tyr Glu
```

-continued

```
                225                 230                 235                 240
Leu Leu Leu Ala Asn Asp Ile Asp Asn Ser Asn Pro Ala Val Gln Ala
                    245                 250                 255
Glu Gln Leu Asn Trp Leu His Tyr Ile Met Asn Ile Gly Ser Ile Leu
                260                 265                 270
Gly Asn Asp Pro Ser Ala Asn Phe Asp Gly Val Arg Ile Asp Ala Val
                275                 280                 285
Asp Asn Val Asp Ala Asp Leu Leu Gln Ile Ala Ser Asp Tyr Phe Lys
            290                 295                 300
Glu Lys Tyr Arg Val Ala Asp Asn Glu Ala Asn Ala Ile Ala His Leu
305                 310                 315                 320
Ser Ile Leu Glu Ala Trp Ser Tyr Asn Asp His Gln Tyr Asn Lys Asp
                325                 330                 335
Thr Lys Gly Ala Gln Leu Ser Ile Asp Asn Pro Leu Arg Glu Thr Leu
                340                 345                 350
Leu Thr Thr Phe Leu Arg Lys Ser Asn Tyr Arg Gly Ser Leu Glu Arg
                355                 360                 365
Val Ile Thr Asn Ser Leu Asn Asn Arg Ser Ser Glu Gln Lys His Thr
        370                 375                 380
Pro Arg Asp Ala Asn Tyr Ile Phe Val Arg Ala His Asp Ser Glu Val
385                 390                 395                 400
Gln Ala Val Leu Ala Asn Ile Ile Ser Lys Gln Ile Asn Pro Lys Thr
                405                 410                 415
Asp Gly Phe Thr Phe Thr Met Asp Glu Leu Lys Gln Ala Phe Glu Ile
                420                 425                 430
Tyr Asn Ala Asp Met Arg Lys Ala Asp Lys Lys Tyr Thr Gln Tyr Asn
            435                 440                 445
Ile Pro Ala Ala Tyr Ala Thr Met Leu Thr Asn Lys Asp Ser Ile Thr
        450                 455                 460
Arg Val Tyr Tyr Gly Asp Leu Phe Thr Asp Asp Gly Gln Tyr Met Ala
465                 470                 475                 480
Glu Lys Ser Pro Tyr Tyr Asn Ala Ile Asp Ala Leu Leu Arg Ala Arg
                485                 490                 495
Ile Lys Tyr Val Ala Gly Gly Gln Asp Met Lys Val Thr Lys Leu Asn
                500                 505                 510
Gly Tyr Glu Ile Met Ser Ser Val Arg Tyr Gly Lys Gly Ala Glu Glu
            515                 520                 525
Ala Asn Gln Leu Gly Thr Ala Glu Thr Arg Asn Gln Gly Met Leu Val
        530                 535                 540
Leu Thr Ala Asn Arg Pro Asp Met Lys Leu Gly Thr Asn Asp Arg Leu
545                 550                 555                 560
Val Val Asn Met Gly Ala Ala His Lys Asn Gln Ala Tyr Arg Pro Leu
                565                 570                 575
Leu Leu Ser Lys Ser Thr Gly Leu Ala Thr Tyr Leu Lys Asp Ser Asp
                580                 585                 590
Val Pro Ala Gly Leu Val Arg Tyr Thr Asp Asn Gln Gly Asn Leu Thr
            595                 600                 605
Phe Thr Ala Asp Asp Ile Thr Gly His Ser Thr Val Glu Val Ser Gly
        610                 615                 620
Tyr Leu Ala Val Trp Val Pro Val Gly Ala Ser Glu Asn Gln Asp Ala
625                 630                 635                 640
Arg Thr Lys Ala Ser Thr Thr Lys Lys Gly Glu Gln Val Phe Glu Ser
                645                 650                 655
```

```
Ser Ala Ala Leu Asp Ser Gln Val Ile Tyr Glu Gly Phe Ser Asn Phe
            660                 665                 670

Gln Asp Phe Val Lys Thr Pro Ser Gln Tyr Thr Asn Arg Val Ile Ala
        675                 680                 685

Gln Asn Ala Lys Arg Phe Lys Glu Trp Gly Ile Thr Ser Phe Glu Phe
690                 695                 700

Ala Pro Gln Tyr Val Ser Ser Gln Asp Gly Thr Phe Leu Asp Ser Ile
705                 710                 715                 720

Ile Glu Asn Gly Tyr Ala Phe Glu Asp Arg Tyr Asp Ile Ala Met Ser
                725                 730                 735

Lys Asn Asn Lys Tyr Gly Ser Leu Lys Asp Leu Met Asp Ala Leu Arg
            740                 745                 750

Ala Leu His Ala Glu Gly Ile Ser Ala Ile Ala Asp Trp Val Pro Asp
        755                 760                 765

Gln Ile Tyr Asn Leu Pro Gly Lys Glu Val Val Thr Ala Ser Arg Thr
770                 775                 780

Asn Ser Tyr Gly Thr Pro Arg Pro Asn Ala Glu Ile Tyr Asn Ser Leu
785                 790                 795                 800

Tyr Ala Ala Lys Thr Arg Thr Phe Gly Asn Asp Phe Gln Gly Lys Tyr
                805                 810                 815

Gly Gly Ala Phe Leu Asp Glu Leu Lys Ala Lys Tyr Pro Ala Ile Phe
            820                 825                 830

Glu Arg Val Gln Ile Ser Asn Gly Arg Lys Leu Thr Thr Asn Glu Lys
        835                 840                 845

Ile Thr Gln Trp Ser Ala Lys Tyr Phe Asn Gly Ser Asn Ile Gln Gly
850                 855                 860

Thr Gly Ala Arg Tyr Val Leu Gln Asp Asn Ala Thr Asn Gln Tyr Phe
865                 870                 875                 880

Asn Leu Lys Ala Gly Gln Thr Phe Leu Pro Lys Gln Met Thr Glu Ile
                885                 890                 895

Thr Ala Thr Gly Phe Arg Arg Val Gly Asp Lys Val Gln Tyr Leu Ser
            900                 905                 910

Thr Ser Gly Tyr Leu Ala Lys Asn Thr Phe Ile Gln Ile Gly Ala Asn
        915                 920                 925

Gln Trp Tyr Tyr Phe Asp Lys Asn Gly Asn Met Val Thr Gly Glu Gln
930                 935                 940

Val Ile Asp Gly Lys Lys Tyr Phe Phe Leu Asp Asn Gly Leu Gln Leu
945                 950                 955                 960

Arg His Val Leu Arg Gln Gly Ser Asp Gly His Val Tyr Tyr Tyr Asp
                965                 970                 975

Pro Lys Gly Val Gln Ala Phe Asn Gly Phe Tyr Asp Phe Ala Gly Pro
            980                 985                 990

Arg Gln Asp Val Arg Tyr Phe Asp  Gly Asn Gly Gln Met  Tyr Arg Gly
        995                 1000                1005

Leu His  Asp Met Tyr Gly Thr  Thr Phe Tyr Phe Asp  Glu Lys Thr
        1010                1015                1020

Gly Ile  Gln Ala Lys Asp Lys  Phe Ile Arg Phe Ala  Asp Gly Arg
        1025                1030                1035

Thr Arg  Tyr Phe Ile Pro Asp  Thr Gly Asn Leu Ala  Val Asn Arg
        1040                1045                1050

Phe Ala  Gln Asn Pro Glu Asn  Lys Ala Trp Tyr Tyr  Leu Asp Ser
        1055                1060                1065
```

| | | | | | | | | | | | |
|---|---|---|---|---|---|---|---|---|---|---|---|
|Asn|Gly|Tyr|Ala|Val|Thr|Gly|Leu|Gln|Thr|Ile|Asn|Gly|Lys|Gln|
| |1070| | | |1075| | | |1080| | | | | |

Asn Gly Tyr Ala Val Thr Gly Leu Gln Thr Ile Asn Gly Lys Gln
          1070            1075            1080

Tyr Tyr Phe Asp Asn Glu Gly Arg Gln Val Lys Gly His Phe Val
          1085            1090            1095

Thr Ile Asn Asn Gln Arg Tyr Phe Leu Asp Gly Asp Ser Gly Glu
          1100            1105            1110

Ile Ala Arg Ser Arg Phe Val Thr Glu Asn Asn Lys Trp Tyr Tyr
          1115            1120            1125

Val Asp Gly Asn Gly Lys Leu Val Lys Gly Ala Gln Val Ile Asn
          1130            1135            1140

Gly Asn His Tyr Tyr Phe Asn Asn Asp Tyr Ser Gln Val Lys Gly
          1145            1150            1155

Ala Trp Ala Asn Gly Arg Tyr Tyr Asp Gly Asp Ser Gly Gln Ala
          1160            1165            1170

Val Thr Asn Arg Phe Val Gln Val Gly Ala Asn Gln Trp Ala Tyr
          1175            1180            1185

Leu Asn Gln Asn Gly Gln Lys Val Val Gly Leu Gln His Ile Asn
          1190            1195            1200

Gly Lys Leu Tyr Tyr Phe Glu Gly Asn Gly Val Gln Ala Lys Gly
          1205            1210            1215

Lys Leu Leu Thr Tyr Lys Gly Lys Lys Tyr Tyr Phe Asp Ala Asn
          1220            1225            1230

Ser Gly Glu Ala Val Thr Asn Arg Phe Ile Gln Ile Ser Arg Gly
          1235            1240            1245

Val Trp Tyr Tyr Phe Asn Ala Ser Gly Gln Ala Val Thr Gly Glu
          1250            1255            1260

Gln Val Ile Asn Gly Gln His Leu Tyr Phe Asp Ala Ser Gly Arg
          1265            1270            1275

Gln Val Lys Gly Arg Tyr Val Trp Ile Lys Gly Gln Arg Arg Tyr
          1280            1285            1290

Tyr Asp Ala Asn Thr Gly Ala Trp Val Arg Asn Arg
          1295            1300            1305

<210> SEQ ID NO 39
<211> LENGTH: 3933
<212> TYPE: DNA
<213> ORGANISM: Streptococcus gallolyticus

<400> SEQUENCE: 39

```
atgatcgacg gcaaatacta ctatgttcag gcagatggca gcgttaagaa gaatttcgcg     60
attacggtca acggtcagct gctgtacttt gatgctgaga ctggcgctct gacgagcacg    120
agcacttata gctttaccga aggcctgacc aatctggtgg ataactttag caagaacaat    180
caagcgtatg acagcacgga gaaatccttt gagctggttg atggctacct gacggcgaac    240
agctggtatc gtccgactaa agttttggag aatggcgaaa cctgggttga cagcaccgaa    300
gagagcttcc gtccactggt gatggcttgg tggcctgacg tcgatacccg attaactac     360 ctgaacagca tgagcgaata ctttggtttg aataagaagt attctgcatc ggatagccaa    420
gcatctctga atgtggcggc tgaagcgatc caggtgaaaa ttgagcagga gattgcgcgt    480
cgtggttcga ccgagtggtt gcgtgaggtc attagctctt ttgttacgac ccaagataag    540
tggaatatga cagcgaaga tcgcgacact gaccacctgc aaggtggcgc actgctgtat    600
gtcaacagcg atctgactga gtgggccaat agcgattacc gctgctgaa ccgcgctccg    660 acctatcaaa ctggtgaaac taagtaccac aaagccgacc gcacgggtgg ctacgacttc    720
```

```
ctgctggcga atgatgttga caatagcaat ccggttgttc aggccgaaca actgaatcag    780
ctgtactacc tgatgaactg ggtaagatt gtgttcggtg acgcagatgc aaacttcgat     840
ggcgtccgtg ttgacgcggt ggacaacgtg gatgctgatc tgttgcaaat ctacacgaat    900
ctgtttgaag cggcctacgg cgtcgataag accgaagcac aagcgctggc gcatattagc    960
atcttggaag cgtggagctt caacgacccg gactataatc acgacaccaa cggtgcagca   1020
ctggccatcg acaacggtct gcgtatggcc ttcctggatg ctctgactcg tcctctggac   1080
tcccgcacta atttggagag cctgattcac aacgatctgg gcatgactga ccgtaccgtc   1140
gatagcgcgt atggtgatgc tatgccgagc tatgccttcg tccgtgccca cgactctgaa   1200
gttcagggca tcattgcatc tatcatcgcc ggtcagatca atccgaaaac ggacggtttt   1260
acctttacct tggatgagct gcaaaaggca ttcgaaatct acaacgccga catgaactcc   1320
gtgcacaaga agtataccca tttcaatatc ccagcagcat acgctttgct gctgaccaac   1380
atggagagcg ttccgcgtgt atactatggc gatttgttca ccgataacgg tcagtacatg   1440
gccgttaaaa gcccgtacta cgaccagatc accgcgctgc tgaagtctcg tatcaagtac   1500
gcggcaggcg gtcaagccat gaatgtgcaa tacccggatg gtgcgggtgc gggtatcctg   1560
acttctgtgc gcttcggcta tggcattatg acggcggatc aaaaagcgac cgacgacagc   1620
gttactacca gcggcattgt caccattgtt ccaacaaccc gaacctgaa actgaatagc    1680
agcgacaaaa ttgcggtgca agttggtctg gcacacgcag gccaatacta ccgtccgctg   1740
ctgtctccga cggagaatgg tctgcaagtg ttcctgaatg attccgacac cgacatcacc   1800
aagctggtcg atgataacgg ttacatctat ttcacgggtg atgagatcaa aggtttcgag   1860
actgtggaca tgaatggctt cctgaccgtt tgggttccgg tgggtgcggc agccgatcag   1920
gatattcgcg tcaaggcgag cacggaagcg aagaaggatg gtgagctgac ctatgaaacc   1980
tctgcggcgc tggattctca ggtcattttt gaaggcttta gcaactttca agactttgtt   2040
caggacccaa gccagtacac caataaggtg attgcggaga atgcggatct gttcgcgagc   2100
tggggcatca cgtctttcga gctggcaccg cagtatgtta gcagcacgga cggtacgttc   2160
ctggacagca ttattcagaa cggttatgct tttacggatc gttatgactt ggcgatgtct   2220
aagaacaata gtatggtag cgcagaagat ttgcgcaatg cgattaaagc gctgcacgca    2280
cgcggtattc aagtgattgc tgattgggtc cctgaccaga tttatgcgct gcctggtgaa   2340
gagattgtga cggcgacccg tgttaatgac tacggcgaag aacgtgaagg cgcgcaaatc   2400
aagaacaaac cgtatgcggc gaatacgaaa agctccggtg aggattacca gcccaatac    2460
ggtggcgagt tcttggaata tctgcaagag aattacccgg agttgtttga aaaggtcatg   2520
attagcacgg gtaagaccat tgacccatcg acgaagatca aggtctggaa agcggagtat   2580
ttcaacggca cgaatattct gggtaagggt gccgattacg tcctgaacga tgcggccacc   2640
ggcacctact tcaccgtaac ggagaacggc gccttcctgc cgaaacaaat gacgagcgat   2700
accgcccaaa cgggtttcta ttatgatggc accggcatga cgtactattc tacctcgggt   2760
taccaagcta agtctagctt cgtgctgtac aacggcaacc gttactattt cgatgaaaac   2820
ggtcacatgg ttacgggtat gcgcgatatt gatggtcaga cgtactactt tctgccgaat   2880
ggtatcgaac tgcgtgacgc gatctatgag gacgcgaacg gtaatcagta ttactttggc   2940
aaatcgggta accgctacgc gggtcattac tacgcctttg aaaccacgag caccgttgac   3000
ggtgtcacca agaccactac taactggcgc tattttgatg aaaacggcgt tatggcacgc   3060
```

-continued

```
ggcctggtga aaatcggtaa tgattatcaa tactacgacg ataacggcaa tcagatcaag    3120
ggtcaactgg tgacggacaa ggacggcaac acccgttact ttaaagctga cagcggtgca    3180
atggttacgg gtgagtttgc actggtgaat ggtggttggt actacttcga tgacaatggt    3240
gttgcagtca aaggtgctca gaccattaac ggtcaacagt tgtacttcga cgagaatggt    3300
gtccaagcaa aaggtgtgtt cgtgaccaat gaggatggca cccgtagcta ttacgacgcc    3360
aagtccggtg agaagtttgt tggcgacttc tttacgaccg cgacaaccac ttggtactat    3420
gccgacgaga acggcaattt ggcaacgggt agccaggtta tccgtggtca gaagttgtat    3480
tttgcagccg atggtttgca ggcgaaaggt atctttacca ccgacgccga aggtaaccgc    3540
cacttctacg acccggactc cggcgatctg gcggaaaaca agtttatcgc ggatggtgac    3600
gactggtact attttgacga aacgggtcat gttgttaccg gcgagcaagt gatcaacggc    3660
caacagctgt atttcgacga aaatggcgtt caggcgaagg gtgttttcgt gaccgatgat    3720
aatggtaata gcgttacta tgatgcacag acgggtgaga tggtggtgaa ccagacgctg    3780
acggtggatg gtgtggaata tacctttggt gcggatggca tcgcggtggt taatgcacaa    3840
gatagcgacg aacaaagcga aagcacggat gaaacgcaag tgaccagcga tgacgcgacg    3900
gttgcaaaga cggaaaccag ctctgctgaa taa                                 3933
```

<210> SEQ ID NO 40
<211> LENGTH: 1310
<212> TYPE: PRT
<213> ORGANISM: Streptococcus gallolyticus

<400> SEQUENCE: 40

```
Met Ile Asp Gly Lys Tyr Tyr Val Gln Ala Asp Gly Ser Val Lys
1               5                   10                  15

Lys Asn Phe Ala Ile Thr Val Asn Gly Gln Leu Leu Tyr Phe Asp Ala
                20                  25                  30

Glu Thr Gly Ala Leu Thr Ser Thr Ser Thr Tyr Ser Phe Thr Glu Gly
            35                  40                  45

Leu Thr Asn Leu Val Asp Asn Phe Ser Lys Asn Asn Gln Ala Tyr Asp
        50                  55                  60

Ser Thr Glu Lys Ser Phe Glu Leu Val Asp Gly Tyr Leu Thr Ala Asn
65                  70                  75                  80

Ser Trp Tyr Arg Pro Thr Lys Val Leu Glu Asn Gly Glu Thr Trp Val
                85                  90                  95

Asp Ser Thr Glu Glu Ser Phe Arg Pro Leu Val Met Ala Trp Trp Pro
            100                 105                 110

Asp Val Asp Thr Gln Ile Asn Tyr Leu Asn Ser Met Ser Glu Tyr Phe
        115                 120                 125

Gly Leu Asn Lys Lys Tyr Ser Ala Ser Asp Ser Gln Ala Ser Leu Asn
    130                 135                 140

Val Ala Ala Glu Ala Ile Gln Val Lys Ile Glu Gln Glu Ile Ala Arg
145                 150                 155                 160

Arg Gly Ser Thr Glu Trp Leu Arg Glu Val Ile Ser Ser Phe Val Thr
                165                 170                 175

Thr Gln Asp Lys Trp Asn Met Asn Ser Glu Asp Arg Asp Thr Asp His
            180                 185                 190

Leu Gln Gly Gly Ala Leu Leu Tyr Val Asn Ser Asp Leu Thr Glu Trp
        195                 200                 205

Ala Asn Ser Asp Tyr Arg Leu Leu Asn Arg Ala Pro Thr Tyr Gln Thr
    210                 215                 220
```

```
Gly Glu Thr Lys Tyr His Lys Ala Asp Arg Thr Gly Tyr Asp Phe
225                 230                 235                 240

Leu Leu Ala Asn Asp Val Asp Asn Ser Asn Pro Val Val Gln Ala Glu
        245                 250                 255

Gln Leu Asn Gln Leu Tyr Tyr Leu Met Asn Trp Gly Lys Ile Val Phe
            260                 265                 270

Gly Asp Ala Asp Ala Asn Phe Asp Gly Val Arg Val Asp Ala Val Asp
                275                 280                 285

Asn Val Asp Ala Asp Leu Leu Gln Ile Tyr Thr Asn Leu Phe Glu Ala
290                 295                 300

Ala Tyr Gly Val Asp Lys Thr Glu Ala Gln Ala Leu His Ile Ser
305                 310                 315                 320

Ile Leu Glu Ala Trp Ser Phe Asn Asp Pro Asp Tyr Asn His Asp Thr
                325                 330                 335

Asn Gly Ala Ala Leu Ala Ile Asp Asn Gly Leu Arg Met Ala Phe Leu
            340                 345                 350

Asp Ala Leu Thr Arg Pro Leu Asp Ser Arg Thr Asn Leu Glu Ser Leu
                355                 360                 365

Ile His Asn Asp Leu Gly Met Thr Asp Arg Thr Val Asp Ser Ala Tyr
370                 375                 380

Gly Asp Ala Met Pro Ser Tyr Ala Phe Val Arg Ala His Asp Ser Glu
385                 390                 395                 400

Val Gln Gly Ile Ile Ala Ser Ile Ile Ala Gly Gln Ile Asn Pro Lys
                405                 410                 415

Thr Asp Gly Phe Thr Phe Thr Leu Asp Glu Leu Gln Lys Ala Phe Glu
                420                 425                 430

Ile Tyr Asn Ala Asp Met Asn Ser Val His Lys Lys Tyr Thr His Phe
                435                 440                 445

Asn Ile Pro Ala Ala Tyr Ala Leu Leu Leu Thr Asn Met Glu Ser Val
450                 455                 460

Pro Arg Val Tyr Tyr Gly Asp Leu Phe Thr Asp Asn Gly Gln Tyr Met
465                 470                 475                 480

Ala Val Lys Ser Pro Tyr Tyr Asp Gln Ile Thr Ala Leu Leu Lys Ser
                485                 490                 495

Arg Ile Lys Tyr Ala Ala Gly Gly Gln Ala Met Asn Val Gln Tyr Pro
                500                 505                 510

Asp Gly Ala Gly Ala Gly Ile Leu Thr Ser Val Arg Phe Gly Tyr Gly
            515                 520                 525

Ile Met Thr Ala Asp Gln Lys Ala Thr Asp Asp Ser Val Thr Thr Ser
530                 535                 540

Gly Ile Val Thr Ile Val Ser Asn Asn Pro Asn Leu Lys Leu Asn Ser
545                 550                 555                 560

Ser Asp Lys Ile Ala Val Gln Val Gly Leu Ala His Ala Gly Gln Tyr
                565                 570                 575

Tyr Arg Pro Leu Leu Ser Pro Thr Glu Asn Gly Leu Gln Val Phe Leu
                580                 585                 590

Asn Asp Ser Asp Thr Asp Ile Thr Lys Leu Val Asp Asp Asn Gly Tyr
            595                 600                 605

Ile Tyr Phe Thr Gly Asp Glu Ile Lys Gly Phe Glu Thr Val Asp Met
            610                 615                 620

Asn Gly Phe Leu Thr Val Trp Val Pro Val Gly Ala Ala Ala Asp Gln
625                 630                 635                 640
```

-continued

```
Asp Ile Arg Val Lys Ala Ser Thr Glu Ala Lys Lys Asp Gly Glu Leu
                645                 650                 655
Thr Tyr Glu Thr Ser Ala Ala Leu Asp Ser Gln Val Ile Phe Glu Gly
            660                 665                 670
Phe Ser Asn Phe Gln Asp Phe Val Gln Asp Pro Ser Gln Tyr Thr Asn
        675                 680                 685
Lys Val Ile Ala Glu Asn Ala Asp Leu Phe Ala Ser Trp Gly Ile Thr
    690                 695                 700
Ser Phe Glu Leu Ala Pro Gln Tyr Val Ser Ser Thr Asp Gly Thr Phe
705                 710                 715                 720
Leu Asp Ser Ile Ile Gln Asn Gly Tyr Ala Phe Thr Asp Arg Tyr Asp
                725                 730                 735
Leu Ala Met Ser Lys Asn Asn Lys Tyr Gly Ser Ala Glu Asp Leu Arg
            740                 745                 750
Asn Ala Ile Lys Ala Leu His Ala Arg Gly Ile Gln Val Ile Ala Asp
        755                 760                 765
Trp Val Pro Asp Gln Ile Tyr Ala Leu Pro Gly Glu Glu Ile Val Thr
    770                 775                 780
Ala Thr Arg Val Asn Asp Tyr Gly Glu Arg Glu Gly Ala Gln Ile
785                 790                 795                 800
Lys Asn Lys Pro Tyr Ala Ala Asn Thr Lys Ser Ser Gly Glu Asp Tyr
                805                 810                 815
Gln Ala Gln Tyr Gly Gly Glu Phe Leu Glu Tyr Leu Gln Glu Asn Tyr
            820                 825                 830
Pro Glu Leu Phe Glu Lys Val Met Ile Ser Thr Gly Lys Thr Ile Asp
        835                 840                 845
Pro Ser Thr Lys Ile Lys Val Trp Lys Ala Glu Tyr Phe Asn Gly Thr
    850                 855                 860
Asn Ile Leu Gly Lys Gly Ala Asp Tyr Val Leu Asn Asp Ala Ala Thr
865                 870                 875                 880
Gly Thr Tyr Phe Thr Val Thr Glu Asn Gly Ala Phe Leu Pro Lys Gln
                885                 890                 895
Met Thr Ser Asp Thr Ala Gln Thr Gly Phe Tyr Tyr Asp Gly Thr Gly
            900                 905                 910
Met Thr Tyr Tyr Ser Thr Ser Gly Tyr Gln Ala Lys Ser Ser Phe Val
        915                 920                 925
Leu Tyr Asn Gly Asn Arg Tyr Tyr Phe Asp Glu Asn Gly His Met Val
    930                 935                 940
Thr Gly Met Arg Asp Ile Asp Gly Gln Thr Tyr Tyr Phe Leu Pro Asn
945                 950                 955                 960
Gly Ile Glu Leu Arg Asp Ala Ile Tyr Glu Asp Ala Asn Gly Asn Gln
                965                 970                 975
Tyr Tyr Phe Gly Lys Ser Gly Asn Arg Tyr Ala Gly His Tyr Tyr Ala
            980                 985                 990
Phe Glu Thr Thr Ser Thr Val Asp Gly Val Thr Lys Thr Thr Thr Asn
        995                 1000                1005
Trp Arg Tyr Phe Asp Glu Asn Gly Val Met Ala Arg Gly Leu Val
    1010                1015                1020
Lys Ile Gly Asn Asp Tyr Gln Tyr Tyr Asp Asp Asn Gly Asn Gln
    1025                1030                1035
Ile Lys Gly Gln Leu Val Thr Asp Lys Asp Gly Asn Thr Arg Tyr
    1040                1045                1050
Phe Lys Ala Asp Ser Gly Ala Met Val Thr Gly Glu Phe Ala Leu
```

```
                1055                1060                1065
Val Asn Gly Gly Trp Tyr Tyr Phe Asp Asp Asn Gly Val Ala Val
         1070                1075                1080
Lys Gly Ala Gln Thr Ile Asn Gly Gln Gln Leu Tyr Phe Asp Glu
         1085                1090                1095
Asn Gly Val Gln Ala Lys Gly Val Phe Val Thr Asn Glu Asp Gly
         1100                1105                1110
Thr Arg Ser Tyr Tyr Asp Ala Lys Ser Gly Glu Lys Phe Val Gly
         1115                1120                1125
Asp Phe Phe Thr Thr Gly Asp Asn His Trp Tyr Tyr Ala Asp Glu
         1130                1135                1140
Asn Gly Asn Leu Ala Thr Gly Ser Gln Val Ile Arg Gly Gln Lys
         1145                1150                1155
Leu Tyr Phe Ala Ala Asp Gly Leu Gln Ala Lys Gly Ile Phe Thr
         1160                1165                1170
Thr Asp Ala Glu Gly Asn Arg His Phe Tyr Asp Pro Asp Ser Gly
         1175                1180                1185
Asp Leu Ala Glu Asn Lys Phe Ile Ala Asp Gly Asp Asp Trp Tyr
         1190                1195                1200
Tyr Phe Asp Glu Thr Gly His Val Val Thr Gly Glu Gln Val Ile
         1205                1210                1215
Asn Gly Gln Gln Leu Tyr Phe Asp Glu Asn Gly Val Gln Ala Lys
         1220                1225                1230
Gly Val Phe Val Thr Asp Asp Asn Gly Asn Lys Arg Tyr Tyr Asp
         1235                1240                1245
Ala Gln Thr Gly Glu Met Val Val Asn Gln Thr Leu Thr Val Asp
         1250                1255                1260
Gly Val Glu Tyr Thr Phe Gly Ala Asp Gly Val Ala Val Val Asn
         1265                1270                1275
Ala Gln Asp Ser Asp Glu Gln Ser Glu Ser Thr Asp Glu Thr Gln
         1280                1285                1290
Val Thr Ser Asp Asp Ala Val Ala Lys Thr Glu Thr Ser Ser
         1295                1300                1305
Ala Glu
   1310

<210> SEQ ID NO 41
<211> LENGTH: 3804
<212> TYPE: DNA
<213> ORGANISM: Streptococcus mutans

<400> SEQUENCE: 41
atggtcaatg gcaaatacta ctactacaaa gaggacggta cgttgcagaa gaactacgca       60
ctgaacatta cggcaagac ctttttcttt gacgagactg gcgccctgag caataacacc      120
ctgccgagca agaaaggtaa catcaccaat aacgacaata ccaatagctt cgcgcaatac      180
aatcaggtgt attcgacgga tgcagcgaac ttcgaacatg tcgatcacta cctgacggcg      240
gagtcctggt atcgcccgaa gtatattctg aaagatggca agacgtggac tcagtccacg      300
gagaaagatt ttcgcccgtt gttgatgacc tggtggccgg atcaggaaac ccagcgtcag      360
tatgtaaact atatgaatgc ccagctgggt attcaccaga cctacaacac ggcgaccagc      420
ccgttgcaac tgaatctggc ggcacagacg atccagacca agattgaaga gaagatcacg      480
gcggagaaga acactaattg gctgcgtcaa acgatttcgg cctttgtcaa aacccagagc      540
```

```
gcgtggaact cggacagcga aaaaccgttt gacgatcatc tgcaaaaggg tgcactgctg    600
tactctaaca atagcaagtt gacctctcaa gctaatagca actaccgtat tctgaaccgt    660
accccaacca accaaaccgg caagaaagat ccgcgttata ccgctgaccg taccatcggt    720
ggttatgagt tcttgctggc gaacgatgtg gataatagca atcctgttgt tcaagcggaa    780
cagctgaact ggctgcactt cctgatgaac tttggcaata tctatgcaaa cgaccctgac    840
gccaactttg acagcatccg tgtagacgcc gtggacaacg tggatgcaga tttgttgcaa    900
atcgctggtg actatctgaa ggctgcaaag ggcatccata agaacgacaa agcagcgaac    960
gaccacctgt cgatcctgga agcatggagc tataatgaca ccccgtatct gcacgacgac   1020
ggtgacaaca tgatcaatat ggacaaccgt ctgcgtctga gcctgctgta tagcctggcg   1080
aagccgttga accagcgttc gggcatgaac ccgctgatca cgaacagcct ggttaaccgt   1140
accgatgaca acgcagaaac cgcagcggtc ccgagctaca gctttatccg tgcacacgat   1200
agcgaggttc aagacctgat tcgtaacatt attcgtgctg agattaatcc gaacgtcgtc   1260
ggttatagct tcacgatgga agagatcaag aaggcctttg agatttacaa caaggatctg   1320
ctggcgacgg aaaagaaata cacccactat aacaccgcgc tgagctacgc gctgctgctg   1380
accaataaga gcagcgttcc gcgtgtgtat tacggtgata tgtttactga cgacggtcag   1440
tacatggcac ataaaacgat caactacgag gctatcgaaa cgctgttgaa ggcgcgcatt   1500
aagtacgtgt ctggtggcca agcgatgcgt aatcaacagg tgggtaatag cgaaatcatt   1560
acgagcgtcc gctatggcaa gggcgcactg aaagcgacgg ataccggcga tcgtaccacg   1620
cgcaccagcg gcgttgcggt tattgaaggc aataacccga gcctgcgctt gaaggcgagc   1680
gaccgcgtcg ttgttaacat gggtgcagca cacaagaacc aggcatatcg tccgctgttg   1740
ctgaccactg ataatggcat caaagcgtat cacagcgatc aggaagctgc gggcctggtg   1800
cgctatacca atgatcgtgg tgaattgatc ttcacggcag ctgacattaa aggttatgca   1860
aatccgcaag tcagcggtta tctgggcgtc tgggtgccgg tcggcgcagc ggctgatcaa   1920
gacgtgcgtg tggccgcgag caccgcgcca tcgaccgacg gtaaaagcgt gcaccagaat   1980
gcggcgctgg acagccgtgt catgtttgag ggttttagca actttcaagc ctttgcaacg   2040
aagaaagaag agtacaccaa cgtcgtcatc gcgaagaacg tcgataagtt cgcggaatgg   2100
ggcgttaccg atttcgaaat ggcaccgcag tatgtgtcta gcaccgatgg ctcgtttctg   2160
gattccgtga tccaaaatgg ttatgcattt accgaccgct atgacctggg cattagcaag   2220
ccgaataagt atggtacggc ggatgatctg gttaaagcga tcaaggcgct gcattctaaa   2280
ggtattaagg ttatggccga ctgggttcca gatcagatgt atgctttccc ggaaaaagaa   2340
gtggtgacgg ccacccgcgt ggacaaatat ggtacgccgg tcgcgggcag ccagatcaaa   2400
aacactctgt atgtcgtgga tggcaaaagc tccggtaaag atcagcaagc gaaatatggc   2460
ggtgccttcc tggaagagtt gcaggcgaaa tacccggaac tgttcgcgcg taagcagatc   2520
agcactggtg ttccgatgga cccgagcgtg aagattaaac aatggtccgc gaaatacttt   2580
aacggcacga acatcctggg tcgtggtgcc ggctacgtgc tgaaagacca ggcaacgaat   2640
acgtacttta gcttggtgtc cgacaatacg tttctgccga agtctctggt caacccgaac   2700
cacggtacga gcagctctgt gaccggcctg gtgttcgatg gtaagggcta cgtgtactac   2760
tctaccagcg gttaccaggc caagaatacg ttcatcagcc tgggtaacaa ctggtattac   2820
ttcgacaata acgttacata ggtcacgggt gcgcagagca tcaacggtgc caactactat   2880
tttctgagca acggcattca gctgcgtaat gcgatttacg acaatggcaa taaggttctg   2940
```

```
agctactacg gtaatgacgg tcgtcgttat gagaatggct attacctgtt tggccaacag    3000
tggcgctact ttcaaaatgg tattatggcc gtcggtctga cccgtgtcca cggtgcggtg    3060
cagtattttg acgccagcgg cttccaagcc aagggccagt tcatcaccac tgcggacggt    3120
aaactgcgtt actttgaccg tgacagcggc aaccaaatca gcaatcgttt tgttcgtaac    3180
agcaagggtg aatggttttt gttcgatcat aacggcgtgg cggttaccgg caccgttact    3240
ttcaatggtc aacgtctgta ctttaagccg aacggtgttc aggcaaaggg tgagttcatt    3300
cgcgacgcgg atggtcactt gcgttactac gaccctaatt ccggtaatga ggttcgtaac    3360
cgtttcgtcc gcaactctaa gggcgaatgg ttcctgtttg accacaatgg catcgcagtc    3420
accggcgctc gtgtggtcaa cggccaacgc ttgtacttca aaagcaatgg cgtccaagct    3480
aagggtgagc tgattaccga acgtaagggc cgtattaagt attatgatcc taacagcggt    3540
aacgaagtgc gtaaccgcta cgtccgcacc agcagcggta attggtacta ttttggtaac    3600
gatggttacg cgctgatcgg ctggcatgtt gttgagggtc gtcgtgtgta ctttgatgag    3660
aacggtgtct atcgttacgc gagccacgac cagcgtaatc attggaacta cgactatcgt    3720
cgcgatttcg gtcgtggtag cagctccgct atccgttttc gccatagccg taacggcttt    3780
ttcgacaact tcttccgctt ctaa                                           3804

<210> SEQ ID NO 42
<211> LENGTH: 1267
<212> TYPE: PRT
<213> ORGANISM: Streptococcus mutans

<400> SEQUENCE: 42

Met Val Asn Gly Lys Tyr Tyr Tyr Lys Glu Asp Gly Thr Leu Gln
1               5                   10                  15

Lys Asn Tyr Ala Leu Asn Ile Asn Gly Lys Thr Phe Phe Phe Asp Glu
                20                  25                  30

Thr Gly Ala Leu Ser Asn Asn Thr Leu Pro Ser Lys Lys Gly Asn Ile
            35                  40                  45

Thr Asn Asn Asp Asn Thr Asn Ser Phe Ala Gln Tyr Asn Gln Val Tyr
        50                  55                  60

Ser Thr Asp Ala Ala Asn Phe Glu His Val Asp His Tyr Leu Thr Ala
65                  70                  75                  80

Glu Ser Trp Tyr Arg Pro Lys Tyr Ile Leu Lys Asp Gly Lys Thr Trp
                85                  90                  95

Thr Gln Ser Thr Glu Lys Asp Phe Arg Pro Leu Leu Met Thr Trp Trp
            100                 105                 110

Pro Asp Gln Glu Thr Gln Arg Gln Tyr Val Asn Tyr Met Asn Ala Gln
        115                 120                 125

Leu Gly Ile His Gln Thr Tyr Asn Thr Ala Thr Ser Pro Leu Gln Leu
    130                 135                 140

Asn Leu Ala Ala Gln Thr Ile Gln Thr Lys Ile Glu Glu Lys Ile Thr
145                 150                 155                 160

Ala Glu Lys Asn Thr Asn Trp Leu Arg Gln Thr Ile Ser Ala Phe Val
                165                 170                 175

Lys Thr Gln Ser Ala Trp Asn Ser Asp Ser Glu Lys Pro Phe Asp Asp
            180                 185                 190

His Leu Gln Lys Gly Ala Leu Leu Tyr Ser Asn Asn Ser Lys Leu Thr
        195                 200                 205

Ser Gln Ala Asn Ser Asn Tyr Arg Ile Leu Asn Arg Thr Pro Thr Asn
```

```
            210                 215                 220
Gln Thr Gly Lys Lys Asp Pro Arg Tyr Thr Ala Asp Arg Thr Ile Gly
225                 230                 235                 240

Gly Tyr Glu Phe Leu Leu Ala Asn Asp Val Asp Asn Ser Asn Pro Val
                245                 250                 255

Val Gln Ala Glu Gln Leu Asn Trp Leu His Phe Leu Met Asn Phe Gly
            260                 265                 270

Asn Ile Tyr Ala Asn Asp Pro Asp Ala Asn Phe Asp Ser Ile Arg Val
        275                 280                 285

Asp Ala Val Asp Asn Val Asp Ala Asp Leu Leu Gln Ile Ala Gly Asp
    290                 295                 300

Tyr Leu Lys Ala Ala Lys Gly Ile His Lys Asn Asp Lys Ala Ala Asn
305                 310                 315                 320

Asp His Leu Ser Ile Leu Glu Ala Trp Ser Tyr Asn Asp Thr Pro Tyr
                325                 330                 335

Leu His Asp Asp Gly Asp Asn Met Ile Asn Met Asp Asn Arg Leu Arg
                340                 345                 350

Leu Ser Leu Leu Tyr Ser Leu Ala Lys Pro Leu Asn Gln Arg Ser Gly
            355                 360                 365

Met Asn Pro Leu Ile Thr Asn Ser Leu Val Asn Arg Thr Asp Asp Asn
        370                 375                 380

Ala Glu Thr Ala Ala Val Pro Ser Tyr Ser Phe Ile Arg Ala His Asp
385                 390                 395                 400

Ser Glu Val Gln Asp Leu Ile Arg Asn Ile Ile Arg Ala Glu Ile Asn
                405                 410                 415

Pro Asn Val Val Gly Tyr Ser Phe Thr Met Glu Glu Ile Lys Lys Ala
                420                 425                 430

Phe Glu Ile Tyr Asn Lys Asp Leu Leu Ala Thr Glu Lys Lys Tyr Thr
            435                 440                 445

His Tyr Asn Thr Ala Leu Ser Tyr Ala Leu Leu Leu Thr Asn Lys Ser
        450                 455                 460

Ser Val Pro Arg Val Tyr Tyr Gly Asp Met Phe Thr Asp Asp Gly Gln
465                 470                 475                 480

Tyr Met Ala His Lys Thr Ile Asn Tyr Glu Ala Ile Glu Thr Leu Leu
                485                 490                 495

Lys Ala Arg Ile Lys Tyr Val Ser Gly Gly Gln Ala Met Arg Asn Gln
                500                 505                 510

Gln Val Gly Asn Ser Glu Ile Ile Thr Ser Val Arg Tyr Gly Lys Gly
            515                 520                 525

Ala Leu Lys Ala Thr Asp Thr Gly Asp Arg Thr Thr Arg Thr Ser Gly
        530                 535                 540

Val Ala Val Ile Glu Gly Asn Asn Pro Ser Leu Arg Leu Lys Ala Ser
545                 550                 555                 560

Asp Arg Val Val Val Asn Met Gly Ala Ala His Lys Asn Gln Ala Tyr
                565                 570                 575

Arg Pro Leu Leu Leu Thr Thr Asp Asn Gly Ile Lys Ala Tyr His Ser
                580                 585                 590

Asp Gln Glu Ala Ala Gly Leu Val Arg Tyr Thr Asn Asp Arg Gly Glu
            595                 600                 605

Leu Ile Phe Thr Ala Ala Asp Ile Lys Gly Tyr Ala Asn Pro Gln Val
        610                 615                 620

Ser Gly Tyr Leu Gly Val Trp Val Pro Val Gly Ala Ala Asp Gln
625                 630                 635                 640
```

```
Asp Val Arg Val Ala Ala Ser Thr Ala Pro Ser Thr Asp Gly Lys Ser
                645                 650                 655

Val His Gln Asn Ala Ala Leu Asp Ser Arg Val Met Phe Glu Gly Phe
                660                 665                 670

Ser Asn Phe Gln Ala Phe Ala Thr Lys Lys Glu Glu Tyr Thr Asn Val
                675                 680                 685

Val Ile Ala Lys Asn Val Asp Lys Phe Ala Glu Trp Gly Val Thr Asp
                690                 695                 700

Phe Glu Met Ala Pro Gln Tyr Val Ser Ser Thr Asp Gly Ser Phe Leu
705                 710                 715                 720

Asp Ser Val Ile Gln Asn Gly Tyr Ala Phe Thr Asp Arg Tyr Asp Leu
                725                 730                 735

Gly Ile Ser Lys Pro Asn Lys Tyr Gly Thr Ala Asp Asp Leu Val Lys
                740                 745                 750

Ala Ile Lys Ala Leu His Ser Lys Gly Ile Lys Val Met Ala Asp Trp
                755                 760                 765

Val Pro Asp Gln Met Tyr Ala Phe Pro Glu Lys Glu Val Val Thr Ala
                770                 775                 780

Thr Arg Val Asp Lys Tyr Gly Thr Pro Val Ala Gly Ser Gln Ile Lys
785                 790                 795                 800

Asn Thr Leu Tyr Val Val Asp Gly Lys Ser Ser Gly Lys Asp Gln Gln
                805                 810                 815

Ala Lys Tyr Gly Gly Ala Phe Leu Glu Glu Leu Gln Ala Lys Tyr Pro
                820                 825                 830

Glu Leu Phe Ala Arg Lys Gln Ile Ser Thr Gly Val Pro Met Asp Pro
                835                 840                 845

Ser Val Lys Ile Lys Gln Trp Ser Ala Lys Tyr Phe Asn Gly Thr Asn
                850                 855                 860

Ile Leu Gly Arg Gly Ala Gly Tyr Val Leu Lys Asp Gln Ala Thr Asn
865                 870                 875                 880

Thr Tyr Phe Ser Leu Val Ser Asp Asn Thr Phe Leu Pro Lys Ser Leu
                885                 890                 895

Val Asn Pro Asn His Gly Thr Ser Ser Val Thr Gly Leu Val Phe
                900                 905                 910

Asp Gly Lys Gly Tyr Val Tyr Tyr Ser Thr Ser Gly Tyr Gln Ala Lys
                915                 920                 925

Asn Thr Phe Ile Ser Leu Gly Asn Asn Trp Tyr Tyr Phe Asp Asn Asn
                930                 935                 940

Gly Tyr Met Val Thr Gly Ala Gln Ser Ile Asn Gly Ala Asn Tyr Tyr
945                 950                 955                 960

Phe Leu Ser Asn Gly Ile Gln Leu Arg Asn Ala Ile Tyr Asp Asn Gly
                965                 970                 975

Asn Lys Val Leu Ser Tyr Tyr Gly Asn Asp Gly Arg Arg Tyr Glu Asn
                980                 985                 990

Gly Tyr Tyr Leu Phe Gly Gln Gln Trp Arg Tyr Phe Gln Asn Gly Ile
                995                 1000                1005

Met Ala Val Gly Leu Thr Arg Val His Gly Ala Val Gln Tyr Phe
1010                1015                1020

Asp Ala Ser Gly Phe Gln Ala Lys Gly Gln Phe Ile Thr Thr Ala
         1025                1030                1035

Asp Gly Lys Leu Arg Tyr Phe Asp Arg Asp Ser Gly Asn Gln Ile
         1040                1045                1050
```

```
Ser Asn Arg Phe Val Arg Asn Ser Lys Gly Glu Trp Phe Leu Phe
    1055                1060                1065

Asp His Asn Gly Val Ala Val Thr Gly Thr Val Thr Phe Asn Gly
    1070                1075                1080

Gln Arg Leu Tyr Phe Lys Pro Asn Gly Val Gln Ala Lys Gly Glu
    1085                1090                1095

Phe Ile Arg Asp Ala Asp Gly His Leu Arg Tyr Tyr Asp Pro Asn
    1100                1105                1110

Ser Gly Asn Glu Val Arg Asn Arg Phe Val Arg Asn Ser Lys Gly
    1115                1120                1125

Glu Trp Phe Leu Phe Asp His Asn Gly Ile Ala Val Thr Gly Ala
    1130                1135                1140

Arg Val Val Asn Gly Gln Arg Leu Tyr Phe Lys Ser Asn Gly Val
    1145                1150                1155

Gln Ala Lys Gly Glu Leu Ile Thr Glu Arg Lys Gly Arg Ile Lys
    1160                1165                1170

Tyr Tyr Asp Pro Asn Ser Gly Asn Glu Val Arg Asn Arg Tyr Val
    1175                1180                1185

Arg Thr Ser Ser Gly Asn Trp Tyr Tyr Phe Gly Asn Asp Gly Tyr
    1190                1195                1200

Ala Leu Ile Gly Trp His Val Val Glu Gly Arg Arg Val Tyr Phe
    1205                1210                1215

Asp Glu Asn Gly Val Tyr Arg Tyr Ala Ser His Asp Gln Arg Asn
    1220                1225                1230

His Trp Asn Tyr Asp Tyr Arg Arg Asp Phe Gly Arg Gly Ser Ser
    1235                1240                1245

Ser Ala Ile Arg Phe Arg His Ser Arg Asn Gly Phe Phe Asp Asn
    1250                1255                1260

Phe Phe Arg Phe
    1265
```

```
<210> SEQ ID NO 43
<211> LENGTH: 3864
<212> TYPE: DNA
<213> ORGANISM: Streptococcus mutans

<400> SEQUENCE: 43
```

| | | | | | |
|---|---|---|---|---|---|
| atgattgacg | gcaaatacta | ctacatcggc | agcgacggtc | agccaaagaa | gaattttgcg | 60 |
| ttgacggtta | caataaaagt | cctgtatttt | gacaagaaca | cgggtgcgct | gaccgacacc | 120 |
| agccaatatc | agttcaaaca | aggtctgacg | aagctgaaca | cgactacac | ccctcacaat | 180 |
| cagattgtca | actttgaaaa | tactagcctg | gaaactattg | ataactatgt | tactgccgac | 240 |
| tcttggtatc | gtccgaaaga | cattctgaag | aacggtaaga | cgtggaccgc | gtcctctgag | 300 |
| agcgatctgc | gtccgctgct | gatgtcctgg | tggcctgata | gcagaccca | gatcgcatac | 360 |
| ctgaactaca | tgaaccaaca | aggcttgggc | actggcgaga | actataccgc | tgatagctct | 420 |
| caagagagcc | tgaacctggc | ggcacaaacc | gttcaagtca | aaatcgaaac | caagatcagc | 480 |
| caaacgcaac | agactcagtg | gctgcgtgac | atcattaact | ctttcgttaa | gacgcaaccg | 540 |
| aactggaata | gccaaaccga | gtctgacacg | agcgctggtg | aaaagatca | tttgcagggc | 600 |
| ggtgccctgc | tgtatagcaa | ttcggacaaa | accgcatacg | caaatagcga | ctatcgtctg | 660 |
| ctgaaccgta | ccccgaccag | ccagactggt | aagccgaaat | acttcgagga | caatagcagc | 720 |
| ggtggttacg | acttcctgtt | ggcaaacgat | attgataatt | ccaatccggt | ggtgcaggct | 780 |

-continued

```
gagcagctga attggctgca ttacctgatg aattacggta gcattgtcgc aaatgacccg      840
gaagcgaatt tcgatggtgt ccgtgttgac gcggtggata cgtgaacgc agacctgttg       900 cagatcgcaa gcgattatct gaaagcccat tatggtgttg ataagagcga aagaatgcg      960 atcaaccacc tgagcatcct ggaagcgtgg tctgacaacg acccacagta taacaaagac    1020
accaaaggtg cccagctgcc gatcgacaac aaactgcgtc tgtcgttgct gtacgcactg     1080
acccgtccgc tggagaagga tgcaagcaac aaaaatgaga ttcgtagcgg tctggagccg    1140
gttattacca attccctgaa taatcgttcc gctgagggca agaactctga acgcatggcg    1200
aattacatct tcatccgtgc tcacgattct gaagttcaaa cggtgatcgc aaagatcatc    1260
aaagcgcaga ttaacccgaa aacggatggc ctgaccttca ccctggatga gctgaaacag    1320
gcgttcaaaa tctataacga ggatatgcgc caggcgaaga gaagtatac ccagagcaat    1380 atcccgacgg catacgccct gatgctgagc aataaggact ccatcacgcg cctgtattac    1440
ggtgatatgt acagcgatga tggccaatac atggcgacca atccccgta ctacgatgcg    1500 attgacaccc tgctgaaggc gcgcattaag tatgccgctg gcggtcagga tatgaagatc    1560
acctacgttg agggtgacaa aagccacatg gactgggact atacgggtgt cctgacgagc    1620
gttcgctacg gcacgggcgc aaacgaagcg accgaccagg gcagcgaagc taccaagacg    1680
caaggtatgg ccgtcatcac ttctaacaac ccgtccctga agctgaatca aacgacaag    1740 gtcattgtca atatgggcac cgctcacaaa aatcaggaat accgtccgtt gctgctgacc    1800
accaaagacg gtctgaccag ctacaccagc gacgccgctg ccaagagcct gtaccgtaaa    1860
acgaacgata agggcgagtt ggtgttcgat gcaagcgaca ttcagggcta tctgaatccg    1920
caagtgagcg gttacctggc tgtttgggtg cctgtgggtg cgagcgacaa ccaggatgtg    1980
cgtgtcgcgc ccagcaataa agccaatgcg accggccaag tctatgaaag cagcagcgca    2040
ctggatagcc aactgattta tgagggtttt tccaactttc aggacttcgt caccaaggat    2100
tctgattaca ccaataaaaa gatcgcgcaa aatgtccagc tgtttaagag ctggggcgtc    2160
accagctttg agatggctcc gcaatacgtc agcagcgagg acggcagctt tttggacagc    2220
attatccaga acggctatgc gttcgaggat cgttacgacc tggcgatgag caaaaacaac    2280
aaatacggct cccagcagga catgatcaac gcggttaagg cgctgcataa gagcggtatc    2340
caagtgatcg cggactgggt cccggatcaa atctacaatt tgccgggtaa agaggtcgtc    2400
accgcgaccc gtgtgaacga ctacggcgag tatcgcaagg actccgaaat caaaaacacc    2460
ctgtacgccg ccaacaccaa aagcaacggt aaagattatc aagcaaagta cggtggcgcc    2520
tttttgagcg agctggccgc caaatatccg agcatcttta accgcactca gattagcaat    2580
ggcaagaaga tcgacccgtc tgaaaagatc accgcctgga aggccaaata cttcaatggt    2640
acgaacattt tgggtcgcgg cgttggttac gtcttgaaag acaatgccag cgacaagtat    2700
tttgagctga agggcaatca gacttatctg ccgaagcaaa tgacgaataa agaagcctcg    2760
actggtttcg ttaatgacgg caatggtatg acctttttaca gcacgagcgg ttatcaagcg    2820
aagaacagct tcgttcagga cgcaaaaggc aactggtact actttgacaa caatggccac    2880
atggtttacg gtctgcaaca tctgaacggc gaggtgcaat acttcctgag caatggcgtg    2940
caactgcgtg aatccttctt ggaaaatgcc gacggcagca aaaactattt cggtcacctg    3000
ggcaaccgtt atagcaatgg ttactacagc ttcgataatg atagcaaatg gcgctatttc    3060
gatgcgagcg gtgttatggc agtgggtctg aaaactatta acggtaacac ccagtatttc    3120
gatcaagacg gctaccaagt gaagggtgca tggattaccg gcagcgatgg taagaagcgt    3180
```

-continued

```
tacttcgacg acggtagcgg caatatggca gttaatcgct ttgctaacga caagaatggc    3240
gattggtatt acctgaatag cgacggtatt gcactggtgg gtgttcagac catcaacggc    3300
aaaacgtatt actttggcca agatggtaaa caaatcaaag gcaaaatcat taccgataat    3360
ggtaaactga atactttct ggcgaacagc ggtgagctgg cgcgtaacat ttttgcgacc     3420
gacagccaga caactggta ttacttcggc tcggatggtg ttgcggttac gggttcgcag     3480
acgattgcgg gtaaaaagtt gtactttgcg tccgacggta acaggtgaa gggtagcttt     3540 gttacttaca atggtaaagt gcactattac catgcggaca gcggcgaact gcaagtcaac    3600
cgtttcgagg cggataaaga cggtaattgg tactatctgg acagcaacgg tgaggcactg    3660
acgggtagcc agcgtatcaa tggtcaacgt gtgtttttca cccgcgaggg caaacaggtt    3720
aagggtgatg tcgcgtatga tgaacgcggc ttgctgcgct attacgacaa aaacagcggt    3780
aatatggtgt acaacaaggt ggtcacgctg gcgaacggtc gtcgtattgg tattgaccgc    3840
tggggtattg ctcgctatta ctaa                                           3864
```

<210> SEQ ID NO 44
<211> LENGTH: 1287
<212> TYPE: PRT
<213> ORGANISM: Streptococcus mutans

<400> SEQUENCE: 44

```
Met Ile Asp Gly Lys Tyr Tyr Ile Gly Ser Asp Gly Gln Pro Lys
 1               5                  10                  15

Lys Asn Phe Ala Leu Thr Val Asn Asn Lys Val Leu Tyr Phe Asp Lys
                20                  25                  30

Asn Thr Gly Ala Leu Thr Asp Thr Ser Gln Tyr Gln Phe Lys Gln Gly
            35                  40                  45

Leu Thr Lys Leu Asn Asn Asp Tyr Thr Pro His Asn Gln Ile Val Asn
        50                  55                  60

Phe Glu Asn Thr Ser Leu Glu Thr Ile Asp Asn Tyr Val Thr Ala Asp
    65                  70                  75                  80

Ser Trp Tyr Arg Pro Lys Asp Ile Leu Lys Asn Gly Lys Thr Trp Thr
                85                  90                  95

Ala Ser Ser Glu Ser Asp Leu Arg Pro Leu Leu Met Ser Trp Trp Pro
               100                 105                 110

Asp Lys Gln Thr Gln Ile Ala Tyr Leu Asn Tyr Met Asn Gln Gln Gly
           115                 120                 125

Leu Gly Thr Gly Glu Asn Tyr Thr Ala Asp Ser Gln Glu Ser Leu
       130                 135                 140

Asn Leu Ala Ala Gln Thr Val Gln Val Lys Ile Glu Thr Lys Ile Ser
145                 150                 155                 160

Gln Thr Gln Gln Thr Gln Trp Leu Arg Asp Ile Ile Asn Ser Phe Val
                165                 170                 175

Lys Thr Gln Pro Asn Trp Asn Ser Gln Thr Glu Ser Thr Ser Ala
           180                 185                 190

Gly Glu Lys Asp His Leu Gln Gly Gly Ala Leu Leu Tyr Ser Asn Ser
       195                 200                 205

Asp Lys Thr Ala Tyr Ala Asn Ser Asp Tyr Arg Leu Leu Asn Arg Thr
   210                 215                 220

Pro Thr Ser Gln Thr Gly Lys Pro Lys Tyr Phe Glu Asp Asn Ser Ser
225                 230                 235                 240

Gly Gly Tyr Asp Phe Leu Leu Ala Asn Asp Ile Asp Asn Ser Asn Pro
```

```
            245                 250                 255
Val Val Gln Ala Glu Gln Leu Asn Trp Leu His Tyr Leu Met Asn Tyr
            260                 265                 270
Gly Ser Ile Val Ala Asn Asp Pro Glu Ala Asn Phe Asp Gly Val Arg
            275                 280                 285
Val Asp Ala Val Asp Asn Val Asn Ala Asp Leu Leu Gln Ile Ala Ser
            290                 295                 300
Asp Tyr Leu Lys Ala His Tyr Gly Val Asp Lys Ser Glu Lys Asn Ala
305                 310                 315                 320
Ile Asn His Leu Ser Ile Leu Glu Ala Trp Ser Asp Asn Asp Pro Gln
            325                 330                 335
Tyr Asn Lys Asp Thr Lys Gly Ala Gln Leu Pro Ile Asp Asn Lys Leu
            340                 345                 350
Arg Leu Ser Leu Leu Tyr Ala Leu Thr Arg Pro Leu Glu Lys Asp Ala
            355                 360                 365
Ser Asn Lys Asn Glu Ile Arg Ser Gly Leu Glu Pro Val Ile Thr Asn
            370                 375                 380
Ser Leu Asn Asn Arg Ser Ala Glu Gly Lys Asn Ser Glu Arg Met Ala
385                 390                 395                 400
Asn Tyr Ile Phe Ile Arg Ala His Asp Ser Glu Val Gln Thr Val Ile
                405                 410                 415
Ala Lys Ile Ile Lys Ala Gln Ile Asn Pro Lys Thr Asp Gly Leu Thr
            420                 425                 430
Phe Thr Leu Asp Glu Leu Lys Gln Ala Phe Lys Ile Tyr Asn Glu Asp
            435                 440                 445
Met Arg Gln Ala Lys Lys Lys Tyr Thr Gln Ser Asn Ile Pro Thr Ala
        450                 455                 460
Tyr Ala Leu Met Leu Ser Asn Lys Asp Ser Ile Thr Arg Leu Tyr Tyr
465                 470                 475                 480
Gly Asp Met Tyr Ser Asp Asp Gly Gln Tyr Met Ala Thr Lys Ser Pro
                485                 490                 495
Tyr Tyr Asp Ala Ile Asp Thr Leu Leu Lys Ala Arg Ile Lys Tyr Ala
            500                 505                 510
Ala Gly Gly Gln Asp Met Lys Ile Thr Tyr Val Glu Gly Asp Lys Ser
        515                 520                 525
His Met Asp Trp Asp Tyr Thr Gly Val Leu Thr Ser Val Arg Tyr Gly
        530                 535                 540
Thr Gly Ala Asn Glu Ala Thr Asp Gln Gly Ser Glu Ala Thr Lys Thr
545                 550                 555                 560
Gln Gly Met Ala Val Ile Thr Ser Asn Asn Pro Ser Leu Lys Leu Asn
                565                 570                 575
Gln Asn Asp Lys Val Ile Val Asn Met Gly Thr Ala His Lys Asn Gln
            580                 585                 590
Glu Tyr Arg Pro Leu Leu Leu Thr Thr Lys Asp Gly Leu Thr Ser Tyr
            595                 600                 605
Thr Ser Asp Ala Ala Ala Lys Ser Leu Tyr Arg Lys Thr Asn Asp Lys
        610                 615                 620
Gly Glu Leu Val Phe Asp Ala Ser Asp Ile Gln Gly Tyr Leu Asn Pro
625                 630                 635                 640
Gln Val Ser Gly Tyr Leu Ala Val Trp Val Pro Val Gly Ala Ser Asp
                645                 650                 655
Asn Gln Asp Val Arg Val Ala Ala Ser Asn Lys Ala Asn Ala Thr Gly
            660                 665                 670
```

```
Gln Val Tyr Glu Ser Ser Ala Leu Asp Ser Gln Leu Ile Tyr Glu
        675                 680                 685

Gly Phe Ser Asn Phe Gln Asp Phe Val Thr Lys Asp Ser Asp Tyr Thr
690                 695                 700

Asn Lys Lys Ile Ala Gln Asn Val Gln Leu Phe Lys Ser Trp Gly Val
705                 710                 715                 720

Thr Ser Phe Glu Met Ala Pro Gln Tyr Val Ser Ser Glu Asp Gly Ser
                725                 730                 735

Phe Leu Asp Ser Ile Ile Gln Asn Gly Tyr Ala Phe Glu Asp Arg Tyr
                740                 745                 750

Asp Leu Ala Met Ser Lys Asn Lys Tyr Gly Ser Gln Gln Asp Met
            755                 760                 765

Ile Asn Ala Val Lys Ala Leu His Lys Ser Gly Ile Gln Val Ile Ala
770                 775                 780

Asp Trp Val Pro Asp Gln Ile Tyr Asn Leu Pro Gly Lys Glu Val Val
785                 790                 795                 800

Thr Ala Thr Arg Val Asn Asp Tyr Gly Glu Tyr Arg Lys Asp Ser Glu
                805                 810                 815

Ile Lys Asn Thr Leu Tyr Ala Ala Asn Thr Lys Ser Asn Gly Lys Asp
                820                 825                 830

Tyr Gln Ala Lys Tyr Gly Gly Ala Phe Leu Ser Glu Leu Ala Ala Lys
            835                 840                 845

Tyr Pro Ser Ile Phe Asn Arg Thr Gln Ile Ser Asn Gly Lys Lys Ile
850                 855                 860

Asp Pro Ser Glu Lys Ile Thr Ala Trp Lys Ala Lys Tyr Phe Asn Gly
865                 870                 875                 880

Thr Asn Ile Leu Gly Arg Gly Val Gly Tyr Val Leu Lys Asp Asn Ala
                885                 890                 895

Ser Asp Lys Tyr Phe Glu Leu Lys Gly Asn Gln Thr Tyr Leu Pro Lys
            900                 905                 910

Gln Met Thr Asn Lys Glu Ala Ser Thr Gly Phe Val Asn Asp Gly Asn
        915                 920                 925

Gly Met Thr Phe Tyr Ser Thr Ser Gly Tyr Gln Ala Lys Asn Ser Phe
        930                 935                 940

Val Gln Asp Ala Lys Gly Asn Trp Tyr Phe Asp Asn Asn Gly His
945                 950                 955                 960

Met Val Tyr Gly Leu Gln His Leu Asn Gly Glu Val Gln Tyr Phe Leu
                965                 970                 975

Ser Asn Gly Val Gln Leu Arg Glu Ser Phe Leu Glu Asn Ala Asp Gly
            980                 985                 990

Ser Lys Asn Tyr Phe Gly His Leu Gly Asn Arg Tyr Ser Asn Gly Tyr
        995                 1000                1005

Tyr Ser  Phe Asp Asn Asp Ser  Lys Trp Arg Tyr Phe  Asp Ala Ser
    1010                1015                1020

Gly Val  Met Ala Val Gly Leu  Lys Thr Ile Asn Gly  Asn Thr Gln
    1025                1030                1035

Tyr Phe  Asp Gln Asp Gly Tyr  Gln Val Lys Gly Ala  Trp Ile Thr
    1040                1045                1050

Gly Ser  Asp Gly Lys Lys Arg  Tyr Phe Asp Asp Gly  Ser Gly Asn
    1055                1060                1065

Met Ala  Val Asn Arg Phe Ala  Asn Asp Lys Asn Gly  Asp Trp Tyr
    1070                1075                1080
```

| | | | | | | | | | | |
|---|---|---|---|---|---|---|---|---|---|---|
|Tyr|Leu|Asn|Ser|Asp|Gly|Ile|Ala|Leu|Val|Gly|Val|Gln|Thr|Ile|
| |1085| | | | |1090| | | | |1095| | | |

Asn Gly Lys Thr Tyr Tyr Phe Gly Gln Asp Gly Lys Gln Ile Lys
    1100                1105                1110

Gly Lys Ile Ile Thr Asp Asn Gly Lys Leu Lys Tyr Phe Leu Ala
    1115                1120                1125

Asn Ser Gly Glu Leu Ala Arg Asn Ile Phe Ala Thr Asp Ser Gln
    1130                1135                1140

Asn Asn Trp Tyr Tyr Phe Gly Ser Asp Gly Val Ala Val Thr Gly
    1145                1150                1155

Ser Gln Thr Ile Ala Gly Lys Lys Leu Tyr Phe Ala Ser Asp Gly
    1160                1165                1170

Lys Gln Val Lys Gly Ser Phe Val Thr Tyr Asn Gly Lys Val His
    1175                1180                1185

Tyr Tyr His Ala Asp Ser Gly Glu Leu Gln Val Asn Arg Phe Glu
    1190                1195                1200

Ala Asp Lys Asp Gly Asn Trp Tyr Tyr Leu Asp Ser Asn Gly Glu
    1205                1210                1215

Ala Leu Thr Gly Ser Gln Arg Ile Asn Gly Gln Arg Val Phe Phe
    1220                1225                1230

Thr Arg Glu Gly Lys Gln Val Lys Gly Asp Val Ala Tyr Asp Glu
    1235                1240                1245

Arg Gly Leu Leu Arg Tyr Tyr Asp Lys Asn Ser Gly Asn Met Val
    1250                1255                1260

Tyr Asn Lys Val Val Thr Leu Ala Asn Gly Arg Arg Ile Gly Ile
    1265                1270                1275

Asp Arg Trp Gly Ile Ala Arg Tyr Tyr
    1280                1285

<210> SEQ ID NO 45
<211> LENGTH: 4068
<212> TYPE: DNA
<213> ORGANISM: Streptococcus gallolyticus

<400> SEQUENCE: 45

```
atgatcgacg gcaaatacta ctatattgac gaggacggta acgtaaagaa gaatttcgcg      60
attacggtgg atggtcagtt gctgtacttc gacgctgaaa cgggtgctct gaccagcacg     120
tccacctata gcttctccga gggcctgact aatctggtcg ataacttcag cattaacaac     180
cagtcctacg acagcaccga agagtcgttt gagctgatcg acggttacct gaccgtcaat     240
acttggtacc gtccgaccaa aattctggaa acggtgaaa cctgggtcga tagcaccgaa     300
acggatttcc gtccgctgct gatggcctgg tggccggatg ttgacaccca aattgactac     360
ttgaactaca tgagcgatta cttcgatctg ggtacgacct atagcgctga cgattcccaa     420
gcgagcctga atctggcagc tgaggcggtt caggtgaaaa ttgaacaaga aattacccgt     480
caagagaaca ccgcctggct gcgcgagatc atctctagct tgttaccac ccaggataaa     540
tggaatatca ataccgagaa tgagggcacc gaccatctgc aaggtggtgc cctgctgtac     600
gttaacagcg acttgactcc gtgggcaaac agcgattatc gcctgctgaa ccgcaccccg     660
acgtaccaga cgggtgagac taattacttt aaagcagatc gtactggtgg ctacgaattt     720
ctgctggcaa atgacgtgga taattctaac ccggtcgttc aagccgaaca gttgaaccag     780
ctgtactact tgatgaattg gggctctatt gtattcggtg atgacgacgc caattttgat     840
ggcgtgcgtg ttgacgcggt ggacaatgtg aacgctgacc tgttgcagat ttacacgaac     900
```

```
ctgttcgaag cggcgtatgg tgttaacgag tctgaggcgc aggccctggc tcacattagc    960
atcctggaag cgtggtctta taacgacccg gactacaacc acgacacgaa tggcgctgcc   1020
ctggcaatcg acaatggtct gcgtctgagc tttctgtact ctttgacgcg ccctacggac   1080
gagcgcagcg gtttggagcc actgatcacc tctgagattg gcctgaccga tcgttccgag   1140
gactctgcat acggtgacac catgccgagc tatgttttcg tccgtgcaca tgacagcgag   1200
gttcagacca ttattgcgag cattatcgca gaacagatca cccggaaaac cgatggctat   1260
accttcaccc tggacgagct gaaccaggcg tttgagattt acaacgcgga tatgaacagc   1320
gtggataaag agtatacgca ttacaatatc ccggctgcgt atagcctgct gctgaccaac   1380
atggaaagcg tcccgcgtgt ttactacggt gacctgtata cggataacgg tcagtacatg   1440
gcgactaaga gcccgtatta tgaccagatc accaccctgc tgcaagcgcg cattcgttac   1500
gcggcgggtg gccaatctat ggctgttacg tactacaccc ctgcgtcgag catgtctacc   1560
gacaatgcgg atagcgtcct gaatgagact ggtgtgctga cttctgtgcg ttacggctat   1620
ggcatcatga ccgccgacca agaggccacg gacgactccg ttctgacctc tggtattgtt   1680
actattatca gcaacaaccc taatttgcag ctggatgatt ccgaagtgat tgcagtccag   1740
gttggtgtgg cgcacgctgg tcagtattat cgtccgctgt tgtacccgac ggcggatggt   1800
ctgcaaagct acctgaacga tagcgatacc gacattacta gctggtcga tgataatggt   1860
tatatctact ttacggcaga tgagattaaa ggctacgaaa cggttgacat gaatggctac   1920
ctgagcgttt gggtcccggt tggtgcagac gagaatcagg acatccgtgt cagcgcagac   1980
accagcgcgt acaccgaggg tgaattgatc tatcaagcaa ccgcagcgct ggatagccaa   2040
gtgatctacg agggtttcag caacttccaa gatttcgtta cctctaacag cgagtacact   2100
aacaagctga tcgcggagaa cgtcgatctg tttaccagct ggggcattac gagctttgag   2160
atggcgccac agtatgtgag caccgatgac ggtactttc tggatagcat cattcaaaac   2220
ggttatgcat ttgacgatcg ctacgacctg gcaatgagcc agaataacaa gtatggtagc   2280
gctgaagatt tgcgtaatgc catcaaggcc ctgcacgctg ctggcattca ggtcattgct   2340
gactgggtgc cggatcaaat ctattcgctg ccaggcgaag aagtcgttac ggcgactcgc   2400
gtgaatgact atggcgaaga aaccgaaggc gcgtacatta acaatacgtt gtatgtggcg   2460
aacagcaaaa gcagcggcga ggactaccag gcacagtatg tggtgagtt cctggattac   2520
ttgcaagaaa cctacccgga aatgttcgaa gttgcgatga ttagcacggg tgagccgatt   2580
gatccgagca ccaagatcaa gatttggaaa gcagaatact ttaatggtac gaacattctg   2640
ggtaagggcg ctggttacgt gctgagcgat gccgcgactg gcacgtactt taccgtgact   2700
gagaatggca cgtttctgcc gaagcagctg accaccgact ccgccattac gggtttctat   2760
tacgacggta cgggtatgtc ttacttagc acctcgggt atcgcgctaa agcgagcttc   2820
attgtttaca cggctacta ctactatttt gatgataacg gctacatggt cactggcacg   2880
gtggaaatca acggtaagac ctactatttc ctgccgaatg gtattcagct gcgtgatgcg   2940
atttacgaag acgagaacgg taatcagtac tatttcggtc cgttgggcaa ccagtatttc   3000
aacaactatt acagctttga cgttgaagag gtggtggacg tgtaacgac tacggtaacg   3060
aagtggcgtc attttgacga gaacggcgtg atggcgcgtg gtttggtcga gattgatggt   3120
gtctaccagt attacgatga aaacggctac caggtcaaag gtgagctgat caccgatgct   3180
gatggtaatt tgcgttattt caaagaagat agcggtgaaa tggttgttag cgattttgtg   3240
```

-continued

```
aagatcggcg ataacaactg gtactacttt gacgaaaacg gtattgcagt cacgggtgcc   3300
caaaccattg ccggccagaa cttgtatttc gatgacaacg gtgtgcaggc gaaaggtgcc   3360
tttgtcacga acgccgatgg cacgcgcagc tattatgacg cggacagcgg tgagaagatc   3420
gtggcagatt tcttcactac gggcgataat gactggtatt atgcagatga aaatggcaat   3480
ctggtgactg gtagccaaac tatcaatggt caaaacctgt actttgctga ggacggtttg   3540
caggccaagg gtgtgtttgt taccgatacg gctggtaaca ttcactatta tgatgcgaac   3600
tctggcgagt tggcggttaa taccttcgtt ggtgatggcg acgactggta ttactttgat   3660
gagaatggca tcgcagttac cggcgcacaa gtcattaacg gtcaacacct gtatttcgca   3720
gacaacggca tccaagtgaa aggtgaaatc gtcaccgacg caaacggcaa ccgctattac   3780
tacgatgcag attccggcga aatggcagtt aacaccttg tggagattga cggtgtttgg   3840
tactattttg gtgccgatgg tatcgcggtg acgggtgcac aagtaattga tggtcagaat   3900
ttgtacttta acgcagacgg tagccaagtc aagggtgacg ttgtccgtat caacggtttg   3960
cgttactact acgacgctaa tagcggcgaa caggtgcgca atcagtgggt cacgctgccg   4020
gatggtactg ttgttttctt taatgcgcgt ggctatactt ggggctaa               4068
```

```
<210> SEQ ID NO 46
<211> LENGTH: 1355
<212> TYPE: PRT
<213> ORGANISM: Streptococcus gallolyticus

<400> SEQUENCE: 46
```

```
Met Ile Asp Gly Lys Tyr Tyr Tyr Ile Asp Glu Asp Gly Asn Val Lys
1               5                   10                  15

Lys Asn Phe Ala Ile Thr Val Asp Gly Gln Leu Leu Tyr Phe Asp Ala
            20                  25                  30

Glu Thr Gly Ala Leu Thr Ser Thr Ser Thr Tyr Ser Phe Ser Glu Gly
        35                  40                  45

Leu Thr Asn Leu Val Asp Asn Phe Ser Ile Asn Asn Gln Ser Tyr Asp
    50                  55                  60

Ser Thr Glu Glu Ser Phe Glu Leu Ile Asp Gly Tyr Leu Thr Val Asn
65                  70                  75                  80

Thr Trp Tyr Arg Pro Thr Lys Ile Leu Glu Asn Gly Glu Thr Trp Val
                85                  90                  95

Asp Ser Thr Glu Thr Asp Phe Arg Pro Leu Leu Met Ala Trp Trp Pro
            100                 105                 110

Asp Val Asp Thr Gln Ile Asp Tyr Leu Asn Tyr Met Ser Asp Tyr Phe
        115                 120                 125

Asp Leu Gly Thr Thr Tyr Ser Ala Asp Ser Gln Ala Ser Leu Asn
    130                 135                 140

Leu Ala Ala Glu Ala Val Gln Val Lys Ile Glu Gln Glu Ile Thr Arg
145                 150                 155                 160

Gln Glu Asn Thr Ala Trp Leu Arg Glu Ile Ile Ser Ser Phe Val Thr
                165                 170                 175

Thr Gln Asp Lys Trp Asn Ile Asn Thr Glu Asn Glu Gly Thr Asp His
            180                 185                 190

Leu Gln Gly Gly Ala Leu Leu Tyr Val Asn Ser Asp Leu Thr Pro Trp
        195                 200                 205

Ala Asn Ser Asp Tyr Arg Leu Leu Asn Arg Thr Pro Thr Tyr Gln Thr
    210                 215                 220

Gly Glu Thr Asn Tyr Phe Lys Ala Asp Arg Thr Gly Gly Tyr Glu Phe
```

```
            225                 230                 235                 240
Leu Leu Ala Asn Asp Val Asp Asn Ser Asn Pro Val Val Gln Ala Glu
                245                 250                 255

Gln Leu Asn Gln Leu Tyr Tyr Leu Met Asn Trp Gly Ser Ile Val Phe
            260                 265                 270

Gly Asp Asp Ala Asn Phe Asp Gly Val Arg Val Asp Ala Val Asp
            275                 280                 285

Asn Val Asn Ala Asp Leu Leu Gln Ile Tyr Thr Asn Leu Phe Glu Ala
            290                 295                 300

Ala Tyr Gly Val Asn Glu Ser Glu Ala Gln Ala Leu Ala His Ile Ser
305                 310                 315                 320

Ile Leu Glu Ala Trp Ser Tyr Asn Asp Pro Asp Tyr Asn His Asp Thr
                325                 330                 335

Asn Gly Ala Ala Leu Ala Ile Asp Asn Gly Leu Arg Leu Ser Phe Leu
            340                 345                 350

Tyr Ser Leu Thr Arg Pro Thr Asp Glu Arg Ser Gly Leu Glu Pro Leu
            355                 360                 365

Ile Thr Ser Glu Ile Gly Leu Thr Asp Arg Ser Glu Asp Ser Ala Tyr
            370                 375                 380

Gly Asp Thr Met Pro Ser Tyr Val Phe Val Arg Ala His Asp Ser Glu
385                 390                 395                 400

Val Gln Thr Ile Ile Ala Ser Ile Ile Ala Glu Gln Ile Asn Pro Glu
                405                 410                 415

Thr Asp Gly Tyr Thr Phe Thr Leu Asp Glu Leu Asn Gln Ala Phe Glu
            420                 425                 430

Ile Tyr Asn Ala Asp Met Asn Ser Val Asp Lys Glu Tyr Thr His Tyr
            435                 440                 445

Asn Ile Pro Ala Ala Tyr Ser Leu Leu Leu Thr Asn Met Glu Ser Val
            450                 455                 460

Pro Arg Val Tyr Tyr Gly Asp Leu Tyr Thr Asp Asn Gly Gln Tyr Met
465                 470                 475                 480

Ala Thr Lys Ser Pro Tyr Tyr Asp Gln Ile Thr Thr Leu Leu Gln Ala
                485                 490                 495

Arg Ile Arg Tyr Ala Ala Gly Gly Gln Ser Met Ala Val Thr Tyr Tyr
            500                 505                 510

Thr Pro Ala Ser Ser Met Ser Thr Asp Asn Ala Asp Ser Val Leu Asn
            515                 520                 525

Glu Thr Gly Val Leu Thr Ser Val Arg Tyr Gly Tyr Gly Ile Met Thr
            530                 535                 540

Ala Asp Gln Glu Ala Thr Asp Ser Val Leu Thr Ser Gly Ile Val
545                 550                 555                 560

Thr Ile Ile Ser Asn Asn Pro Asn Leu Gln Leu Asp Asp Ser Glu Val
                565                 570                 575

Ile Ala Val Gln Val Gly Val Ala His Ala Gly Gln Tyr Tyr Arg Pro
            580                 585                 590

Leu Leu Tyr Pro Thr Ala Asp Gly Leu Gln Ser Tyr Leu Asn Asp Ser
            595                 600                 605

Asp Thr Asp Ile Thr Lys Leu Val Asp Asp Asn Gly Tyr Ile Tyr Phe
            610                 615                 620

Thr Ala Asp Glu Ile Lys Gly Tyr Glu Thr Val Asp Met Asn Gly Tyr
625                 630                 635                 640

Leu Ser Val Trp Val Pro Val Gly Ala Asp Glu Asn Gln Asp Ile Arg
                645                 650                 655
```

```
Val Ser Ala Asp Thr Ser Ala Tyr Thr Glu Gly Glu Leu Ile Tyr Gln
                660                 665                 670

Ala Thr Ala Ala Leu Asp Ser Gln Val Ile Tyr Glu Gly Phe Ser Asn
            675                 680                 685

Phe Gln Asp Phe Val Thr Ser Asn Ser Glu Tyr Thr Asn Lys Leu Ile
        690                 695                 700

Ala Glu Asn Val Asp Leu Phe Thr Ser Trp Gly Ile Thr Ser Phe Glu
705                 710                 715                 720

Met Ala Pro Gln Tyr Val Ser Thr Asp Gly Thr Phe Leu Asp Ser
                725                 730                 735

Ile Ile Gln Asn Gly Tyr Ala Phe Asp Asp Arg Tyr Asp Leu Ala Met
                740                 745                 750

Ser Gln Asn Asn Lys Tyr Gly Ser Ala Glu Asp Leu Arg Asn Ala Ile
            755                 760                 765

Lys Ala Leu His Ala Ala Gly Ile Gln Val Ile Ala Asp Trp Val Pro
        770                 775                 780

Asp Gln Ile Tyr Ser Leu Pro Gly Glu Glu Val Val Thr Ala Thr Arg
785                 790                 795                 800

Val Asn Asp Tyr Gly Glu Glu Thr Glu Gly Ala Tyr Ile Asn Asn Thr
                805                 810                 815

Leu Tyr Val Ala Asn Ser Lys Ser Ser Gly Glu Asp Tyr Gln Ala Gln
            820                 825                 830

Tyr Gly Gly Glu Phe Leu Asp Tyr Leu Gln Glu Thr Tyr Pro Glu Met
        835                 840                 845

Phe Glu Val Ala Met Ile Ser Thr Gly Glu Pro Ile Asp Pro Ser Thr
        850                 855                 860

Lys Ile Lys Ile Trp Lys Ala Glu Tyr Phe Asn Gly Thr Asn Ile Leu
865                 870                 875                 880

Gly Lys Gly Ala Gly Tyr Val Leu Ser Asp Ala Ala Thr Gly Thr Tyr
                885                 890                 895

Phe Thr Val Thr Glu Asn Gly Thr Phe Leu Pro Lys Gln Leu Thr Thr
            900                 905                 910

Asp Ser Ala Ile Thr Gly Phe Tyr Tyr Asp Gly Thr Gly Met Ser Tyr
        915                 920                 925

Phe Ser Thr Ser Gly Tyr Arg Ala Lys Ala Ser Phe Ile Val Tyr Asn
        930                 935                 940

Gly Tyr Tyr Tyr Tyr Phe Asp Asp Asn Gly Tyr Met Val Thr Gly Thr
945                 950                 955                 960

Val Glu Ile Asn Gly Lys Thr Tyr Tyr Phe Leu Pro Asn Gly Ile Gln
                965                 970                 975

Leu Arg Asp Ala Ile Tyr Glu Asp Glu Asn Gly Asn Gln Tyr Tyr Phe
            980                 985                 990

Gly Pro Leu Gly Asn Gln Tyr Phe Asn Asn Tyr Tyr Ser Phe Asp Val
        995                 1000                1005

Glu Glu Val Val Asp Gly Val Thr Thr Thr Val Thr Lys Trp Arg
        1010                1015                1020

His Phe Asp Glu Asn Gly Val Met Ala Arg Gly Leu Val Glu Ile
        1025                1030                1035

Asp Gly Val Tyr Gln Tyr Tyr Asp Glu Asn Gly Tyr Gln Val Lys
        1040                1045                1050

Gly Glu Leu Ile Thr Asp Ala Asp Gly Asn Leu Arg Tyr Phe Lys
        1055                1060                1065
```

| | | | | | | | | | | |
|---|---|---|---|---|---|---|---|---|---|---|
|Glu|Asp|Ser|Gly|Glu|Met|Val|Val|Ser|Asp|Phe|Val|Lys|Ile|Gly|
| |1070| | | | |1075| | | | |1080| | | |

Asp Asn Asn Trp Tyr Tyr Phe Asp Glu Asn Gly Ile Ala Val Thr
    1085                1090               1095

Gly Ala Gln Thr Ile Ala Gly Gln Asn Leu Tyr Phe Asp Asp Asn
    1100                1105               1110

Gly Val Gln Ala Lys Gly Ala Phe Val Thr Asn Ala Asp Gly Thr
    1115                1120               1125

Arg Ser Tyr Tyr Asp Ala Asp Ser Gly Glu Lys Ile Val Ala Asp
    1130                1135               1140

Phe Phe Thr Thr Gly Asp Asn Asp Trp Tyr Tyr Ala Asp Glu Asn
    1145                1150               1155

Gly Asn Leu Val Thr Gly Ser Gln Thr Ile Asn Gly Gln Asn Leu
    1160                1165               1170

Tyr Phe Ala Glu Asp Gly Leu Gln Ala Lys Gly Val Phe Val Thr
    1175                1180               1185

Asp Thr Ala Gly Asn Ile His Tyr Tyr Asp Ala Asn Ser Gly Glu
    1190                1195               1200

Leu Ala Val Asn Thr Phe Val Gly Asp Gly Asp Trp Tyr Tyr
    1205                1210               1215

Phe Asp Glu Asn Gly Ile Ala Val Thr Gly Ala Gln Val Ile Asn
    1220                1225               1230

Gly Gln His Leu Tyr Phe Ala Asp Asn Gly Ile Gln Val Lys Gly
    1235                1240               1245

Glu Ile Val Thr Asp Ala Asn Gly Asn Arg Tyr Tyr Tyr Asp Ala
    1250                1255               1260

Asp Ser Gly Glu Met Ala Val Asn Thr Phe Val Glu Ile Asp Gly
    1265                1270               1275

Val Trp Tyr Tyr Phe Gly Ala Asp Gly Ile Ala Val Thr Gly Ala
    1280                1285               1290

Gln Val Ile Asp Gly Gln Asn Leu Tyr Phe Asn Ala Asp Gly Ser
    1295                1300               1305

Gln Val Lys Gly Asp Val Val Arg Ile Asn Gly Leu Arg Tyr Tyr
    1310                1315               1320

Tyr Asp Ala Asn Ser Gly Glu Gln Val Arg Asn Gln Trp Val Thr
    1325                1330               1335

Leu Pro Asp Gly Thr Val Val Phe Phe Asn Ala Arg Gly Tyr Thr
    1340                1345               1350

Trp Gly
    1355

<210> SEQ ID NO 47
<211> LENGTH: 4047
<212> TYPE: DNA
<213> ORGANISM: Streptococcus sanguinis

<400> SEQUENCE: 47

```
atgatcgatg gcaagaaata ctatgttcag gacgacggta cggtaaagaa gaatttcgcg      60
gttgaactga acggcaaggt cctgtatttc gatgcagaaa ccgtgccct ggtcgacagc     120 gcggagtacc agtttcaaca gggtacgagc tccctgaata acgagttcag ccgcatgaat    180
gcgttccatg gcacgacgga gaaagatatt gaaaccgtcg atggctatct gaccgcagat    240
acgtggtacc gcccgaaggc catcctgaaa gatggcaaaa cctggactca gagcaccgaa    300
accgatctgc gtccgctgct gatggcatgg tggccggaca acaaacgca ggtaagctac     360
```

```
ttgaactata tgaaccagca gggtctgggt gcgggtgcgt ttgagaacaa agttgagcag     420
gcaatcttga cgggcgcaag ccagcaggtg cagcgcaaga tcgaagaacg tattggcaaa     480
gacggcgata ccaaatggct gcgtaccctg atgggtgcat tgtgaaaaac ccagccgaat     540
tggaatatca agacggagag cgaaaccacg ggtactaata aggatcatct gcaaggtggt     600
gcgctgctgt acaccaactc tgaaaagacg agccacgcga acagcaaata ccgtattctg     660
aatcgtaccc cgaccaatca gaccggtacg ccgaagtatt tcatcgacaa atcgaatggt     720
ggttacgagt tcttgctggc aaatgatttt gataatagca acccagcagt ccaagcggaa     780
cagctgaatt ggctgcactt tatgatgaat ttcggcagca ttgttgcaaa tgacccgacc     840
gcaaacttcg atggcgtgcg tgtggatgcg gtggacaatg ttaatgccga tttgctgcaa     900
attgccagcg actatttcaa atctcgttac aaagtgggcg agagcgaaga acaagcgatt     960
aaacatctga gcatcctgga agcctggagc gacaacgatc cggactataa caaagacacc    1020
aaaggcgccc aactgccgat cgacaataag ctgcgtctga gcctgttgta cagctttatg    1080
cgtaagctga gcattcgcag cggtgtcgaa ccgacgatta ccaacagcct gaacgaccgt    1140
tctgcggaga agaagaacgg tgagcgcatg gcaaactata tctttgttcg tgcgcatgat    1200
tccgaagtgc agacggtcat tgccgacatt attcgcgaga atatcaatcc gaacacggat    1260
ggtctgacct ttaccatgga cgagctgaaa caggcgttca agatctacaa tgaagatatg    1320
cgcaaggcgg ataagaagta tacccaattc aatattccga ccgctcacgc gttgatgttg    1380
agcaacaagg attccattac gcgtgtgtac tacggtgacc tgtatacgga tgatggtcag    1440
tatatggaaa agaaaagccc ttattacgac gcgatcgacg cgctgctgcg cgcacgcatt    1500
aagtacgttg cgggtggcca ggacatgaaa gttacctaca tgggtgtgcc gcgtgaaacc    1560
gacaaatgga gctacaacgg catcctgacc agcgtccgct acggcaccgg cgcaaatgag    1620
gctacggacg agggtactgc cgagactcgc acccagggta tggccgtcat cgcaagcaac    1680
aatccgaatt tgaaactgaa cgagtgggat aagttgcagg tcaacatggg tgcggcacac    1740
aagaaccaat actatcgtcc ggtgctgctg accaccaagg acggtattag ccgttacctg    1800
accgacgaag aagttccgca aagcctgtgg aagaaaaccg atgcaaacgg catcttgacg    1860
ttcgacatga acgatatcgc aggttacagc aatgtccaag tatctggcta cttggctgtg    1920
tgggtgccgg ttggtgccaa agcggatcaa gacgcgcgtg ttactgcgtc gaagaagaaa    1980
aacgccagcg gtcaggtgta tgagtccagc gctgcactgg acagccaact gatttatgaa    2040
ggcttctcta acttccaaga cttcgcgacc cgcgacgatc aatacaccaa caagttatt     2100 gccaaaaatg ttaatctgtt taaagagtgg ggtgtgacca gctttgagct gccacctcag    2160
tatgtttcca gccaggatgg cacgttttg gatagcatca tccagaatgg ctacgcattt     2220
gaagatcgtt atgacatggc gatgagcaaa acaataagt acggtagcct ggacgacctg     2280
ctgaacgcgc tgcgtgcctt gcacagcgtc aacatccaag cgatcgcgga ctgggtcccg    2340
gatcagattt acaacctgcc gggcaaagaa gtggttacgg ctacgcgtgt caacaattat     2400
ggtacctatc gtgagggtgc ggaaatcaaa gaaatctgt acgtggcaaa cacgaaaacc     2460
aacggcaccg actatcaagg caaatacggt ggtgcgttcc tggacgaact gaaagcgaaa    2520
tatcctgaga tcttcgaacg tgttcaaatt ccaatggtc aaaagatgac caccgatgag     2580
aagattacga aatggagcgc gaaacacttc aatggtacca acattctggg ccgtggtgca    2640
tactacgtgc tgaaagattg ggccagcaat gagtatctga acaataagaa tggtgagatg    2700
```

```
gtgttgccga agcaactggt taacaaaaac gcgtacaccg gctttgttaa ggacaccacc    2760
ggttttaagt actatagcac ctcgggctat caagcgcgta atagcttcat ccaagatgag    2820
aacggtaatt ggtactactt tgacaaacgt ggttacctgg cgactggtgc acacgaaatc    2880
gacggcaagc aggtctattt cctgaaaaac ggcattcaac tgcgcgactc tctgcgtgag    2940
gacgagaacg gcaatcagta ctattacgac aagaccggtg cgcaggtgct gaaccgctac    3000
tacaccaccg acggcagaa ctggcgttac ttcgacgcca aggtgtttat ggcgcgtggc    3060
ctggttacca tgggtggtaa ccaacaattc ttcgaccaga acggttatca ggtgaaaggc    3120
aagatcgcgc gtgccaagga tggtaaactg cgctacttcg acaaagacag cggtaacgca    3180
gcggcgaatc gctttgcaca gggcgataat ccgagcgatt ggtattactt tggtgccgat    3240
ggcgtcgctg ttaccggttt gcaaaaactg ggtcaacaaa ctctgtactt tgatcaagaa    3300
ggtaaacaag tgaagggcaa gattgtcacg ctggctgata agtccatccg ttacttcgat    3360
gcgaacagcg gcgagatggc tgtcggtaag tttgctgagg gtagcaagaa cgaatggtac    3420
tatttcgatc agacgggcaa agcggttacg ggtctgcaaa agattggcca gcagaccctg    3480
tattttgacc aagatggtaa gcaggtaaag ggtaaagtgg taaccctggc agataagtcg    3540
attcgctact ttgatgcaaa ctccggcgaa atggcggtgg taagttcgc cgagggtgct    3600 aagaatgagt ggtactactt tgaccaggcg ggcaaggcgg tgaccggctt gcagaaaatt    3660
ggtcagcaaa cgctgtattt tgatcaggac ggcaaacaag tcaaaggcca actggtgacg    3720
ctggcggaca gagcattcg ttatttcgac gcaaacagcg gtgagatggc ctctaacaag    3780
ttcgttgagg gtgccaaaaa cgaatggtac tatttcgacc aagccggtaa agcagtgacc    3840
ggtctgcaac aaatcggtca gcagaccttg tacttcgacc aaaacggtaa acaggtcaaa    3900
ggtaaaatcg tgtatgttaa cggtgccaat cgttactttg acgccaattc gggtgaaatg    3960
gcgcgcaata agtggatcca actggaagat ggtagctgga tgtacttcga tcgtaacggt    4020
cgtggtcgtc gtttcggctg gaattaa                                        4047
```

<210> SEQ ID NO 48
<211> LENGTH: 1348
<212> TYPE: PRT
<213> ORGANISM: Streptococcus sanguinis

<400> SEQUENCE: 48

```
Met Ile Asp Gly Lys Lys Tyr Tyr Val Gln Asp Asp Gly Thr Val Lys
1               5                   10                  15

Lys Asn Phe Ala Val Glu Leu Asn Gly Lys Val Leu Tyr Phe Asp Ala
            20                  25                  30

Glu Thr Gly Ala Leu Val Asp Ser Ala Glu Tyr Gln Phe Gln Gln Gly
        35                  40                  45

Thr Ser Ser Leu Asn Asn Glu Phe Ser Arg Met Asn Ala Phe His Gly
    50                  55                  60

Thr Thr Glu Lys Asp Ile Glu Val Asp Gly Tyr Leu Thr Ala Asp
65                  70                  75                  80

Thr Trp Tyr Arg Pro Lys Ala Ile Leu Lys Asp Gly Lys Thr Trp Thr
                85                  90                  95

Gln Ser Thr Glu Thr Asp Leu Arg Pro Leu Met Ala Trp Trp Pro
            100                 105                 110

Asp Lys Gln Thr Gln Val Ser Tyr Leu Asn Tyr Met Asn Gln Gln Gly
        115                 120                 125

Leu Gly Ala Gly Ala Phe Glu Asn Lys Val Glu Gln Ala Ile Leu Thr
```

```
                130               135                140
Gly Ala Ser Gln Gln Val Gln Arg Lys Ile Glu Arg Ile Gly Lys
145                 150                 155                 160

Asp Gly Asp Thr Lys Trp Leu Arg Thr Leu Met Gly Ala Phe Val Lys
            165                 170                 175

Thr Gln Pro Asn Trp Asn Ile Lys Thr Glu Ser Glu Thr Thr Gly Thr
                180                 185                 190

Asn Lys Asp His Leu Gln Gly Gly Ala Leu Leu Tyr Thr Asn Ser Glu
            195                 200                 205

Lys Thr Ser His Ala Asn Ser Lys Tyr Arg Ile Leu Asn Arg Thr Pro
210                 215                 220

Thr Asn Gln Thr Gly Thr Pro Lys Tyr Phe Ile Asp Lys Ser Asn Gly
225                 230                 235                 240

Gly Tyr Glu Phe Leu Leu Ala Asn Asp Phe Asp Asn Ser Asn Pro Ala
                245                 250                 255

Val Gln Ala Glu Gln Leu Asn Trp Leu His Phe Met Met Asn Phe Gly
            260                 265                 270

Ser Ile Val Ala Asn Asp Pro Thr Ala Asn Phe Asp Gly Val Arg Val
            275                 280                 285

Asp Ala Val Asp Asn Val Asn Ala Asp Leu Leu Gln Ile Ala Ser Asp
        290                 295                 300

Tyr Phe Lys Ser Arg Tyr Lys Val Gly Glu Ser Glu Gln Ala Ile
305                 310                 315                 320

Lys His Leu Ser Ile Leu Glu Ala Trp Ser Asp Asn Asp Pro Asp Tyr
                325                 330                 335

Asn Lys Asp Thr Lys Gly Ala Gln Leu Pro Ile Asp Asn Lys Leu Arg
            340                 345                 350

Leu Ser Leu Leu Tyr Ser Phe Met Arg Lys Leu Ser Ile Arg Ser Gly
            355                 360                 365

Val Glu Pro Thr Ile Thr Asn Ser Leu Asn Asp Arg Ser Ala Glu Lys
370                 375                 380

Lys Asn Gly Glu Arg Met Ala Asn Tyr Ile Phe Val Arg Ala His Asp
385                 390                 395                 400

Ser Glu Val Gln Thr Val Ile Ala Asp Ile Ile Arg Glu Asn Ile Asn
                405                 410                 415

Pro Asn Thr Asp Gly Leu Thr Phe Thr Met Asp Glu Leu Lys Gln Ala
            420                 425                 430

Phe Lys Ile Tyr Asn Glu Asp Met Arg Lys Ala Asp Lys Lys Tyr Thr
            435                 440                 445

Gln Phe Asn Ile Pro Thr Ala His Ala Leu Met Leu Ser Asn Lys Asp
450                 455                 460

Ser Ile Thr Arg Val Tyr Tyr Gly Asp Leu Tyr Thr Asp Asp Gly Gln
465                 470                 475                 480

Tyr Met Glu Lys Lys Ser Pro Tyr Tyr Asp Ala Ile Asp Ala Leu Leu
                485                 490                 495

Arg Ala Arg Ile Lys Tyr Val Ala Gly Gly Gln Asp Met Lys Val Thr
            500                 505                 510

Tyr Met Gly Val Pro Arg Glu Thr Asp Lys Trp Ser Tyr Asn Gly Ile
            515                 520                 525

Leu Thr Ser Val Arg Tyr Gly Thr Gly Ala Asn Glu Ala Thr Asp Glu
            530                 535                 540

Gly Thr Ala Glu Thr Arg Thr Gln Gly Met Ala Val Ile Ala Ser Asn
545                 550                 555                 560
```

```
Asn Pro Asn Leu Lys Leu Asn Glu Trp Asp Lys Leu Gln Val Asn Met
            565                 570                 575

Gly Ala Ala His Lys Asn Gln Tyr Tyr Arg Pro Val Leu Leu Thr Thr
                580                 585                 590

Lys Asp Gly Ile Ser Arg Tyr Leu Thr Asp Glu Val Pro Gln Ser
            595                 600                 605

Leu Trp Lys Lys Thr Asp Ala Asn Gly Ile Leu Thr Phe Asp Met Asn
    610                 615                 620

Asp Ile Ala Gly Tyr Ser Asn Val Gln Val Ser Gly Tyr Leu Ala Val
625                 630                 635                 640

Trp Val Pro Val Gly Ala Lys Ala Asp Gln Asp Ala Arg Val Thr Ala
                645                 650                 655

Ser Lys Lys Lys Asn Ala Ser Gly Gln Val Tyr Glu Ser Ser Ala Ala
                660                 665                 670

Leu Asp Ser Gln Leu Ile Tyr Glu Gly Phe Ser Asn Phe Gln Asp Phe
                675                 680                 685

Ala Thr Arg Asp Asp Gln Tyr Thr Asn Lys Val Ile Ala Lys Asn Val
    690                 695                 700

Asn Leu Phe Lys Glu Trp Gly Val Thr Ser Phe Glu Leu Pro Pro Gln
705                 710                 715                 720

Tyr Val Ser Ser Gln Asp Gly Thr Phe Leu Asp Ser Ile Ile Gln Asn
                725                 730                 735

Gly Tyr Ala Phe Glu Asp Arg Tyr Asp Met Ala Met Ser Lys Asn Asn
                740                 745                 750

Lys Tyr Gly Ser Leu Asp Asp Leu Asn Ala Leu Arg Ala Leu His
                755                 760                 765

Ser Val Asn Ile Gln Ala Ile Ala Asp Trp Val Pro Asp Gln Ile Tyr
    770                 775                 780

Asn Leu Pro Gly Lys Glu Val Val Thr Ala Thr Arg Val Asn Asn Tyr
785                 790                 795                 800

Gly Thr Tyr Arg Glu Gly Ala Glu Ile Lys Glu Asn Leu Tyr Val Ala
                805                 810                 815

Asn Thr Lys Thr Asn Gly Thr Asp Tyr Gln Gly Lys Tyr Gly Gly Ala
                820                 825                 830

Phe Leu Asp Glu Leu Lys Ala Lys Tyr Pro Glu Ile Phe Glu Arg Val
    835                 840                 845

Gln Ile Ser Asn Gly Gln Lys Met Thr Thr Asp Glu Lys Ile Thr Lys
    850                 855                 860

Trp Ser Ala Lys His Phe Asn Gly Thr Asn Ile Leu Gly Arg Gly Ala
865                 870                 875                 880

Tyr Tyr Val Leu Lys Asp Trp Ala Ser Asn Glu Tyr Leu Asn Asn Lys
                885                 890                 895

Asn Gly Glu Met Val Leu Pro Lys Gln Leu Val Asn Lys Asn Ala Tyr
                900                 905                 910

Thr Gly Phe Val Lys Asp Thr Thr Gly Phe Lys Tyr Tyr Ser Thr Ser
    915                 920                 925

Gly Tyr Gln Ala Arg Asn Ser Phe Ile Gln Asp Glu Asn Gly Asn Trp
    930                 935                 940

Tyr Tyr Phe Asp Lys Arg Gly Tyr Leu Ala Thr Gly Ala His Glu Ile
945                 950                 955                 960

Asp Gly Lys Gln Val Tyr Phe Leu Lys Asn Gly Ile Gln Leu Arg Asp
                965                 970                 975
```

Ser Leu Arg Glu Asp Glu Asn Gly Asn Gln Tyr Tyr Asp Lys Thr
            980                 985                 990

Gly Ala Gln Val Leu Asn Arg Tyr Tyr Thr Asp Gly Gln Asn Trp
        995                 1000                1005

Arg Tyr Phe Asp Ala Lys Gly Val Met Ala Arg Gly Leu Val Thr
    1010                1015                1020

Met Gly Gly Asn Gln Gln Phe Phe Asp Gln Asn Gly Tyr Gln Val
    1025                1030                1035

Lys Gly Lys Ile Ala Arg Ala Lys Asp Gly Lys Leu Arg Tyr Phe
    1040                1045                1050

Asp Lys Asp Ser Gly Asn Ala Ala Ala Asn Arg Phe Ala Gln Gly
    1055                1060                1065

Asp Asn Pro Ser Asp Trp Tyr Tyr Phe Gly Ala Asp Gly Val Ala
    1070                1075                1080

Val Thr Gly Leu Gln Lys Leu Gly Gln Gln Thr Leu Tyr Phe Asp
    1085                1090                1095

Gln Glu Gly Lys Gln Val Lys Gly Lys Ile Val Thr Leu Ala Asp
    1100                1105                1110

Lys Ser Ile Arg Tyr Phe Asp Ala Asn Ser Gly Glu Met Ala Val
    1115                1120                1125

Gly Lys Phe Ala Glu Gly Ser Lys Asn Glu Trp Tyr Tyr Phe Asp
    1130                1135                1140

Gln Thr Gly Lys Ala Val Thr Gly Leu Gln Lys Ile Gly Gln Gln
    1145                1150                1155

Thr Leu Tyr Phe Asp Gln Asp Gly Lys Gln Val Lys Gly Lys Val
    1160                1165                1170

Val Thr Leu Ala Asp Lys Ser Ile Arg Tyr Phe Asp Ala Asn Ser
    1175                1180                1185

Gly Glu Met Ala Val Gly Lys Phe Ala Glu Gly Ala Lys Asn Glu
    1190                1195                1200

Trp Tyr Tyr Phe Asp Gln Ala Gly Lys Ala Val Thr Gly Leu Gln
    1205                1210                1215

Lys Ile Gly Gln Gln Thr Leu Tyr Phe Asp Gln Asp Gly Lys Gln
    1220                1225                1230

Val Lys Gly Gln Leu Val Thr Leu Ala Asp Lys Ser Ile Arg Tyr
    1235                1240                1245

Phe Asp Ala Asn Ser Gly Glu Met Ala Ser Asn Lys Phe Val Glu
    1250                1255                1260

Gly Ala Lys Asn Glu Trp Tyr Tyr Phe Asp Gln Ala Gly Lys Ala
    1265                1270                1275

Val Thr Gly Leu Gln Gln Ile Gly Gln Gln Thr Leu Tyr Phe Asp
    1280                1285                1290

Gln Asn Gly Lys Gln Val Lys Gly Lys Ile Val Tyr Val Asn Gly
    1295                1300                1305

Ala Asn Arg Tyr Phe Asp Ala Asn Ser Gly Glu Met Ala Arg Asn
    1310                1315                1320

Lys Trp Ile Gln Leu Glu Asp Gly Ser Trp Met Tyr Phe Asp Arg
    1325                1330                1335

Asn Gly Arg Gly Arg Arg Phe Gly Trp Asn
    1340                1345

<210> SEQ ID NO 49
<211> LENGTH: 4284
<212> TYPE: DNA

<213> ORGANISM: Streptococcus salivarius

<400> SEQUENCE: 49

```
atgaaggatg gcaaatacta ctacttgttg aagatggct cgcacaaaaa gaatttcgca      60
atcaccgtca atggtcaagt gctgtatttt gacgagaacg gtgcgctgag cagcaccagc     120
acgtacagct tcacgcagga aaccaccaat ctggttacgg actttacgaa gaataatgcg     180
gcgtatgact ccacgaaagc gtctttcgaa ttggtggacg gctatctgac cgcagacagc     240
tggtatcgcc cgaaagagat tctggaagcc ggcaccacct ggaaggcgag caccgaaaag     300
gacttccgtc cgctgctgat gtcctggtgg ccggataagg acacgcaagt tgcttatctg     360
aattacatga cgaaagcact gtcgaacggc gaagaaacca aggatgtctt tacgatcgaa     420
aacagccaag cgagcctgaa tgcggcagcg caaatcctgc aacgtaagat tgaggtcaag     480
attgcggcca acaagagcac cgactggctg cgccaaagca tcgaggcgtt tgtcaaagac     540
caagataagt ggaatatcaa tagcgaaagc cctggcaaag agcatttcca gaagggtgcg     600
ctgctgtttg ttaatagcga cagcaccaag tgggcgaact ccgattatcg taaactgaat     660
cagaccgcga cgtcttacat caagaatcat aagatcgtga acggtagcga tggtggttac     720
gagttcttgc tgagcaacga catcgacaac agcaacccgg tggtccaggc agagatgctg     780
aatcaactgt actactttat gaactggggt cagattgtgt tcggcgataa agataaagac     840
gcacatttcg atggcatccg tgtggacgcg gtggacaatg ttagcgttga catgctgcaa     900
ctggtcagca gctacatgaa ggcggcatac aaggtcaatg aatctgaagc ccgtgcgctg     960
gcgaatatca gcattttgga agcgtggagc cataatgacc cgtattatgt gaacgagcac    1020
aatacggcag cactgagcat ggataacggt ctgcgtctgt ctattgtgca tggtctgacg    1080
cgtccggtga ctaacaaagg cacgggtgct cgtaacgcca gcatgaagga cctgatcaac    1140
ggcggttact ttggcttgag caaccgtgcg gaagttacta gctacgacca gctgggcttt    1200
gccacttacc tgtttgtgcg tgcgcatgac agcgaggttc agacggttat cgctgatatt    1260
atttctaaaa agattgaccc gaccaccgac ggttttacct ttaccctgga ccagctgaag    1320
caggcttttg atatttataa gcggacatg ttgaaggttg ataaagagta tacgcatagc    1380
aacatcccgg ctgcgtatgc gctgatgctg caaacgatgg gtgcagcgac ccgcgtgtat    1440
tacggcgatc tgtacactga taacggccaa tacatggcga aaaagagccc gtatttttgat   1500
cagattacca cgctgttgaa ggcccgtccg aagtacgtgg cgggtggcca gacgagctac    1560
atccacaacc tggcaggcga tggtgtcagc tcggccaaag ataacaaaga ggttctggtt    1620
agcgtgcgct acggtcagga tctgatgagc aaaacggata ctgagggcgg taaatacggt    1680
cgtaacagcg gtatgctgac tctgatcgcg aacaacccgg acctgaagct ggccgatggt    1740
gagactatca cggttaacat gggtgctgcc cacaaaaatc aggcgtatcg tccgttgctg    1800
ctgggcacgg aaaagggtat tgtcagcagc ctgaacgata cgacaccaa aatcgtgaag    1860
tatacggacg cccaaggtaa cctggttttc accgccgacg agatcaaggg cttcaaaacc    1920
gtggacatgt ctggctacct gtctgtttgg gttccggttg gtgccacgga tgaccagaac    1980
gtcctggcga aaccgagcac caaagcatac aaagaaggtg ataaggttta cagcagcagc    2040
gcggctctgg aagctcaggt tatctatgaa ggttttagca atttccagga tttcgtgaaa    2100
gaagatagcc agtataccaa taagctgatt gcggctaatg cggacctgtt taagagctgg    2160
ggtatcacga gctttgagat cgcaccgcaa tatgtgagca gcaaagatgg tacttttctg    2220
gacagcatca ttgaaaatgg ttacgcgttc accgatcgtt atgacttcgc gatgagcaag    2280
```

-continued

```
aacaataagt atggtagcaa agaggatctg cgcgacgcgc tgaaggcact gcacaaacaa    2340
ggcatccaag tcatcgcgga ttgggtgccg gatcagctgt atacctgcc gggcaaagag    2400 gtggttacgg caacccgtac cgatacgcac ggtaaagtgc tggatgacac gagcctggtg    2460
aataaactgt atgtgaccaa tacgaagtct agcggtaacg atttccaggc acagtatggt    2520
ggtgcgttcc tggataaact gcaaaagctg tacccagaga ttttcaaaga agttatggaa    2580
gcgtccggca agaccatcga cccaagcgtc aagattaaac aatgggaagc taaatacttt    2640
aatggcacga atattcaaaa gcgtggttcc gattatgttc tgagcgatgg caaactgtac    2700
tttacggtta acgataaggg caccttcctg cctgctgccc tgacgggtga caccaaggct    2760
aaaacgggtt ttgcctacga tggtacgggt gtcacgtatt acactaccag cggtactcaa    2820
gctaagagcc agtttgtgac gtataatggt aagcaatact acttcaacga caagggttac    2880
ttggttaccg gcgagcagac gattgatggc tccaactatt tcttcctgcc gaatggtgtt    2940
atgtttaccg atggtgtgcg taaaaacgcg aagggtcaga gcctggttta tggcaagtct    3000
ggtaagctga ccacgcaaac gggctggaaa gaagtgaccg ttaaagatga tagcggcaaa    3060
gaagaaaagt tttaccagta tttcttcaag ggtggcatca tggcgaccgg cctgacggaa    3120
gttgaaggta agagaagta tttctatgac aatggctacc aggctaaagg cgtctttgtc    3180
ccgaccaaag acggccacct gatgttcttt tgcggcgaca gcggtgagcg taaatacagc    3240
ggtttctttg aacaagacgg taactggtac tatgcgaatg acaagggcta cgtcgcgacc    3300
ggctttacca aggtgggtaa acaaaatctg tatttcaatg agaaaggcgt ccaggtcaaa    3360
aaccgctttt tccaagtggg tgacgccacc tattacgcga taacgaggg cgacgtgctg    3420 cgtggtgcgc aaaccatcaa tggtgatgag ctgtacttcg acgaaagcgg caaacaagtt    3480
aagggtgagt tcgtgaataa cccagacggc acgacctctt actatgatgc gatcacgggc    3540
gttaagctgg tcgatacctc gctggttgtt gatggtcaga cgttcaacgt ggatgcgaag    3600
ggtgtcgtaa ccaaggcgca cacgccgggt ttctacacca cgggcgacaa caactggttc    3660
tacgcagata gctatggtcg taatgttacc ggtgcgcaag taatcaacgg ccaacacctg    3720
tatttcgatg caaatggtcg tcaagtgaaa ggcggctttg tcacgaacac ggacggtagc    3780
cgtagctttt accactggaa taccggcgac aaactggtgt ccacgttctt tgcgacgggt    3840
cacgatcgct ggtactacgc tgatgatcgt ggcaacgtcg tcacgggtgc acaggtcatc    3900
aacggtcaga agctgttctt tgacaccgat ggtaaacaag tcaaaggtgc tttcgcgacc    3960
aacgcgaatg gttcccgtag ctattatcat tggaatacgg gcaacaagct ggtgagcacc    4020
ttcttcacct cgggtgacaa taactggtat tacgcggacg ccaaaggtga ggttgtggtc    4080
ggtgaacaga cgattaatgg ccagcacctg tactttgacc agactggcaa gcaagtgaag    4140
ggcgcgactg caacgaaccc ggacggctcg atcagctatt atgatgtgca cacgggtgaa    4200
aaggctatca tcgttgggt gaagattccg agcggtcaat gggtgtactt caatgcgcag    4260
ggcaaaggtt acgtcagcaa ctaa                                            4284
```

<210> SEQ ID NO 50
<211> LENGTH: 1427
<212> TYPE: PRT
<213> ORGANISM: Streptococcus salivarius

<400> SEQUENCE: 50

```
Met Lys Asp Gly Lys Tyr Tyr Tyr Leu Leu Glu Asp Gly Ser His Lys
1               5                   10                  15
```

```
Lys Asn Phe Ala Ile Thr Val Asn Gly Gln Val Leu Tyr Phe Asp Glu
                20                  25                  30

Asn Gly Ala Leu Ser Ser Thr Ser Thr Tyr Ser Phe Thr Gln Glu Thr
            35                  40                  45

Thr Asn Leu Val Thr Asp Phe Thr Lys Asn Asn Ala Ala Tyr Asp Ser
 50                      55                  60

Thr Lys Ala Ser Phe Glu Leu Val Asp Gly Tyr Leu Thr Ala Asp Ser
 65                  70                  75                  80

Trp Tyr Arg Pro Lys Glu Ile Leu Glu Ala Gly Thr Thr Trp Lys Ala
                85                  90                  95

Ser Thr Glu Lys Asp Phe Arg Pro Leu Leu Met Ser Trp Pro Asp
                100                 105                 110

Lys Asp Thr Gln Val Ala Tyr Leu Asn Tyr Met Thr Lys Ala Leu Ser
            115                 120                 125

Asn Gly Glu Glu Thr Lys Asp Val Phe Thr Ile Glu Asn Ser Gln Ala
            130                 135                 140

Ser Leu Asn Ala Ala Ala Gln Ile Leu Gln Arg Lys Ile Glu Val Lys
145                 150                 155                 160

Ile Ala Ala Asn Lys Ser Thr Asp Trp Leu Arg Gln Ser Ile Glu Ala
                165                 170                 175

Phe Val Lys Asp Gln Asp Lys Trp Asn Ile Asn Ser Glu Ser Pro Gly
            180                 185                 190

Lys Glu His Phe Gln Lys Gly Ala Leu Leu Phe Val Asn Ser Asp Ser
            195                 200                 205

Thr Lys Trp Ala Asn Ser Asp Tyr Arg Lys Leu Asn Gln Thr Ala Thr
210                 215                 220

Ser Tyr Ile Lys Asn His Lys Ile Val Asn Gly Ser Asp Gly Gly Tyr
225                 230                 235                 240

Glu Phe Leu Leu Ser Asn Asp Ile Asp Asn Ser Asn Pro Val Val Gln
                245                 250                 255

Ala Glu Met Leu Asn Gln Leu Tyr Tyr Phe Met Asn Trp Gly Gln Ile
            260                 265                 270

Val Phe Gly Asp Lys Asp Lys Asp Ala His Phe Asp Gly Ile Arg Val
            275                 280                 285

Asp Ala Val Asp Asn Val Ser Val Asp Met Leu Gln Leu Val Ser Ser
290                 295                 300

Tyr Met Lys Ala Ala Tyr Lys Val Asn Glu Ser Glu Ala Arg Ala Leu
305                 310                 315                 320

Ala Asn Ile Ser Ile Leu Glu Ala Trp Ser His Asn Asp Pro Tyr Tyr
                325                 330                 335

Val Asn Glu His Asn Thr Ala Ala Leu Ser Met Asp Asn Gly Leu Arg
            340                 345                 350

Leu Ser Ile Val His Gly Leu Thr Arg Pro Val Thr Asn Lys Gly Thr
            355                 360                 365

Gly Ala Arg Asn Ala Ser Met Lys Asp Leu Ile Asn Gly Gly Tyr Phe
            370                 375                 380

Gly Leu Ser Asn Arg Ala Glu Val Thr Ser Tyr Asp Gln Leu Gly Phe
385                 390                 395                 400

Ala Thr Tyr Leu Phe Val Arg Ala His Asp Ser Glu Val Gln Thr Val
                405                 410                 415

Ile Ala Asp Ile Ile Ser Lys Lys Ile Asp Pro Thr Thr Asp Gly Phe
            420                 425                 430
```

```
Thr Phe Thr Leu Asp Gln Leu Lys Gln Ala Phe Asp Ile Tyr Asn Ala
        435                 440                 445

Asp Met Leu Lys Val Asp Lys Glu Tyr Thr His Ser Asn Ile Pro Ala
450                 455                 460

Ala Tyr Ala Leu Met Leu Gln Thr Met Gly Ala Ala Thr Arg Val Tyr
465                 470                 475                 480

Tyr Gly Asp Leu Tyr Thr Asp Asn Gly Gln Tyr Met Ala Lys Lys Ser
                485                 490                 495

Pro Tyr Phe Asp Gln Ile Thr Thr Leu Leu Lys Ala Arg Pro Lys Tyr
            500                 505                 510

Val Ala Gly Gly Gln Thr Ser Tyr Ile His Asn Leu Ala Gly Asp Gly
            515                 520                 525

Val Ser Ser Ala Lys Asp Asn Lys Glu Val Leu Val Ser Val Arg Tyr
530                 535                 540

Gly Gln Asp Leu Met Ser Lys Thr Asp Thr Glu Gly Gly Lys Tyr Gly
545                 550                 555                 560

Arg Asn Ser Gly Met Leu Thr Leu Ile Ala Asn Asn Pro Asp Leu Lys
                565                 570                 575

Leu Ala Asp Gly Glu Thr Ile Thr Val Asn Met Gly Ala Ala His Lys
            580                 585                 590

Asn Gln Ala Tyr Arg Pro Leu Leu Gly Thr Glu Lys Gly Ile Val
            595                 600                 605

Ser Ser Leu Asn Asp Ser Asp Thr Lys Ile Val Lys Tyr Thr Asp Ala
610                 615                 620

Gln Gly Asn Leu Val Phe Thr Ala Asp Glu Ile Lys Gly Phe Lys Thr
625                 630                 635                 640

Val Asp Met Ser Gly Tyr Leu Ser Val Trp Val Pro Val Gly Ala Thr
                645                 650                 655

Asp Asp Gln Asn Val Leu Ala Lys Pro Ser Thr Lys Ala Tyr Lys Glu
            660                 665                 670

Gly Asp Lys Val Tyr Ser Ser Ala Ala Leu Glu Ala Gln Val Ile
            675                 680                 685

Tyr Glu Gly Phe Ser Asn Phe Gln Asp Phe Val Lys Glu Asp Ser Gln
690                 695                 700

Tyr Thr Asn Lys Leu Ile Ala Ala Asn Ala Asp Leu Phe Lys Ser Trp
705                 710                 715                 720

Gly Ile Thr Ser Phe Glu Ile Ala Pro Gln Tyr Val Ser Ser Lys Asp
                725                 730                 735

Gly Thr Phe Leu Asp Ser Ile Ile Glu Asn Gly Tyr Ala Phe Thr Asp
            740                 745                 750

Arg Tyr Asp Phe Ala Met Ser Lys Asn Asn Lys Tyr Gly Ser Lys Glu
            755                 760                 765

Asp Leu Arg Asp Ala Leu Lys Ala Leu His Lys Gln Gly Ile Gln Val
770                 775                 780

Ile Ala Asp Trp Val Pro Asp Gln Leu Tyr Thr Leu Pro Gly Lys Glu
785                 790                 795                 800

Val Val Thr Ala Thr Arg Thr Asp Thr His Gly Lys Val Leu Asp Asp
                805                 810                 815

Thr Ser Leu Val Asn Lys Leu Tyr Val Thr Asn Thr Lys Ser Ser Gly
            820                 825                 830

Asn Asp Phe Gln Ala Gln Tyr Gly Gly Ala Phe Leu Asp Lys Leu Gln
            835                 840                 845

Lys Leu Tyr Pro Glu Ile Phe Lys Glu Val Met Glu Ala Ser Gly Lys
```

```
            850                 855                 860
Thr Ile Asp Pro Ser Val Lys Ile Lys Gln Trp Glu Ala Lys Tyr Phe
865                 870                 875                 880

Asn Gly Thr Asn Ile Gln Lys Arg Gly Ser Asp Tyr Val Leu Ser Asp
                    885                 890                 895

Gly Lys Leu Tyr Phe Thr Val Asn Asp Lys Gly Thr Phe Leu Pro Ala
                900                 905                 910

Ala Leu Thr Gly Asp Thr Lys Ala Lys Thr Gly Phe Ala Tyr Asp Gly
            915                 920                 925

Thr Gly Val Thr Tyr Tyr Thr Thr Ser Gly Thr Gln Ala Lys Ser Gln
        930                 935                 940

Phe Val Thr Tyr Asn Gly Lys Gln Tyr Tyr Phe Asn Asp Lys Gly Tyr
945                 950                 955                 960

Leu Val Thr Gly Glu Gln Thr Ile Asp Gly Ser Asn Tyr Phe Phe Leu
                965                 970                 975

Pro Asn Gly Val Met Phe Thr Asp Gly Val Arg Lys Asn Ala Lys Gly
                980                 985                 990

Gln Ser Leu Val Tyr Gly Lys Ser  Gly Lys Leu Thr Thr  Gln Thr Gly
            995                 1000                1005

Trp Lys  Glu Val Thr Val Lys  Asp Asp Ser Gly Lys  Glu Glu Lys
    1010                1015                1020

Phe Tyr  Gln Tyr Phe Phe Lys  Gly Gly Ile Met Ala  Thr Gly Leu
    1025                1030                1035

Thr Glu  Val Glu Gly Lys Glu  Lys Tyr Phe Tyr Asp  Asn Gly Tyr
    1040                1045                1050

Gln Ala  Lys Gly Val Phe Val  Pro Thr Lys Asp Gly  His Leu Met
    1055                1060                1065

Phe Phe  Cys Gly Asp Ser Gly  Glu Arg Lys Tyr Ser  Gly Phe Phe
    1070                1075                1080

Glu Gln  Asp Gly Asn Trp Tyr  Tyr Ala Asn Asp Lys  Gly Tyr Val
    1085                1090                1095

Ala Thr  Gly Phe Thr Lys Val  Gly Lys Gln Asn Leu  Tyr Phe Asn
    1100                1105                1110

Glu Lys  Gly Val Gln Val Lys  Asn Arg Phe Phe Gln  Val Gly Asp
    1115                1120                1125

Ala Thr  Tyr Tyr Ala Asn Asn  Glu Gly Asp Val Leu  Arg Gly Ala
    1130                1135                1140

Gln Thr  Ile Asn Gly Asp Glu  Leu Tyr Phe Asp Glu  Ser Gly Lys
    1145                1150                1155

Gln Val  Lys Gly Glu Phe Val  Asn Asn Pro Asp Gly  Thr Thr Ser
    1160                1165                1170

Tyr Tyr  Asp Ala Ile Thr Gly  Val Lys Leu Val Asp  Thr Ser Leu
    1175                1180                1185

Val Val  Asp Gly Gln Thr Phe  Asn Val Asp Ala Lys  Gly Val Val
    1190                1195                1200

Thr Lys  Ala His Thr Pro Gly  Phe Tyr Thr Thr Gly  Asp Asn Asn
    1205                1210                1215

Trp Phe  Tyr Ala Asp Ser Tyr  Gly Arg Asn Val Thr  Gly Ala Gln
    1220                1225                1230

Val Ile  Asn Gly Gln His Leu  Tyr Phe Asp Ala Asn  Gly Arg Gln
    1235                1240                1245

Val Lys  Gly Gly Phe Val Thr  Asn Thr Asp Gly Ser  Arg Ser Phe
    1250                1255                1260
```

Tyr His Trp Asn Thr Gly Asp Lys Leu Val Ser Thr Phe Phe Ala
1265                 1270                1275

Thr Gly His Asp Arg Trp Tyr Tyr Ala Asp Asp Arg Gly Asn Val
     1280                1285                1290

Val Thr Gly Ala Gln Val Ile Asn Gly Gln Lys Leu Phe Phe Asp
1295                1300                1305

Thr Asp Gly Lys Gln Val Lys Gly Ala Phe Ala Thr Asn Ala Asn
     1310                1315                1320

Gly Ser Arg Ser Tyr Tyr His Trp Asn Thr Gly Asn Lys Leu Val
1325                1330                1335

Ser Thr Phe Phe Thr Ser Gly Asp Asn Asn Trp Tyr Tyr Ala Asp
     1340                1345                1350

Ala Lys Gly Glu Val Val Val Gly Glu Gln Thr Ile Asn Gly Gln
1355                1360                1365

His Leu Tyr Phe Asp Gln Thr Gly Lys Gln Val Lys Gly Ala Thr
     1370                1375                1380

Ala Thr Asn Pro Asp Gly Ser Ile Ser Tyr Tyr Asp Val His Thr
1385                1390                1395

Gly Glu Lys Ala Ile Asn Arg Trp Val Lys Ile Pro Ser Gly Gln
     1400                1405                1410

Trp Val Tyr Phe Asn Ala Gln Gly Lys Gly Tyr Val Ser Asn
1415                1420                1425

<210> SEQ ID NO 51
<211> LENGTH: 4182
<212> TYPE: DNA
<213> ORGANISM: Unknown
<220> FEATURE:
<223> OTHER INFORMATION: unknown Streptococcus species

<400> SEQUENCE: 51

| | | |
|---|---|---|
| atgatcaatg gcaaacagta ctatgtaaat tcggacggta gcgtgcgtaa gaatttcgtt | 60 |
| tttgaacagg atggtaagag ctactacttt gacgcggaaa ctggcgcgct ggccactaaa | 120 |
| agccaagatg aatttagcac ggagccgatt aaagcagcag tggacttctc tagcggcaac | 180 |
| cagctgtaca aaaatgacaa caaatcgctg gatcagctgg atacgtttat caccgctgac | 240 |
| gcatggtacc gccctaagtc tattctgaag gatggcaaaa cctggaccgc gtctaccgaa | 300 |
| gctgataagc gtccgttgct gatggtgtgg tggccggaca gtccacccca gttaactac | 360 |
| ctgaactaca tgcagaacca gggtttgggt gcgggtagct tcagcaccaa tagcagccaa | 420 |
| gaatccctga atctggctgc gaaagcagtt cagaccaaga tcgaagaacg catcgcacgt | 480 |
| gagggtaaca ccaattggct gcgtaccagc attgaccaat tcattaagac gcagccaggc | 540 |
| tggaacagca gcactgagaa tagcagctat gatcacttgc agggtggtca actgctgttc | 600 |
| aataacagca aggtgatac gggtaaccgc accagctatg cgaatagcga ctatcgtctg | 660 |
| ctgaaccgta ccccaactaa tcaaagcggc acccgtaagt actttaagga taattccatc | 720 |
| ggtggtctgg aatttctgct ggcaaacgac atcgacaaca gcaaccctgc cgttcaggcg | 780 |
| gagcagctga actggctgca cttcatgatg aacattggtt ctatcatggc gaatgacccg | 840 |
| acggcgaact tgatggtttt gcgtgtggac gcgttggata cgtggatgc ggacctgttg | 900 |
| cagatcgcga gcgattactt caaggcagtc tacggtgttg ataaatccga ggcgaatgcg | 960 |
| atcaagcacc tgagctatct ggaggcgtgg agcgccaatg accgtatta caacaaggat | 1020 |
| accaaaggcg cgcaactgcc gattgacaac gcgctgcgca acgcactgac caacctgttg | 1080 |

```
atgcgtgaca agaatacgcg catgcagctg ggtgacatga cggcgtttat gaatagctct      1140
ctgaacccac gtggtgcgaa tgacaaaaac ggcgagcgta tggcgaatta cattttcacc      1200
cgcgcacacg ataccgaggc gcagaccatc attcagcgta ttatccgcga tcgtatcaat      1260
ccgaacctgt ttggctacaa tttcacccgc gatgaaatca aaaaggcgtt tgagatctac      1320
aacgcggaca ttaacacggc gcataagacg tacgcgagct acaatctgcc gtccgtctac      1380
gcactgatgc tgacgaataa ggacagcgtg acccgtgtgt attacggtga cctgtatcgt      1440
gaggacggtc actacatggc caagaaaacg ccttatttcg atgcaatcga taccctgctg      1500
cgtgcgcgca tcaaatacgt ggcgggtggt caagacatgg aggtgaagaa agttggtaat      1560
gacggcttgc tgacgagcgt ccgctatggc aagggtgcga acaatagcac cgactggggc      1620
acgactgaaa cccgtaccca aggtatgggc gttatcctga cgaacaacta tgatttccgc      1680
ctgggcagca acgaaaccgt cacgatgaac atgggccgtg cgcatcgcaa tcagctgtat      1740
cgtccgctgc tgctgacgac caaggatggt ctggccacgt acctgaatga tagcgacgtg      1800
ccttcgaatt tgctgaaacg cacggactgg aatggtaact tgacctttaa tgccaacgat      1860
gtgtttggtg tagagaacgt ccaggtcagc ggttacctgg tgtttgggt accggttggt       1920 gctaaagcta accaggatgc gcgtacccaa ccgagcaacc gtgcgaacag cgatggtcag      1980
gtctataagt cgtctgcggc attggacagc caggtcatgt atgaggcgtt tagcaatttt      2040
caggcatttg cggacgatca accggaactg tacatgaacc gcgttctggc gaagaacacc      2100
gatctgctga agcgtggggg cgttactagc gttggcttgc cgccacaata cgttagcagc      2160
aaagacggca ccttcctgga tagcactatt gataacggct atgcgttcga tgatcgttac      2220
gacatggcgc tgagccagaa caacaaatac ggttctctgg aggacttgct gaacgttctg      2280
cgcgctctgc acaaagacgg tattcaggcg attgcggact gggtcccgga tcaaatctac      2340
aatttgccgg gtaaagaggt tgttaatgcg acgcgtgtta acggttacgg ttaccatcag      2400
cagggctacc agattgttga ccaggcgtac gttgcaaaca cccgtacgga tggtaccgat      2460
tatcagggtc gttacggtgg tgcttttctg gacgaactga aggcgaagta cccgagcatt      2520
ttcaatcgtg tccagattag caacggtaaa cagctgccaa ccaatgagaa aatcacgaaa      2580
tggtccgcga atacttcaa tggcacgaac atcctgggcc gtggtattaa ctatgtgctg       2640
cgcgacgaca agaccaatca gtatttcaac accagcgcaa acggccaact gctgccgacg      2700
ccactgcgcg acaccggtgc catcaccagc acgcaagttt tccagcgtcg tggccaagac      2760
gtctattttc tgcgtgataa ccaggttatc aaaaacgagt ttgtgcaaga tggtaacggt      2820
aattggtact acttcggtgc cgacggtaaa atgacgaagg gtgcacaaaa catcaatagc      2880
aaggattact atttcttcga taatggcgtc cagctgcgta atgcgctgcg tcgcgcgtcc      2940
aatggttaca cctactatta tggcctggac ggtgccatga tcaagaacgc tttcgtcgat      3000
tttgatgata agcaccaaca ggtgcgtgcg tttactacgc agggcacgat ggtggtcggt      3060
aatttgcact ggagcggtca ccacttctat tttgaccgcg aaacgggtat ccaagccaaa      3120
gaccgcattg tgcgtaccga tgatggcaag ctgcactatt atgtcgcaca aaccggcgat      3180
atgggccgca atgtgtttgc gaccgacagc cgcacgggca agcgctatta ctttgatgcg      3240
gacggcaaca ccgttacggg ctcccgtgtc atcgacggca agacctacta cttcaaccag      3300
gacggttcgg tcggtaccgc gtacagcaat cgtgcggata gcattatctt tgagaatggc      3360
aaggctcgct atatcactcc ggctggcgag attggccgtt ccattttgt ctacaacccg        3420
```

-continued

```
gcgaccaaag cgtggaatta cttcgacaag gaaggtaacc gtgtcaccgg tcgtcagtat    3480
attgacggca atctgtacta ctttaaagag gacggctccc aagtgaaagg tgcgattgtt    3540
gaagagaacg gtatcaagta ctactacgaa ccgggcagcg gtatcctggc gagcggtcgt    3600
tatctgcaag tcggtgacga ccaatggatc tacttcaaac acgacggtag cctggcgatc    3660
ggtcaggttc gtgcagacgg tggttacttg aaatactttg ataagaatgg catccaggtc    3720
aagggccaaa ccattgtgga ggatggtcat acctattact acgatgccga ctccggtgct    3780
ctggtgacct ctagcttcgc ggagattgct ccgaaccagt gggcctactt caataccgag    3840
ggccaagccc tgaagggcaa atggaccatc aatggtaaag agtactattt tgatcagaac    3900
ggcattcagt ataaaggcaa ggcagttaag gtcggcagcc gttacaaata ctatgacgag    3960
aatgacggtc aaccggtcac taaccgtttt gcccagattg agccgaacgt ctgggcgtac    4020
tttggtgccg atggctacgc agttactggc gaacaggtga ttaatggcca gcacctgtac    4080
ttcgatcagt cgggtcgtca ggttaaaggt gcgtacgtca ccgtgaatgg tcaacgtcgt    4140
tactacgacg caaacacggg tgaatacatt ccgggtcgtt aa                      4182
```

<210> SEQ ID NO 52
<211> LENGTH: 1393
<212> TYPE: PRT
<213> ORGANISM: Unknown
<220> FEATURE:
<223> OTHER INFORMATION: unknown Streptococcus species

<400> SEQUENCE: 52

```
Met Ile Asn Gly Lys Gln Tyr Tyr Val Asn Ser Asp Gly Ser Val Arg
1               5                   10                  15

Lys Asn Phe Val Phe Glu Gln Asp Gly Lys Ser Tyr Tyr Phe Asp Ala
                20                  25                  30

Glu Thr Gly Ala Leu Ala Thr Lys Ser Gln Asp Glu Phe Ser Thr Glu
            35                  40                  45

Pro Ile Lys Ala Ala Val Asp Phe Ser Ser Gly Asn Gln Leu Tyr Lys
        50                  55                  60

Asn Asp Asn Lys Ser Leu Asp Gln Leu Asp Thr Phe Ile Thr Ala Asp
65                  70                  75                  80

Ala Trp Tyr Arg Pro Lys Ser Ile Leu Lys Asp Gly Lys Thr Trp Thr
                85                  90                  95

Ala Ser Thr Glu Ala Asp Lys Arg Pro Leu Leu Met Val Trp Trp Pro
            100                 105                 110

Asp Lys Ser Thr Gln Val Asn Tyr Leu Asn Tyr Met Gln Asn Gln Gly
        115                 120                 125

Leu Gly Ala Gly Ser Phe Ser Thr Asn Ser Ser Gln Glu Ser Leu Asn
    130                 135                 140

Leu Ala Ala Lys Ala Val Gln Thr Lys Ile Glu Glu Arg Ile Ala Arg
145                 150                 155                 160

Glu Gly Asn Thr Asn Trp Leu Arg Thr Ser Ile Asp Gln Phe Ile Lys
                165                 170                 175

Thr Gln Pro Gly Trp Asn Ser Ser Thr Glu Asn Ser Ser Tyr Asp His
            180                 185                 190

Leu Gln Gly Gly Gln Leu Leu Phe Asn Asn Ser Lys Gly Asp Thr Gly
        195                 200                 205

Asn Arg Thr Ser Tyr Ala Asn Ser Asp Tyr Arg Leu Leu Asn Arg Thr
    210                 215                 220

Pro Thr Asn Gln Ser Gly Thr Arg Lys Tyr Phe Lys Asp Asn Ser Ile
```

-continued

```
            225                 230                 235                 240

Gly Gly Leu Glu Phe Leu Leu Ala Asn Asp Ile Asp Asn Ser Asn Pro
                245                 250                 255

Ala Val Gln Ala Glu Gln Leu Asn Trp Leu His Phe Met Met Asn Ile
                260                 265                 270

Gly Ser Ile Met Ala Asn Asp Pro Thr Ala Asn Phe Asp Gly Leu Arg
                275                 280                 285

Val Asp Ala Leu Asp Asn Val Asp Ala Asp Leu Leu Gln Ile Ala Ser
                290                 295                 300

Asp Tyr Phe Lys Ala Val Tyr Gly Val Asp Lys Ser Glu Ala Asn Ala
305                 310                 315                 320

Ile Lys His Leu Ser Tyr Leu Glu Ala Trp Ser Ala Asn Asp Pro Tyr
                325                 330                 335

Tyr Asn Lys Asp Thr Lys Gly Ala Gln Leu Pro Ile Asn Ala Leu
                340                 345                 350

Arg Asn Ala Leu Thr Asn Leu Leu Met Arg Asp Lys Asn Thr Arg Met
                355                 360                 365

Gln Leu Gly Asp Met Thr Ala Phe Met Asn Ser Ser Leu Asn Pro Arg
                370                 375                 380

Gly Ala Asn Asp Lys Asn Gly Glu Arg Met Ala Asn Tyr Ile Phe Thr
385                 390                 395                 400

Arg Ala His Asp Thr Glu Ala Gln Thr Ile Ile Gln Arg Ile Ile Arg
                405                 410                 415

Asp Arg Ile Asn Pro Asn Leu Phe Gly Tyr Asn Phe Thr Arg Asp Glu
                420                 425                 430

Ile Lys Lys Ala Phe Glu Ile Tyr Asn Ala Asp Ile Asn Thr Ala His
                435                 440                 445

Lys Thr Tyr Ala Ser Tyr Asn Leu Pro Ser Val Tyr Ala Leu Met Leu
                450                 455                 460

Thr Asn Lys Asp Ser Val Thr Arg Val Tyr Tyr Gly Asp Leu Tyr Arg
465                 470                 475                 480

Glu Asp Gly His Tyr Met Ala Lys Lys Thr Pro Tyr Phe Asp Ala Ile
                485                 490                 495

Asp Thr Leu Leu Arg Ala Arg Ile Lys Tyr Val Ala Gly Gly Gln Asp
                500                 505                 510

Met Glu Val Lys Lys Val Gly Asn Asp Gly Leu Leu Thr Ser Val Arg
                515                 520                 525

Tyr Gly Lys Gly Ala Asn Asn Ser Thr Asp Trp Gly Thr Thr Glu Thr
                530                 535                 540

Arg Thr Gln Gly Met Gly Val Ile Leu Thr Asn Asn Tyr Asp Phe Arg
545                 550                 555                 560

Leu Gly Ser Asn Glu Thr Val Thr Met Asn Met Gly Arg Ala His Arg
                565                 570                 575

Asn Gln Leu Tyr Arg Pro Leu Leu Leu Thr Lys Asp Gly Leu Ala
                580                 585                 590

Thr Tyr Leu Asn Asp Ser Asp Val Pro Ser Asn Leu Leu Lys Arg Thr
                595                 600                 605

Asp Trp Asn Gly Asn Leu Thr Phe Asn Ala Asn Asp Val Phe Gly Val
                610                 615                 620

Glu Asn Val Gln Val Ser Gly Tyr Leu Gly Val Trp Val Pro Val Gly
625                 630                 635                 640

Ala Lys Ala Asn Gln Asp Ala Arg Thr Gln Pro Ser Asn Arg Ala Asn
                645                 650                 655
```

```
Ser Asp Gly Gln Val Tyr Lys Ser Ala Ala Leu Asp Ser Gln Val
            660                 665                 670

Met Tyr Glu Ala Phe Ser Asn Phe Gln Ala Phe Ala Asp Asp Gln Pro
            675                 680                 685

Glu Leu Tyr Met Asn Arg Val Leu Ala Lys Asn Thr Asp Leu Leu Lys
            690                 695                 700

Ala Trp Gly Val Thr Ser Val Gly Leu Pro Pro Gln Tyr Val Ser Ser
705                 710                 715                 720

Lys Asp Gly Thr Phe Leu Asp Ser Thr Ile Asp Asn Gly Tyr Ala Phe
                    725                 730                 735

Asp Asp Arg Tyr Asp Met Ala Leu Ser Gln Asn Asn Lys Tyr Gly Ser
            740                 745                 750

Leu Glu Asp Leu Leu Asn Val Leu Arg Ala Leu His Lys Asp Gly Ile
            755                 760                 765

Gln Ala Ile Ala Asp Trp Val Pro Asp Gln Ile Tyr Asn Leu Pro Gly
            770                 775                 780

Lys Glu Val Val Asn Ala Thr Arg Val Asn Gly Tyr Gly Tyr His Gln
785                 790                 795                 800

Gln Gly Tyr Gln Ile Val Asp Gln Ala Tyr Val Ala Asn Thr Arg Thr
            805                 810                 815

Asp Gly Thr Asp Tyr Gln Gly Arg Tyr Gly Gly Ala Phe Leu Asp Glu
            820                 825                 830

Leu Lys Ala Lys Tyr Pro Ser Ile Phe Asn Arg Val Gln Ile Ser Asn
            835                 840                 845

Gly Lys Gln Leu Pro Thr Asn Glu Lys Ile Thr Lys Trp Ser Ala Lys
            850                 855                 860

Tyr Phe Asn Gly Thr Asn Ile Leu Gly Arg Gly Ile Asn Tyr Val Leu
865                 870                 875                 880

Arg Asp Asp Lys Thr Asn Gln Tyr Phe Asn Thr Ser Ala Asn Gly Gln
                    885                 890                 895

Leu Leu Pro Thr Pro Leu Arg Asp Thr Gly Ala Ile Thr Ser Thr Gln
            900                 905                 910

Val Phe Gln Arg Arg Gly Gln Asp Val Tyr Phe Leu Arg Asp Asn Gln
            915                 920                 925

Val Ile Lys Asn Glu Phe Val Gln Asp Gly Asn Gly Asn Trp Tyr Tyr
930                 935                 940

Phe Gly Ala Asp Gly Lys Met Thr Lys Gly Ala Gln Asn Ile Asn Ser
945                 950                 955                 960

Lys Asp Tyr Tyr Phe Phe Asp Asn Gly Val Gln Leu Arg Asn Ala Leu
                    965                 970                 975

Arg Arg Ala Ser Asn Gly Tyr Thr Tyr Tyr Tyr Gly Leu Asp Gly Ala
            980                 985                 990

Met Ile Lys Asn Ala Phe Val Asp Phe Asp Asp Lys His Gln Gln Val
            995                 1000                1005

Arg Ala Phe Thr Thr Gln Gly Thr Met Val Val Gly Asn Leu His
            1010                1015                1020

Trp Ser Gly His His Phe Tyr Phe Asp Arg Glu Thr Gly Ile Gln
            1025                1030                1035

Ala Lys Asp Arg Ile Val Arg Thr Asp Asp Gly Lys Leu His Tyr
            1040                1045                1050

Tyr Val Ala Gln Thr Gly Asp Met Gly Arg Asn Val Phe Ala Thr
            1055                1060                1065
```

| | | | | | | | | | |
|---|---|---|---|---|---|---|---|---|---|
| Asp | Ser | Arg | Thr | Gly | Lys | Arg | Tyr | Tyr | Phe | Asp | Ala | Asp | Gly | Asn |

Asp Ser Arg Thr Gly Lys Arg Tyr Tyr Phe Asp Ala Asp Gly Asn
1070                1075                1080

Thr Val Thr Gly Ser Arg Val Ile Asp Gly Lys Thr Tyr Tyr Phe
1085                1090                1095

Asn Gln Asp Gly Ser Val Gly Thr Ala Tyr Ser Asn Arg Ala Asp
1100                1105                1110

Ser Ile Ile Phe Glu Asn Gly Lys Ala Arg Tyr Ile Thr Pro Ala
1115                1120                1125

Gly Glu Ile Gly Arg Ser Ile Phe Val Tyr Asn Pro Ala Thr Lys
1130                1135                1140

Ala Trp Asn Tyr Phe Asp Lys Glu Gly Asn Arg Val Thr Gly Arg
1145                1150                1155

Gln Tyr Ile Asp Gly Asn Leu Tyr Tyr Phe Lys Glu Asp Gly Ser
1160                1165                1170

Gln Val Lys Gly Ala Ile Val Glu Asn Gly Ile Lys Tyr Tyr
1175                1180                1185

Tyr Glu Pro Gly Ser Gly Ile Leu Ala Ser Gly Arg Tyr Leu Gln
1190                1195                1200

Val Gly Asp Asp Gln Trp Ile Tyr Phe Lys His Asp Gly Ser Leu
1205                1210                1215

Ala Ile Gly Gln Val Arg Ala Asp Gly Tyr Leu Lys Tyr Phe
1220                1225                1230

Asp Lys Asn Gly Ile Gln Val Lys Gly Gln Thr Ile Val Glu Asp
1235                1240                1245

Gly His Thr Tyr Tyr Tyr Asp Ala Asp Ser Gly Ala Leu Val Thr
1250                1255                1260

Ser Ser Phe Ala Glu Ile Ala Pro Asn Gln Trp Ala Tyr Phe Asn
1265                1270                1275

Thr Glu Gly Gln Ala Leu Lys Gly Lys Trp Thr Ile Asn Gly Lys
1280                1285                1290

Glu Tyr Tyr Phe Asp Gln Asn Gly Ile Gln Tyr Lys Gly Lys Ala
1295                1300                1305

Val Lys Val Gly Ser Arg Tyr Lys Tyr Tyr Asp Glu Asn Asp Gly
1310                1315                1320

Gln Pro Val Thr Asn Arg Phe Ala Gln Ile Glu Pro Asn Val Trp
1325                1330                1335

Ala Tyr Phe Gly Ala Asp Gly Tyr Ala Val Thr Gly Glu Gln Val
1340                1345                1350

Ile Asn Gly Gln His Leu Tyr Phe Asp Gln Ser Gly Arg Gln Val
1355                1360                1365

Lys Gly Ala Tyr Val Thr Val Asn Gly Gln Arg Arg Tyr Tyr Asp
1370                1375                1380

Ala Asn Thr Gly Glu Tyr Ile Pro Gly Arg
1385                1390

<210> SEQ ID NO 53
<211> LENGTH: 3789
<212> TYPE: DNA
<213> ORGANISM: Leuconostoc citreum

<400> SEQUENCE: 53
atgattaacg gccacaatta ctatttcgac agcttgggtc aactgaagaa aggtttcacg      60
ggcgtgatcg acggtcaggt ccgttacttc gaccaggagt ccggtcagga agttagcacc     120
accgacagcc aaatcaaaga gggcttgacg agccaaacga ccgactacac cgcccataac     180

```
gcggtccaca gcacggactc cgcagatttt gacaacttca atggttacct gaccgcgagc    240
agctggtatc gtcctaagga cgttctgcgt aacggccaac attgggaagc caccaccgcg    300
aatgacttcc gtcctatcgt cagcgtgtgg tggccgagca agcaaacgca ggtcaactac    360
ctgaactata tgagccagat gggtttgatc gataaccgtc aaatgttctc gttgaaagat    420
aaccaagcga tgctgaacat cgcgtgcacg accgtgcaac aagcaatcga actaaaatc     480 ggtgtggcga atagcaccgc gtggctgaaa accgcgatcg atgactttat ccgtacccag    540
ccgcagtgga acatgagcag cgaagatccg aagaatgacc atctgcaaaa tggcgccctg    600
acgtttgtta acagcccgct gaccccggat acgaatagca atttccgcct gctgaatcgt    660
accccgacca atcaaaccgg tgttccgaaa tacaccatcg accaaagcaa aggtggtttt    720
gaactgctgc tggcgaatga cgtggataat tcgaacccgg ttgtgcaggc cgagcagttg    780
aactggctgc actacctgat gaactttggt agcattactg cgaatgacag cgcagcaaac    840
ttcgacggta ttcgcgttga cgcagtggat aacgtggatg cggacctgct gcaaattgcg    900
gcagattact tcaaagcagc atacggtgtg acaagaacg acgcaacggc aaatcagcat     960
ctgtcgatcc tggaagattg gagccacaac gacccggagt acgttaaaga cttcggcaat   1020
aaccaactga ccatggacga ttacatgcac acgcagctga tctggagcct gacgaaagac   1080
atgcgtatgc gtggtacgat gcagcgcttt atggactact atctggttaa ccgcaatcac   1140
gacagcaccg agaatactgc cattccgaat tacagctttg tccgtgccca tgacagcgaa   1200
gttcaaacgg ttattgcgca gatcatttct gagctgcatc cagacgtgaa gaatagcctg   1260
gcgccgaccg cggatcaact ggctgaggcg ttcaaaatct acaacaacga cgagaagcaa   1320
gctgataaga agtatacccca atacaatatg ccaagcgcgt acgcaatgct gttgaccaat   1380
aaagataccg ttccgcgtgt ttactacggt gacctgtata ccgatgacgg tcagtatatg   1440
gctaacaaat ccccgtattt tgacgctatc aacggtctgc tgaagagccg tatcaaatat   1500
gtggcaggcg gtcaaagcat ggcggtggat cagaatgata tcctgacgaa tgtgcgctat   1560
ggcaaaggtg ccatgagcgt gacggatagc ggcaacgcgg atacgcgtac ccagggcatc   1620
ggcgttattg ttagcaacaa agaaaacctg gctctgaaat ccggcgacac cgttaccctg   1680
cacatgggcg cagcgcacaa gaaccaggcg tttcgcctgc tgttgggtac gacggcggac   1740
aacctgagct actacgacaa tgacaatgcg ccggtgaagt acaccaatga tcaaggtgat   1800
ctgattttcg ataataccga gatttatggt gttcgcaatc cgcaagtctc tggttttctg   1860
gcggtgtggg tcccggttgg tgccgatagc catcaagatg ctcgcacttt gagcgacgat   1920
acggcacacc acgacggcaa gaccttccac tcgaacgcag cactggatag ccaggtgatt   1980
tacgaaggtt ttagcaactt ccaagcattt gcaacgaata cggaagatta cactaacgct   2040
gtgatcgcca aaaacggcca gctgttcaag gattgggcca tcacctcgtt ccagctggct   2100
ccgcagtatc gcagctccac cgatacgagc ttcctggata gcattattca gaacggctat   2160
gccttcacgg accgttatga cctgggctat ggcacccga cgaagtatgg caccgtggac    2220
cagctgcgcg atgcaatcaa ggctctgcac gccaatggca tccaagcaat tgccgactgg   2280
gttccggacc agatctacaa cctgccgggt caggagctgg ccacggtgac ccgtacgaac   2340
tcctatggtg ataaagacac caatagcgat attgatcaga gcttgtacgt gatccaatcg   2400
cgcggtggcg gtaagtatca agcccaatac ggtggtgcat tcctgagcga cattcaaaag   2460
aagtatccgg ctctgttcga gactaaacag atcagcacgg gtctgccgat ggacccgagc   2520
```

-continued

```
caaaagatta ccgagtggag cggcaagtac ttcaacggta gcaatattca aggtaagggc    2580
gctggttacg tcctgaagga cagcggcacc gaccagtact ataaagtgac gagcaacaat    2640
aacaaccgtg atttcctgcc gaaacagctg acggatgatc tgtctgaaac cggttttgtg    2700
cgtgacaata ttggcatggt ctattacacc ctgtctggct acctggcacg caataccttc    2760
atccaggacg acaacggtaa ctattactac tttgatagca ccggtcacct ggttacgggt    2820
ttccagaaca ttaacaacca ccactacttt tccttgccga acggcattga actggttcag    2880
agctttctgc aaaacgctga tggtagcacg atctacttcg atcaaagggg tcgtcaagtt    2940
ttcaaccagt atatcactga tcagactggt accgcgtact acttccagaa cgacggcacc    3000
atggtcactt ctggctttac tgagatcgat ggccacaagc agtatttcta taagaatggc    3060
actcaggtta agggtcagtt tgtgagcgac accgatggtc acgtctttta cctggaagcg    3120
ggtaatggta atgtcgccac gcaacgtttc gcacagaaca gccagggtca atggttctac    3180
ttgggtaatg atggcattgc gttgacgggt ttgcagacga tcaacggtgt tcagaactac    3240
ttttatgcgg acggtcatca aagcaagggt gacttcatca ccatccagaa tcatgtcctg    3300
tacaccaacc cgctgacggg tgccatcacg accggcatgc aacagatcgg cgacaaaatc    3360
ttcgtgtttg ataatacggg taatatgctg acgaaccagt attatcagac gctggatggt    3420
cagtggctgc acctgagcac ccagggtcca gcagatacgg gtctggtcaa tatcaatggt    3480
aatctgaagt atttttcaggc aaatggtcgt caggtgaaag gccaattcgt caccgacccg    3540
attaccaacg tcagctacta catgaacgcg acggacggta gcgcagtgtt caatgactat    3600
ttcacctatc agggccaatg gtatttgacg gactccaact atcagttggt caaaggcttc    3660
aaagtggtga caacaaaact gcaacatttc gatgaaatca ccggtgtgca aaccaagagc    3720
gctcacatta ttgttaacaa tcgtacctac attttgacg accagggcta ttttgtcagc    3780
gtggcataa                                                          3789
```

<210> SEQ ID NO 54
<211> LENGTH: 1262
<212> TYPE: PRT
<213> ORGANISM: Leuconostoc citreum

<400> SEQUENCE: 54

```
Met Ile Asn Gly His Asn Tyr Tyr Phe Asp Ser Leu Gly Gln Leu Lys
 1               5                  10                  15
Lys Gly Phe Thr Gly Val Ile Asp Gly Gln Val Arg Tyr Phe Asp Gln
            20                  25                  30
Glu Ser Gly Gln Glu Val Ser Thr Thr Asp Ser Gln Ile Lys Glu Gly
        35                  40                  45
Leu Thr Ser Gln Thr Thr Asp Tyr Thr Ala His Asn Ala Val His Ser
    50                  55                  60
Thr Asp Ser Ala Asp Phe Asp Asn Phe Asn Gly Tyr Leu Thr Ala Ser
65                  70                  75                  80
Ser Trp Tyr Arg Pro Lys Asp Val Leu Arg Asn Gly Gln His Trp Glu
                85                  90                  95
Ala Thr Thr Ala Asn Asp Phe Arg Pro Ile Val Ser Val Trp Trp Pro
            100                 105                 110
Ser Lys Gln Thr Gln Val Asn Tyr Leu Asn Tyr Met Ser Gln Met Gly
        115                 120                 125
Leu Ile Asp Asn Arg Gln Met Phe Ser Leu Lys Asp Asn Gln Ala Met
    130                 135                 140
```

```
Leu Asn Ile Ala Cys Thr Thr Val Gln Gln Ala Ile Glu Thr Lys Ile
145                 150                 155                 160

Gly Val Ala Asn Ser Thr Ala Trp Leu Lys Thr Ala Ile Asp Asp Phe
                165                 170                 175

Ile Arg Thr Gln Pro Gln Trp Asn Met Ser Glu Asp Pro Lys Asn
                180                 185                 190

Asp His Leu Gln Asn Gly Ala Leu Thr Phe Val Asn Ser Pro Leu Thr
                195                 200                 205

Pro Asp Thr Asn Ser Asn Phe Arg Leu Leu Asn Arg Thr Pro Thr Asn
210                 215                 220

Gln Thr Gly Val Pro Lys Tyr Thr Ile Asp Gln Ser Lys Gly Gly Phe
225                 230                 235                 240

Glu Leu Leu Leu Ala Asn Asp Val Asp Asn Ser Asn Pro Val Val Gln
                245                 250                 255

Ala Glu Gln Leu Asn Trp Leu His Tyr Leu Met Asn Phe Gly Ser Ile
                260                 265                 270

Thr Ala Asn Asp Ser Ala Ala Asn Phe Asp Gly Ile Arg Val Asp Ala
                275                 280                 285

Val Asp Asn Val Asp Ala Asp Leu Leu Gln Ile Ala Ala Asp Tyr Phe
                290                 295                 300

Lys Ala Ala Tyr Gly Val Asp Lys Asn Asp Ala Thr Ala Asn Gln His
305                 310                 315                 320

Leu Ser Ile Leu Glu Asp Trp Ser His Asn Asp Pro Glu Tyr Val Lys
                325                 330                 335

Asp Phe Gly Asn Asn Gln Leu Thr Met Asp Asp Tyr Met His Thr Gln
                340                 345                 350

Leu Ile Trp Ser Leu Thr Lys Asp Met Arg Met Arg Gly Thr Met Gln
                355                 360                 365

Arg Phe Met Asp Tyr Tyr Leu Val Asn Arg Asn His Asp Ser Thr Glu
                370                 375                 380

Asn Thr Ala Ile Pro Asn Tyr Ser Phe Val Arg Ala His Asp Ser Glu
385                 390                 395                 400

Val Gln Thr Val Ile Ala Gln Ile Ile Ser Glu Leu His Pro Asp Val
                405                 410                 415

Lys Asn Ser Leu Ala Pro Thr Ala Asp Gln Leu Ala Glu Ala Phe Lys
                420                 425                 430

Ile Tyr Asn Asn Asp Glu Lys Gln Ala Lys Lys Tyr Thr Gln Tyr
                435                 440                 445

Asn Met Pro Ser Ala Tyr Ala Met Leu Leu Thr Asn Lys Asp Thr Val
450                 455                 460

Pro Arg Val Tyr Tyr Gly Asp Leu Tyr Thr Asp Asp Gly Gln Tyr Met
465                 470                 475                 480

Ala Asn Lys Ser Pro Tyr Phe Asp Ala Ile Asn Gly Leu Leu Lys Ser
                485                 490                 495

Arg Ile Lys Tyr Val Ala Gly Gln Ser Met Ala Val Asp Gln Asn
                500                 505                 510

Asp Ile Leu Thr Asn Val Arg Tyr Gly Lys Gly Ala Met Ser Val Thr
                515                 520                 525

Asp Ser Gly Asn Ala Asp Thr Arg Thr Gln Gly Ile Gly Val Ile Val
                530                 535                 540

Ser Asn Lys Glu Asn Leu Ala Leu Lys Ser Gly Asp Thr Val Thr Leu
545                 550                 555                 560

His Met Gly Ala Ala His Lys Asn Gln Ala Phe Arg Leu Leu Leu Gly
```

-continued

```
                565                 570                 575
Thr Thr Ala Asp Asn Leu Ser Tyr Tyr Asp Asn Asp Asn Ala Pro Val
            580                 585                 590
Lys Tyr Thr Asn Asp Gln Gly Asp Leu Ile Phe Asp Asn Thr Glu Ile
            595                 600                 605
Tyr Gly Val Arg Asn Pro Gln Val Ser Gly Phe Leu Ala Val Trp Val
            610                 615                 620
Pro Val Gly Ala Asp Ser His Gln Asp Ala Arg Thr Leu Ser Asp Asp
625                 630                 635                 640
Thr Ala His His Asp Gly Lys Thr Phe His Ser Asn Ala Ala Leu Asp
                645                 650                 655
Ser Gln Val Ile Tyr Glu Gly Phe Ser Asn Phe Gln Ala Phe Ala Thr
            660                 665                 670
Asn Thr Glu Asp Tyr Thr Asn Ala Val Ile Ala Lys Asn Gly Gln Leu
            675                 680                 685
Phe Lys Asp Trp Gly Ile Thr Ser Phe Gln Leu Ala Pro Gln Tyr Arg
            690                 695                 700
Ser Ser Thr Asp Thr Ser Phe Leu Asp Ser Ile Ile Gln Asn Gly Tyr
705                 710                 715                 720
Ala Phe Thr Asp Arg Tyr Asp Leu Gly Tyr Gly Thr Pro Thr Lys Tyr
                725                 730                 735
Gly Thr Val Asp Gln Leu Arg Asp Ala Ile Lys Ala Leu His Ala Asn
            740                 745                 750
Gly Ile Gln Ala Ile Ala Asp Trp Val Pro Asp Gln Ile Tyr Asn Leu
            755                 760                 765
Pro Gly Gln Glu Leu Ala Thr Val Thr Arg Thr Asn Ser Tyr Gly Asp
            770                 775                 780
Lys Asp Thr Asn Ser Asp Ile Asp Gln Ser Leu Tyr Val Ile Gln Ser
785                 790                 795                 800
Arg Gly Gly Gly Lys Tyr Gln Ala Gln Tyr Gly Gly Ala Phe Leu Ser
                805                 810                 815
Asp Ile Gln Lys Lys Tyr Pro Ala Leu Phe Glu Thr Lys Gln Ile Ser
            820                 825                 830
Thr Gly Leu Pro Met Asp Pro Ser Gln Lys Ile Thr Glu Trp Ser Gly
            835                 840                 845
Lys Tyr Phe Asn Gly Ser Asn Ile Gln Gly Lys Gly Ala Gly Tyr Val
            850                 855                 860
Leu Lys Asp Ser Gly Thr Asp Gln Tyr Tyr Lys Val Thr Ser Asn Asn
865                 870                 875                 880
Asn Asn Arg Asp Phe Leu Pro Lys Gln Leu Thr Asp Leu Ser Glu
                885                 890                 895
Thr Gly Phe Val Arg Asp Asn Ile Gly Met Val Tyr Tyr Thr Leu Ser
            900                 905                 910
Gly Tyr Leu Ala Arg Asn Thr Phe Ile Gln Asp Asp Asn Gly Asn Tyr
            915                 920                 925
Tyr Tyr Phe Asp Ser Thr Gly His Leu Val Thr Gly Phe Gln Asn Ile
            930                 935                 940
Asn Asn His His Tyr Phe Phe Leu Pro Asn Gly Ile Glu Leu Val Gln
945                 950                 955                 960
Ser Phe Leu Gln Asn Ala Asp Gly Ser Thr Ile Tyr Phe Asp Gln Lys
                965                 970                 975
Gly Arg Gln Val Phe Asn Gln Tyr Ile Thr Asp Gln Thr Gly Thr Ala
            980                 985                 990
```

```
Tyr Tyr Phe Gln Asn Asp Gly Thr Met Val Thr Ser Gly Phe Thr Glu
        995                 1000                    1005

Ile Asp Gly His Lys Gln Tyr Phe Tyr Lys Asn Gly Thr Gln Val
    1010                1015                 1020

Lys Gly Gln Phe Val Ser Asp Thr Asp Gly His Val Phe Tyr Leu
    1025                1030                 1035

Glu Ala Gly Asn Gly Asn Val Ala Thr Gln Arg Phe Ala Gln Asn
    1040                1045                 1050

Ser Gln Gly Gln Trp Phe Tyr Leu Gly Asn Asp Gly Ile Ala Leu
    1055                1060                 1065

Thr Gly Leu Gln Thr Ile Asn Gly Val Gln Asn Tyr Phe Tyr Ala
    1070                1075                 1080

Asp Gly His Gln Ser Lys Gly Asp Phe Ile Thr Ile Gln Asn His
    1085                1090                 1095

Val Leu Tyr Thr Asn Pro Leu Thr Gly Ala Ile Thr Thr Gly Met
    1100                1105                 1110

Gln Gln Ile Gly Asp Lys Ile Phe Val Phe Asp Asn Thr Gly Asn
    1115                1120                 1125

Met Leu Thr Asn Gln Tyr Tyr Gln Thr Leu Asp Gly Gln Trp Leu
    1130                1135                 1140

His Leu Ser Thr Gln Gly Pro Ala Asp Thr Gly Leu Val Asn Ile
    1145                1150                 1155

Asn Gly Asn Leu Lys Tyr Phe Gln Ala Asn Gly Arg Gln Val Lys
    1160                1165                 1170

Gly Gln Phe Val Thr Asp Pro Ile Thr Asn Val Ser Tyr Tyr Met
    1175                1180                 1185

Asn Ala Thr Asp Gly Ser Ala Val Phe Asn Asp Tyr Phe Thr Tyr
    1190                1195                 1200

Gln Gly Gln Trp Tyr Leu Thr Asp Ser Asn Tyr Gln Leu Val Lys
    1205                1210                 1215

Gly Phe Lys Val Val Asn Asn Lys Leu Gln His Phe Asp Glu Ile
    1220                1225                 1230

Thr Gly Val Gln Thr Lys Ser Ala His Ile Ile Val Asn Asn Arg
    1235                1240                 1245

Thr Tyr Ile Phe Asp Asp Gly Tyr Phe Val Ser Val Ala
    1250                1255                 1260

<210> SEQ ID NO 55
<211> LENGTH: 4284
<212> TYPE: DNA
<213> ORGANISM: Streptococcus salivarius

<400> SEQUENCE: 55
atgaaagacg gcaagtacta ttacctgttg gaggacggta gccacaagaa aaactttgcg    60
atcacggtca acggccaagt gctgtatttc gatgagaacg gtgcactgag cagcacgtct   120
acctattcgt ttacccagga gactaccaac ctggttaccg atttcactaa gaataatgct   180
gcgtacgaca gcaccaaggc ttccttcgag ctggttgatg ctacctgac tgcggacagc   240 tggtatcgtc cgaaggaaat cctggaggct ggcaccacct ggaaagcgag caccgagaaa   300
gactttcgtc cgctgctgat gagctggtgg ccggataaag acacccaggt tgcgtacctg   360
aattacatga cgaaggcgct gagcaatggc gaggaaacga agacgtgtt tacgatcgag   420 aactcccaag catctctgaa cgcagccgct cagatcatcc aacgcaagat cgaggtcaag   480
```

```
attgcagcga acaaaagcac ggactggctg cgccagagca tcgaggcgtt cgtgaaagat      540
caagacaagt ggaatatcaa ttcggagagc ccgggtaaag agcatttcca aaaaggtgct      600
ctgctgttcg ttaacagcga cctgaccaaa tgggcgaata gcgactatcg taaactggac      660
caaacggcga ccagccgtct gccgaaagac aagattaaga gcggcagcga tgcgggctac      720 gagttttgc tgtcctctga cattgataac agcaacccga ttgttcaggc ggagatgctg       780
aaccaactgt actatttcat gaactggggt cagattgtgt tggcgacaa agataaggat       840 gcccatttcg acggtatccg cgtcgacgcc gtagacaacg ttagcattga tatgctgcaa      900
ctggttagct cttatatgaa ggcggcatac aaagttaatg aaagcgaagc gcgtgcactg      960
gcaaacattt ccattctgga ggcttggagc cagaacgatc cgtactacgt tgatgaacac     1020
aacacggctg cgctgtctat ggacaacggt ctgcgcctga gcatcgttca cggtttgacc     1080
cgtccggtta ctaacaaggg taccggtgcc cgtaatgcaa gcatgaaaga cctgatcaac     1140
ggtggctact tcggcttgtc caatcgtgca gaagttacga gctacgatca gctgggcttc     1200
gccacctacc tgtttgtgcg tgcccatgac tctgaagttc agaccgttat cgcggacatt     1260
atctcgaaga aaatcgatcc aaccacggac ggtttcacgt tcaccctgga ccagttgaaa     1320
caagccttcg acatctacaa cgccgatatg ctgaaggttg ataaggagta cacgcacagc     1380
aacatcccgg ctgcgtatgc cctgatgctg caaactatgg gtgcggctac gcgcgtgtat     1440
tatggtgatt tgtatacgga caatggccag tacatgcgca aaaagagccc gtactttgat     1500
cagatcacga ccctgctgaa ggcgcgtagc aagtacgttg cgggtggcca gaccagctac     1560
atccataacc tggcgggtga tggtgtcagc agcgcgaagg ataacaaaga ggtgttggtc     1620
agcgtccgct acggtcagga tttgatgagc aaaaccgaca ccgagggtgg taagtatggt     1680
cgtaacagcg gtatgctgac cctgatcgcc aacaaccctg atctgaagct ggcagacggt     1740
gaaaccatca ccgtcaacat gggcgcagcg cacaagaatc aagcatatcg tccgttgttg     1800
ctgggcaccg aaaagggcat tgtgagcagc ctgaatgatt ccgacacgaa aattgttaag     1860
tataccgacg cgcaaggcaa tctggttttt accgctgatg agatcaaagg tttcaaaacc     1920
gtggatatga gcggttacct gtccgtgtgg gtgccggttg gcgcgaccga ggaccaaaac     1980
gtgctggcca agccgagcac gaaggtctac aaagagggtg ataaagttta ttcgagcagc     2040
gcggcactgg aagcacaggt gatctacgag ggttttagca atttccaaga cttcgtgaag     2100
gaagatagcc agtataccaa caagctgatt gcggccaatg cggacctgtt caaaagctgg     2160
ggtattacga gctttgaaat cgctccgcag tatgttagct ccaaggatgg caccttcctg     2220
gatagcatca ttgagaatgg ctacgcgttt accgatcgtt acgacttcgc gatgtcgaaa     2280
aacaataagt acggctccaa agaggatctg cgtgacgcgt tgaaagccct gcacaaacaa     2340
ggcattcaag ttattgcaga ttgggtcccg gaccagctgt acaccctgcc gggtaaggaa     2400
gtggtcacgg cgaccgcac ggacacccac ggtaaagtcc tggatgacac ctccctggtc      2460
aataaactgt acgttaccaa taccaaatct agcggtaacg acttccaggc gcaatacggc     2520
ggtgcattcc tggacaaaact gcaaaagttg tacccggaga ttttcaagga agtgatggag    2580
gctagcggca aaaccattga tccgtccgtc aaaatcaagc agtgggaggc aaagtatttc     2640
aacggtacga acattcagaa acgcggtagc gactacgttc tgagcgacgg caaactgtat     2700
ttcacggtaa acgacaaagg taccttcttg ccggcagctc tgaccggtga cacgaaggca     2760
aagaccggtt tcgcctatga cggtactggc gtcacttact atacgacctc cggcacgcag     2820
gcaaagagcc aatttgtcac ctacaatggc aagcagtact atttcaatga caaaggttat     2880
```

```
ctggtcacgg gtgaacaggc gattgacggt agcaactact tcttcctgcc gaacggcgtt    2940
atgtttacgg acggtgtgat caaaaatgct aaaggtcagt ctctggtcta cggcaaatct    3000
ggtaagctga ccacgcaaac cggttggaag gaagttacgg tgaaggatga tagcggcaag    3060
gaagagaaat tctaccaata cttctttaag ggtggcatta tggcgacggg tctgaccgag    3120
gttgaaggta agagaaata cttttatgat aatggttatc aggctaaagg tattttcatc    3180
cctaccaaag acggccatct gatgtttttc tgcggtgata gcggtgagcg taaatacagc    3240
ggtttcttcg aacaagacgg taactggtat tacgcaaacg ataaaggtta cgtcgcgacc    3300
ggttttacca aagtgggtaa gcagaacttg tactttaacg agaaaggtgt gcaggtcaag    3360
aaccgtttct ttcaggttgg tgatgctact tattacgcga ataacgaggg tgatgtactg    3420
cgtggtgcac agacgatcaa cggcgacgaa ctgtacttcg acgaaagcgg caagcaagtc    3480
aaaggtgaat tgtgaataa cccggacggt accacgagct attatgacgc aattaccggt    3540
gtgaaactgg tggacaccag cttggtcgtt aatggtcaaa cgttcaacat tgacgctaaa    3600
ggcgttgtca ccaaggcgca cacgccgggt ttctatacca ctggcgacaa caattggttt    3660
tatgcagata gccacggtcg caatgtcact ggcgcacaga tcattaacgg ccaacacctg    3720
tatttcgatg cgaatggccg tcaggtgaag ggcggctttg ttatgaacac tgatggttct    3780
cgttcgttct atcattggaa taccggtgat aaactggtga gcacgttctt tacgaccggc    3840
cacgatcgtt ggtactacgc cgacgacaaa ggtaacgtgg tgaccggcgc acaagtcatc    3900
aacggtcaga aattgttctt cgcgaccgac ggtaaacaag ttaagggcga tttcgcgacc    3960
aacgcaaatg gttcccgttc ttactatcac ggtgccacgg taataagct ggtcagcacc    4020 ttctttacca cgggcgataa caactggtac tatgcagacg cgaagggcga ggttgtcgtt    4080
ggtgaacaaa cgattaacgg tcaaaatctg tattttgatc agaccggtaa gcaagtgaaa    4140
ggtgcgaccg cgaccaatcc agatggcagc atttcttatt cgatgttca cacgggcgag    4200 aaggtcatca accgctgggt caaaattccg agcggtcaat gggtgtactt caacgcgcag    4260
ggtaagggtt acgtcagcaa ttaa                                          4284
```

<210> SEQ ID NO 56
<211> LENGTH: 1427
<212> TYPE: PRT
<213> ORGANISM: Streptococcus salivarius

<400> SEQUENCE: 56

```
Met Lys Asp Gly Lys Tyr Tyr Tyr Leu Leu Glu Asp Gly Ser His Lys
1               5                   10                  15

Lys Asn Phe Ala Ile Thr Val Asn Gly Gln Val Leu Tyr Phe Asp Glu
            20                  25                  30

Asn Gly Ala Leu Ser Ser Thr Ser Thr Tyr Ser Phe Thr Gln Glu Thr
        35                  40                  45

Thr Asn Leu Val Thr Asp Phe Thr Lys Asn Asn Ala Ala Tyr Asp Ser
    50                  55                  60

Thr Lys Ala Ser Phe Glu Leu Val Asp Gly Tyr Leu Thr Ala Asp Ser
65                  70                  75                  80

Trp Tyr Arg Pro Lys Glu Ile Leu Glu Ala Gly Thr Thr Trp Lys Ala
                85                  90                  95

Ser Thr Glu Lys Asp Phe Arg Pro Leu Leu Met Ser Trp Trp Pro Asp
            100                 105                 110

Lys Asp Thr Gln Val Ala Tyr Leu Asn Tyr Met Thr Lys Ala Leu Ser
```

-continued

```
            115                 120                 125
Asn Gly Glu Glu Thr Lys Asp Val Phe Thr Ile Glu Asn Ser Gln Ala
    130                 135                 140
Ser Leu Asn Ala Ala Ala Gln Ile Ile Gln Arg Lys Ile Glu Val Lys
145                 150                 155                 160
Ile Ala Ala Asn Lys Ser Thr Asp Trp Leu Arg Gln Ser Ile Glu Ala
                165                 170                 175
Phe Val Lys Asp Gln Asp Lys Trp Asn Ile Asn Ser Glu Ser Pro Gly
                180                 185                 190
Lys Glu His Phe Gln Lys Gly Ala Leu Leu Phe Val Asn Ser Asp Leu
            195                 200                 205
Thr Lys Trp Ala Asn Ser Asp Tyr Arg Lys Leu Asp Gln Thr Ala Thr
    210                 215                 220
Ser Arg Leu Pro Lys Asp Lys Ile Lys Ser Gly Ser Asp Ala Gly Tyr
225                 230                 235                 240
Glu Phe Leu Leu Ser Ser Asp Ile Asp Asn Ser Asn Pro Ile Val Gln
                245                 250                 255
Ala Glu Met Leu Asn Gln Leu Tyr Tyr Phe Met Asn Trp Gly Gln Ile
                260                 265                 270
Val Phe Gly Asp Lys Asp Lys Asp Ala His Phe Asp Gly Ile Arg Val
            275                 280                 285
Asp Ala Val Asp Asn Val Ser Ile Asp Met Leu Gln Leu Val Ser Ser
    290                 295                 300
Tyr Met Lys Ala Ala Tyr Lys Val Asn Glu Ser Glu Ala Arg Ala Leu
305                 310                 315                 320
Ala Asn Ile Ser Ile Leu Glu Ala Trp Ser Gln Asn Asp Pro Tyr Tyr
                325                 330                 335
Val Asp Glu His Asn Thr Ala Ala Leu Ser Met Asp Asn Gly Leu Arg
            340                 345                 350
Leu Ser Ile Val His Gly Leu Thr Arg Pro Val Thr Asn Lys Gly Thr
    355                 360                 365
Gly Ala Arg Asn Ala Ser Met Lys Asp Leu Ile Asn Gly Gly Tyr Phe
370                 375                 380
Gly Leu Ser Asn Arg Ala Glu Val Thr Ser Tyr Asp Gln Leu Gly Phe
385                 390                 395                 400
Ala Thr Tyr Leu Phe Val Arg Ala His Asp Ser Glu Val Gln Thr Val
                405                 410                 415
Ile Ala Asp Ile Ile Ser Lys Lys Ile Asp Pro Thr Thr Asp Gly Phe
                420                 425                 430
Thr Phe Thr Leu Asp Gln Leu Lys Gln Ala Phe Asp Ile Tyr Asn Ala
            435                 440                 445
Asp Met Leu Lys Val Asp Lys Glu Tyr Thr His Ser Asn Ile Pro Ala
    450                 455                 460
Ala Tyr Ala Leu Met Leu Gln Thr Met Gly Ala Ala Thr Arg Val Tyr
465                 470                 475                 480
Tyr Gly Asp Leu Tyr Thr Asp Asn Gly Gln Tyr Met Ala Lys Lys Ser
                485                 490                 495
Pro Tyr Phe Asp Gln Ile Thr Thr Leu Leu Lys Ala Arg Ser Lys Tyr
                500                 505                 510
Val Ala Gly Gly Gln Thr Ser Tyr Ile His Asn Leu Ala Gly Asp Gly
            515                 520                 525
Val Ser Ser Ala Lys Asp Asn Lys Glu Val Leu Val Ser Val Arg Tyr
    530                 535                 540
```

```
Gly Gln Asp Leu Met Ser Lys Thr Asp Thr Glu Gly Lys Tyr Gly
545                 550                 555                 560

Arg Asn Ser Gly Met Leu Thr Leu Ile Ala Asn Pro Asp Leu Lys
                565                 570                 575

Leu Ala Asp Gly Glu Thr Ile Thr Val Asn Met Gly Ala Ala His Lys
            580                 585                 590

Asn Gln Ala Tyr Arg Pro Leu Leu Gly Thr Glu Lys Gly Ile Val
            595                 600                 605

Ser Ser Leu Asn Asp Ser Asp Thr Lys Ile Val Lys Tyr Thr Asp Ala
610                 615                 620

Gln Gly Asn Leu Val Phe Thr Ala Asp Glu Ile Lys Gly Phe Lys Thr
625                 630                 635                 640

Val Asp Met Ser Gly Tyr Leu Ser Val Trp Val Pro Val Gly Ala Thr
                645                 650                 655

Glu Asp Gln Asn Val Leu Ala Lys Pro Ser Thr Lys Val Tyr Lys Glu
            660                 665                 670

Gly Asp Lys Val Tyr Ser Ser Ala Ala Leu Glu Ala Gln Val Ile
            675                 680                 685

Tyr Glu Gly Phe Ser Asn Phe Gln Asp Phe Val Lys Glu Asp Ser Gln
690                 695                 700

Tyr Thr Asn Lys Leu Ile Ala Ala Asn Ala Asp Leu Phe Lys Ser Trp
705                 710                 715                 720

Gly Ile Thr Ser Phe Glu Ile Ala Pro Gln Tyr Val Ser Ser Lys Asp
                725                 730                 735

Gly Thr Phe Leu Asp Ser Ile Ile Glu Asn Gly Tyr Ala Phe Thr Asp
            740                 745                 750

Arg Tyr Asp Phe Ala Met Ser Lys Asn Lys Tyr Gly Ser Lys Glu
            755                 760                 765

Asp Leu Arg Asp Ala Leu Lys Ala Leu His Lys Gln Gly Ile Gln Val
770                 775                 780

Ile Ala Asp Trp Val Pro Asp Gln Leu Tyr Thr Leu Pro Gly Lys Glu
785                 790                 795                 800

Val Val Thr Ala Thr Arg Thr Asp Thr His Gly Lys Val Leu Asp Asp
                805                 810                 815

Thr Ser Leu Val Asn Lys Leu Tyr Val Thr Asn Thr Lys Ser Ser Gly
            820                 825                 830

Asn Asp Phe Gln Ala Gln Tyr Gly Gly Ala Phe Leu Asp Lys Leu Gln
            835                 840                 845

Lys Leu Tyr Pro Glu Ile Phe Lys Glu Val Met Glu Ala Ser Gly Lys
850                 855                 860

Thr Ile Asp Pro Ser Val Lys Ile Lys Gln Trp Glu Ala Lys Tyr Phe
865                 870                 875                 880

Asn Gly Thr Asn Ile Gln Lys Arg Gly Ser Asp Tyr Val Leu Ser Asp
                885                 890                 895

Gly Lys Leu Tyr Phe Thr Val Asn Asp Lys Gly Thr Phe Leu Pro Ala
            900                 905                 910

Ala Leu Thr Gly Asp Thr Lys Ala Lys Thr Gly Phe Ala Tyr Asp Gly
            915                 920                 925

Thr Gly Val Thr Tyr Tyr Thr Thr Ser Gly Thr Gln Ala Lys Ser Gln
930                 935                 940

Phe Val Thr Tyr Asn Gly Lys Gln Tyr Tyr Phe Asn Asp Lys Gly Tyr
945                 950                 955                 960
```

-continued

Leu Val Thr Gly Glu Gln Ala Ile Asp Gly Ser Asn Tyr Phe Phe Leu
                965                 970                 975

Pro Asn Gly Val Met Phe Thr Asp Gly Val Ile Lys Asn Ala Lys Gly
        980                 985                 990

Gln Ser Leu Val Tyr Gly Lys Ser Gly Lys Leu Thr Thr Gln Thr Gly
        995                 1000                1005

Trp Lys Glu Val Thr Val Lys Asp Asp Ser Gly Lys Glu Glu Lys
        1010                1015                1020

Phe Tyr Gln Tyr Phe Phe Lys Gly Gly Ile Met Ala Thr Gly Leu
        1025                1030                1035

Thr Glu Val Glu Gly Lys Glu Lys Tyr Phe Tyr Asp Asn Gly Tyr
        1040                1045                1050

Gln Ala Lys Gly Ile Phe Ile Pro Thr Lys Asp Gly His Leu Met
        1055                1060                1065

Phe Phe Cys Gly Asp Ser Gly Glu Arg Lys Tyr Ser Gly Phe Phe
        1070                1075                1080

Glu Gln Asp Gly Asn Trp Tyr Tyr Ala Asn Asp Lys Gly Tyr Val
        1085                1090                1095

Ala Thr Gly Phe Thr Lys Val Gly Lys Gln Asn Leu Tyr Phe Asn
        1100                1105                1110

Glu Lys Gly Val Gln Val Lys Asn Arg Phe Phe Gln Val Gly Asp
        1115                1120                1125

Ala Thr Tyr Tyr Ala Asn Asn Glu Gly Asp Val Leu Arg Gly Ala
        1130                1135                1140

Gln Thr Ile Asn Gly Asp Glu Leu Tyr Phe Asp Glu Ser Gly Lys
        1145                1150                1155

Gln Val Lys Gly Glu Phe Val Asn Asn Pro Asp Gly Thr Thr Ser
        1160                1165                1170

Tyr Tyr Asp Ala Ile Thr Gly Val Lys Leu Val Asp Thr Ser Leu
        1175                1180                1185

Val Val Asn Gly Gln Thr Phe Asn Ile Asp Ala Lys Gly Val Val
        1190                1195                1200

Thr Lys Ala His Thr Pro Gly Phe Tyr Thr Thr Gly Asp Asn Asn
        1205                1210                1215

Trp Phe Tyr Ala Asp Ser His Gly Arg Asn Val Thr Gly Ala Gln
        1220                1225                1230

Ile Ile Asn Gly Gln His Leu Tyr Phe Asp Ala Asn Gly Arg Gln
        1235                1240                1245

Val Lys Gly Gly Phe Val Met Asn Thr Asp Gly Ser Arg Ser Phe
        1250                1255                1260

Tyr His Trp Asn Thr Gly Asp Lys Leu Val Ser Thr Phe Phe Thr
        1265                1270                1275

Thr Gly His Asp Arg Trp Tyr Tyr Ala Asp Asp Lys Gly Asn Val
        1280                1285                1290

Val Thr Gly Ala Gln Val Ile Asn Gly Gln Lys Leu Phe Phe Ala
        1295                1300                1305

Thr Asp Gly Lys Gln Val Lys Gly Asp Phe Ala Thr Asn Ala Asn
        1310                1315                1320

Gly Ser Arg Ser Tyr Tyr His Gly Ala Thr Gly Asn Lys Leu Val
        1325                1330                1335

Ser Thr Phe Phe Thr Thr Gly Asp Asn Asn Trp Tyr Tyr Ala Asp
        1340                1345                1350

Ala Lys Gly Glu Val Val Val Gly Glu Gln Thr Ile Asn Gly Gln

```
                1355              1360               1365
Asn Leu Tyr Phe Asp Gln Thr Gly Lys Gln Val Lys Gly Ala Thr
            1370              1375              1380

Ala Thr Asn Pro Asp Gly Ser Ile Ser Tyr Tyr Asp Val His Thr
        1385              1390              1395

Gly Glu Lys Val Ile Asn Arg Trp Val Lys Ile Pro Ser Gly Gln
    1400              1405              1410

Trp Val Tyr Phe Asn Ala Gln Gly Lys Gly Tyr Val Ser Asn
    1415              1420              1425

<210> SEQ ID NO 57
<211> LENGTH: 5208
<212> TYPE: DNA
<213> ORGANISM: Lactobacillus reuteri

<400> SEQUENCE: 57
```

| | | | | | |
|---|---|---|---|---|---|
| atggatcagc | aagtacaaag | cagcaccacc | caggagcaga | cgagcacggt | taacgcggac | 60 |
| acgactaaaa | ccgtcaatct | ggataccaac | actgaccagc | cggctcagac | gaccgataag | 120 |
| aatcaggtcg | cgaatgatac | caccaccaac | caaagcaaga | cggacagcac | cagcacgacg | 180 |
| gttaagaatc | cgacgtttat | tcctgttagc | actttgtcca | gctccgataa | cgaaaagcag | 240 |
| agccagaatt | acaataaacc | agataacggt | aattacggta | atgttgatgc | ggcctacttc | 300 |
| aataacaatc | agctgcacat | tagcggttgg | cacgcaacca | acgcgagcca | gggtacggat | 360 |
| agccgccaag | taatcgtacg | cgacattacc | accaagaccg | agctgggtcg | tactaatgtg | 420 |
| accaacaatg | ttctgcgtcc | ggacgtgaaa | aatgttcaca | cgtctacaa  | cgctgacaac | 480 |
| agcggctttg | atgtgaatat | caatattgat | ttcagcaaga | tgaaagacta | tcgtgacagc | 540 |
| atcgagatcg | tttctcgtta | tagcggcaac | ggcaagagcc | ttgactggtg | gtcgcagccg | 600 |
| atcacgtttg | acaaaaacaa | ttatgcttat | ctggacactt | tcgaggtgaa | gaacggtgaa | 660 |
| ctgcatgcaa | cgggctggaa | tgccaccaac | aaggctatca | attacaatca | ccacttcgtt | 720 |
| attctgtttg | atcgtacgaa | tggcaaagaa | gtcacccgcc | aagaggtgcg | tgatggtcaa | 780 |
| agccgtccgg | atgtggcgaa | ggtatacccg | caagtcgttg | gcgcgaacaa | tagcggtttt | 840 |
| gacgttacgt | ttaacattgg | tgatttggac | tacacccatc | agtaccagat | cctgtctcgt | 900 |
| tacagcaacg | cagacaacgg | tgaaggcgat | tatgtgacct | attggtttgc | gccgcagagc | 960 |
| atcgctccgg | cgaatcaaag | caaccaaggt | tacctggaca | gcttcgatat | ttcgaaaaac | 1020 |
| ggtgaggtga | ccgtgacggg | ttggaatgcg | acggatctga | gcgagttgca | aacgaatcac | 1080 |
| tacgtgatcc | tgtttgatca | gacggcgggt | caacaggttg | catccgctaa | ggtcgacctg | 1140 |
| atcagccgtc | cagacgtcgc | gaaggcgtac | cctaccgtta | aaacggcaga | aacctccggt | 1200 |
| ttcaaggtca | cgtttaaggt | tagcaatctg | caaccgggcc | accaatacag | cgtcgttagc | 1260 |
| cgctttagcg | ccgatgaaaa | cggtaatggc | aacgacaaac | gccacacgga | ctactggtac | 1320 |
| tctccggtta | ccctgaacca | aacggctagc | aacattgaca | ctatcaccat | gacttccaac | 1380 |
| ggtctgcaca | tcaccggctg | gatggcgagc | gataatagca | ttaacgaagc | gaccccgtac | 1440 |
| gcgattatcc | tgaacaacgg | tcgcgaggtg | acgcgccaga | aactgaccct | gatcgcgcgt | 1500 |
| ccggatgttg | cggcagtgta | tccgagcctg | tacaatagcg | cggttagcgg | cttcgacacc | 1560 |
| accatcaagc | tgactaacgc | gcaatatcaa | gcattgaacg | ccagctgca  | agtgctgctg | 1620 |
| cgctttagca | aggcggtgga | cggtaacccg | aatggtacca | ataccgtcac | ggatcaattt | 1680 |
| agcaaaaaact | acgcaacgac | cggtggtaat | ttcgattacg | tcaaggttaa | tggtaaccaa | 1740 |

-continued

```
attgagtttt ctggctggca cgcgacgaat cagagcaatg ataagaacag ccaatggatt    1800
atcgtcttgg ttaacggtaa agaggtcaaa cgccagctgg tcaatgacac gaaagacggc    1860
gcagccggct tcaatcgtaa tgatgtgtat aaagtgaacc cagcgatcga aaatagcatt    1920
atgtctggct tccagggcat tatcacgttg ccggttacgg tgaaagacga aaacgtgcag    1980
ctggtgcacc gcttctccaa tgacgcaaaa acgggtgagg gcaattatgt cgatttctgg    2040
agcgaggtga tgtctgtgaa ggactctttc caaaagggta atggtccgct gaaccagttt    2100
ggcctgcaaa ccatcaacgg ccaacaatac tatattgacc cgacgaccgg ccagccgcgt    2160
aagaatttcc tgctgcaaaa cggcaacgat tggatttact tcgacaaaga cactggcgca    2220
ggcaccaacg cgctgaaatt gcagtttgat aagggcacga ttagcgctga cgaacaatac    2280
cgtcgcggca acgaggcgta ctcctacgat gataagagca ttgaaaatgt caacggttac    2340
ttgacggcgg acacgtggta ccgcccgaag cagatcctga aggatggcac cacttggacc    2400
gattccaaag aaaccgatat gcgtccgatc ttgatggtct ggtggccaaa cacggtgact    2460
caggcgtact atctgaacta catgaaacaa tatggcaatc tgctgccggc gagcctgccg    2520
agctttagca ccgacgccga tagcgcggag ttgaatcatt attccgagct ggtccaacag    2580
aatatcgaga aacgtattag cgagactggt agcactgatt ggctgcgtac cctgatgcac    2640
gagttcgtga cgaagaatag catgtggaac aaagatagcg agaacgttga ctacggtggc    2700
ctgcaactgc aaggtggttt cctgaagtac gttaacagcg acctgacgaa gtacgcaaac    2760
tctgattggc gtctgatgaa ccgtaccgcg acgaacattg acggtaagaa ttacggtggt    2820
gccgagtttc tgctggcgaa tgacatcgac aactctaacc cggtggtgca ggccgaagaa    2880
ttgaattggc tgtattatct gatgaacttc ggtaccatca ccggtaacaa cccagaagct    2940
aacttcgacg gcatccgtgt cgacgcggtc gataatgtgg atgttgatct gctgagcatt    3000
gcccgtgact actttaatgc agcgtataac atggaacaaa gcgatgctag cgcgaataag    3060
cacatcaata ttctggaaga ttggggctgg gacgatccgg cgtacgtgaa caaaatcggc    3120
aatccacagt tgaccatgga tgaccgcctg cgtaatgcaa ttatggacac cctgagcggt    3180
gcgccggata agaaccaagc gctgaacaag ctgattactc agtctctggt gaatcgcgca    3240
aatgataata ctgaaaacgc ggtgatccct tcctacaact ttgtccgcgc tcatgacagc    3300
aatgcccagg accagatccg tcaagcgatc caggcggcaa ccggcaaacc ttatggcgag    3360
ttcaacttgg atgatgagaa aaagggtatg gaggcttaca tcaatgacca aaatagcacc    3420
aataagaaat ggaacctgta caacatgccg agcgcatata ccatcctgct gacgaataag    3480
gactcggtcc cgcgtgtcta ctatggcgac ttgtaccagg atggtggcca gtacatggaa    3540
cacaaaactc gttactttga caccatcacg aatctgctga aaccccgcgt caagtatgtc    3600
gcaggcggcc agaccatgtc tgtggataag aatggcattt tgactaatgt ccgtttcggt    3660
aagggtgcga tgaacgcaac tgacacgggt accgatgaaa cccgcaccga aggtatcggc    3720
gttgttatca gcaacaatac gaatttgaaa ctgaatgacg gcgaaagcgt tgtgctgcac    3780
atgggcgctg cccataagaa tcagaagtat cgtgcagtga tcctgaccac ggaggacggt    3840
gtgaagaatt acaccaacga caccgatgcg ccggtcgcat acaccgacgc gaacggcgat    3900
ttgcatttca ccaatactaa cctggacggt cagcaatata ccgccgttcg tggctacgca    3960
aacccggacg ttacgggtta tctggccgtc tgggttcctg ctggtgccgc cgatgaccaa    4020
gacgcacgta ccgctccgag cgacgaggcc cacaccacga aaacggcgta tcgttccaat    4080
```

```
gcggcattgg actccaacgt catctacgaa ggcttttcga actttatcta ttggccgacg    4140
accgagagcg agcgcacgaa tgtccgcatc gcgcagaacg cggatctgtt caaatcgtgg    4200
ggtatcacca ccttcgagct ggcgccacag tacaatagca gcaaggacgg tacgtttctg    4260
gattcgatca ttgacaatgg ttacgcgttt accgatcgtt atgacctggg tatgtctacc    4320
ccgaacaagt acggtagcga tgaggatctg cgtaacgccc tgcaagcact gcacaaggcc    4380
ggtctgcaag ccatcgcaga ttgggttccg gaccaaatct acaatctgcc gggcaaagag    4440
gctgtcacgg ttactcgtag cgatgaccac ggcactacct gggaggttag cccgatcaag    4500
aatgtggtgt atatcactaa taccatcggt ggtggcgaat accagaaaaa gtatggtggt    4560
gaatttctgg acaccttgca aaagaatat ccgcagctgt ttagccaagt ttacccggtg    4620
acccaaacga cgattgaccc tagcgttaag attaaagagt ggtccgcgaa gtacttcaat    4680
ggtactaata tcctgcatcg cggtgcgggt tacgtcctgc gtagcaatga tggtaagtat    4740
tacaacctgg gtactagcac ccagcagttc ctgccgagcc agctgagcgt tcaagataat    4800
gagggttacg gtttcgttaa agagggtaac aactatcact attatgacga gaacaaacaa    4860
atggttaagg acgcgtttat ccaggatagc gtcggcaatt ggtactattt tgataagaac    4920
ggcaatatgg ttgcaaacca agcccggtt gaaatcagca gcaacggtgc gagcggcacc    4980
tacttgtttt tgaataatgg taccagcttc cgcagcggcc tggtcaaaac ggatgcaggc    5040
acctattact acgatggtga cggtcgcatg gttcgtaatc aaacggtttc tgacggtgcc    5100
atgacgtacg ttctggacga aaatggtaaa ctggtcagcg aatcttttga tagcagcgcg    5160
accgaggccc atccgctgaa accgggcgat ctgaacggtc aaaagtaa              5208
```

<210> SEQ ID NO 58
<211> LENGTH: 1735
<212> TYPE: PRT
<213> ORGANISM: Lactobacillus reuteri

<400> SEQUENCE: 58

Met Asp Gln Gln Val Gln Ser Ser Thr Thr Gln Glu Gln Thr Ser Thr
1               5                   10                  15

Val Asn Ala Asp Thr Thr Lys Thr Val Asn Leu Asp Thr Asn Thr Asp
            20                  25                  30

Gln Pro Ala Gln Thr Thr Asp Lys Asn Gln Val Ala Asn Asp Thr Thr
        35                  40                  45

Thr Asn Gln Ser Lys Thr Asp Ser Thr Ser Thr Thr Val Lys Asn Pro
    50                  55                  60

Thr Phe Ile Pro Val Ser Thr Leu Ser Ser Ser Asp Asn Glu Lys Gln
65                  70                  75                  80

Ser Gln Asn Tyr Asn Lys Pro Asp Asn Gly Asn Tyr Gly Asn Val Asp
                85                  90                  95

Ala Ala Tyr Phe Asn Asn Asn Gln Leu His Ile Ser Gly Trp His Ala
            100                 105                 110

Thr Asn Ala Ser Gln Gly Thr Asp Ser Arg Gln Val Ile Val Arg Asp
        115                 120                 125

Ile Thr Thr Lys Thr Glu Leu Gly Arg Thr Asn Val Thr Asn Asn Val
    130                 135                 140

Leu Arg Pro Asp Val Lys Asn Val His Asn Val Tyr Asn Ala Asp Asn
145                 150                 155                 160

Ser Gly Phe Asp Val Asn Ile Asn Ile Asp Phe Ser Lys Met Lys Asp
                165                 170                 175

```
Tyr Arg Asp Ser Ile Glu Ile Val Ser Arg Tyr Ser Gly Asn Gly Lys
            180                 185                 190

Ser Val Asp Trp Trp Ser Gln Pro Ile Thr Phe Asp Lys Asn Asn Tyr
        195                 200                 205

Ala Tyr Leu Asp Thr Phe Glu Val Lys Asn Gly Glu Leu His Ala Thr
    210                 215                 220

Gly Trp Asn Ala Thr Asn Lys Ala Ile Asn Tyr Asn His His Phe Val
225                 230                 235                 240

Ile Leu Phe Asp Arg Thr Asn Gly Lys Glu Val Thr Arg Gln Glu Val
                245                 250                 255

Arg Asp Gly Gln Ser Arg Pro Asp Val Ala Lys Val Tyr Pro Gln Val
            260                 265                 270

Val Gly Ala Asn Asn Ser Gly Phe Asp Val Thr Phe Asn Ile Gly Asp
        275                 280                 285

Leu Asp Tyr Thr His Gln Tyr Gln Ile Leu Ser Arg Tyr Ser Asn Ala
    290                 295                 300

Asp Asn Gly Glu Gly Asp Tyr Val Thr Tyr Trp Phe Ala Pro Gln Ser
305                 310                 315                 320

Ile Ala Pro Ala Asn Gln Ser Asn Gln Gly Tyr Leu Asp Ser Phe Asp
                325                 330                 335

Ile Ser Lys Asn Gly Glu Val Thr Val Thr Gly Trp Asn Ala Thr Asp
            340                 345                 350

Leu Ser Glu Leu Gln Thr Asn His Tyr Val Ile Leu Phe Asp Gln Thr
        355                 360                 365

Ala Gly Gln Gln Val Ala Ser Ala Lys Val Asp Leu Ile Ser Arg Pro
    370                 375                 380

Asp Val Ala Lys Ala Tyr Pro Thr Val Lys Thr Ala Glu Thr Ser Gly
385                 390                 395                 400

Phe Lys Val Thr Phe Lys Val Ser Asn Leu Gln Pro Gly His Gln Tyr
                405                 410                 415

Ser Val Val Ser Arg Phe Ser Ala Asp Glu Asn Gly Asn Gly Asn Asp
            420                 425                 430

Lys Arg His Thr Asp Tyr Trp Tyr Ser Pro Val Thr Leu Asn Gln Thr
        435                 440                 445

Ala Ser Asn Ile Asp Thr Ile Thr Met Thr Ser Asn Gly Leu His Ile
    450                 455                 460

Thr Gly Trp Met Ala Ser Asp Asn Ser Ile Asn Glu Ala Thr Pro Tyr
465                 470                 475                 480

Ala Ile Ile Leu Asn Asn Gly Arg Glu Val Thr Arg Gln Lys Leu Thr
                485                 490                 495

Leu Ile Ala Arg Pro Asp Val Ala Ala Val Tyr Pro Ser Leu Tyr Asn
            500                 505                 510

Ser Ala Val Ser Gly Phe Asp Thr Thr Ile Lys Leu Thr Asn Ala Gln
        515                 520                 525

Tyr Gln Ala Leu Asn Gly Gln Leu Gln Val Leu Leu Arg Phe Ser Lys
    530                 535                 540

Ala Val Asp Gly Asn Pro Asn Gly Thr Asn Thr Val Thr Asp Gln Phe
545                 550                 555                 560

Ser Lys Asn Tyr Ala Thr Thr Gly Gly Asn Phe Asp Tyr Val Lys Val
                565                 570                 575

Asn Gly Asn Gln Ile Glu Phe Ser Gly Trp His Ala Thr Asn Gln Ser
            580                 585                 590

Asn Asp Lys Asn Ser Gln Trp Ile Ile Val Leu Val Asn Gly Lys Glu
```

```
                  595                 600                 605
Val Lys Arg Gln Leu Val Asn Asp Thr Lys Asp Gly Ala Ala Gly Phe
610                 615                 620

Asn Arg Asn Asp Val Tyr Lys Val Asn Pro Ala Ile Glu Asn Ser Ile
625                 630                 635                 640

Met Ser Gly Phe Gln Gly Ile Ile Thr Leu Pro Val Thr Val Lys Asp
                    645                 650                 655

Glu Asn Val Gln Leu Val His Arg Phe Ser Asn Asp Ala Lys Thr Gly
                    660                 665                 670

Glu Gly Asn Tyr Val Asp Phe Trp Ser Glu Val Met Ser Val Lys Asp
                    675                 680                 685

Ser Phe Gln Lys Gly Asn Gly Pro Leu Asn Gln Phe Gly Leu Gln Thr
690                 695                 700

Ile Asn Gly Gln Gln Tyr Tyr Ile Asp Pro Thr Thr Gly Gln Pro Arg
705                 710                 715                 720

Lys Asn Phe Leu Leu Gln Asn Gly Asn Asp Trp Ile Tyr Phe Asp Lys
                    725                 730                 735

Asp Thr Gly Ala Gly Thr Asn Ala Leu Lys Leu Gln Phe Asp Lys Gly
                    740                 745                 750

Thr Ile Ser Ala Asp Glu Gln Tyr Arg Arg Gly Asn Glu Ala Tyr Ser
                    755                 760                 765

Tyr Asp Asp Lys Ser Ile Glu Asn Val Asn Gly Tyr Leu Thr Ala Asp
770                 775                 780

Thr Trp Tyr Arg Pro Lys Gln Ile Leu Lys Asp Gly Thr Thr Trp Thr
785                 790                 795                 800

Asp Ser Lys Glu Thr Asp Met Arg Pro Ile Leu Met Val Trp Trp Pro
                    805                 810                 815

Asn Thr Val Thr Gln Ala Tyr Tyr Leu Asn Tyr Met Lys Gln Tyr Gly
                    820                 825                 830

Asn Leu Leu Pro Ala Ser Leu Pro Ser Phe Ser Thr Asp Ala Asp Ser
                    835                 840                 845

Ala Glu Leu Asn His Tyr Ser Glu Leu Val Gln Gln Asn Ile Glu Lys
850                 855                 860

Arg Ile Ser Glu Thr Gly Ser Thr Asp Trp Leu Arg Thr Leu Met His
865                 870                 875                 880

Glu Phe Val Thr Lys Asn Ser Met Trp Asn Lys Asp Ser Glu Asn Val
                    885                 890                 895

Asp Tyr Gly Gly Leu Gln Leu Gln Gly Gly Phe Leu Lys Tyr Val Asn
                    900                 905                 910

Ser Asp Leu Thr Lys Tyr Ala Asn Ser Asp Trp Arg Leu Met Asn Arg
                    915                 920                 925

Thr Ala Thr Asn Ile Asp Gly Lys Asn Tyr Gly Gly Ala Glu Phe Leu
930                 935                 940

Leu Ala Asn Asp Ile Asp Asn Ser Asn Pro Val Val Gln Ala Glu Glu
945                 950                 955                 960

Leu Asn Trp Leu Tyr Tyr Leu Met Asn Phe Gly Thr Ile Thr Gly Asn
                    965                 970                 975

Asn Pro Glu Ala Asn Phe Asp Gly Ile Arg Val Asp Ala Val Asp Asn
                    980                 985                 990

Val Asp Val Asp Leu Leu Ser Ile Ala Arg Asp Tyr Phe Asn Ala Ala
                    995                 1000                1005

Tyr Asn  Met Glu Gln Ser Asp  Ala Ser Ala Asn Lys  His Ile Asn
                    1010                1015                1020
```

```
Ile Leu Glu Asp Trp Gly Trp Asp Asp Pro Ala Tyr Val Asn Lys
1025                1030                1035

Ile Gly Asn Pro Gln Leu Thr Met Asp Asp Arg Leu Arg Asn Ala
1040                1045                1050

Ile Met Asp Thr Leu Ser Gly Ala Pro Asp Lys Asn Gln Ala Leu
1055                1060                1065

Asn Lys Leu Ile Thr Gln Ser Leu Val Asn Arg Ala Asn Asp Asn
1070                1075                1080

Thr Glu Asn Ala Val Ile Pro Ser Tyr Asn Phe Val Arg Ala His
1085                1090                1095

Asp Ser Asn Ala Gln Asp Gln Ile Arg Gln Ala Ile Gln Ala Ala
1100                1105                1110

Thr Gly Lys Pro Tyr Gly Glu Phe Asn Leu Asp Asp Glu Lys Lys
1115                1120                1125

Gly Met Glu Ala Tyr Ile Asn Asp Gln Asn Ser Thr Asn Lys Lys
1130                1135                1140

Trp Asn Leu Tyr Asn Met Pro Ser Ala Tyr Thr Ile Leu Leu Thr
1145                1150                1155

Asn Lys Asp Ser Val Pro Arg Val Tyr Tyr Gly Asp Leu Tyr Gln
1160                1165                1170

Asp Gly Gly Gln Tyr Met Glu His Lys Thr Arg Tyr Phe Asp Thr
1175                1180                1185

Ile Thr Asn Leu Leu Lys Thr Arg Val Lys Tyr Val Ala Gly Gly
1190                1195                1200

Gln Thr Met Ser Val Asp Lys Asn Gly Ile Leu Thr Asn Val Arg
1205                1210                1215

Phe Gly Lys Gly Ala Met Asn Ala Thr Asp Thr Gly Thr Asp Glu
1220                1225                1230

Thr Arg Thr Glu Gly Ile Gly Val Val Ile Ser Asn Asn Thr Asn
1235                1240                1245

Leu Lys Leu Asn Asp Gly Glu Ser Val Val Leu His Met Gly Ala
1250                1255                1260

Ala His Lys Asn Gln Lys Tyr Arg Ala Val Ile Leu Thr Thr Glu
1265                1270                1275

Asp Gly Val Lys Asn Tyr Thr Asn Asp Thr Asp Ala Pro Val Ala
1280                1285                1290

Tyr Thr Asp Ala Asn Gly Asp Leu His Phe Thr Asn Thr Asn Leu
1295                1300                1305

Asp Gly Gln Gln Tyr Thr Ala Val Arg Gly Tyr Ala Asn Pro Asp
1310                1315                1320

Val Thr Gly Tyr Leu Ala Val Trp Val Pro Ala Gly Ala Ala Asp
1325                1330                1335

Asp Gln Asp Ala Arg Thr Ala Pro Ser Asp Glu Ala His Thr Thr
1340                1345                1350

Lys Thr Ala Tyr Arg Ser Asn Ala Ala Leu Asp Ser Asn Val Ile
1355                1360                1365

Tyr Glu Gly Phe Ser Asn Phe Ile Tyr Trp Pro Thr Thr Glu Ser
1370                1375                1380

Glu Arg Thr Asn Val Arg Ile Ala Gln Asn Ala Asp Leu Phe Lys
1385                1390                1395

Ser Trp Gly Ile Thr Thr Phe Glu Leu Ala Pro Gln Tyr Asn Ser
1400                1405                1410
```

```
Ser Lys Asp Gly Thr Phe Leu Asp Ser Ile Ile Asp Asn Gly Tyr
    1415                1420                1425

Ala Phe Thr Asp Arg Tyr Asp Leu Gly Met Ser Thr Pro Asn Lys
    1430                1435                1440

Tyr Gly Ser Asp Glu Asp Leu Arg Asn Ala Leu Gln Ala Leu His
    1445                1450                1455

Lys Ala Gly Leu Gln Ala Ile Ala Asp Trp Val Pro Asp Gln Ile
    1460                1465                1470

Tyr Asn Leu Pro Gly Lys Glu Ala Val Thr Val Thr Arg Ser Asp
    1475                1480                1485

Asp His Gly Thr Thr Trp Glu Val Ser Pro Ile Lys Asn Val Val
    1490                1495                1500

Tyr Ile Thr Asn Thr Ile Gly Gly Gly Glu Tyr Gln Lys Lys Tyr
    1505                1510                1515

Gly Gly Glu Phe Leu Asp Thr Leu Gln Lys Glu Tyr Pro Gln Leu
    1520                1525                1530

Phe Ser Gln Val Tyr Pro Val Thr Gln Thr Thr Ile Asp Pro Ser
    1535                1540                1545

Val Lys Ile Lys Glu Trp Ser Ala Lys Tyr Phe Asn Gly Thr Asn
    1550                1555                1560

Ile Leu His Arg Gly Ala Gly Tyr Val Leu Arg Ser Asn Asp Gly
    1565                1570                1575

Lys Tyr Tyr Asn Leu Gly Thr Ser Thr Gln Gln Phe Leu Pro Ser
    1580                1585                1590

Gln Leu Ser Val Gln Asp Asn Glu Gly Tyr Gly Phe Val Lys Glu
    1595                1600                1605

Gly Asn Asn Tyr His Tyr Tyr Asp Glu Asn Lys Gln Met Val Lys
    1610                1615                1620

Asp Ala Phe Ile Gln Asp Ser Val Gly Asn Trp Tyr Tyr Phe Asp
    1625                1630                1635

Lys Asn Gly Asn Met Val Ala Asn Gln Ser Pro Val Glu Ile Ser
    1640                1645                1650

Ser Asn Gly Ala Ser Gly Thr Tyr Leu Phe Leu Asn Asn Gly Thr
    1655                1660                1665

Ser Phe Arg Ser Gly Leu Val Lys Thr Asp Ala Gly Thr Tyr Tyr
    1670                1675                1680

Tyr Asp Gly Asp Gly Arg Met Val Arg Asn Gln Thr Val Ser Asp
    1685                1690                1695

Gly Ala Met Thr Tyr Val Leu Asp Glu Asn Gly Lys Leu Val Ser
    1700                1705                1710

Glu Ser Phe Asp Ser Ser Ala Thr Glu Ala His Pro Leu Lys Pro
    1715                1720                1725

Gly Asp Leu Asn Gly Gln Lys
    1730                1735

<210> SEQ ID NO 59
<211> LENGTH: 1242
<212> TYPE: PRT
<213> ORGANISM: Unknown
<220> FEATURE:
<223> OTHER INFORMATION: unknown Streptococcus species

<400> SEQUENCE: 59

Met Ile Asn Gly Lys Glu Tyr Tyr Val Glu Asp Asp Gly Thr Val Arg
1               5                   10                  15
```

```
Lys Asn Tyr Val Leu Glu Arg Asn Gly Ser Gln Tyr Phe Asn Ala
            20                  25                  30

Glu Thr Gly Glu Leu Ser Asn Gln Lys Asp Tyr Arg Phe Asp Lys Asn
        35                  40                  45

Gly Gly Thr Gly Ser Ala Ala Asp Ser Thr Thr Asn Thr Asn Val Thr
    50                  55                  60

Val Asn Gly Asp Lys Asn Ala Phe Tyr Gly Thr Thr Glu Lys Asp Ile
65                  70                  75                  80

Glu Leu Val Asp Gly Tyr Phe Thr Ala Asn Thr Trp Tyr Arg Pro Lys
                85                  90                  95

Glu Ile Leu Lys Asp Gly Lys Glu Trp Thr Ala Ser Thr Glu Asn Asp
            100                 105                 110

Lys Arg Pro Leu Leu Thr Val Trp Trp Pro Ser Lys Ala Ile Gln Ala
        115                 120                 125

Ser Tyr Leu Asn Tyr Met Arg Glu Glu Gly Leu Gly Thr Asn Gln Thr
    130                 135                 140

Phe Thr Ser Tyr Ser Ser Gln Thr Gln Met Asp Gln Ala Ala Leu Glu
145                 150                 155                 160

Val Gln Lys Arg Ile Glu Glu Arg Ile Ala Arg Glu Gly Asn Thr Asp
                165                 170                 175

Trp Leu Arg Thr Thr Ile Lys Asn Phe Val Lys Thr Gln Pro Gly Trp
            180                 185                 190

Asn Ser Thr Ser Glu Asn Leu Asp Asn Ser Asp His Leu Gln Gly Gly
        195                 200                 205

Ala Leu Leu Tyr Asn Asn Ser Asn Arg Thr Ser Tyr Ala Asn Ser Asp
    210                 215                 220

Tyr Arg Leu Leu Asn Arg Thr Pro Thr Gln Gln Asp Gly Thr Arg Arg
225                 230                 235                 240

Tyr Phe Lys Asp Asn Ser Ser Gly Gly Phe Glu Phe Leu Leu Ala Asn
                245                 250                 255

Asp Ile Asp Asn Ser Asn Pro Ala Val Gln Ala Glu Gln Leu Asn Trp
            260                 265                 270

Leu His Tyr Ile Met Asn Ile Gly Ser Leu Thr Gly Gly Ser Glu Asp
        275                 280                 285

Glu Asn Phe Asp Gly Val Arg Val Asp Ala Val Asp Asn Val Asn Ala
    290                 295                 300

Asp Leu Leu Gln Ile Ala Ser Asp Tyr Phe Lys Ala Lys Tyr Gly Val
305                 310                 315                 320

Glu Lys Ser Glu Glu Ala Ile Lys His Leu Ser Ile Leu Glu Ala
                325                 330                 335

Trp Ser His Asn Asp Ala Tyr Tyr Asn Glu Asp Thr Lys Gly Ala Gln
            340                 345                 350

Leu Pro Met Asp Asp Pro Leu Arg Leu Ala Met Val Phe Ser Phe Leu
        355                 360                 365

Arg Pro Ile Gly Asn Arg Ser Gly Leu Glu Pro Leu Ile Thr Asn Ser
    370                 375                 380

Leu Asn Asp Arg Ser Glu Ser Lys Lys Asn Thr Lys Arg Met Ala Asn
385                 390                 395                 400

Tyr Thr Phe Val Arg Ala His Asp Ser Glu Val Gln Ser Val Ile Gly
                405                 410                 415

Gln Ile Ile Lys Asn Glu Ile Asn Pro Gln Ser Thr Gly Asn Thr Phe
            420                 425                 430

Thr Leu Asp Glu Met Lys Lys Ala Phe Lys Ile Tyr Asn Ala Asp Met
```

```
                435                 440                 445
Arg Ser Ala Asn Lys Arg Tyr Thr Gln Tyr Asn Ile Pro Ser Ala Tyr
450                 455                 460
Ala Phe Met Leu Thr Asn Lys Asp Thr Val Pro Arg Val Tyr Tyr Gly
465                 470                 475                 480
Asp Leu Tyr Thr Asp Asp Gly Gln Tyr Met Ala Gln Lys Ser Pro Tyr
                485                 490                 495
His Asp Ala Ile Ser Thr Leu Leu Gln Ala Arg Ile Arg Tyr Ala Ala
                500                 505                 510
Gly Gly Gln Asp Met Lys Met Ser Tyr Val Gly Ser Gly Asn Thr Asn
                515                 520                 525
Gly Trp Asp Ala Ser Gly Val Leu Thr Ser Val Arg Tyr Gly Lys Gly
                530                 535                 540
Ala Asn Asn Ala Ser Asp Ala Gly Thr Ala Glu Thr Arg Asn Gln Gly
545                 550                 555                 560
Met Ala Val Ile Leu Ser Asn Gln Pro Ala Leu Arg Leu Asn Ser Asn
                565                 570                 575
Leu Thr Ile Asn Met Gly Ala Ala His Arg Asn Gln Ala Tyr Arg Pro
                580                 585                 590
Leu Leu Leu Thr Thr Ser Asn Gly Val Ala Ser Tyr Leu Asn Asp Gly
                595                 600                 605
Asp Ala Asn Gly Ile Val Lys Tyr Thr Asp Ala Asn Gly Tyr Leu Thr
                610                 615                 620
Phe Asn Pro Gly Glu Ile Ser Gly Val Arg Asn Ala Gln Val Asp Gly
625                 630                 635                 640
Tyr Leu Ala Val Trp Val Pro Leu Gly Ala Ser Glu Asn Gln Asp Val
                645                 650                 655
Arg Val Ala Ala Ser Lys Ser Lys Asn Ser Ser Gly Leu Val Tyr Asp
                660                 665                 670
Ser Ser Ala Ala Leu Asp Ser Gln Val Ile Tyr Glu Gly Phe Ser Asn
                675                 680                 685
Phe Gln Asp Phe Val Gln Asp Pro Ser Gln Tyr Thr Asn Lys Lys Ile
                690                 695                 700
Ala Glu Asn Ala Asn Leu Phe Lys Ser Trp Gly Ile Thr Ser Phe Glu
705                 710                 715                 720
Phe Ala Pro Gln Tyr Val Ser Ser Asp Asp Gly Thr Phe Leu Asp Ser
                725                 730                 735
Val Ile Gln Asn Gly Tyr Ala Phe Ser Asp Arg Tyr Asp Ile Gly Met
                740                 745                 750
Ser Lys Asp Asn Lys Tyr Gly Ser Leu Ala Asp Leu Lys Ala Ala Leu
                755                 760                 765
Lys Ser Leu His Ala Val Gly Ile Ser Ala Ile Ala Asp Trp Val Pro
                770                 775                 780
Asp Gln Ile Tyr Asn Leu Pro Gly Asp Glu Val Val Thr Ala Thr Arg
785                 790                 795                 800
Val Asn Asn Tyr Gly Glu Thr Lys Asp Gly Ala Ile Ile Asp His Ser
                805                 810                 815
Leu Tyr Val Ala Lys Thr Arg Thr Phe Gly Asn Asp Tyr Gln Gly Lys
                820                 825                 830
Tyr Gly Gly Ala Tyr Leu Asp Glu Leu Lys Arg Leu Tyr Pro Gln Phe
                835                 840                 845
Phe Asp Arg Val Gln Ile Ser Thr Gly Lys Arg Leu Thr Asp Glu
                850                 855                 860
```

```
Lys Ile Thr Lys Trp Ser Ala Lys Tyr Met Asn Gly Thr Asn Ile Leu
865                 870                 875                 880

Asp Arg Gly Ser Glu Tyr Val Leu Lys Asn Gly Leu Ser Gly Tyr Tyr
                885                 890                 895

Gly Thr Asn Gly Gly Lys Val Ser Leu Pro Lys Val Val Gly Ser Asn
                900                 905                 910

Gln Ser Thr Asn Asn Asn Gln Asn Gly Asp Gly Ser Gly Arg Phe
            915                 920                 925

Glu Lys Ser Trp Gly Ser Val Tyr Tyr Arg Tyr Asn Asp Gly Gln Arg
930                 935                 940

Ala Arg Asn Ala Phe Ile Lys Asp Asn Asp Gly Asn Val Tyr Tyr Phe
945                 950                 955                 960

Asp Asn Thr Gly Arg Met Ala Ile Gly Glu Lys Thr Ile Asp Gly Lys
                965                 970                 975

Gln Tyr Phe Phe Leu Ala Asn Gly Val Gln Leu Arg Asp Gly Tyr Arg
            980                 985                 990

Gln Asn Arg Arg Gly Gln Val Phe Tyr Tyr Asp Glu Asn Gly Ile Met
            995                 1000                1005

Ser Gln Thr Gly Lys Pro Ser Pro Lys Pro Glu Pro Lys Pro Asp
    1010                1015                1020

Asn Asn Thr Phe Ser Arg Asn Gln Phe Ile Gln Ile Gly Asn Asn
    1025                1030                1035

Val Trp Ala Tyr Tyr Asp Gly Asn Gly Lys Arg Val Ile Gly Arg
    1040                1045                1050

Gln Asn Ile Asn Gly Gln Glu Leu Phe Phe Asp Asn Asn Gly Val
    1055                1060                1065

Gln Val Lys Gly Arg Thr Ala Gln Val Asp Gly Val Thr Arg Tyr
    1070                1075                1080

Phe Asp Ala Asn Ser Gly Glu Met Ala Arg Asn Arg Phe Ala Glu
    1085                1090                1095

Val Glu Pro Gly Val Trp Ala Tyr Phe Asn Asn Asp Gly Ala Ala
    1100                1105                1110

Val Thr Gly Ser Gln Asn Ile Asn Gly Gln Thr Leu Tyr Phe Asp
    1115                1120                1125

Gln Asn Gly His Gln Val Lys Gly Ala Leu Val Thr Val Asp Gly
    1130                1135                1140

Asn Leu Arg Tyr Tyr Asp Ala Asn Ser Gly Asp Leu Tyr Arg Asn
    1145                1150                1155

Arg Phe Gln Glu Val Asn Gly Ser Trp Tyr Tyr Phe Asp Gly Asn
    1160                1165                1170

Gly Asn Ala Val Lys Gly Met Val Asn Ile Asn Gly Gln Asn Leu
    1175                1180                1185

Leu Phe Asp Asn Asp Gly Lys Gln Val Lys Gly His Leu Val Arg
    1190                1195                1200

Val Asn Gly Val Ile Arg Tyr Tyr Asp Pro Asn Ser Gly Glu Met
    1205                1210                1215

Ala Val Asn Arg Trp Val Glu Ile Ser Ser Gly Trp Trp Val Tyr
    1220                1225                1230

Phe Asp Gly Glu Gly Arg Gly Gln Ile
    1235                1240

<210> SEQ ID NO 60
<211> LENGTH: 1518
```

```
<212> TYPE: PRT
<213> ORGANISM: Streptococcus salivarius

<400> SEQUENCE: 60

Met Glu Asn Lys Ile His Tyr Lys Leu His Lys Val Lys Lys Gln Trp
1               5                   10                  15

Val Thr Ile Ala Val Ala Ser Val Ala Leu Ala Thr Val Leu Gly Gly
                20                  25                  30

Leu Ser Val Thr Thr Ser Ser Val Ser Ala Asp Glu Thr Gln Asp Lys
            35                  40                  45

Thr Val Thr Gln Ser Asn Ser Gly Thr Thr Ala Ser Leu Val Thr Ser
        50                  55                  60

Pro Glu Ala Thr Lys Glu Ala Asp Lys Arg Thr Asn Thr Lys Glu Ala
65                  70                  75                  80

Asp Val Leu Thr Pro Ala Lys Glu Thr Asn Ala Val Glu Thr Ala Thr
                85                  90                  95

Thr Thr Asn Thr Gln Ala Thr Ala Glu Ala Ala Thr Thr Ala Thr Thr
            100                 105                 110

Ala Asp Val Ala Val Ala Ala Val Pro Asn Lys Glu Ala Val Val Thr
        115                 120                 125

Thr Asp Ala Pro Ala Val Thr Thr Glu Lys Ala Glu Glu Gln Pro Ala
130                 135                 140

Thr Val Lys Ala Glu Val Val Asn Thr Glu Val Lys Ala Pro Glu Ala
145                 150                 155                 160

Ala Leu Lys Asp Ser Glu Val Glu Ala Ala Leu Ser Leu Lys Asn Ile
                165                 170                 175

Lys Asn Ile Asp Gly Lys Tyr Tyr Tyr Val Asn Glu Asp Gly Ser His
            180                 185                 190

Lys Glu Asn Phe Ala Ile Thr Val Asn Gly Gln Leu Leu Tyr Phe Gly
        195                 200                 205

Lys Asp Gly Ala Leu Thr Ser Ser Thr Tyr Ser Phe Thr Pro Gly
    210                 215                 220

Thr Thr Asn Ile Val Asp Gly Phe Ser Ile Asn Asn Arg Ala Tyr Asp
225                 230                 235                 240

Ser Ser Glu Ala Ser Phe Glu Leu Ile Asp Gly Tyr Leu Thr Ala Asp
                245                 250                 255

Ser Trp Tyr Arg Pro Ala Ser Ile Ile Lys Asp Gly Val Thr Trp Gln
            260                 265                 270

Ala Ser Thr Ala Glu Asp Phe Arg Pro Leu Leu Met Ala Trp Trp Pro
        275                 280                 285

Asn Val Asp Thr Gln Val Asn Tyr Leu Asn Tyr Met Ser Lys Val Phe
    290                 295                 300

Asn Leu Asp Ala Lys Tyr Ser Ser Thr Asp Lys Gln Glu Thr Leu Lys
305                 310                 315                 320

Val Ala Ala Lys Asp Ile Gln Ile Lys Ile Glu Gln Lys Ile Gln Ala
                325                 330                 335

Glu Lys Ser Thr Gln Trp Leu Arg Glu Thr Ile Ser Ala Phe Val Lys
            340                 345                 350

Thr Gln Pro Gln Trp Asn Lys Glu Thr Glu Asn Tyr Ser Lys Gly Gly
        355                 360                 365

Gly Glu Asp His Leu Gln Gly Gly Ala Leu Leu Tyr Val Asn Asp Ser
    370                 375                 380

Arg Thr Pro Trp Ala Asn Ser Asp Tyr Arg Arg Leu Asn Arg Thr Ala
385                 390                 395                 400
```

```
Thr Asn Gln Thr Gly Thr Ile Asp Lys Ser Ile Leu Asp Glu Gln Ser
                405                 410                 415

Asp Pro Asn His Met Gly Gly Phe Asp Phe Leu Leu Ala Asn Asp Val
            420                 425                 430

Asp Leu Ser Asn Pro Val Val Gln Ala Glu Gln Leu Asn Gln Ile His
        435                 440                 445

Tyr Leu Met Asn Trp Gly Ser Ile Val Met Gly Asp Lys Asp Ala Asn
450                 455                 460

Phe Asp Gly Ile Arg Val Asp Ala Val Asp Asn Val Asp Ala Asp Met
465                 470                 475                 480

Leu Gln Leu Tyr Thr Asn Tyr Phe Arg Glu Tyr Tyr Gly Val Asn Lys
                485                 490                 495

Ser Glu Ala Asn Ala Leu Ala His Ile Ser Val Leu Glu Ala Trp Ser
            500                 505                 510

Leu Asn Asp Asn His Tyr Asn Asp Lys Thr Asp Gly Ala Ala Leu Ala
        515                 520                 525

Met Glu Asn Lys Gln Arg Leu Ala Leu Leu Phe Ser Leu Ala Lys Pro
530                 535                 540

Ile Lys Glu Arg Thr Pro Ala Val Ser Pro Leu Tyr Asn Asn Thr Phe
545                 550                 555                 560

Asn Thr Thr Gln Arg Asp Glu Lys Thr Asp Trp Ile Asn Lys Asp Gly
                565                 570                 575

Ser Lys Ala Tyr Asn Glu Asp Gly Thr Val Lys Gln Ser Thr Ile Gly
            580                 585                 590

Lys Tyr Asn Glu Lys Tyr Gly Asp Ala Ser Gly Asn Tyr Val Phe Ile
        595                 600                 605

Arg Ala His Asp Asn Asn Val Gln Asp Ile Ile Ala Glu Ile Ile Lys
610                 615                 620

Lys Glu Ile Asn Pro Lys Ser Asp Gly Phe Thr Ile Thr Asp Ala Glu
625                 630                 635                 640

Met Lys Gln Ala Phe Glu Ile Tyr Asn Lys Asp Met Leu Ser Ser Asp
                645                 650                 655

Lys Lys Tyr Thr Leu Asn Asn Ile Pro Ala Ala Tyr Ala Val Met Leu
            660                 665                 670

Gln Asn Met Glu Thr Ile Thr Arg Val Tyr Tyr Gly Asp Leu Tyr Thr
        675                 680                 685

Asp Asp Gly His Tyr Met Glu Thr Lys Ser Pro Tyr Tyr Asp Thr Ile
690                 695                 700

Val Asn Leu Met Lys Ser Arg Ile Lys Tyr Val Ser Gly Gly Gln Ala
705                 710                 715                 720

Gln Arg Ser Tyr Trp Leu Pro Thr Asp Gly Lys Met Asp Asn Ser Asp
                725                 730                 735

Val Glu Leu Tyr Arg Thr Asn Glu Val Tyr Thr Ser Val Arg Tyr Gly
            740                 745                 750

Lys Asp Ile Met Thr Ala Asn Asp Thr Glu Gly Ser Lys Tyr Ser Arg
        755                 760                 765

Thr Ser Gly Gln Val Thr Leu Val Ala Asn Asn Pro Lys Leu Asn Leu
770                 775                 780

Asp Gln Ser Ala Lys Leu Asn Val Glu Met Gly Lys Ile His Ala Asn
785                 790                 795                 800

Gln Lys Tyr Arg Ala Leu Ile Val Gly Thr Ala Asp Gly Ile Lys Asn
                805                 810                 815
```

```
Phe Thr Ser Asp Ala Asp Ala Ile Ala Ala Gly Tyr Val Lys Glu Thr
            820                 825                 830

Asp Ser Asn Gly Val Leu Thr Phe Gly Ala Asn Asp Ile Lys Gly Tyr
        835                 840                 845

Glu Thr Phe Asp Met Ser Gly Phe Val Ala Val Trp Val Pro Val Gly
    850                 855                 860

Ala Ser Asp Asn Gln Asp Ile Arg Val Ala Pro Ser Thr Glu Ala Lys
865                 870                 875                 880

Lys Glu Gly Glu Leu Thr Leu Lys Ala Thr Glu Ala Tyr Asp Ser Gln
                885                 890                 895

Leu Ile Tyr Glu Gly Phe Ser Asn Phe Gln Thr Ile Pro Asp Gly Ser
            900                 905                 910

Asp Pro Ser Val Tyr Thr Asn Arg Lys Ile Ala Glu Asn Val Asp Leu
        915                 920                 925

Phe Lys Ser Trp Gly Val Thr Ser Phe Glu Met Ala Pro Gln Phe Val
    930                 935                 940

Ser Ala Asp Asp Gly Thr Phe Leu Asp Ser Val Ile Gln Asn Gly Tyr
945                 950                 955                 960

Ala Phe Ala Asp Arg Tyr Asp Leu Ala Met Ser Lys Asn Asn Lys Tyr
                965                 970                 975

Gly Ser Lys Glu Asp Leu Arg Asp Ala Leu Lys Ala Leu His Lys Ala
            980                 985                 990

Gly Ile Gln Ala Ile Ala Asp Trp Val Pro Asp Gln Ile Tyr Gln Leu
        995                 1000                1005

Pro Gly Lys Glu Val Val Thr Ala Thr Arg Thr Asp Gly Ala Gly
    1010                1015                1020

Arg Lys Ile Ala Asp Ala Ile Ile Asp His Ser Leu Tyr Val Ala
    1025                1030                1035

Asn Ser Lys Ser Ser Gly Lys Asp Tyr Gln Ala Lys Tyr Gly Gly
    1040                1045                1050

Glu Phe Leu Ala Glu Leu Lys Ala Lys Tyr Pro Glu Met Phe Lys
    1055                1060                1065

Val Asn Met Ile Ser Thr Gly Lys Pro Ile Asp Asp Ser Val Lys
    1070                1075                1080

Leu Lys Gln Trp Lys Ala Glu Tyr Phe Asn Gly Thr Asn Val Leu
    1085                1090                1095

Glu Arg Gly Val Gly Tyr Val Leu Ser Asp Glu Ala Thr Gly Lys
    1100                1105                1110

Tyr Phe Thr Val Thr Lys Glu Gly Asn Phe Ile Pro Leu Gln Leu
    1115                1120                1125

Thr Gly Lys Glu Lys Val Ile Thr Gly Phe Ser Ser Asp Gly Lys
    1130                1135                1140

Gly Ile Thr Tyr Phe Gly Thr Ser Gly Thr Gln Ala Lys Ser Ala
    1145                1150                1155

Phe Val Thr Phe Asn Gly Asn Thr Tyr Tyr Phe Asp Ala Arg Gly
    1160                1165                1170

His Met Val Thr Asn Ser Glu Tyr Ser Pro Asn Gly Lys Asp Val
    1175                1180                1185

Tyr Arg Phe Leu Pro Asn Gly Ile Met Leu Ser Asn Ala Phe Tyr
    1190                1195                1200

Ile Asp Ala Asn Gly Asn Thr Tyr Leu Tyr Asn Ser Lys Gly Gln
    1205                1210                1215

Met Tyr Lys Gly Gly Tyr Thr Lys Phe Asp Val Ser Glu Thr Asp
```

```
                   1220                1225                1230

Lys Asp Gly Lys Glu Ser Lys Val Val Lys Phe Arg Tyr Phe Thr
            1235                1240                1245

Asn Glu Gly Val Met Ala Lys Gly Val Thr Val Ile Asp Gly Phe
        1250                1255                1260

Thr Gln Tyr Phe Gly Glu Asp Gly Phe Gln Ala Lys Asp Lys Leu
    1265                1270                1275

Val Thr Phe Lys Gly Lys Thr Tyr Tyr Phe Asp Ala His Thr Gly
1280                1285                1290

Asn Gly Ile Lys Asp Thr Trp Arg Asn Ile Asn Gly Lys Trp Tyr
        1295                1300                1305

Tyr Phe Asp Ala Asn Gly Val Ala Ala Thr Gly Ala Gln Val Ile
    1310                1315                1320

Asn Gly Gln Lys Leu Tyr Phe Asn Glu Asp Gly Ser Gln Val Lys
1325                1330                1335

Gly Gly Val Val Lys Asn Ala Asp Gly Thr Tyr Ser Lys Tyr Lys
        1340                1345                1350

Glu Gly Phe Gly Glu Leu Val Thr Asn Glu Phe Phe Thr Thr Asp
    1355                1360                1365

Gly Asn Val Trp Tyr Tyr Ala Gly Ala Asn Gly Lys Thr Val Thr
1370                1375                1380

Gly Ala Gln Val Ile Asn Gly Gln His Leu Tyr Phe Asn Ala Asp
        1385                1390                1395

Gly Ser Gln Val Lys Gly Val Val Lys Asn Ala Asp Gly Thr
    1400                1405                1410

Tyr Ser Lys Tyr Asn Ala Ser Thr Gly Glu Arg Leu Thr Asn Glu
1415                1420                1425

Phe Phe Thr Thr Gly Asp Asn Asn Trp Tyr Tyr Ile Gly Ala Asn
        1430                1435                1440

Gly Lys Ser Val Thr Gly Glu Val Lys Ile Gly Asp Asp Thr Tyr
    1445                1450                1455

Phe Phe Ala Lys Asp Gly Lys Gln Val Lys Gly Gln Thr Val Ser
1460                1465                1470

Ala Gly Asn Gly Arg Ile Ser Tyr Tyr Gly Asp Ser Gly Lys
        1475                1480                1485

Arg Ala Val Ser Thr Trp Ile Glu Ile Gln Pro Gly Val Tyr Val
    1490                1495                1500

Tyr Phe Asp Lys Asn Gly Leu Ala Tyr Pro Pro Arg Val Leu Asn
1505                1510                1515

<210> SEQ ID NO 61
<211> LENGTH: 1528
<212> TYPE: PRT
<213> ORGANISM: Streptococcus salivarius

<400> SEQUENCE: 61

Met Thr Asn Lys Ile Thr Gly Lys Ile Ile Met Glu Asn Lys Val His
1               5                   10                  15

Tyr Lys Leu His Lys Val Lys Lys Gln Trp Val Thr Ile Ala Val Ala
            20                  25                  30

Ser Ala Ala Leu Ala Thr Val Val Gly Gly Leu Ser Ala Thr Thr Ser
        35                  40                  45

Ser Val Ser Ala Asp Glu Thr Gln Asp Lys Ile Val Thr Gln Pro Asn
    50                  55                  60
```

```
Leu Asp Thr Thr Ala Asp Leu Val Thr Ser Thr Glu Ala Thr Lys Glu
 65                  70                  75                  80

Val Asp Lys Arg Thr Asn Thr Lys Glu Ala Asp Val Leu Thr Pro Ala
                 85                  90                  95

Lys Glu Thr Asn Ala Val Glu Thr Ala Thr Thr Thr Asn Thr Gln Ala
            100                 105                 110

Thr Ala Glu Ala Ala Thr Thr Ala Thr Thr Ser Asp Val Ala Val Ala
        115                 120                 125

Ala Val Pro Asn Lys Glu Ala Val Val Thr Thr Asp Ala Pro Ala Val
    130                 135                 140

Thr Thr Glu Lys Ala Glu Glu Gln Pro Ala Thr Val Lys Ala Glu Val
145                 150                 155                 160

Val Asn Thr Glu Val Lys Ala Pro Gln Ala Ala Leu Lys Asp Ser Glu
                165                 170                 175

Val Glu Ala Ala Leu Ser Leu Lys Asn Ile Lys Tyr Thr Asp Gly Lys
            180                 185                 190

Tyr Tyr Tyr Val Asn Glu Asp Gly Ser His Lys Glu Asn Phe Ala Ile
        195                 200                 205

Thr Val Asn Gly Gln Leu Leu Tyr Phe Gly Lys Asp Gly Ala Leu Thr
    210                 215                 220

Ser Ser Ser Thr His Ser Phe Thr Pro Gly Thr Thr Asn Ile Val Asp
225                 230                 235                 240

Gly Phe Ser Ile Asn Asn Arg Ala Tyr Asp Ser Ser Glu Ala Ser Phe
                245                 250                 255

Glu Leu Ile Asn Gly Tyr Leu Thr Ala Asp Ser Trp Tyr Arg Pro Val
            260                 265                 270

Ser Ile Ile Lys Asp Gly Val Thr Trp Gln Ala Ser Thr Ala Glu Asp
        275                 280                 285

Phe Arg Pro Leu Leu Met Ala Trp Trp Pro Asn Val Asp Thr Gln Val
    290                 295                 300

Asn Tyr Leu Asn Tyr Met Ser Lys Val Phe Asn Leu Glu Ala Lys Tyr
305                 310                 315                 320

Thr Ser Thr Asp Lys Gln Ala Asp Leu Asn Arg Ala Ala Lys Asp Ile
                325                 330                 335

Gln Val Lys Ile Glu Gln Lys Ile Gln Ala Glu Lys Ser Thr Gln Trp
            340                 345                 350

Leu Arg Glu Thr Ile Ser Ala Phe Val Lys Thr Gln Pro Gln Trp Asn
        355                 360                 365

Lys Glu Thr Glu Asn Tyr Ser Lys Gly Gly Glu Asp His Leu Gln
    370                 375                 380

Gly Gly Ala Leu Leu Tyr Val Asn Asp Ser Arg Thr Pro Trp Ala Asn
385                 390                 395                 400

Ser Asn Tyr Arg Leu Leu Asn Arg Thr Ala Thr Asn Gln Thr Gly Thr
                405                 410                 415

Ile Asn Lys Ser Val Leu Asp Glu Gln Ser Asp Pro Asn His Met Gly
            420                 425                 430

Gly Phe Asp Phe Leu Leu Ala Asn Asp Val Asp Leu Ser Asn Pro Val
        435                 440                 445

Val Gln Ala Glu Gln Leu Asn Gln Ile His Tyr Leu Met Asn Trp Gly
    450                 455                 460

Ser Ile Val Met Gly Asp Lys Asp Ala Asn Phe Asp Gly Ile Arg Val
465                 470                 475                 480

Asp Ala Val Asp Asn Val Asn Ala Asp Met Leu Gln Leu Tyr Thr Asn
```

```
                    485                 490                 495
Tyr Phe Arg Glu Tyr Tyr Gly Val Asn Lys Ser Glu Ala Gln Ala Leu
                500                 505                 510

Ala His Ile Ser Val Leu Glu Ala Trp Ser Leu Asn Asp Asn His Tyr
                515                 520                 525

Asn Asp Lys Thr Asp Gly Ala Ala Leu Ala Met Glu Asn Lys Gln Arg
                530                 535                 540

Leu Ala Leu Leu Phe Ser Leu Ala Lys Pro Ile Lys Asp Arg Thr Pro
545                 550                 555                 560

Ala Val Ser Pro Leu Tyr Asn Asn Thr Phe Asn Thr Thr Gln Arg Asp
                565                 570                 575

Phe Lys Thr Asp Trp Ile Asn Lys Asp Gly Ser Thr Ala Tyr Asn Glu
                580                 585                 590

Asp Gly Thr Ala Lys Gln Ser Thr Ile Gly Lys Tyr Asn Glu Lys Tyr
                595                 600                 605

Gly Asp Ala Ser Gly Asn Tyr Val Phe Ile Arg Ala His Asp Asn Asn
                610                 615                 620

Val Gln Asp Ile Ile Ala Glu Ile Ile Lys Lys Glu Ile Asn Lys Lys
625                 630                 635                 640

Ser Asp Gly Phe Thr Ile Ser Asp Ser Glu Met Lys Gln Ala Phe Glu
                645                 650                 655

Ile Tyr Asn Lys Asp Met Leu Ser Ser Asn Lys Lys Tyr Thr Leu Asn
                660                 665                 670

Asn Ile Pro Ala Ala Tyr Ala Val Met Leu Gln Asn Met Glu Thr Ile
                675                 680                 685

Thr Arg Val Tyr Tyr Gly Asp Leu Tyr Thr Asp Asp Gly His Tyr Met
690                 695                 700

Glu Thr Lys Ser Pro Tyr His Asp Thr Ile Val Asn Leu Met Lys Asn
705                 710                 715                 720

Arg Ile Lys Tyr Val Ser Gly Gln Ala Gln Arg Ser Tyr Trp Leu
                725                 730                 735

Pro Thr Asp Gly Lys Met Asp Asn Ser Asp Val Glu Leu Tyr Arg Thr
                740                 745                 750

Ser Glu Val Tyr Thr Ser Val Arg Tyr Gly Lys Asp Ile Met Thr Ala
                755                 760                 765

Asp Asp Thr Glu Gly Ser Lys Tyr Ser Arg Thr Ser Gly Gln Val Thr
                770                 775                 780

Leu Val Val Asn Asn Pro Lys Leu Thr Leu His Glu Ser Ala Lys Leu
785                 790                 795                 800

Asn Val Glu Met Gly Lys Ile His Ala Asn Gln Lys Tyr Arg Ala Leu
                805                 810                 815

Ile Val Gly Thr Ala Asp Gly Ile Lys Asn Phe Thr Ser Asp Ala Glu
                820                 825                 830

Ala Ile Ala Ala Gly Tyr Val Lys Glu Thr Asp Ser Asn Gly Val Leu
                835                 840                 845

Thr Phe Gly Ala Asn Asp Ile Lys Gly Tyr Glu Thr Phe Asp Met Ser
                850                 855                 860

Gly Phe Val Ala Val Trp Val Pro Val Gly Ala Ser Asp Gln Asp
865                 870                 875                 880

Ile Arg Val Ala Pro Ser Thr Glu Ala Lys Lys Glu Gly Glu Leu Thr
                885                 890                 895

Leu Lys Ala Thr Glu Ala Tyr Asp Ser Gln Leu Ile Tyr Glu Gly Phe
                900                 905                 910
```

```
Ser Asn Phe Gln Thr Ile Pro Asp Gly Ser Asp Pro Ser Val Tyr Thr
        915                 920                 925

Asn Arg Lys Ile Ala Glu Asn Val Asp Leu Phe Lys Ser Trp Gly Val
930                 935                 940

Thr Ser Phe Glu Met Ala Pro Gln Phe Val Ser Ala Asp Asp Gly Thr
945                 950                 955                 960

Phe Leu Asp Ser Val Ile Gln Asn Gly Tyr Ala Phe Ala Asp Arg Tyr
            965                 970                 975

Asp Leu Ala Met Ser Lys Asn Asn Lys Tyr Gly Ser Lys Glu Asp Leu
                980                 985                 990

Arg Asp Ala Leu Lys Ala Leu His  Lys Ala Gly Ile Gln  Ala Ile Ala
            995                 1000                 1005

Asp Trp Val Pro Asp Gln Ile  Tyr Gln Leu Pro Gly  Lys Glu Val
    1010                 1015                 1020

Val Thr Ala Thr Arg Thr Asp  Gly Ala Gly Arg Lys  Ile Ala Asp
    1025                 1030                 1035

Ala Ile Ile Asp His Ser Leu  Tyr Val Ala Asn Ser  Lys Ser Ser
    1040                 1045                 1050

Gly Arg Asp Tyr Gln Ala Gln  Tyr Gly Gly Glu Phe  Leu Ala Glu
    1055                 1060                 1065

Leu Lys Ala Lys Tyr Pro Lys  Met Phe Thr Glu Asn  Met Ile Ser
    1070                 1075                 1080

Thr Gly Lys Pro Ile Asp Asp  Ser Val Lys Leu Lys  Gln Trp Lys
    1085                 1090                 1095

Ala Lys Tyr Phe Asn Gly Thr  Asn Val Leu Asp Arg  Gly Val Gly
    1100                 1105                 1110

Tyr Val Leu Ser Asp Glu Ala  Thr Gly Lys Tyr Phe  Thr Val Thr
    1115                 1120                 1125

Lys Glu Gly Asn Phe Ile Pro  Leu Gln Leu Thr Gly  Asn Glu Lys
    1130                 1135                 1140

Ala Val Thr Gly Phe Ser Asn  Asp Gly Lys Gly Ile  Thr Tyr Phe
    1145                 1150                 1155

Gly Thr Ser Gly Asn Gln Ala  Lys Ser Ala Phe Val  Thr Phe Asn
    1160                 1165                 1170

Gly Asn Thr Tyr Tyr Phe Asp  Ala Arg Gly His Met  Val Thr Asn
    1175                 1180                 1185

Gly Glu Tyr Ser Pro Asn Gly  Lys Asp Val Tyr Arg  Phe Leu Pro
    1190                 1195                 1200

Asn Gly Ile Met Leu Ser Asn  Ala Phe Tyr Val Asp  Ala Asn Gly
    1205                 1210                 1215

Asn Thr Tyr Leu Tyr Asn Tyr  Lys Gly Gln Met Tyr  Lys Gly Gly
    1220                 1225                 1230

Tyr Thr Lys Phe Asp Val Thr  Glu Thr Asp Lys Asp  Gly Asn Glu
    1235                 1240                 1245

Ser Lys Val Val Lys Phe Arg  Tyr Phe Thr Asn Glu  Gly Val Met
    1250                 1255                 1260

Ala Lys Gly Leu Thr Val Ile  Asp Gly Ser Thr Gln  Tyr Phe Gly
    1265                 1270                 1275

Glu Asp Gly Phe Gln Thr Lys  Asp Lys Leu Ala Thr  Tyr Lys Gly
    1280                 1285                 1290

Lys Thr Tyr Tyr Phe Glu Ala  His Thr Gly Asn Ala  Ile Lys Asn
    1295                 1300                 1305
```

Thr Trp Arg Asn Ile Asp Gly Lys Trp Tyr His Phe Asp Glu Asn
    1310                1315                1320

Gly Val Ala Ala Thr Gly Ala Gln Val Ile Asn Gly Gln Lys Leu
    1325                1330                1335

Tyr Phe Asn Glu Asp Gly Ser Gln Val Lys Gly Gly Val Val Lys
    1340                1345                1350

Asn Ala Asp Gly Thr Tyr Ser Lys Tyr Lys Glu Gly Ser Gly Glu
    1355                1360                1365

Leu Val Thr Asn Glu Phe Phe Thr Thr Asp Gly Asn Val Trp Tyr
    1370                1375                1380

Tyr Ala Gly Ala Asp Gly Lys Thr Val Thr Gly Ala Gln Val Ile
    1385                1390                1395

Asn Gly Gln His Leu Tyr Phe Lys Glu Asp Gly Ser Gln Val Lys
    1400                1405                1410

Gly Gly Val Val Lys Asn Ala Asp Gly Thr Tyr Ser Lys Tyr Asp
    1415                1420                1425

Ala Ala Thr Gly Glu Arg Leu Thr Asn Glu Phe Phe Thr Thr Gly
    1430                1435                1440

Asp Asn Asn Trp Tyr Tyr Ile Gly Ser Asn Gly Lys Thr Val Thr
    1445                1450                1455

Gly Glu Val Lys Ile Gly Ala Asp Thr Tyr Tyr Phe Ala Lys Asp
    1460                1465                1470

Gly Lys Gln Val Lys Gly Gln Thr Val Thr Ala Gly Asn Gly Arg
    1475                1480                1485

Ile Ser Tyr Tyr Tyr Gly Asp Ser Gly Lys Lys Ala Ile Ser Thr
    1490                1495                1500

Trp Ile Glu Ile Gln Pro Gly Ile Tyr Val Tyr Phe Asp Lys Thr
    1505                1510                1515

Gly Ile Ala Tyr Pro Pro Arg Val Leu Asn
    1520                1525

<210> SEQ ID NO 62
<211> LENGTH: 1518
<212> TYPE: PRT
<213> ORGANISM: Streptococcus salivarius

<400> SEQUENCE: 62

Met Glu Asn Lys Ile His Tyr Lys Leu His Lys Val Lys Lys Gln Trp
1               5                   10                  15

Val Thr Ile Ala Val Ala Ser Val Ala Leu Ala Thr Val Leu Gly Gly
            20                  25                  30

Leu Ser Val Thr Thr Ser Ser Val Ser Ala Asp Glu Thr Gln Asp Lys
        35                  40                  45

Thr Val Thr Gln Ser Asn Ser Gly Thr Thr Ala Ser Leu Val Thr Ser
    50                  55                  60

Pro Glu Ala Thr Lys Glu Ala Asp Lys Arg Thr Asn Thr Lys Glu Ala
65                  70                  75                  80

Asp Val Leu Thr Pro Ala Lys Glu Thr Asn Ala Val Glu Thr Ala Thr
                85                  90                  95

Thr Thr Asn Thr Gln Ala Thr Ala Glu Ala Ala Thr Thr Ala Thr Thr
            100                 105                 110

Ala Asp Val Ala Val Ala Ala Val Pro Asn Lys Glu Ala Val Val Thr
        115                 120                 125

Thr Asp Ala Pro Ala Val Thr Thr Glu Lys Ala Glu Glu Gln Pro Ala
    130                 135                 140

```
Thr Val Lys Ala Glu Val Val Asn Thr Glu Val Lys Ala Pro Glu Ala
145                 150                 155                 160

Ala Leu Lys Asp Ser Glu Val Glu Ala Ala Leu Ser Leu Lys Asn Ile
                165                 170                 175

Lys Asn Ile Asp Gly Lys Tyr Tyr Tyr Val Asn Glu Asp Gly Ser His
            180                 185                 190

Lys Glu Asn Phe Ala Ile Thr Val Asn Gly Gln Leu Leu Tyr Phe Gly
            195                 200                 205

Lys Asp Gly Ala Leu Thr Ser Ser Thr Tyr Ser Phe Thr Pro Gly
210                 215                 220

Thr Thr Asn Ile Val Asp Gly Phe Ser Ile Asn Asn Arg Ala Tyr Asp
225                 230                 235                 240

Ser Ser Glu Ala Ser Phe Glu Leu Ile Asp Gly Tyr Leu Thr Ala Asp
                245                 250                 255

Ser Trp Tyr Arg Pro Ala Ser Ile Ile Lys Asp Gly Val Thr Trp Gln
                260                 265                 270

Ala Ser Thr Ala Glu Asp Phe Arg Pro Leu Leu Met Ala Trp Trp Pro
            275                 280                 285

Asn Val Asp Thr Gln Val Asn Tyr Leu Asn Tyr Met Ser Lys Val Phe
290                 295                 300

Asn Leu Asp Ala Lys Tyr Ser Ser Thr Asp Lys Gln Glu Thr Leu Lys
305                 310                 315                 320

Val Ala Ala Lys Asp Ile Gln Ile Lys Ile Glu Gln Lys Ile Gln Ala
                325                 330                 335

Glu Lys Ser Thr Gln Trp Leu Arg Glu Thr Ile Ser Ala Phe Val Lys
            340                 345                 350

Thr Gln Pro Gln Trp Asn Lys Glu Thr Glu Asn Tyr Ser Lys Gly Gly
            355                 360                 365

Gly Glu Asp His Leu Gln Gly Gly Ala Leu Leu Tyr Val Asn Asp Ser
370                 375                 380

Arg Thr Pro Trp Ala Asn Ser Asp Tyr Arg Arg Leu Asn Arg Thr Ala
385                 390                 395                 400

Thr Asn Gln Thr Gly Thr Ile Asp Lys Ser Ile Leu Asp Glu Gln Ser
            405                 410                 415

Asp Pro Asn His Met Gly Gly Phe Asp Phe Leu Leu Ala Asn Asp Val
            420                 425                 430

Asp Leu Ser Asn Pro Val Val Gln Ala Glu Gln Leu Asn Gln Ile His
            435                 440                 445

Tyr Leu Met Asn Trp Gly Ser Ile Val Met Gly Asp Lys Asp Ala Asn
            450                 455                 460

Phe Asp Gly Ile Arg Val Asp Ala Val Asp Asn Val Asp Ala Asp Met
465                 470                 475                 480

Leu Gln Leu Tyr Thr Asn Tyr Phe Arg Glu Tyr Tyr Gly Val Asn Lys
                485                 490                 495

Ser Glu Ala Asn Ala Leu Ala His Ile Ser Val Leu Glu Ala Trp Ser
                500                 505                 510

Leu Asn Asp Asn His Tyr Asn Asp Lys Thr Asp Gly Ala Ala Leu Ala
                515                 520                 525

Met Glu Asn Lys Gln Arg Leu Ala Leu Leu Phe Ser Leu Ala Lys Pro
            530                 535                 540

Ile Lys Glu Arg Thr Pro Ala Val Ser Pro Leu Tyr Asn Asn Thr Phe
545                 550                 555                 560
```

```
Asn Thr Thr Gln Arg Asp Glu Lys Thr Asp Trp Ile Asn Lys Asp Gly
            565                 570                 575

Ser Lys Ala Tyr Asn Glu Asp Gly Thr Val Lys Gln Ser Thr Ile Gly
        580                 585                 590

Lys Tyr Asn Glu Lys Tyr Gly Asp Ala Ser Gly Asn Tyr Val Phe Ile
            595                 600                 605

Arg Ala His Asp Asn Asn Val Gln Asp Ile Ile Ala Glu Ile Ile Lys
        610                 615                 620

Lys Glu Ile Asn Pro Lys Ser Asp Gly Phe Thr Ile Thr Asp Ala Glu
625                 630                 635                 640

Met Lys Gln Ala Phe Glu Ile Tyr Asn Lys Asp Met Leu Ser Ser Asp
                645                 650                 655

Lys Lys Tyr Thr Leu Asn Asn Ile Pro Ala Ala Tyr Ala Val Met Leu
            660                 665                 670

Gln Asn Met Glu Thr Ile Thr Arg Val Tyr Tyr Gly Asp Leu Tyr Thr
        675                 680                 685

Asp Asp Gly His Tyr Met Glu Thr Lys Ser Pro Tyr Tyr Asp Thr Ile
        690                 695                 700

Val Asn Leu Met Lys Ser Arg Ile Lys Tyr Val Ser Gly Gly Gln Ala
705                 710                 715                 720

Gln Arg Ser Tyr Trp Leu Pro Thr Asp Gly Lys Met Asp Asn Ser Asp
                725                 730                 735

Val Glu Leu Tyr Arg Thr Asn Glu Val Tyr Thr Ser Val Arg Tyr Gly
            740                 745                 750

Lys Asp Ile Met Thr Ala Asn Asp Thr Glu Gly Ser Lys Tyr Ser Arg
        755                 760                 765

Thr Ser Gly Gln Val Thr Leu Val Ala Asn Asn Pro Lys Leu Thr Leu
770                 775                 780

Asp Gln Ser Ala Lys Leu Asn Val Glu Met Gly Lys Ile His Ala Asn
785                 790                 795                 800

Gln Lys Tyr Arg Ala Leu Ile Val Gly Thr Ala Asp Gly Ile Lys Asn
            805                 810                 815

Phe Thr Ser Asp Ala Asp Ala Ile Ala Ala Gly Tyr Val Lys Glu Thr
        820                 825                 830

Asp Ser Asn Gly Val Leu Thr Phe Gly Ala Asn Asp Ile Lys Gly Tyr
        835                 840                 845

Glu Thr Phe Asp Met Ser Gly Phe Val Ala Val Trp Val Pro Val Gly
        850                 855                 860

Ala Ser Asp Asp Gln Asp Ile Arg Val Ala Pro Ser Thr Glu Ala Lys
865                 870                 875                 880

Lys Glu Gly Glu Leu Thr Leu Lys Ala Thr Glu Ala Tyr Asp Ser Gln
            885                 890                 895

Leu Ile Tyr Glu Gly Phe Ser Asn Phe Gln Thr Ile Pro Asp Gly Ser
        900                 905                 910

Asp Pro Ser Val Tyr Thr Asn Arg Lys Ile Ala Glu Asn Val Asp Leu
        915                 920                 925

Phe Lys Ser Trp Gly Val Thr Ser Phe Glu Met Ala Pro Gln Phe Val
        930                 935                 940

Ser Ala Asp Asp Gly Thr Phe Leu Asp Ser Val Ile Gln Asn Gly Tyr
945                 950                 955                 960

Ala Phe Ala Asp Arg Tyr Asp Leu Ala Met Ser Lys Asn Asn Lys Tyr
                965                 970                 975

Gly Ser Lys Glu Asp Leu Arg Asp Ala Leu Lys Ala Leu His Lys Ala
```

```
                    980             985                 990
Gly Ile Gln Ala Ile Ala Asp Trp  Val Pro Asp Gln Ile  Tyr Gln Leu
            995                 1000                1005
Pro Gly Lys Glu Val Val Thr Ala Thr Arg Thr Asp  Gly Ala Gly
    1010              1015                1020
Arg Lys Ile Ala Asp Ala Ile  Ile Asp His Ser Leu  Tyr Val Ala
    1025              1030                1035
Asn Thr Lys Ser Ser Gly Lys  Asp Tyr Gln Ala Lys  Tyr Gly Gly
    1040              1045                1050
Glu Phe Leu Ala Glu Leu Lys  Ala Lys Tyr Pro Glu  Met Phe Lys
    1055              1060                1065
Val Asn Met Ile Ser Thr Gly  Lys Pro Ile Asp Asp  Ser Val Lys
    1070              1075                1080
Leu Lys Gln Trp Lys Ala Glu  Tyr Phe Asn Gly Thr  Asn Val Leu
    1085              1090                1095
Glu Arg Gly Val Gly Tyr Val  Leu Ser Asp Glu Ala  Thr Gly Lys
    1100              1105                1110
Tyr Phe Thr Val Thr Lys Asp  Gly Asn Phe Ile Pro  Leu Gln Leu
    1115              1120                1125
Thr Gly Asn Glu Lys Val Val  Thr Gly Phe Ser Asn  Asp Gly Lys
    1130              1135                1140
Gly Ile Thr Tyr Phe Gly Thr  Ser Gly Thr Gln Ala  Lys Ser Ala
    1145              1150                1155
Phe Val Thr Phe Asn Gly Asn  Thr Tyr Tyr Phe Asp  Ala Arg Gly
    1160              1165                1170
His Met Val Thr Asn Gly Glu  Tyr Ser Pro Asn Gly  Lys Asp Val
    1175              1180                1185
Tyr Arg Phe Leu Pro Asn Gly  Ile Met Leu Ser Asn  Ala Phe Tyr
    1190              1195                1200
Val Asp Ala Asn Gly Asn Thr  Tyr Leu Tyr Asn Ser  Lys Gly Gln
    1205              1210                1215
Met Tyr Lys Gly Gly Tyr Thr  Lys Phe Asp Val Thr  Glu Thr Asp
    1220              1225                1230
Lys Asp Gly Lys Glu Ser Lys  Val Val Lys Phe Arg  Tyr Phe Thr
    1235              1240                1245
Asn Glu Gly Val Met Ala Lys  Gly Val Thr Val Ile  Asp Gly Phe
    1250              1255                1260
Thr Gln Tyr Phe Gly Glu Asp  Gly Phe Gln Ala Lys  Asp Lys Leu
    1265              1270                1275
Val Thr Phe Lys Gly Lys Thr  Tyr Tyr Phe Asp Ala  His Thr Gly
    1280              1285                1290
Asn Ala Ile Lys Asp Thr Trp  Arg Asn Ile Asn Gly  Lys Trp Tyr
    1295              1300                1305
His Phe Asp Ala Asn Gly Val  Ala Ala Thr Gly Ala  Gln Val Ile
    1310              1315                1320
Asn Gly Gln Lys Leu Tyr Phe  Asn Glu Asp Gly Ser  Gln Val Lys
    1325              1330                1335
Gly Gly Val Val Lys Asn Ala  Asp Gly Thr Tyr Ser  Lys Tyr Lys
    1340              1345                1350
Glu Gly Ser Gly Glu Leu Val  Thr Asn Glu Phe Phe  Thr Thr Asp
    1355              1360                1365
Gly Asn Val Trp Tyr Tyr Ala  Gly Ala Asn Gly Lys  Thr Val Thr
    1370              1375                1380
```

```
Gly Ala Gln Val Ile Asn Gly Gln His Leu Tyr Phe Asn Ala Asp
    1385                1390                1395

Gly Ser Gln Val Lys Gly Val Val Lys Asn Ala Asp Gly Thr
    1400                1405                1410

Tyr Ser Lys Tyr Asp Ala Ser Thr Gly Glu Arg Leu Thr Asn Glu
    1415                1420                1425

Phe Phe Thr Thr Gly Asp Asn Asn Trp Tyr Tyr Ile Gly Ala Asn
    1430                1435                1440

Gly Lys Ser Val Thr Gly Glu Val Lys Ile Gly Asp Thr Tyr
    1445                1450                1455

Phe Phe Ala Lys Asp Gly Lys Gln Val Lys Gly Gln Thr Val Ser
    1460                1465                1470

Ala Gly Asn Gly Arg Ile Ser Tyr Tyr Tyr Gly Asp Ser Gly Lys
    1475                1480                1485

Arg Ala Val Ser Thr Trp Ile Glu Ile Gln Pro Gly Val Tyr Val
    1490                1495                1500

Tyr Phe Asp Lys Asn Gly Ile Ala Tyr Pro Pro Arg Val Leu Asn
    1505                1510                1515

<210> SEQ ID NO 63
<211> LENGTH: 1431
<212> TYPE: PRT
<213> ORGANISM: Streptococcus salivarius

<400> SEQUENCE: 63

Met Thr Lys Glu Thr Asn Thr Val Asp Ala Thr Thr Thr Asn Thr
1               5                   10                  15

Gln Ala Ala Asp Ala Ala Thr Lys Thr Ala Asp Ala Ala Val Thr
                20                  25                  30

Ala Leu Pro Asn Lys Glu Ala Val Val Thr Thr Asp Ala Pro Ala Val
            35                  40                  45

Thr Thr Glu Lys Ala Ala Glu Gln Pro Ala Thr Val Lys Ser Glu Val
    50                  55                  60

Val Asn Thr Glu Val Lys Ala Pro Glu Ala Ala Leu Lys Asp Ser Glu
65                  70                  75                  80

Val Glu Ala Ala Leu Ser Leu Lys Asn Ile Lys Asn Ile Asp Gly Lys
                85                  90                  95

Tyr Tyr Tyr Val Asn Lys Asp Gly Ser His Lys Glu Asn Phe Ala Ile
                100                 105                 110

Thr Val Asn Gly Gln Leu Leu Tyr Phe Gly Lys Asp Gly Ala Leu Thr
            115                 120                 125

Ser Ser Ser Thr Tyr Ser Phe Thr Gln Gly Thr Thr Asn Ile Val Asp
        130                 135                 140

Gly Phe Ser Lys Asn Asn Arg Ala Tyr Asp Ser Ser Glu Ala Ser Phe
145                 150                 155                 160

Glu Leu Ile Asp Gly Tyr Leu Thr Ala Asp Ser Trp Tyr Arg Pro Val
                165                 170                 175

Ser Ile Ile Lys Asp Gly Val Thr Trp Gln Ala Ser Thr Lys Glu Asp
            180                 185                 190

Phe Arg Pro Leu Leu Met Ala Trp Trp Pro Asn Val Asp Thr Gln Val
        195                 200                 205

Asn Tyr Leu Asn Tyr Met Ser Lys Val Phe Asn Leu Asp Ala Lys Tyr
    210                 215                 220

Thr Ser Thr Asp Lys Gln Val Asp Leu Asn Arg Ala Ala Lys Asp Ile
```

```
               225                 230                 235                 240
        Gln Val Lys Ile Glu Gln Lys Ile Gln Ala Glu Lys Ser Thr Gln Trp
                            245                 250                 255

Leu Arg Glu Ala Ile Ser Ala Phe Val Lys Thr Gln Pro Gln Trp Asn
                        260                 265                 270

Lys Glu Thr Glu Asn Phe Ser Lys Gly Gly Glu Asp His Leu Gln
                    275                 280                 285

Gly Gly Ala Leu Leu Tyr Val Asn Asp Pro Arg Thr Pro Trp Ala Asn
                290                 295                 300

Ser Asn Tyr Arg Leu Leu Asn Arg Thr Ala Thr Asn Gln Thr Gly Thr
        305                 310                 315                 320

Ile Asp Lys Ser Val Leu Asp Glu Gln Ser Asp Pro Asn His Met Gly
                        325                 330                 335

Gly Phe Asp Phe Leu Leu Ala Asn Asp Val Asp Thr Ser Asn Pro Val
                    340                 345                 350

Val Gln Ala Glu Gln Leu Asn Gln Ile His Tyr Leu Met Asn Trp Gly
                355                 360                 365

Ser Ile Val Met Gly Asp Lys Asp Ala Asn Phe Asp Gly Ile Arg Val
        370                 375                 380

Asp Ala Val Asp Asn Val Asp Ala Asp Met Leu Gln Leu Tyr Thr Asn
        385                 390                 395                 400

Tyr Phe Arg Glu Tyr Tyr Gly Val Asn Lys Ser Glu Ala Asn Ala Leu
                        405                 410                 415

Ala His Ile Ser Val Leu Glu Ala Trp Ser Leu Asn Asp Asn His Tyr
                    420                 425                 430

Asn Asp Lys Thr Asp Gly Ala Ala Leu Ala Met Glu Asn Lys Gln Arg
                435                 440                 445

Leu Ala Leu Leu Phe Ser Leu Ala Lys Pro Ile Lys Glu Arg Thr Pro
        450                 455                 460

Ala Val Ser Pro Leu Tyr Asn Asn Thr Phe Asn Thr Thr Gln Arg Asp
        465                 470                 475                 480

Glu Lys Thr Asp Trp Ile Asn Lys Asp Gly Ser Lys Ala Tyr Asn Glu
                        485                 490                 495

Asp Gly Thr Val Lys Gln Ser Thr Ile Gly Lys Tyr Asn Glu Lys Tyr
                    500                 505                 510

Gly Asp Ala Ser Gly Asn Tyr Val Phe Ile Arg Ala His Asp Asn Asn
                515                 520                 525

Val Gln Asp Ile Ile Ala Glu Ile Lys Lys Glu Ile Asn Pro Lys
        530                 535                 540

Ser Asp Gly Phe Thr Ile Thr Asp Ala Glu Met Lys Lys Ala Phe Glu
        545                 550                 555                 560

Ile Tyr Asn Lys Asp Met Leu Ser Ser Asp Lys Lys Tyr Thr Leu Asn
                        565                 570                 575

Asn Ile Pro Ala Ala Tyr Ala Val Met Leu Gln Asn Met Glu Thr Ile
                    580                 585                 590

Thr Arg Val Tyr Tyr Gly Asp Leu Tyr Thr Asp Asp Gly His Tyr Met
                595                 600                 605

Glu Thr Lys Ser Pro Tyr Tyr Asp Thr Ile Val Asn Leu Met Lys Asn
                610                 615                 620

Arg Ile Lys Tyr Val Ser Gly Gly Gln Ala Gln Arg Ser Tyr Trp Leu
        625                 630                 635                 640

Pro Thr Asp Gly Lys Met Asp Lys Ser Asp Val Glu Leu Tyr Arg Thr
                        645                 650                 655
```

```
Asn Glu Val Tyr Thr Ser Val Arg Tyr Gly Lys Asp Ile Met Thr Ala
            660                 665                 670

Asp Asp Thr Gln Gly Ser Lys Tyr Ser Arg Thr Ser Gly Gln Val Thr
        675                 680                 685

Leu Val Val Asn Asn Pro Lys Leu Ser Leu Asp Lys Ser Ala Lys Leu
690                 695                 700

Asp Val Glu Met Gly Lys Ile His Ala Asn Gln Lys Tyr Arg Ala Leu
705                 710                 715                 720

Ile Val Gly Thr Pro Asn Gly Ile Lys Asn Phe Thr Ser Asp Ala Glu
                725                 730                 735

Ala Ile Ala Ala Gly Tyr Val Lys Glu Thr Asp Gly Asn Gly Val Leu
            740                 745                 750

Thr Phe Gly Ala Asn Asp Ile Lys Gly Tyr Glu Thr Phe Asp Met Ser
        755                 760                 765

Gly Phe Val Ala Val Trp Val Pro Val Gly Ala Ser Asp Asp Gln Asp
    770                 775                 780

Ile Arg Val Ala Ala Ser Thr Ala Ala Lys Lys Glu Gly Glu Leu Thr
785                 790                 795                 800

Leu Lys Ala Thr Glu Ala Tyr Asp Ser Gln Leu Ile Tyr Glu Gly Phe
                805                 810                 815

Ser Asn Phe Gln Thr Ile Pro Asp Gly Ser Asp Pro Ser Val Tyr Thr
            820                 825                 830

Asn Arg Lys Ile Ala Glu Asn Val Asp Leu Phe Lys Ser Trp Gly Val
        835                 840                 845

Thr Ser Phe Glu Met Ala Pro Gln Phe Val Ser Ala Asp Gly Thr
    850                 855                 860

Phe Leu Asp Ser Val Ile Gln Asn Gly Tyr Ala Phe Ala Asp Arg Tyr
865                 870                 875                 880

Asp Leu Ala Met Ser Lys Asn Asn Lys Tyr Gly Ser Lys Glu Asp Leu
                885                 890                 895

Arg Asn Ala Leu Lys Ala Leu His Lys Ala Gly Ile Gln Ala Ile Ala
            900                 905                 910

Asp Trp Val Pro Asp Gln Ile Tyr Gln Leu Pro Gly Lys Glu Val Val
        915                 920                 925

Thr Ala Thr Arg Thr Asp Gly Ala Gly Arg Lys Ile Ser Asp Ala Ile
    930                 935                 940

Ile Asp His Ser Leu Tyr Val Ala Asn Ser Lys Ser Ser Gly Lys Asp
945                 950                 955                 960

Tyr Gln Ala Lys Tyr Gly Gly Glu Phe Leu Ala Glu Leu Lys Ala Lys
                965                 970                 975

Tyr Pro Glu Met Phe Lys Val Asn Met Ile Ser Thr Lys Pro Ile
            980                 985                 990

Asp Asp Ser Val Lys Leu Lys Gln Trp Lys Ala Glu Tyr Phe Asn Gly
        995                 1000                1005

Thr Asn Val Leu Asp Arg Gly Val Gly Tyr Val Leu Ser Asp Glu
    1010                1015                1020

Ala Thr Gly Lys Tyr Phe Val Thr Lys Glu Gly Asn Phe Ile
    1025                1030                1035

Pro Leu Gln Leu Lys Gly Asn Glu Lys Val Ile Thr Gly Phe Ser
    1040                1045                1050

Ser Asp Gly Lys Gly Ile Thr Tyr Phe Gly Thr Ser Gly Asn Gln
    1055                1060                1065
```

```
Ala Lys Ser Ala Phe Val Thr Phe Asn Gly Asn Thr Tyr Tyr Phe
1070            1075                1080

Asp Ala Arg Gly His Met Val Thr Asn Gly Glu Tyr Ser Pro Asn
1085            1090                1095

Gly Lys Asp Val Tyr Arg Phe Leu Pro Asn Gly Ile Met Leu Ser
1100            1105                1110

Asn Ala Phe Tyr Val Asp Gly Asn Gly Asn Thr Tyr Leu Tyr Asn
1115            1120                1125

Ser Lys Gly Gln Met Tyr Lys Gly Gly Tyr Ser Lys Phe Asp Val
1130            1135                1140

Thr Glu Thr Lys Asp Gly Lys Glu Ser Lys Val Val Lys Phe Arg
1145            1150                1155

Tyr Phe Thr Asn Glu Gly Val Met Ala Lys Gly Val Thr Val Val
1160            1165                1170

Asp Gly Phe Thr Gln Tyr Phe Asn Glu Asp Gly Ile Gln Ser Lys
1175            1180                1185

Asp Glu Leu Val Thr Tyr Asn Gly Lys Thr Tyr Tyr Phe Glu Ala
1190            1195                1200

His Thr Gly Asn Ala Ile Lys Asn Thr Trp Arg Asn Ile Lys Gly
1205            1210                1215

Lys Trp Tyr His Phe Asp Ala Asn Gly Val Ala Ala Thr Gly Ala
1220            1225                1230

Gln Val Ile Asn Gly Gln His Leu Tyr Phe Asn Glu Asp Gly Ser
1235            1240                1245

Gln Val Lys Gly Gly Val Val Lys Asn Ala Asp Gly Thr Phe Ser
1250            1255                1260

Lys Tyr Lys Asp Gly Ser Gly Asp Leu Val Val Asn Glu Phe Phe
1265            1270                1275

Thr Thr Gly Asp Asn Val Trp Tyr Tyr Ala Gly Ala Asn Gly Lys
1280            1285                1290

Thr Val Thr Gly Ala Gln Val Ile Asn Gly Gln His Leu Phe Phe
1295            1300                1305

Lys Glu Asp Gly Ser Gln Val Lys Gly Asp Phe Val Lys Asn Ser
1310            1315                1320

Asp Gly Thr Tyr Ser Lys Tyr Asp Ala Ala Ser Gly Glu Arg Leu
1325            1330                1335

Thr Asn Glu Phe Phe Thr Thr Gly Asp Asn His Trp Tyr Tyr Ile
1340            1345                1350

Gly Ala Asn Gly Lys Thr Val Thr Gly Glu Val Lys Ile Gly Asp
1355            1360                1365

Asp Thr Tyr Phe Phe Ala Lys Asp Gly Lys Gln Leu Lys Gly Gln
1370            1375                1380

Ile Val Thr Thr Arg Ser Gly Arg Ile Ser Tyr Tyr Phe Gly Asp
1385            1390                1395

Ser Gly Lys Lys Ala Ile Ser Thr Trp Val Glu Ile Gln Pro Gly
1400            1405                1410

Val Phe Val Phe Phe Asp Lys Asn Gly Leu Ala Tyr Pro Pro Glu
1415            1420                1425

Asn Met Asn
1430

<210> SEQ ID NO 64
<211> LENGTH: 1532
<212> TYPE: PRT
```

<213> ORGANISM: Unknown
<220> FEATURE:
<223> OTHER INFORMATION: unknown Streptococcus species

<400> SEQUENCE: 64

```
Met Glu Asn Lys Val His Tyr Lys Leu His Lys Val Lys Lys Gln Trp
1               5                   10                  15

Val Thr Ile Ala Val Ala Ser Ala Ala Leu Ala Thr Val Val Gly Gly
                20                  25                  30

Leu Ser Ala Thr Thr Ser Ser Val Ser Ala Asp Glu Thr Gln Asp Lys
            35                  40                  45

Thr Val Thr Gln Pro Asn Ser Asp Thr Thr Ala Asp Leu Val Thr Ser
    50                  55                  60

Thr Glu Ala Thr Lys Glu Val Asp Lys Arg Thr Asn Thr Lys Glu Ala
65                  70                  75                  80

Asp Val Leu Thr Pro Ala Lys Glu Thr Asn Thr Val Glu Thr Ala Ala
                85                  90                  95

Thr Thr Asn Thr Gln Ala Thr Ala Glu Ala Ala Lys Thr Ala Thr Thr
            100                 105                 110

Thr Asn Thr Gln Ala Thr Ala Glu Val Ala Lys Thr Ala Thr Thr Ala
        115                 120                 125

Asp Val Ala Val Ala Val Pro Asn Lys Glu Ala Val Val Thr Thr
    130                 135                 140

Asp Ala Pro Ala Val Thr Thr Glu Lys Ala Glu Gln Pro Ala Thr
145                 150                 155                 160

Val Lys Ala Glu Val Val Asn Thr Glu Val Lys Ala Pro Glu Ala Ala
                165                 170                 175

Leu Lys Asp Ser Glu Val Glu Ala Ala Leu Ser Leu Lys Asn Ile Lys
            180                 185                 190

Asn Ile Asp Gly Lys Tyr Tyr Tyr Val Asn Glu Asp Gly Ser His Lys
        195                 200                 205

Glu Asn Phe Ala Ile Thr Val Asn Gly Gln Leu Leu Tyr Phe Gly Lys
    210                 215                 220

Asp Gly Ala Leu Thr Ser Ser Ser Thr Tyr Ser Phe Thr Gln Gly Thr
225                 230                 235                 240

Thr Asn Ile Val Asp Gly Phe Ser Ile Asn Asn Arg Ala Tyr Asp Ser
                245                 250                 255

Ser Glu Ala Ser Phe Glu Leu Ile Asp Gly Tyr Leu Thr Ala Asp Ser
            260                 265                 270

Trp Tyr Arg Pro Ala Ser Ile Ile Lys Asp Gly Val Thr Trp Gln Ala
        275                 280                 285

Ser Thr Ala Glu Asp Phe Arg Pro Leu Leu Met Ala Trp Trp Pro Asn
    290                 295                 300

Val Asp Thr Gln Val Asn Tyr Leu Asn Tyr Met Ser Lys Val Phe Asn
305                 310                 315                 320

Leu Asp Ala Lys Tyr Ser Ser Thr Asp Lys Gln Glu Thr Leu Lys Val
                325                 330                 335

Ala Ala Lys Asp Ile Gln Ile Lys Ile Glu Gln Lys Ile Gln Ala Glu
            340                 345                 350

Lys Ser Thr Gln Trp Leu Arg Glu Thr Ile Ser Ala Phe Val Lys Thr
        355                 360                 365

Gln Pro Gln Trp Asn Lys Glu Thr Gly Asn Tyr Ser Lys Gly Gly Gly
    370                 375                 380

Glu Asp His Leu Gln Gly Gly Ala Leu Leu Tyr Val Asn Asp Ser Arg
```

```
                385                 390                 395                 400
Thr Pro Trp Ala Asn Ser Asn Tyr Arg Leu Leu Asn Arg Thr Ala Thr
                    405                 410                 415
Asn Gln Thr Gly Thr Ile Asp Lys Ser Ile Leu Asp Glu Gln Ser Asp
                420                 425                 430
Pro Asn His Met Gly Gly Phe Asp Phe Leu Leu Ala Asn Asp Val Asp
            435                 440                 445
Leu Ser Asn Pro Val Val Gln Ala Glu Gln Leu Asn Gln Ile His Tyr
450                 455                 460
Leu Met Asn Trp Gly Ser Ile Val Met Gly Asp Lys Asp Ala Asn Phe
465                 470                 475                 480
Asp Gly Ile Arg Val Asp Ala Val Asp Asn Val Asp Ala Asp Met Leu
                485                 490                 495
Gln Leu Tyr Thr Asn Tyr Phe Arg Glu Tyr Tyr Gly Val Asn Lys Ser
                500                 505                 510
Glu Ala Asn Ala Leu Ala His Ile Ser Val Leu Glu Ala Trp Ser Leu
                515                 520                 525
Asn Asp Asn His Tyr Asn Asp Lys Thr Asp Val Ala Ala Leu Ala Met
530                 535                 540
Glu Asn Lys Gln Arg Leu Ala Leu Leu Phe Ser Leu Ala Lys Pro Ile
545                 550                 555                 560
Lys Glu Arg Thr Pro Ala Val Ser Pro Leu Tyr Asn Asn Thr Phe Asn
                565                 570                 575
Thr Thr Gln Arg Asp Glu Lys Thr Asp Trp Ile Asn Lys Asp Gly Ser
                580                 585                 590
Lys Ala Tyr Asn Glu Asp Gly Thr Val Lys Lys Ser Thr Ile Gly Lys
                595                 600                 605
Tyr Asn Glu Lys Tyr Gly Asp Ala Ser Gly Asn Tyr Val Phe Ile Arg
                610                 615                 620
Ala His Asp Asn Val Gln Asp Ile Ile Ala Glu Ile Ile Lys Lys
625                 630                 635                 640
Glu Ile Asn Glu Lys Ser Asp Gly Phe Thr Ile Thr Asp Ser Glu Met
                645                 650                 655
Lys Arg Ala Phe Glu Ile Tyr Asn Lys Asp Met Leu Ser Asn Asp Lys
                660                 665                 670
Lys Tyr Thr Leu Asn Asn Ile Pro Ala Ala Tyr Ala Val Met Leu Gln
                675                 680                 685
Asn Met Glu Thr Ile Thr Arg Val Tyr Tyr Gly Asp Leu Tyr Thr Asp
690                 695                 700
Asp Gly Asn Tyr Met Glu Ala Lys Ser Pro Tyr Tyr Asp Thr Ile Val
705                 710                 715                 720
Asn Leu Met Lys Ser Arg Ile Lys Tyr Val Ser Gly Gly Gln Ala Gln
                725                 730                 735
Arg Ser Tyr Trp Leu Pro Thr Asp Gly Lys Met Asp Lys Ser Asp Val
                740                 745                 750
Glu Leu Tyr Arg Thr Asn Glu Val Tyr Thr Ser Val Arg Tyr Gly Lys
                755                 760                 765
Asp Ile Met Thr Ala Asp Thr Gln Gly Ser Lys Tyr Ser Arg Thr
                770                 775                 780
Ser Gly Gln Val Thr Leu Val Val Asn Asn Pro Lys Leu Thr Leu Asp
785                 790                 795                 800
Gln Ser Ala Lys Leu Asn Val Val Met Gly Lys Ile His Ala Asn Gln
                805                 810                 815
```

```
Lys Tyr Arg Ala Leu Ile Val Gly Thr Pro Asn Gly Ile Lys Asn Phe
            820                 825                 830

Thr Ser Asp Ala Glu Ala Ile Ala Ala Gly Tyr Val Lys Glu Thr Asp
        835                 840                 845

Gly Asn Gly Val Leu Thr Phe Gly Ala Asn Asp Ile Lys Gly Tyr Glu
    850                 855                 860

Thr Phe Asp Met Ser Gly Phe Val Ala Val Trp Val Pro Val Gly Ala
865                 870                 875                 880

Ser Asp Asp Gln Asp Ile Arg Val Ala Ala Ser Thr Ala Ala Lys Lys
                885                 890                 895

Glu Gly Glu Leu Thr Leu Lys Ala Thr Glu Ala Tyr Asp Ser Gln Leu
            900                 905                 910

Ile Tyr Glu Gly Phe Ser Asn Phe Gln Thr Ile Pro Asp Gly Ser Asp
        915                 920                 925

Pro Ser Val Tyr Thr Asn Arg Lys Ile Ala Glu Asn Val Asp Leu Phe
    930                 935                 940

Lys Ser Trp Gly Val Thr Ser Phe Glu Met Ala Pro Gln Phe Val Ser
945                 950                 955                 960

Ala Asp Asp Gly Thr Phe Leu Asp Ser Val Ile Gln Asn Gly Tyr Ala
                965                 970                 975

Phe Ala Asp Arg Tyr Asp Leu Ala Met Ser Lys Asn Asn Lys Tyr Gly
            980                 985                 990

Ser Lys Glu Asp Leu Arg Asn Ala  Leu Lys Ala Leu His  Lys Ala Gly
        995                 1000                1005

Ile Gln  Ala Ile Ala Asp Trp  Val Pro Asp Gln Ile  Tyr Gln Leu
    1010                1015                1020

Pro Gly Lys Glu Val Val Thr  Ala Thr Arg Thr Asp  Gly Ala Gly
    1025                1030                1035

Arg Lys  Ile Ser Asp Ala Ile  Ile Asp His Ser Leu  Tyr Val Ala
    1040                1045                1050

Asn Ser  Lys Ser Ser Gly Lys  Asp Tyr Gln Ala Lys  Tyr Gly Gly
    1055                1060                1065

Glu Phe  Leu Ala Glu Leu Lys  Ala Lys Tyr Pro Glu  Met Phe Lys
    1070                1075                1080

Val Asn  Met Ile Ser Thr Gly  Lys Pro Ile Asp Asp  Ser Val Lys
    1085                1090                1095

Leu Lys  Gln Trp Lys Ala Glu  Tyr Phe Asn Gly Thr  Asn Val Leu
    1100                1105                1110

Asp Arg  Gly Val Gly Tyr Val  Leu Ser Asp Glu Ala  Thr Gly Lys
    1115                1120                1125

Tyr Phe  Thr Val Thr Lys Glu  Gly Asn Phe Ile Pro  Leu Gln Leu
    1130                1135                1140

Lys Gly  Asn Lys Lys Val Ile  Thr Gly Phe Ser Ser  Asp Gly Lys
    1145                1150                1155

Gly Ile  Thr Tyr Phe Gly Thr  Ser Gly Asn Gln Ala  Lys Ser Ala
    1160                1165                1170

Phe Val  Thr Phe Asn Gly Asn  Thr Tyr Tyr Phe Asp  Ala Arg Gly
    1175                1180                1185

His Met  Val Thr Asn Gly Glu  Tyr Ser Pro Asn Gly  Lys Asp Val
    1190                1195                1200

Tyr Arg  Phe Leu Pro Asn Gly  Ile Met Leu Ser Asn  Ala Phe Tyr
    1205                1210                1215
```

```
Val Asp Gly Asn Gly Asn Thr Tyr Leu Tyr Asn Ser Lys Gly Gln
1220                    1225                1230

Met Tyr Lys Gly Gly Tyr Ser Lys Phe Asp Val Thr Glu Thr Lys
1235                    1240                1245

Asp Gly Lys Glu Ser Lys Val Val Lys Phe Arg Tyr Phe Thr Asn
1250                    1255                1260

Glu Gly Val Met Ala Lys Gly Val Thr Val Val Asp Gly Phe Thr
1265                    1270                1275

Gln Tyr Phe Asn Glu Asp Gly Ile Gln Ser Lys Asp Glu Leu Val
1280                    1285                1290

Thr Tyr Asn Gly Lys Thr Tyr Tyr Phe Glu Ala His Thr Gly Asn
1295                    1300                1305

Ala Ile Lys Asn Thr Trp Arg Asn Ile Lys Gly Lys Trp Tyr His
1310                    1315                1320

Phe Asp Ala Asn Gly Val Ala Ala Thr Gly Ala Gln Val Ile Asn
1325                    1330                1335

Gly Gln His Leu Tyr Phe Asn Glu Asp Gly Ser Gln Val Lys Gly
1340                    1345                1350

Ser Ile Val Lys Asn Ala Asp Gly Thr Phe Ser Lys Tyr Lys Asp
1355                    1360                1365

Ser Ser Gly Asp Leu Val Val Asn Glu Phe Phe Thr Thr Gly Asp
1370                    1375                1380

Asn Val Trp Tyr Tyr Ala Gly Ala Asn Gly Lys Thr Val Thr Gly
1385                    1390                1395

Ala Gln Val Ile Asn Gly Gln His Leu Phe Phe Lys Glu Asp Gly
1400                    1405                1410

Ser Gln Val Lys Gly Asp Phe Val Lys Asn Ser Asp Gly Thr Tyr
1415                    1420                1425

Ser Lys Tyr Asp Ala Ala Ser Gly Glu Arg Leu Thr Asn Glu Phe
1430                    1435                1440

Phe Thr Thr Gly Asp Asn His Trp Tyr Tyr Ile Gly Ala Asn Gly
1445                    1450                1455

Lys Thr Val Thr Gly Glu Val Lys Ile Gly Asp Asp Thr Tyr Phe
1460                    1465                1470

Phe Ala Lys Asp Gly Lys Gln Leu Lys Gly Gln Ile Val Thr Thr
1475                    1480                1485

Arg Ser Gly Arg Ile Ser Tyr Tyr Phe Gly Asp Ser Gly Lys Lys
1490                    1495                1500

Ala Ile Ser Thr Trp Val Glu Ile Gln Pro Gly Val Phe Val Phe
1505                    1510                1515

Phe Asp Lys Asn Gly Leu Ala Tyr Pro Pro Glu Asn Met Asn
1520                    1525                1530
```

GLUCOSYLTRANSFERASE ENZYMES FOR PRODUCTION OF GLUCAN POLYMERS

This application is a divisional of pending application Ser. No. 14/036,049, filed Sep. 25, 2013, which claims the benefit of U.S. Provisional Application Nos. 61/705,177; 61/705,178; 61/705,179; 61/705,180 and 61/705,181, each filed Sep. 25, 2012. All of these prior applications are incorporated herein by reference in their entirety.

FIELD OF INVENTION

The invention is in the field of enzyme catalysis. Specifically, this invention pertains to producing high molecular weight, insoluble poly alpha-1,3-glucan using a glucosyltransferase enzyme.

BACKGROUND

Driven by a desire to find new structural polysaccharides using enzymatic syntheses or genetic engineering of microorganisms or plant hosts, researchers have discovered polysaccharides that are biodegradable and can be made economically from renewably sourced feedstocks. One such polysaccharide is poly alpha-1,3-glucan, a glucan polymer characterized by having alpha-1,3-glycosidic linkages. This polymer has been isolated by contacting an aqueous solution of sucrose with a glucosyltransferase (gtf) enzyme isolated from *Streptococcus salivarius* (Simpson et al., *Microbiology* 141:1451-1460, 1995). Films prepared from poly alpha-1,3-glucan tolerate temperatures up to 150° C. and provide an advantage over polymers obtained from beta-1,4-linked polysaccharides (Ogawa et al., *Fiber Differentiation Methods* 47:353-362, 1980).

U.S. Pat. No. 7,000,000 disclosed the preparation of a polysaccharide fiber using an *S. salivarius* gtfJ enzyme. At least 50% of the hexose units within the polymer of this fiber were linked via alpha-1,3-glycosidic linkages. *S. salivarius* gtfJ enzyme utilizes sucrose as a substrate in a polymerization reaction producing poly alpha-1,3-glucan and fructose as end-products (Simpson et al., 1995). The disclosed polymer formed a liquid crystalline solution when it was dissolved above a critical concentration in a solvent or in a mixture comprising a solvent. Continous, strong, cotton-like fibers were obtained from this solution that could be spun and used in textile applications.

Not all glucosyltransferase enzymes can produce glucan with a molecular weight and percentage of alpha-1,3 glycosidic linkages suitable for use in spinning fibers. For example, most glucosyltransferase enzymes do not produce glucan having at least 50% alpha-1,3 glycosidic linkages and a number average degree of polymerization of at least 100. Therefore, it is desirable to identify glucosyltransferase enzymes that can convert sucrose to glucan polymers having a high percentage of alpha-1,3 glycosidic linkages and high molecular weight.

SUMMARY OF INVENTION

In one embodiment, the invention concerns a reaction solution comprising water, sucrose and a glucosyltransferase enzyme that synthesizes poly alpha-1,3-glucan. The glucosyltransferase enzyme comprises an amino acid sequence that is at least 90% identical to the amino acid sequence of SEQ ID NO:4, SEQ ID NO:10, SEQ ID NO:12, SEQ ID NO:14, SEQ ID NO:20, SEQ ID NO:26, SEQ ID NO:28, SEQ ID NO:30, or SEQ ID NO:34.

In a second embodiment, the glucosyltransferase enzyme in the reaction solution synthesizes poly alpha-1,3-glucan having at least 50% alpha-1,3 glycosidic linkages and a number average degree of polymerization of at least 100. In a third embodiment, the glucosyltransferase synthesizes poly alpha-1,3-glucan having 100% alpha-1,3 glycosidic linkages and a number average degree of polymerization of at least 100. In a fourth embodiment, the glucosyltransferase enzyme synthesizes poly alpha-1,3-glucan having 100% alpha-1,3 glycosidic linkages and a number average degree of polymerization of at least 250.

In a fifth embodiment, the reaction solution comprises a primer. In a sixth embodiment, this primer can be dextran or hydrolyzed glucan.

In a seventh embodiment, the invention concerns a method for producing poly alpha-1,3-glucan comprising the step of contacting at least water, sucrose, and a glucosyltransferase enzyme that synthesizes poly alpha-1,3-glucan. The glucosyltransferase enzyme comprises an amino acid sequence that is at least 90% identical to the amino acid sequence of SEQ ID NO:4, SEQ ID NO:10, SEQ ID NO:12, SEQ ID NO:14, SEQ ID NO:20, SEQ ID NO:26, SEQ ID NO:28, SEQ ID NO:30, or SEQ ID NO:34. The poly alpha-1,3-glucan produced in this method can optionally be isolated.

In an eighth embodiment, the glucosyltransferase enzyme used in the method synthesizes poly alpha-1,3-glucan having at least 50% alpha-1,3 glycosidic linkages and a number average degree of polymerization of at least 100. In a ninth embodiment, the glucosyltransferase enzyme synthesizes poly alpha-1,3-glucan having 100% alpha-1,3 glycosidic linkages and a number average degree of polymerization of at least 100. In a tenth embodiment, the glucosyltransferase enzyme synthesizes poly alpha-1,3-glucan having 100% alpha-1,3 glycosidic linkages and a number average degree of polymerization of at least 250.

In an eleventh embodiment, the contacting step of the method further comprises contacting a primer with the water, sucrose, and glucosyltransferase enzyme. In a twelfth embodiment, this primer can be dextran or hydrolyzed glucan.

BRIEF DESCRIPTION OF THE SEQUENCES

TABLE 1

Summary of Nucleic Acid and Protein SEQ ID Numbers

| Description | Nucleic acid SEQ ID NO. | Protein SEQ ID NO. |
|---|---|---|
| "0874 gtf", *Streptococcus sobrinus*. DNA codon-optimized for expression in *E. coli*. The first 156 amino acids of the protein are deleted compared to GENBANK Identification No. 450874, which discloses "glucosyltransferase-I". | 1 | 2 (1435 aa) |
| "6855 gtf", *Streptococcus salivarius* SK126. DNA codon-optimized for expression in *E. coli*. The first 178 amino acids of the protein are deleted compared to GENBANK Identification No. 228476855, which discloses "glucosyltransferase-SI". | 3 | 4 (1341 aa) |
| "2379 gtf", *Streptococcus salivarius*. DNA codon-optimized for expression in *E. coli*. The first 203 amino acids of the protein are deleted compared to GENBANK Identification No. 662379, which discloses "glucosyltransferase". | 5 | 6 (1247 aa) |

TABLE 1-continued

Summary of Nucleic Acid and Protein SEQ ID Numbers

| Description | Nucleic acid SEQ ID NO. | Protein SEQ ID NO. |
|---|---|---|
| "7527" or "gtfJ", *Streptococcus salivarius*. DNA codon-optimized for expression in *E. coli*. The first 42 amino acids of the protein are deleted compared to GENBANK Identification No. 47527, which discloses "glucosyltransferase-I". | 7 | 8 (1477 aa) |
| "1724 gtf", *Streptococcus downei*. DNA codon-optimized for expression in *E. coli*. The first 162 amino acids of the protein are deleted compared to GENBANK Identification No. 121724, which discloses "glucosyltransferase-I". | 9 | 10 (1436 aa) |
| "0544 gtf", *Streptococcus mutans*. DNA codon-optimized for expression in *E. coli*. The first 164 amino acids of the protein are deleted compared to GENBANK Identification No. 290580544, which discloses "glucosyltransferase-I". | 11 | 12 (1313 aa) |
| "5926 gtf", *Streptococcus dentirousetti*. DNA codon-optimized for expression in *E. coli*. The first 144 amino acids of the protein are deleted compared to GENBANK Identification No. 167735926, which discloses "glucosyltransferase-I". | 13 | 14 (1323 aa) |
| "4297 gtf", *Streptococcus oralis*. DNA codon-optimized for expression in *E. coli*. The first 228 amino acids of the protein are deleted compared to GENBANK Identification No. 7684297, which discloses "glucosyltransferase". | 15 | 16 (1348 aa) |
| "5618 gtf", *Streptococcus sanguinis*. DNA codon-optimized for expression in *E. coli*. The first 223 amino acids of the protein are deleted compared to GENBANK Identification No. 328945618, which discloses "glucosyltransferase-S". | 17 | 18 (1348 aa) |
| "2765 gtf", unknown *Streptococcus* sp. C150. DNA codon-optimized for expression in *E. coli*. The first 193 amino acids of the protein are deleted compared to GENBANK Identification No. 322372765, which discloses "glucosyltransferase-S". | 19 | 20 (1340 aa) |
| "4700 gtf", *Leuconostoc mesenteroides*. DNA codon-optimized for expression in *E. coli*. The first 36 amino acids of the protein are deleted compared to GENBANK Identification No. 21654700, which discloses "dextransucrase DsrD". | 21 | 22 (1492 aa) |
| "1366 gtf", *Streptococcus criceti*. DNA codon-optimized for expression in *E. coli*. The first 139 amino acids of the protein are deleted compared to GENBANK Identification No. 146741366, which discloses "glucosyltransferase". | 23 | 24 (1323 aa) |
| "0427 gtf", *Streptococcus sobrinus*. DNA codon-optimized for expression in *E. coli*. The first 156 amino acids of the protein are deleted compared to GENBANK Identification No. 940427, which discloses "GTF-I". | 25 | 26 (1435 aa) |
| "2919 gtf", *Streptococcus salivarius* PS4. DNA codon-optimized for expression in *E. coli*. The first 92 amino acids of the protein are deleted compared to GENBANK Identification No. 383282919, which discloses "putative glucosyltransferase". | 27 | 28 (1340 aa) |
| "2678 gtf", *Streptococcus salivarius* K12. DNA codon-optimized for expression in *E. coli*. The first 188 amino acids of the protein are deleted compared to GENBANK Identification No. 400182678, which discloses "dextransucrase-S". | 29 | 30 (1341 aa) |
| "2381 gtf", *Streptococcus salivarius*. DNA codon-optimized for expression in *E. coli*. The first 273 amino acids of the protein are deleted compared to GENBANK Identification No. 662381, which discloses "glucosyltransferase". | 31 | 32 (1305 aa) |
| "3929 gtf", *Streptococcus salivarius* JIM8777. DNA codon-optimized for expression in *E. coli*. The first 178 amino acids of the protein are deleted compared to GENBANK Identification No. 387783929, which discloses "glucosyltransferase-S precursor (GTF-S) (Dextransucrase) (Sucrose 6-glucosyltransferase)". | 33 | 34 (1341 aa) |
| "6907 gtf", *Streptococcus salivarius* SK126. DNA codon-optimized for expression in *E. coli*. The first 161 amino acids of the protein are deleted compared to GENBANK Identification No. 228476907, which discloses "glucosyltransferase-SI". | 35 | 36 (1331 aa) |
| "6661 gtf", *Streptococcus salivarius* SK126. DNA codon-optimized for expression in *E. coli*. The first 265 amino acids of the protein are deleted compared to GENBANK Identification No. 228476661, which discloses "glucosyltransferase-SI". | 37 | 38 (1305 aa) |
| "0339 gtf", *Streptococcus gallolyticus* ATCC 43143. DNA codon-optimized for expression in *E. coli*. The first 213 amino acids of the protein are deleted compared to GENBANK Identification No. 334280339, which discloses "glucosyltransferase". | 39 | 40 (1310 aa) |
| "0088 gtf", *Streptococcus mutans*. DNA codon-optimized for expression in *E. coli*. The first 189 amino acids of the protein are deleted compared to GENBANK Identification No. 3130088, which discloses "glucosyltransferase-SI". | 41 | 42 (1267 aa) |
| "9358 gtf", *Streptococcus mutans* UA159. DNA codon-optimized for expression in *E. coli*. The first 176 amino acids of the protein are deleted compared to GENBANK Identification No. 24379358, which discloses "glucosyltransferase-S". | 43 | 44 (1287 aa) |
| "8242 gtf", *Streptococcus gallolyticus* ATCC BAA-2069. DNA codon-optimized for expression in *E. coli*. The first 191 amino acids of the protein are deleted compared to GENBANK Identification No. 325978242, which discloses "glucosyltransferase-I". | 45 | 46 (1355 aa) |
| "3442 gtf", *Streptococcus sanguinis* SK405. DNA codon-optimized for expression in *E. coli*. The first 228 amino acids of the protein are deleted compared to GENBANK Identification No. 324993442, which discloses a ". . . signal domain protein". | 47 | 48 (1348 aa) |
| "7528 gtf", *Streptococcus salivarius*. DNA codon-optimized for expression in *E. coli*. The first 173 amino acids of the protein are deleted compared to GENBANK Identification No. 47528, which discloses "glucosyltransferase S". | 49 | 50 (1427 aa) |
| "3279 gtf", *Streptococcus* sp. C150. DNA codon-optimized for expression in *E. coli*. The first 178 amino acids of the protein are deleted compared to GENBANK Identification No. 322373279, which discloses "glucosyltransferase S". | 51 | 52 (1393 aa) |
| "6491 gtf", *Leuconostoc citreum* KM20. DNA codon-optimized for expression in *E. coli*. The first 244 amino acids of the protein are deleted compared to GENBANK Identification No. 170016491, which discloses "glucosyltransferase". | 53 | 54 (1262 aa) |
| "6889 gtf", *Streptococcus salivarius* SK126. DNA codon-optimized for expression in *E. coli*. The first 173 amino acids of the protein are deleted compared to GENBANK Identification No. 228476889, which discloses "glucosyltransferase-I". | 55 | 56 (1427 aa) |
| "4154 gtf", *Lactobacillus reuteri*. DNA codon-optimized for expression in *E. coli*. The first 38 amino acids of the protein are deleted compared to GENBANK Identification No. 51574154, which discloses "glucansucrase". | 57 | 58 (1735 aa) |
| "3298 gtf", *Streptococcus* sp. C150. The first 209 amino acids of the protein are deleted compared to GENBANK Identification No. 322373298, which discloses "glucosyltransferase-S". |  | 59 (1242 aa) |
| "Wild type gtfJ", *Streptococcus salivarius*. GENBANK Identification No. 47527. |  | 60 (1518 aa) |
| Wild type gtf corresponding to 2678 gtf, *Streptococcus salivarius* K12. GENBANK Identification No. 400182678, which discloses "dextransucrase-S". |  | 61 (1528 aa) |
| Wild type gtf corresponding to 6855 gtf, *Streptococcus salivarius* SK126. GENBANK Identification No. 228476855, which discloses "glucosyltransferase-SI". |  | 62 (1518 aa) |

TABLE 1-continued

Summary of Nucleic Acid and Protein SEQ ID Numbers

| Description | Nucleic acid SEQ ID NO. | Protein SEQ ID NO. |
|---|---|---|
| Wild type gtf corresponding to 2919 gtf, *Streptococcus salivarius* PS4. GENBANK Identification No. 383282919, which discloses "putative glucosyltransferase". | | 63 (1431 aa) |
| Wild type gtf corresponding to 2765 gtf, *Streptococcus* sp. C150. GENBANK Identification No. 322372765, which discloses "glucosyltransferase-S". | | 64 (1532 aa) |

DETAILED DESCRIPTION OF THE INVENTION

The disclosures of all cited patent and non-patent literature are incorporated herein by reference in their entirety.

As used herein, the term "invention" or "disclosed invention" is not meant to be limiting, but applies generally to any of the inventions defined in the claims or described herein. These terms are used interchangeably herein.

The terms "poly alpha-1,3-glucan", "alpha-1,3-glucan polymer" and "glucan polymer" are used interchangeably herein. Poly alpha-1,3-glucan is a polymer comprising glucose monomeric units linked together by glycosidic linkages, wherein at least about 50% of the glycosidic linkages are alpha-1,3-glycosidic linkages. Poly alpha-1,3-glucan is a type of polysaccharide. The structure of poly alpha-1,3-glucan can be illustrated as follows:

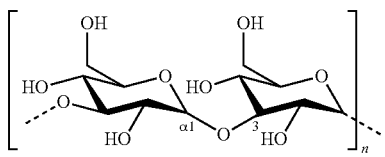

The terms "glycosidic linkage" and "glycosidic bond" are used interchangeably herein and refer to the type of covalent bond that joins a carbohydrate (sugar) molecule to another group such as another carbohydrate. The term "alpha-1,3-glycosidic linkage" as used herein refers to the type of covalent bond that joins alpha-D-glucose molecules to each other through carbons 1 and 3 on adjacent alpha-D-glucose rings. This linkage is illustrated in the poly alpha-1,3-glucan structure provided above. Herein, "alpha-D-glucose" will be referred to as "glucose".

The term "sucrose" herein refers to a non-reducing disaccharide composed of an alpha-D-glucose molecule and a beta-D-fructose molecule linked by an alpha-1,2-glycosidic bond. Sucrose is known commonly as table sugar.

The "molecular weight" of the poly alpha-1,3-glucan herein can be represented as number-average molecular weight ($M_n$) or as weight-average molecular weight ($M_w$). Alternatively, molecular weight can be represented as Daltons, grams/mole, DPw (weight average degree of polymerization), or DPn (number average degree of polymerization). Various means are known in the art for calculating these molecular weight measurements such as with high-pressure liquid chromatography (HPLC), size exclusion chromatography (SEC), or gel permeation chromatography (GPC).

The terms "glucosyltransferase enzyme", "gtf enzyme", "gtf enzyme catalyst", "gtf", and "glucansucrase" are used interchangeably herein. The activity of a gtf enzyme herein catalyzes the reaction of the substrate sucrose to make the products poly alpha-1,3-glucan and fructose. Other products (byproducts) of a gtf reaction can include glucose (where glucose is hydrolyzed from the glucosyl-gtf enzyme intermediate complex), various soluble oligosaccharides (DP2-DP7), and leucrose (where glucose of the glucosyl-gtf enzyme intermediate complex is linked to fructose). Leucrose is a disaccharide composed of glucose and fructose linked by an alpha-1,5 linkage. Wild type forms of glucosyltransferase enzymes generally contain (in the N-terminal to C-terminal direction) a signal peptide, a variable domain, a catalytic domain, and a glucan-binding domain. A gtf herein is classified under the glycoside hydrolase family 70 (GH70) according to the CAZy (Carbohydrate-Active EnZymes) database (Cantarel et al., *Nucleic Acids Res.* 37:D233-238, 2009).

The terms "reaction" and "enzymatic reaction" are used interchangeably herein and refer to a reaction that is performed by a glucosyltransferase enzyme. A "reaction solution" as used herein generally refers to a solution comprising at least one active glucosyltransferase enzyme in a solution comprising sucrose and water, and optionally other components. It is in the reaction solution where the step of contacting water, sucrose and a glucosyltransferase enzyme is performed. The term "under suitable reaction conditions" as used herein, refers to reaction conditions that support conversion of sucrose to poly alpha-1,3-glucan via glucosyltransferase enzyme activity. The reaction herein is not naturally occurring.

The terms "percent by volume", "volume percent", "vol %" and "v/v %" are used interchangeably herein. The percent by volume of a solute in a solution can be determined using the formula: [(volume of solute)/(volume of solution)]× 100%.

The terms "percent by weight", "weight percentage (wt %)" and "weight-weight percentage (% w/w)" are used interchangeably herein. Percent by weight refers to the percentage of a material on a mass basis as it is comprised in a composition, mixture, or solution.

The terms "increased", "enhanced" and "improved" are used interchangeably herein. These terms refer to a greater quantity or activity such as a quantity or activity slightly greater than the original quantity or activity, or a quantity or activity in large excess compared to the original quantity or activity, and including all quantities or activities in between. Alternatively, these terms may refer to, for example, a quantity or activity that is at least 1%, 2%, 3%, 4%, 5%, 6%, 7%, 8%, 9%, 10%, 11%, 12%, 13%, 14%, 15%, 16%, 17%, 18%, 19% or 20% more than the quantity or activity for which the increased quantity or activity is being compared.

The terms "polynucleotide", "polynucleotide sequence", and "nucleic acid sequence" are used interchangeably herein. These terms encompass nucleotide sequences and the like. A polynucleotide may be a polymer of DNA or RNA that is single- or double-stranded, that optionally contains synthetic, non-natural or altered nucleotide bases. A polynucleotide may be comprised of one or more segments of cDNA, genomic DNA, synthetic DNA, or mixtures thereof.

The term "gene" as used herein refers to a polynucleotide sequence that expresses a protein, and which may refer to the coding region alone or may include regulatory sequences upstream and/or downstream to the coding region (e.g., 5' untranslated regions upstream of the transcription start site of the coding region). A gene that is "native" or "endogenous" refers to a gene as found in nature with its own regulatory sequences; this gene is located in its natural location in the genome of an organism. "Chimeric gene" refers to any gene that is not a native gene, comprising regulatory and coding sequences that are not found together in nature. A "foreign" or "heterologous" gene refers to a gene that is introduced into the host organism by gene transfer. Foreign genes can comprise native genes inserted into a non-native organism, native genes introduced into a new location within the native host, or chimeric genes. The polynucleotide sequences in certain embodiments disclosed herein are heterologous. A "transgene" is a gene that has been introduced into the genome by a transformation procedure. A "codon-optimized gene" is a gene having its frequency of codon usage designed to mimic the frequency of preferred codon usage of the host cell.

A native amino acid sequence or polynucleotide sequence is naturally occurring, whereas a non-native amino acid sequence or polynucleotide sequence does not occur in nature.

"Coding sequence" as used herein refers to a DNA sequence that codes for a specific amino acid sequence. "Regulatory sequences" as used herein refer to nucleotide sequences located upstream of the coding sequence's transcription start site, 5' untranslated regions and 3' non-coding regions, and which may influence the transcription, RNA processing or stability, or translation of the associated coding sequence. Regulatory sequences may include promoters, enhancers, silencers, 5' untranslated leader sequence, introns, polyadenylation recognition sequences, RNA processing sites, effector binding sites, stem-loop structures and other elements involved in regulation of gene expression.

The term "recombinant" as used herein refers to an artificial combination of two otherwise separated segments of sequence, e.g., by chemical synthesis or by the manipulation of isolated segments of nucleic acids by genetic engineering techniques. The terms "recombinant", "transgenic", "transformed", "engineered" or "modified for exogenous gene expression" are used interchangeably herein.

The term "transformation" as used in certain embodiments refers to the transfer of a nucleic acid molecule into a host organism. The nucleic acid molecule may be a plasmid that replicates autonomously, or it may integrate into the genome of the host organism. Host organisms containing the transformed nucleic acid fragments are referred to as "transgenic" or "recombinant" or "transformed" organisms or "transformants".

The term "recombinant" or "heterologous" refers to an artificial combination of two otherwise separate segments of sequence, e.g., by chemical synthesis or by the manipulation of isolated segments of nucleic acids by genetic engineering techniques.

The terms "sequence identity" or "identity" as used herein with respect to polynucleotide or polypeptide sequences refer to the nucleic acid bases or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

The Basic Local Alignment Search Tool (BLAST) algorithm, which is available online at the National Center for Biotechnology Information (NCBI) website, may be used, for example, to measure percent identity between or among two or more of the polynucleotide sequences (BLASTN algorithm) or polypeptide sequences (BLASTP algorithm) disclosed herein. Alternatively, percent identity between sequences may be performed using a Clustal algorithm (e.g., ClustalW or ClustalV). For multiple alignments using a Clustal method of alignment, the default values may correspond to GAP PENALTY=10 and GAP LENGTH PENALTY=10. Default parameters for pairwise alignments and calculation of percent identity of protein sequences using a Clustal method may be KTUPLE=1, GAP PENALTY=3, WINDOW=5 and DIAGONALS SAVED=5. For nucleic acids, these parameters may be KTUPLE=2, GAP PENALTY=5, WINDOW=4 and DIAGONALS SAVED=4. Alternatively still, percent identity between sequences may be performed using an EMBOSS algorithm (e.g., needle) with parameters such as GAP OPEN=10, GAP EXTEND=0.5, END GAP PENALTY=false, END GAP OPEN=10, END GAP EXTEND=0.5 using a BLOSUM matrix (e.g., BLOSUM62).

Various polypeptide amino acid sequences and polynucleotide sequences are disclosed herein as features of certain embodiments of the disclosed invention. Variants of these sequences that are at least about 70-85%, 85-90%, or 90%-95% identical to the sequences disclosed herein can be used. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function/activity of the disclosed sequence, or at least about 85%, 86%, 87%, 88%, 89%, 90%, 91%, 92%, 93%, 94%, 95%, 96%, 97%, 98%, or 99% of the function/activity of the disclosed sequence.

The term "isolated" as used in certain embodiments refers to any cellular component that has been completely or partially purified from its native source (e.g., an isolated polynucleotide or polypeptide molecule). In some instances, an isolated polynucleotide or polypeptide molecule is part of a greater composition, buffer system or reagent mix. For example, the isolated polynucleotide or polypeptide molecule can be comprised within a cell or organism in a heterologous manner. Another example is an isolated glucosyltransferase enzyme.

Embodiments of the disclosed invention concern a reaction solution comprising water, sucrose and a glucosyltransferase enzyme that synthesizes poly alpha-1,3-glucan. The glucosyltransferase enzyme comprises an amino acid sequence that is at least 90% identical to the amino acid sequence of SEQ ID NO:4, SEQ ID NO:10, SEQ ID NO:12, SEQ ID NO:14, SEQ ID NO:20, SEQ ID NO:26, SEQ ID NO:28, SEQ ID NO:30, or SEQ ID NO:34. Significantly, these glucosyltransferase enzymes can synthesize poly alpha-1,3-glucan having at least 50% alpha-1,3 glycosidic linkages and a number average degree of polymerization of at least 100. Such glucan is suitable for use in spinning fibers and in other industrial applications.

The molecular weight of the poly alpha-1,3-glucan produced by the glucosyltransferase enzymes herein can be measured as $DP_n$ (number average degree of polymerization). Alternatively, the molecular weight of the poly alpha-1,3-glucan can be measured in terms of Daltons, grams/mole, or as $DP_w$ (weight average degree of polymerization). The poly alpha-1,3-glucan in certain embodiments of the invention can have a molecular weight in $DP_n$ or $DP_w$ of at least about 100. The molecular weight of the poly alpha-1,3-glucan can alternatively be at least about 250 $DP_n$ or $DP_w$. Alternatively still, the $DP_n$ or $DP_w$ of the poly alpha-1,3-glucan can be at least about 100, 150, 200, 250, 300, 350, 400, 450, 500, 550, 600, 650, 700, 750, 800, 850, 900, 950, or 1000 (or any integer between 100 and 1000).

The molecular weight of the poly alpha-1,3-glucan herein can be measured using any of several means known in the art. For example, glucan polymer molecular weight can be measured using high-pressure liquid chromatography (HPLC), size exclusion chromatography (SEC), or gel permeation chromatography (GPC).

The poly alpha-1,3-glucan herein is preferably linear/unbranched. The percentage of glycosidic linkages between the glucose monomer units of the poly alpha-1,3-glucan that are alpha-1,3 is at least about 50%, 60%, 70%, 80%, 90%, 95%, 96%, 97%, 98%, 99%, or 100%. In such embodiments, accordingly, the poly alpha-1,3-glucan has less than about 50%, 40%, 30%, 20%, 10%, 5%, 4%, 3%, 2%, 1%, or 0% of glycosidic linkages that are not alpha-1,3.

It is understood that the higher the percentage of alpha-1, 3-glycosidic linkages present in the poly alpha-1,3-glucan, the greater the probability that the poly alpha-1,3-glucan is linear, since there are lower occurrences of certain glycosidic linkages forming branch points in the polymer. In certain embodiments, the poly alpha-1,3-glucan has no branch points or less than about 10%, 9%, 8%, 7%, 6%, 5%, 4%, 3%, 2%, or 1% branch points as a percent of the glycosidic linkages in the polymer. Examples of branch points include alpha-1,6 branch points, such as those that are present in mutan polymer.

The glycosidic linkage profile of the poly alpha-1,3-glucan can be determined using any method known in the art. For example, the linkage profile can be determined using methods that use nuclear magnetic resonance (NMR) spectroscopy (e.g., $^{13}C$ NMR or $^{1}H$ NMR). These and other methods that can be used are disclosed in *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, Fla., 2005), which is incorporated herein by reference.

The poly alpha-1,3-glucan herein may be characterized by any combination of the aforementioned percentages of alpha-1,3 linkages and molecular weights. For example, the poly alpha-1,3-glucan produced in a reaction solution herein can have at least 50% alpha-1,3 glycosidic linkages and a $DP_n$ or $DP_w$ of at least 100. As another example, the poly alpha-1,3-glucan can have 100% alpha-1,3 glycosidic linkages and a $DP_n$ or $DP_w$ of at least 100. The poly alpha-1,3-glucan in still another example can have 100% alpha-1,3 glycosidic linkages and a $DP_n$ or $DP_w$ of at least 250.

The glucosyltransferase enzyme in certain embodiments of the invention may be derived from a *Streptococcus* species, *Leuconostoc* species or *Lactobacillus* species, for example. Examples of *Streptococcus* species from which the glucosyltransferase may be derived include *S. salivarius, S. sobrinus, S. dentirousetti, S. downei, S. mutans, S. oralis, S. gallolyticus* and *S. sanguinis*. Examples of *Leuconostoc* species from which the glucosyltransferase may be derived include *L. mesenteroides, L. amelibiosum, L. argentinum, L. carnosum, L. citreum, L. cremoris, L. dextranicum* and *L. fructosum*. Examples of *Lactobacillus* species from which the glucosyltransferase may be derived include *L. acidophilus, L. del-*

*brueckii, L. helveticus, L. salivarius, L. casei, L. curvatus, L. plantarum, L. sakei, L. brevis, L. buchneri, L. fermentum* and *L. reuteri*.

The glucosyltransferase enzyme herein can comprise, or consist of, an amino acid sequence that is at least 90% identical to the amino acid sequence provided in SEQ ID NO:4, SEQ ID NO:10, SEQ ID NO:12, SEQ ID NO:14, SEQ ID NO:20, SEQ ID NO:26, SEQ ID NO:28, SEQ ID NO:30, or SEQ ID NO:34, wherein the glucosyltransferase enzyme has activity. Alternatively, the glucosyltransferase enzyme can comprise, or consist of, an amino acid sequence that is at least 90%, 91%, 92%, 93%, 94%, 95%, 96%, 97%, 98%, or 99% identical to SEQ ID NO:4, SEQ ID NO:10, SEQ ID NO:12, SEQ ID NO:14, SEQ ID NO:20, SEQ ID NO:26, SEQ ID NO:28, SEQ ID NO:30, or SEQ ID NO:34, wherein the glucosyltransferase enzyme has activity.

All the amino acid residues disclosed herein at each amino acid position of the glucosyltransferase enzyme sequences are examples. Given that certain amino acids share similar structural and/or charge features with each other (i.e., conserved), the amino acid at each position in the glucosyltransferase enzyme sequences can be as provided in the disclosed sequences or substituted with a conserved amino acid residue ("conservative amino acid substitution") as follows:
1. The following small aliphatic, nonpolar or slightly polar residues can substitute for each other: Ala (A), Ser (S), Thr (T), Pro (P), Gly (G);
2. The following polar, negatively charged residues and their amides can substitute for each other: Asp (D), Asn (N), Glu (E), Gln (Q);
3. The following polar, positively charged residues can substitute for each other: H is (H), Arg (R), Lys (K);
4. The following aliphatic, nonpolar residues can substitute for each other: Ala (A), Leu (L), Ile (I), Val (V), Cys (C), Met (M); and
5. The following large aromatic residues can substitute for each other: Phe (F), Tyr (Y), Trp (W).

Examples of glucosyltransferase enzymes may be any of the amino acid sequences disclosed herein and that further include 1-300 (or any integer there between) residues on the N-terminus and/or C-terminus. Such additional residues may be from a corresponding wild type sequence from which the glucosyltransferase enzyme is derived, or may be another sequence such as an epitope tag (at either N- or C-terminus) or a heterologous signal peptide (at N-terminus), for example. Thus, examples of glucosyltransferase enzymes include SEQ ID NOs:61, 62, 63 and 64, which represent the wild type sequences from which SEQ ID NOs:30, 4, 28 and 20 are derived, respectively.

The glucosyltransferase enzyme can be encoded by the polynucleotide sequence provided in SEQ ID NO:3, SEQ ID NO:9, SEQ ID NO:11, SEQ ID NO:13, SEQ ID NO:19, SEQ ID NO:25, SEQ ID NO:27, SEQ ID NO:29, or SEQ ID NO:33, for example. Alternatively, the glucosyltransferase enzyme can be encoded by a polynucleotide sequence that is at least 90%, 91%, 92%, 93%, 94%, 95%, 96%, 97%, 98%, or 99% identical to SEQ ID NO:3, SEQ ID NO:9, SEQ ID NO:11, SEQ ID NO:13, SEQ ID NO:19, SEQ ID NO:25, SEQ ID NO:27, SEQ ID NO:29, or SEQ ID NO:33.

The glucosyltransferase enzyme in certain embodiments synthesizes poly alpha-1,3-glucan in which at least about 50%, 60%, 70%, 80%, 90%, 95%, 96%, 97%, 98%, 99%, or 100% (or any integer between 50% and 100%) of the constituent glycosidic linkages are alpha-1,3 linkages. In such embodiments, accordingly, the glucosyltransferase enzyme synthesizes poly alpha-1,3-glucan in which there is less than about 50%, 40%, 30%, 20%, 10%, 5%, 4%, 3%, 2%, or 1% of glycosidic linkages that are not alpha-1,3.

In other aspects, the glucosyltransferase enzyme synthesizes poly alpha-1,3-glucan with no branch points or less than about 10%, 9%, 8%, 7%, 6%, 5%, 4%, 3%, 2%, or 1% branch points as a percent of the glycosidic linkages in the polymer. Examples of branch points include alpha-1,6 branch points, such as those that are present in mutan polymer.

The glucosyltransferase enzyme can synthesize poly alpha-1,3-glucan having a molecular weight in $DP_n$ or $DP_w$ of at least about 100. Alternatively, the glucosyltransferase enzyme can synthesize poly alpha-1,3-glucan having a molecular weight in $DP_n$ or $DP_w$ of at least about 400. Alternatively still, the glucosyltransferase enzyme can synthesize poly alpha-1,3-glucan having a molecular weight in $DP_n$ or $DP_w$ of at least about 100, 150, 200, 250, 300, 350, 400, 450, 500, 550, 600, 650, 700, 750, 800, 850, 900, 950, or 1000 (or any integer between 100 and 1000).

One or more different glucosyltransferase enzymes may be used in the disclosed invention. The glucosyltransferase enzyme preferably does not have, or has very little (less than 1%), dextransucrase, reuteransucrase, or alternansucrase activity. The glucosyltransferase in certain embodiments does not comprise amino acid residues 2-1477 of SEQ ID NO:8 or amino acid residues 138-1477 of SEQ ID NO:8, which are derived from the glucosyltransferase identified in GENBANK under GI number 47527 (SEQ ID NO:60).

The glucosyltransferase enzyme herein can be primer-independent or primer-dependent. Primer-independent glucosyltransferase enzymes do not require the presence of a primer to perform glucan synthesis. A primer-dependent glucosyltransferase enzyme requires the presence of an initiating molecule in the reaction solution to act as a primer for the enzyme during glucan polymer synthesis. The term "primer" as used herein refers to any molecule that can act as the initiator for a glucosyltransferase enzyme. Oligosaccharides and polysaccharides can serve a primers herein, for example. Primers that can be used in certain embodiments include dextran and other carbohydrate-based primers, such as hydrolyzed glucan, for example. Hydrolyzed glucan can be prepared by acid hydrolysis of a glucan such as poly alpha-glucan. International Appl. Publ. No. WO2013/036918, which is incorporated herein by reference, discloses such preparation of hydrolyzed glucan using poly alpha-1,3-glucan as the starting material. Dextran for use as a primer herein can be dextran T10 (i.e., dextran having a molecular weight of 10 kD). Alternatively, the dextran can have a molecular weight of about 2, 4, 6, 8, 10, 12, 14, 16, 18, 20, or 25 kD, for example.

The glucosyltransferase enzyme used herein may be produced by any means known in the art (e.g., U.S. Pat. No. 7,000,000, which is incorporated herein by reference). For example, the glucosyltransferase enzyme may be produced recombinantly in any bacterial (e.g., *E. coli* such as TOP10, *Bacillus* sp.) or eukaryotic (e.g., yeasts such as *Pichia* sp. and *Saccharomyces* sp.) heterologous gene expression system. Any of the above-listed nucleic acid sequences can be used for this purpose, for example.

The glucosyltransferase enzyme used herein may be purified and/or isolated prior to its use, or may be used in the form of a cell lysate, for example. A cell lysate or extract may be prepared from a bacteria (e.g., *E. coli*) used to heterologously express the enzyme. For example, the bacteria may be subjected to disruption using a French pressure cell (French press). The glucosyltransferase enzyme is soluble in these type of preparations. The lysate or extract may be used at about 0.15-0.3% (v/v) in a reaction solution for producing poly alpha-1,3-glucan from sucrose. In certain embodiments, a bacterial cell lysate is first cleared of insoluble material by means such as centrifugation or filtration.

In certain embodiments, the heterologous gene expression system may be one that is designed for protein secretion. The glucosyltransferase enzyme comprises a signal peptide (signal sequence) in such embodiments. The signal peptide may be either its native signal peptide or a heterologous signal peptide.

The activity of the glucosyltransferase enzyme can be determined using any method known in the art. For example, glucosyltransferase enzyme activity can be determined by measuring the production of reducing sugars (fructose and glucose) in a reaction solution containing sucrose (50 g/L), dextran T10 (1 mg/mL) and potassium phosphate buffer (pH 6.5, 50 mM), where the solution is held at 22-25° C. for 24-30 hours. The reducing sugars can be measured by adding 0.01 mL of the reaction solution to a mixture containing 1 N NaOH and 0.1% triphenyltetrazolium chloride and then monitoring the increase in absorbance at $OD_{480nm}$ for five minutes.

The temperature of the reaction solution herein can be controlled, if desired. In certain embodiments, the solution has a temperature between about 5° C. to about 50° C. The temperature of the solution in certain other embodiments is between about 20° C. to about 40° C. Alternatively, the temperature of the solution may be about 20, 21, 22, 23, 24, 25, 26, 27, 28, 29, 30, 31, 32, 33, 34, 35, 36, 37, 38, 39, or 40° C.

The temperature of the reaction solution may be maintained using various means known in the art. For example, the temperature of reaction solution can be maintained by placing the vessel containing the reaction solution in an air or water bath incubator set at the desired temperature.

The initial concentration of the sucrose in the solution can be about 20 g/L to about 400 g/L, for example. Alternatively, the initial concentration of the sucrose can be about 75 g/L to about 175 g/L, or from about 50 g/L to about 150 g/L. Alternatively still, the initial concentration of the sucrose can be about 40, 50, 60, 70, 80, 90, 100, 110, 120, 130, 140, 150, or 160 g/L (or any integer between 40 and 160 g/L), for example. The "initial concentration of sucrose" refers to the sucrose concentration in the solution just after all the reaction solution components have been added (water, sucrose, gtf enzyme).

Sucrose used in the reaction solution can be highly pure 99.5%) or be of any other purity or grade. For example, the sucrose can have a purity of at least 99.0%, or be reagent grade sucrose. The sucrose may be derived from any renewable sugar source such as sugar cane, sugar beets, cassava, sweet sorghum, or corn. The sucrose can be provided in any form such as crystalline form or non-crystalline form (e.g., syrup or cane juice).

The pH of the reaction solution herein can be between about 4.0 to about 8.0. Alternatively, the pH can be about 4.0, 4.5, 5.0, 5.5, 6.0, 6.5, 7.0, 7.5, or 8.0. In certain embodiments, the pH of a solution containing water and sucrose may be set before adding the glucosyltransferase enzyme. The pH of the reaction solution can be adjusted or controlled by the addition or incorporation of a suitable buffer, including but not limited to: phosphate, tris, citrate, or a combination thereof. The concentration of the buffer can be from 0 mM to about 100 mM, or about 10, 20, or 50 mM, for example. A suitable amount of DTT (dithiothreitol, e.g., about 1.0 mM) can optionally be added to the reaction solution.

The disclosed invention also concerns a method for producing poly alpha-1,3-glucan comprising the step of contacting at least water, sucrose, and a glucosyltransferase enzyme that synthesizes poly alpha-1,3-glucan. The glucosyltransferase enzyme can comprise an amino acid sequence that is at least 90% identical to the amino acid sequence of SEQ ID NO:4, SEQ ID NO:10, SEQ ID NO:12, SEQ ID NO:14, SEQ ID NO:20, SEQ ID NO:26, SEQ ID NO:28, SEQ ID NO:30, or SEQ ID NO:34. The poly alpha-1,3-glucan produced in this method can optionally be isolated.

Water, sucrose, and a glucosyltransferase enzyme as described herein are contacted in a reaction solution. Thus, the method can comprise providing a reaction solution comprising water, sucrose and a glucosyltransferase enzyme as described herein. It will be understood that, as the glucosyltransferase enzyme synthesizes poly alpha-1,3-glucan, the reaction solution becomes a reaction mixture given that insoluble poly alpha-1,3-glucan falls out of solution as indicated by clouding of the reaction. The contacting step of the disclosed method can be performed in any number of ways. For example, the desired amount of sucrose can first be dissolved in water (optionally, other components may also be added at this stage of preparation, such as buffer components), followed by the addition of the glucosyltransferase enzyme. The solution may be kept still, or agitated via stirring or orbital shaking, for example. The reaction can be, and typically is, cell-free.

The glucosyltransferase enzyme can optionally be added to water or an aqueous solution (e.g., sucrose in water) that does not contain salt or buffer when initially preparing the reaction solution. The pH of such a preparation can then be modified as desired, such as to pH 5-6 for example. The reaction can be carried out to completion without any added buffer, if desired.

Completion of the reaction in certain embodiments can be determined visually (no more accumulation of precipitated poly alpha-1,3-glucan) and/or by measuring the amount of sucrose left in the solution (residual sucrose), where a percent sucrose consumption of over about 90% can indicate reaction completion. Typically, a reaction of the disclosed process will take about 12, 24, 36, 48, 60, 72, 84, or 96 hours to complete, depending on certain parameters such as the amount of sucrose and glucosyltransferase enzyme used in the reaction.

The percent sucrose consumption of a reaction in certain embodiments of the disclosed process is at least 90%, 91%, 92%, 93%, 94%, 95%, 96%, 97%, 98%, 99%, or 100%. Alternatively, the percent sucrose consumption may be >90% or >95%.

The yield of the poly alpha-1,3-glucan produced in the disclosed invention can be at least about 5%, 6%, 7%, 8%, 9%, 10%, 11%, 12%, 13%, 14%, 15%, 16%, 17%, 18%, 19%, or 20%, based on the weight of the sucrose used in the reaction solution.

The poly alpha-1,3-glucan produced in the disclosed method may optionally be isolated. For example, insoluble poly alpha-1,3-glucan may be separated by centrifugation or filtration. In doing so, the poly alpha-1,3-glucan is separated from the rest of the reaction solution, which may comprise water, fructose and certain byproducts (e.g., leucrose, soluble oligosaccharides DP2-DP7). This solution may also comprise residual sucrose and glucose monomer.

Poly alpha-1,3 glucan is a potentially low cost polymer which can be enzymatically produced from renewable resources containing sucrose using glucosyltransferase enzymes. It has been shown that this polymer can form ordered liquid crystalline solutions when the polymer is dissolved in a solvent under certain conditions (U.S. Pat. No. 7,000,000). Such solutions can be spun into continuous, high strength, cotton-like fibers. The poly alpha-1,3-glucan produced using the disclosed invention has comparable utilities.

EXAMPLES

The disclosed invention is further defined in the following Examples. It should be understood that these Examples, while indicating certain preferred aspects of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Abbreviations

The meanings of some of the abbreviations used herein are as follows: "g" means gram(s), "h" means hour(s), "mL" means milliliter(s), "psi" means pound(s) per square inch, "wt %" means weight percentage, "µm" means micrometer(s), "° C." means degrees Celsius, "mg" means milligram(s), "mm" means millimeter(s), "µL" means microliter(s), "mmol" means millimole(s), "min" means minute(s), "mol %" means mole percent, "M" means molar, "rpm" means revolutions per minute, "MPa" means megaPascals.

General Methods

Preparation of Crude Extracts of Glucosyltransferase (Gtf) Enzymes

Gtf enzymes were prepared as follows. E. coli TOP10® cells (Invitrogen, Carlsbad Calif.) were transformed with a pJexpress404®-based construct containing a particular gtf-encoding DNA sequence. Each sequence was codon-optimized to express the gtf enzyme in E. coli. Individual E. coli strains expressing a particular gtf enzyme were grown in LB (Luria broth) medium (Becton, Dickinson and Company, Franklin Lakes, N.J.) with ampicillin (100 µg/mL) at 37° C. with shaking to $OD_{600}$=0.4-0.5, at which time IPTG (isopropyl beta-D-1-thiogalactopyranoside, Cat. No. 16758, Sigma-Aldrich, St. Louis, Mo.) was added to a final concentration of 0.5 mM. The cultures were incubated for 2-4 hours at 37° C. following IPTG induction. Cells were harvested by centrifugation at 5,000×g for 15 minutes and resuspended (20% w/v) in 50 mM phosphate buffer pH 7.0 supplemented with dithiothreitol (DTT, 1.0 mM). Resuspended cells were passed through a French Pressure Cell (SLM Instruments, Rochester, N.Y.) twice to ensure >95% cell lysis. Lysed cells were centrifuged for 30 minutes at 12,000×g at 4° C. The resulting supernatant was analyzed by the BCA (bicinchoninic acid) protein assay (Sigma-Aldrich) and SDS-PAGE to confirm expression of the gtf enzyme, and the supernatant was stored at −20° C.

Determination of Gtf Enzymatic Activity

Gtf enzyme activity was confirmed by measuring the production of reducing sugars (fructose and glucose) in a gtf reaction solution. A reaction solution was prepared by adding a gtf extract (prepared as above) to a mixture containing sucrose (50 or 150 g/L), potassium phosphate buffer (pH 6.5, 50 mM), and optionally dextran (1 mg/mL, dextran T10, Cat. No. D9260, Sigma-Aldrich); the gtf extract was added to 2.5%-5% by volume. The reaction solution was then incubated at 22-25° C. for 24-30 hours, after which it was centrifuged. Supernatant (0.01 mL) was added to a mixture containing 1 N NaOH and 0.1% triphenyltetrazolium chloride (Sigma-Aldrich). The mixture was incubated for five minutes after which its $OD_{480nm}$ was determined using an ULTROSPEC spectrophotometer (Pharmacia LKB, New York, N.Y.) to gauge the presence of the reducing sugars fructose and glucose.

Determination of Glycosidic Linkages

Glycosidic linkages in the glucan product synthesized by a gtf enzyme were determined by $^{13}C$ NMR (nuclear magnetic resonance). Dry glucan polymer (25-30 mg) was dissolved in 1 mL of deuterated dimethyl sulfoxide (DMSO) containing 3% by weight of LiCl with stirring at 50° C. Using a glass pipet, 0.8 mL of the solution was transferred into a 5-mm NMR tube. A quantitative $^{13}$C NMR spectrum was acquired using a Bruker Avance 500-MHz NMR spectrometer (Billerica, Mass.) equipped with a CPDUL cryoprobe at a spectral frequency of 125.76 MHz, using a spectral window of 26041.7 Hz. An inverse gated decoupling pulse sequence using waltz decoupling was used with an acquisition time of 0.629 second, an inter-pulse delay of 5 seconds, and 6000 pulses. The time domain data was transformed using an exponential multiplication of 2.0 Hz.

Determination of Number Average Degree of Polymerization ($DP_n$)

The $DP_n$ of a glucan product synthesized by a gtf enzyme was determined by size-exclusion chromatography (SEC). Dry glucan polymer was dissolved at 5 mg/mL in N,N-dimethyl-acetamide (DMAc) and 5% LiCl with overnight shaking at 100° C. The SEC system used was an Alliance™ 2695 separation module from Waters Corporation (Milford, Mass.) coupled with three on-line detectors: a differential refractometer 2410 from Waters, a multiangle light scattering photometer Heleos™ 8+ from Wyatt Technologies (Santa Barbara, Calif.), and a differential capillary viscometer ViscoStar™ from Wyatt. The columns used for SEC were four styrene-divinyl benzene columns from Shodex (Japan) and two linear KD-806M, KD-802 and KD-801 columns to improve resolution at the low molecular weight region of a polymer distribution. The mobile phase was DMAc with 0.11% LiCl. The chromatographic conditions used were 50° C. in the column and detector compartments, 40° C. in the sample and injector compartment, a flow rate of 0.5 mL/min, and an injection volume of 100 μL. The software packages used for data reduction were Empower™ version 3 from Waters (calibration with broad glucan polymer standard) and Astra® version 6 from Wyatt (triple detection method with column calibration).

Example 1

Production of Gtf Enzyme 0874 (SEQ ID NO:2)

This Example describes preparing an N-terminally truncated version of a *Streptococcus sobrinus* gtf enzyme identified in GENBANK under GI number 450874 (SEQ ID NO:2, encoded by SEQ ID NO:1; herein referred to as "0874").

A nucleotide sequence encoding gtf 0874 was synthesized using codons optimized for protein expression in *E. coli* (DNA2.0, Inc., Menlo Park, Calif.). The nucleic acid product (SEQ ID NO:1), encoding gtf 0874 (SEQ ID NO:2), was subcloned into pJexpress404® (DNA2.0, Inc.) to generate the plasmid construct identified as pMP57. This plasmid construct was used to transform *E. coli* TOP10 cells (Invitrogen, Carlsbad, Calif.) to generate the strain identified as TOP10/pMP57.

Production of gtf 0874 by bacterial expression and determination of its enzymatic activity were performed following the procedures disclosed in the General Methods section. The enzymatic activity of gtf 0874 is shown in Table 2 (see Example 18 below).

Example 2

Production of Gtf Enzyme 6855 (SEQ ID NO:4)

This Example describes preparing an N-terminally truncated version of a *Streptococcus salivarius* gtf enzyme identified in GENBANK under GI number 228476855 (SEQ ID NO:4, encoded by SEQ ID NO:3; herein referred to as "6855").

A nucleotide sequence encoding gtf 6855 was synthesized using codons optimized for protein expression in *E. coli* (DNA2.0, Inc.). The nucleic acid product (SEQ ID NO:3), encoding gtf 6855 (SEQ ID NO:4), was subcloned into pJexpress404® to generate the plasmid construct identified as pMP53. This plasmid construct was used to transform *E. coli* TOP10 cells to generate the strain identified as TOP10/pMP53.

Production of gtf 6855 by bacterial expression and determination of its enzymatic activity were performed following the procedures disclosed in the General Methods section. The enzymatic activity of gtf 6855 is shown in Table 2 (see Example 18 below).

Example 3

Production of Gtf Enzyme 2379 (SEQ ID NO:6)

This Example describes preparing an N-terminally truncated version of a *Streptococcus salivarius* gtf enzyme identified in GENBANK under GI number 662379 (SEQ ID NO:6, encoded by SEQ ID NO:5; herein referred to as "2379").

A nucleotide sequence encoding gtf 2379 was synthesized using codons optimized for protein expression in *E. coli* (DNA2.0, Inc.). The nucleic acid product (SEQ ID NO:5), encoding gtf 2379 (SEQ ID NO:6), was subcloned into pJexpress404® to generate the plasmid construct identified as pMP66. This plasmid construct was used to transform *E. coli* TOP10 cells to generate the strain identified as TOP10/pMP66.

Production of gtf 2379 by bacterial expression and determination of its enzymatic activity were performed following the procedures disclosed in the General Methods section. The enzymatic activity of gtf 2379 is shown in Table 2 (see Example 18 below).

Example 4

Production of Gtf Enzyme 7527 (GtfJ, SEQ ID NO:8)

This Example describes preparing an N-terminally truncated version of a *Streptococcus salivarius* gtf enzyme identified in GENBANK under GI number 47527 (SEQ ID NO:8, encoded by SEQ ID NO:7; herein referred to as "7527" or "GtfJ").

A nucleotide sequence encoding gtf 7527 was synthesized using codons optimized for protein expression in *E. coli* (DNA2.0, Inc.). The nucleic acid product (SEQ ID NO:7), encoding gtf 7527 (SEQ ID NO:8), was subcloned into pJexpress404® to generate the plasmid construct identified as pMP65. This plasmid construct was used to transform *E. coli* TOP10 cells to generate the strain identified as TOP10/pMP65.

Production of gtf 7527 by bacterial expression and determination of its enzymatic activity were performed following the procedures disclosed in the General Methods section. The enzymatic activity of gtf 7527 is shown in Table 2 (see Example 18 below).

Example 5

Production of Gtf Enzyme 1724 (SEQ ID NO:10)

This Example describes preparing an N-terminally truncated version of a *Streptococcus downei* gtf enzyme identified in GENBANK under GI number 121724 (SEQ ID NO:10, encoded by SEQ ID NO:9; herein referred to as "1724").

A nucleotide sequence encoding gtf 1724 was synthesized using codons optimized for protein expression in *E. coli* (DNA2.0, Inc.). The nucleic acid product (SEQ ID NO:9), encoding gtf 1724 (SEQ ID NO:10), was subcloned into pJexpress404® to generate the plasmid construct identified as pMP52. This plasmid construct was used to transform *E. coli* TOP10 cells to generate the strain identified as TOP10/pMP52.

Production of gtf 1724 by bacterial expression and determination of its enzymatic activity were performed following the procedures disclosed in the General Methods section. The enzymatic activity of gtf 1724 is shown in Table 2 (see Example 18 below).

Example 6

Production of Gtf Enzyme 0544 (SEQ ID NO:12)

This Example describes preparing an N-terminally truncated version of a *Streptococcus mutans* gtf enzyme identified in GENBANK under GI number 290580544 (SEQ ID NO:12, encoded by SEQ ID NO:11; herein referred to as "0544").

A nucleotide sequence encoding gtf 0544 was synthesized using codons optimized for protein expression in *E. coli* (DNA2.0, Inc.). The nucleic acid product (SEQ ID NO:11), encoding gtf 0544 (SEQ ID NO:12), was subcloned into pJexpress404® to generate the plasmid construct identified as pMP55. This plasmid construct was used to transform *E. coli* TOP10 cells to generate the strain identified as TOP10/pMP55.

Production of gtf 0544 by bacterial expression and determination of its enzymatic activity were performed following the procedures disclosed in the General Methods section. The enzymatic activity of gtf 0544 is shown in Table 2 (see Example 18 below).

Example 7

Production of Gtf Enzyme 5926 (SEQ ID NO:14)

This Example describes preparing an N-terminally truncated version of a *Streptococcus dentirousetti* gtf enzyme identified in GENBANK under GI number 167735926 (SEQ ID NO:14, encoded by SEQ ID NO:13; herein referred to as "5926").

A nucleotide sequence encoding gtf 5926 was synthesized using codons optimized for protein expression in *E. coli* (DNA2.0, Inc.). The nucleic acid product (SEQ ID NO:13), encoding gtf 5926 (SEQ ID NO:14), was subcloned into pJexpress404® to generate the plasmid construct identified as pMP67. This plasmid construct was used to transform *E. coli* TOP10 cells to generate the strain identified as TOP10/pMP67.

Production of gtf 5926 by bacterial expression and determination of its enzymatic activity were performed following the procedures disclosed in the General Methods section. The enzymatic activity of gtf 5926 is shown in Table 2 (see Example 18 below).

Example 8

Production of Gtf Enzyme 4297 (SEQ ID NO:16)

This Example describes preparing an N-terminally truncated version of a *Streptococcus oralis* gtf enzyme identified in GENBANK under GI number 7684297 (SEQ ID NO:16, encoded by SEQ ID NO:15; herein referred to as "4297").

A nucleotide sequence encoding gtf 4297 was synthesized using codons optimized for protein expression in *E. coli* (DNA2.0, Inc.). The nucleic acid product (SEQ ID NO:15), encoding gtf 4297 (SEQ ID NO:16), was subcloned into pJexpress404® to generate the plasmid construct identified as pMP62. This plasmid construct was used to transform *E. coli* TOP10 cells to generate the strain identified as TOP10/pMP62.

Production of gtf 4297 by bacterial expression and determination of its enzymatic activity were performed following the procedures disclosed in the General Methods section. The enzymatic activity of gtf 4297 is shown in Table 2 (see Example 18 below).

Example 9

Production of Gtf Enzyme 5618 (SEQ ID NO:18)

This Example describes preparing an N-terminally truncated version of a *Streptococcus sanguinis* gtf enzyme identified in GENBANK under GI number 328945618 (SEQ ID NO:18, encoded by SEQ ID NO:17; herein referred to as "5618").

A nucleotide sequence encoding gtf 5618 was synthesized using codons optimized for protein expression in *E. coli* (DNA2.0, Inc.). The nucleic acid product (SEQ ID NO:17), encoding gtf 5618 (SEQ ID NO:18), was subcloned into pJexpress404® to generate the plasmid construct identified as pMP56. This plasmid construct was used to transform *E. coli* TOP10 cells to generate the strain identified as TOP10/pMP56.

Production of gtf 5618 by bacterial expression and determination of its enzymatic activity were performed following the procedures disclosed in the General Methods section. The enzymatic activity of gtf 5618 is shown in Table 2 (see Example 18 below).

Example 10

Production of Gtf Enzyme 2765 (SEQ ID NO:20)

This Example describes preparing an N-terminally truncated version of a *Streptococcus sp.* gtf enzyme identified in GENBANK under GI number 322372765 (SEQ ID NO:20, encoded by SEQ ID NO:19; herein referred to as "2765").

A nucleotide sequence encoding gtf 2765 was synthesized using codons optimized for protein expression in *E. coli* (DNA2.0, Inc.). The nucleic acid product (SEQ ID NO:19), encoding gtf 2765 (SEQ ID NO:20), was subcloned into pJexpress404® to generate the plasmid construct identified as pMP73. This plasmid construct was used to transform *E. coli* TOP10 cells to generate the strain identified as TOP10/pMP73.

Production of gtf 2765 by bacterial expression and determination of its enzymatic activity were performed following the procedures disclosed in the General Methods section. The enzymatic activity of gtf 2765 is shown in Table 2 (see Example 18 below).

Example 11

Production of Gtf Enzyme 4700 (SEQ ID NO:22)

This Example describes preparing an N-terminally truncated version of a *Leuconostoc mesenteroides* gtf enzyme identified in GENBANK under GI number 21654700 (SEQ ID NO:22, encoded by SEQ ID NO:21; herein referred to as "4700").

A nucleotide sequence encoding gtf 2765 was synthesized using codons optimized for protein expression in *E. coli* (DNA2.0, Inc.). The nucleic acid product (SEQ ID NO:21), encoding gtf 4700 (SEQ ID NO:22), was subcloned into pJexpress404® to generate the plasmid construct identified as pMP83. This plasmid construct was used to transform *E. coli* TOP10 cells to generate the strain identified as TOP10/pMP83.

Production of gtf 4700 by bacterial expression and determination of its enzymatic activity were performed following the procedures disclosed in the General Methods section. The enzymatic activity of gtf 4700 is shown in Table 2 (see Example 18 below).

Example 12

Production of Gtf Enzyme 1366 (SEQ ID NO:24)

This Example describes preparing an N-terminally truncated version of a *Streptococcus criceti* gtf enzyme identified in GENBANK under GI number 146741366 (SEQ ID NO:24, encoded by SEQ ID NO:23; herein referred to as "1366").

A nucleotide sequence encoding gtf 1366 was synthesized using codons optimized for protein expression in *E. coli* (DNA2.0, Inc.). The nucleic acid product (SEQ ID NO:23), encoding gtf 1366 (SEQ ID NO:24), was subcloned into pJexpress404® to generate the plasmid construct identified as pMP86. This plasmid construct was used to transform *E. coli* TOP10 cells to generate the strain identified as TOP10/pMP86.

Production of gtf 1366 by bacterial expression and determination of its enzymatic activity were performed following the procedures disclosed in the General Methods section. The enzymatic activity of gtf 1366 is shown in Table 2 (see Example 18 below).

Example 13

Production of Gtf Enzyme 0427 (SEQ ID NO:26)

This Example describes preparing an N-terminally truncated version of a *Streptococcus sobrinus* gtf enzyme identified in GENBANK under GI number 940427 (SEQ ID NO:26, encoded by SEQ ID NO:25; herein referred to as "0427").

A nucleotide sequence encoding gtf 0427 was synthesized using codons optimized for protein expression in *E. coli* (DNA2.0, Inc.). The nucleic acid product (SEQ ID NO:25), encoding gtf 0427 (SEQ ID NO:26), was subcloned into pJexpress404® to generate the plasmid construct identified as pMP87. This plasmid construct was used to transform *E. coli* TOP10 cells to generate the strain identified as TOP10/pMP87.

Production of gtf 0427 by bacterial expression and determination of its enzymatic activity were performed following the procedures disclosed in the General Methods section. The enzymatic activity of gtf 0427 is shown in Table 2 (see Example 18 below).

Example 14

Production of Gtf Enzyme 2919 (SEQ ID NO:28)

This Example describes preparing an N-terminally truncated version of a *Streptococcus salivarius* gtf enzyme identified in GENBANK under GI number 383282919 (SEQ ID NO:28, encoded by SEQ ID NO:27; herein referred to as "2919").

A nucleotide sequence encoding gtf 2919 was synthesized using codons optimized for protein expression in *E. coli* (DNA2.0, Inc.). The nucleic acid product (SEQ ID NO:27), encoding gtf 2919 (SEQ ID NO:28), was subcloned into pJexpress404® to generate the plasmid construct identified as pMP88. This plasmid construct was used to transform *E. coli* TOP10 cells to generate the strain identified as TOP10/pMP88.

Production of gtf 2919 by bacterial expression and determination of its enzymatic activity were performed following the procedures disclosed in the General Methods section. The enzymatic activity of gtf 2919 is shown in Table 2 (see Example 18 below).

Example 15

Production of Gtf Enzyme 2678 (SEQ ID NO:30)

This Example describes preparing an N-terminally truncated version of a *Streptococcus salivarius* gtf enzyme identified in GENBANK under GI number 400182678 (SEQ ID NO:30 encoded by SEQ ID NO:29; herein referred to as "2678").

A nucleotide sequence encoding gtf 2678 was synthesized using codons optimized for protein expression in *E. coli* (DNA2.0, Inc.). The nucleic acid product (SEQ ID NO:29), encoding gtf 2678 (SEQ ID NO:30), was subcloned into pJexpress404® to generate the plasmid construct identified as pMP89. This plasmid construct was used to transform *E. coli* TOP10 cells to generate the strain identified as TOP10/pMP89.

Production of gtf 2678 by bacterial expression and determination of its enzymatic activity were performed following the procedures disclosed in the General Methods section. The enzymatic activity of gtf 2678 is shown in Table 2 (see Example 18 below).

Example 16

Production of Gtf Enzyme 2381 (SEQ ID NO:32)

This Example describes preparing an N-terminally truncated version of a *Streptococcus salivarius* gtf enzyme identified in GENBANK under GI number 662381 (SEQ ID NO:32 encoded by SEQ ID NO:31; herein referred to as "2381").

A nucleotide sequence encoding gtf 2381 was synthesized using codons optimized for protein expression in *E. coli* (DNA2.0, Inc.). The nucleic acid product (SEQ ID NO:31), encoding gtf 2381 (SEQ ID NO:32), was subcloned into pJexpress404® to generate the plasmid construct identified as pMP96. This plasmid construct was used to transform *E. coli* TOP10 cells to generate the strain identified as TOP10/pMP96.

Production of gtf 2381 by bacterial expression and determination of its enzymatic activity were performed following the procedures disclosed in the General Methods section. The enzymatic activity of gtf 2381 is shown in Table 2 (see Example 18 below).

Example 17

Production of Gtf Enzyme 3929 (SEQ ID NO:34) and Additional Gtf Enzymes

This Example describes preparing an N-terminally truncated version of a *Streptococcus salivarius* gtf enzyme identified in GENBANK under GI number 387783929 (SEQ ID NO:34 encoded by SEQ ID NO:33; herein referred to as "3929").

A nucleotide sequence encoding gtf 3929 was synthesized using codons optimized for protein expression in *E. coli* (DNA2.0, Inc.). The nucleic acid product (SEQ ID NO:33), encoding gtf 3929 (SEQ ID NO:34), was subcloned into pJexpress404® to generate the plasmid construct identified as pMP97. This plasmid construct was used to transform *E. coli* TOP10 cells to generate the strain identified as TOP10/pMP97.

Production of gtf 3929 by bacterial expression and determination of its enzymatic activity were performed following the procedures disclosed in the General Methods section. The enzymatic activity of gtf 3929 is shown in Table 2 (see Example 18 below).

Additional gtf enzymes were produced in a similar manner. Briefly, N-terminally truncated versions of enzymes identified in GENBANK under GI numbers 228476907 (a *Streptococcus salivarius* gtf, SEQ ID NO:36, herein referred to as "6907"), 228476661 (a *Streptococcus salivarius* gtf, SEQ ID NO:38, herein referred to as "6661"), 334280339 (a *Streptococcus gallolyticus* gtf, SEQ ID NO:40, herein referred to as "0339"), 3130088 (a *Streptococcus mutans* gtf, SEQ ID NO:42, herein referred to as "0088"), 24379358 (a *Streptococcus mutans* gtf, SEQ ID NO:44, herein referred to as "9358"), 325978242 (a *Streptococcus gallolyticus* gtf, SEQ ID NO:46, herein referred to as "8242"), 324993442 (a *Streptococcus sanguinis* gtf, SEQ ID NO:48, herein referred to as "3442"), 47528 (a *Streptococcus salivarius* gtf, SEQ ID NO:50, herein referred to as "7528"), 322373279 (a *Streptococcus* sp. gtf, SEQ ID NO:52, herein referred to as "3279"), 170016491 (a *Leuconostoc citreum* gtf, SEQ ID NO:54, herein referred to as "6491"), 228476889 (a *Streptococcus salivarius* gtf, SEQ ID NO:56, herein referred to as "6889"), 51574154 (a *Lactobacillus reuteri* gtf, SEQ ID NO:58, herein referred to as "4154"), and 322373298 (a *Streptococcus* sp. gtf, SEQ ID NO:59, herein referred to as "3298") were prepared and tested for enzymatic activity (Table 2, see Example 18 below).

Example 18

Production of Insoluble Glucan Polymer with Gtf Enzymes

This Example describes using the gtf enzymes prepared in the above Examples to synthesize glucan polymer.

Reactions were performed with each of the above gtf enzymes following the procedures disclosed in the General Methods section. Briefly, gtf reaction solutions were prepared comprising sucrose (50 g/L), potassium phosphate buffer (pH 6.5, 50 mM) and a gtf enzyme (2.5% extract by volume). After 24-30 hours at 22-25° C., insoluble glucan polymer product was harvested by centrifugation, washed three times with water, washed once with ethanol, and dried at 50° C. for 24-30 hours.

Following the procedures disclosed in the General Methods section, the glycosidic linkages in the insoluble glucan polymer product from each reaction were determined by $^{13}C$ NMR, and the $DP_n$ for each product was determined by SEC. The results of these analyses are shown in Table 2.

TABLE 2

Linkages and $DP_n$ of Glucan Produced by Various Gtf Enzymes

| Gtf | SEQ ID NO. | Reducing Sugars Produced? | Insoluble Glucan Produced? | Glucan Alpha Linkages | | $DP_n$ |
|---|---|---|---|---|---|---|
| | | | | % 1, 3 | % 1, 6 | |
| 0874 | 2 | yes | yes | 100 | 0 | 60 |
| 6855 | 4 | yes | yes | 100 | 0 | 440 |
| 2379 | 6 | yes | yes | 37 | 63 | 310 |
| 7527 | 8 | yes | yes | 100 | 0 | 440 |
| 1724 | 10 | yes | yes | 100 | 0 | 250 |
| 0544 | 12 | yes | yes | 62 | 36 | 980 |
| 5926 | 14 | yes | yes | 100 | 0 | 260 |
| 4297 | 16 | yes | yes | 31 | 67 | 800 |
| 5618 | 18 | yes | yes | 34 | 66 | 1020 |
| 2765 | 20 | yes | yes | 100 | 0 | 280 |
| 4700 | 22 | yes | no | | | |
| 1366 | 24 | yes | no | | | |
| 0427 | 26 | yes | yes | 100 | 0 | 120 |
| 2919 | 28 | yes | yes | 100 | 0 | 250 |
| 2678 | 30 | yes | yes | 100 | 0 | 390 |
| 2381 | 32 | yes | no | | | |
| 3929 | 34 | yes | yes | 100 | 0 | 280 |
| 6907 | 36 | yes | no | | | |
| 6661 | 38 | yes | no | | | |
| 0339 | 40 | yes | no | | | |
| 0088 | 42 | yes | no | | | |
| 9358 | 44 | yes | no | | | |
| 8242 | 46 | yes | no | | | |
| 3442 | 48 | yes | no | | | |
| 7528 | 50 | yes | no | | | |
| 3279 | 52 | yes | no | | | |
| 6491 | 54 | yes | no | | | |
| 6889 | 56 | yes | no | | | |
| 4154 | 58 | yes | no | | | |
| 3298 | 59 | yes | no | | | |
| none | na | no | no | | | |

Several gtf enzymes produced insoluble glucan products (Table 2). However, only gtf enzymes 6855 (SEQ ID NO:4), 7527 (gtfJ, SEQ ID NO:8), 1724 (SEQ ID NO:10), 0544 (SEQ ID NO:12), 5926 (SEQ ID NO:14), 2765 (SEQ ID NO:20), 0427 (SEQ ID NO:26), 2919 (SEQ ID NO:28), 2678 (SEQ ID NO:30), and 3929 (SEQ ID NO:34) produced glucan comprising at least 50% alpha-1,3 linkages and having a $DP_n$ of at least 100. These enzymes are therefore suitable for producing glucan polymers for fiber applications.

Only gtfs 6855 (SEQ ID NO:4), 7527 (gtfJ, SEQ ID NO:8), 1724 (SEQ ID NO:10), 5926 (SEQ ID NO:14), 2765 (SEQ ID NO:20), 0427 (SEQ ID NO:26), 2919 (SEQ ID NO:28), 2678 (SEQ ID NO:30), and 3929 (SEQ ID NO:34) produced glucan polymer comprising 100% alpha-1,3 linkages and having a $DP_n$ of at least 100. These results, in which only nine out of thirty gtfs were able to produce glucan with 100% alpha-1,3 linkages and a $DP_n$ of at least 100, indicate that not all gtf enzymes are capable of producing high molecular weight, insoluble glucan with a high level of alpha-1,3 linkages. Fewer gtf enzymes were able to produce glucan polymer comprising 100% alpha-1,3 linkages and having a $DP_n$ of at least 250.

Thus, gtf enzymes capable of producing glucan polymer comprising 100% alpha-1,3 linkages and a $DP_n$ of at least 100 were identified. These enzymes can be used to produce glucan suitable for producing fibers.

What is claimed is:

1. A reaction solution comprising water, sucrose and a glucosyltransferase enzyme that synthesizes poly alpha-1,3-glucan, wherein said glucosyltransferase enzyme consists of an amino acid sequence that is at least 93% identical to SEQ ID NO:10.

2. The reaction solution of claim 1, wherein said glucosyltransferase enzyme synthesizes poly alpha-1,3-glucan having at least 50% alpha-1,3 glycosidic linkages and a number average degree of polymerization of at least 100.

3. The reaction solution of claim 2, wherein said glucosyltransferase enzyme synthesizes poly alpha-1,3-glucan having 100% alpha-1,3 glycosidic linkages and a number average degree of polymerization of at least 100.

4. The reaction solution of claim 3, wherein said glucosyltransferase enzyme synthesizes poly alpha-1,3-glucan having 100% alpha-1,3 glycosidic linkages and a number average degree of polymerization of at least 250.

5. The reaction solution of claim 1, further comprising a primer.

6. The reaction solution of claim 5, wherein the primer is dextran.

7. The reaction solution of claim 5, wherein the primer is hydrolyzed glucan.

8. The reaction solution of claim 1, wherein said glucosyltransferase enzyme consists of an amino acid sequence that is at least 95% identical to SEQ ID NO:10.

9. The reaction solution of claim 8, wherein said glucosyltransferase enzyme consists of an amino acid sequence that is at least 97% identical to SEQ ID NO:10.

10. The reaction solution of claim 9, wherein said glucosyltransferase enzyme consists of an amino acid sequence that is at least 99% identical to SEQ ID NO:10.

11. The reaction solution of claim 1, wherein a heterologous amino acid sequence of 1-300 residues is at the N-terminus and/or C-terminus of said glucosyltransferase enzyme.

12. A method for producing poly alpha-1,3-glucan comprising:
   a) contacting at least water, sucrose, and a glucosyltransferase enzyme that synthesizes poly alpha-1,3-glucan, wherein said glucosyltransferase enzyme consists of an amino acid sequence that is at least 93% identical to SEQ ID NO:10;
   whereby poly alpha-1,3-glucan is produced; and
   b) optionally, isolating the poly alpha-1,3-glucan produced in step (a).

13. The method of claim 12, wherein said glucosyltransferase enzyme synthesizes poly alpha-1,3-glucan having at least 50% alpha-1,3 glycosidic linkages and a number average degree of polymerization of at least 100.

14. The method of claim 13, wherein said glucosyltransferase enzyme synthesizes poly alpha-1,3-glucan having 100% alpha-1,3 glycosidic linkages and a number average degree of polymerization of at least 100.

15. The method of claim 14, wherein said glucosyltransferase enzyme synthesizes poly alpha-1,3-glucan having 100% alpha-1,3 glycosidic linkages and a number average degree of polymerization of at least 250.

16. The method of claim 12, wherein step (a) further comprises contacting a primer with the water, sucrose, and glucosyltransferase enzyme.

17. The method of claim 16, wherein the primer is dextran.

18. The method of claim 16, wherein the primer is hydrolyzed glucan.

19. The method of claim 12, wherein said glucosyltransferase enzyme consists of an amino acid sequence that is at least 95% identical to SEQ ID NO:10.

20. The method of claim 19, wherein said glucosyltransferase enzyme consists of an amino acid sequence that is at least 97% identical to SEQ ID NO:10.

21. The method of claim 20, wherein said glucosyltransferase enzyme consists of an amino acid sequence that is at least 99% identical to SEQ ID NO:10.

22. The method of claim 12, wherein a heterologous amino acid sequence of 1-300 residues is at the N-terminus and/or C-terminus of said glucosyltransferase enzyme.

* * * * *